United States Patent
Ichihara et al.

(10) Patent No.: US 9,963,581 B2
(45) Date of Patent: *May 8, 2018

(54) FOOD PRODUCT CONTAINING STARCH GEL, STARCH GRANULE, PRODUCTION METHOD AND USE THEREOF

(75) Inventors: Takashi Ichihara, Osaka (JP); Junya Fukuda, Osaka (JP); Masakazu Kimura, Osaka (JP); Kenichi Kurita, Osaka (JP)

(73) Assignee: Glico Nutrition Co., Ltd., Osaka (JP)

( * ) Notice: Subject to any disclaimer, the term of this patent is extended or adjusted under 35 U.S.C. 154(b) by 145 days.

This patent is subject to a terminal disclaimer.

(21) Appl. No.: 13/564,104

(22) Filed: Aug. 1, 2012

(65) Prior Publication Data

US 2013/0011884 A1 Jan. 10, 2013

Related U.S. Application Data

(63) Continuation-in-part of application No. 13/383,060, filed as application No. PCT/JP2010/005046 on Aug. 11, 2010, now Pat. No. 9,005,681.

(30) Foreign Application Priority Data

Aug. 18, 2009 (JP) ................................. 2009-189567

(51) Int. Cl.
| | |
|---|---|
| C12P 19/04 | (2006.01) |
| C08B 31/00 | (2006.01) |
| C08L 3/02 | (2006.01) |
| C09J 103/02 | (2006.01) |
| C12P 19/14 | (2006.01) |
| C12P 19/16 | (2006.01) |
| C12P 19/18 | (2006.01) |
| C12P 19/20 | (2006.01) |
| C12P 19/22 | (2006.01) |
| D04H 1/4266 | (2012.01) |
| A23L 29/212 | (2016.01) |

(52) U.S. Cl.
CPC ............... *C08L 3/02* (2013.01); *A23L 29/212* (2016.08); *C09J 103/02* (2013.01); *C12P 19/04* (2013.01); *C12P 19/14* (2013.01); *C12P 19/16* (2013.01); *C12P 19/18* (2013.01); *C12P 19/20* (2013.01); *C12P 19/22* (2013.01); *D04H 1/4266* (2013.01); *Y10T 428/1352* (2015.01); *Y10T 442/60* (2015.04)

(58) Field of Classification Search
CPC .......... C12P 19/04; C12P 19/16; A23L 1/0522
USPC .......................................... 435/101; 426/48
See application file for complete search history.

(56) References Cited

U.S. PATENT DOCUMENTS

| 5,445,950 A | 8/1995 | Kobayashi et al. | |
|---|---|---|---|
| 6,461,656 B1* | 10/2002 | Bindzus et al. | ............... 426/242 |
| 2005/0204425 A1 | 9/2005 | Myers et al. | |
| 2007/0110847 A1 | 5/2007 | Okamoto et al. | |

FOREIGN PATENT DOCUMENTS

| CN | 101028101 A | 9/2007 |
|---|---|---|
| JP | 59-196072 A | 11/1984 |
| JP | 1-159047 A | 6/1989 |
| JP | 5-112469 A | 5/1993 |
| JP | 06-269291 A | 9/1994 |
| JP | 7-063324 | 7/1995 |
| JP | 8-277230 A | 10/1996 |
| JP | 10-215795 A | 8/1998 |
| JP | 11-192052 | 7/1999 |
| JP | 11-255802 A | 9/1999 |
| JP | 2001-103991 A | 4/2001 |
| JP | 3312225 | 8/2002 |
| JP | 2003-219813 A | 8/2003 |
| JP | 3723860 B2 | 12/2005 |
| JP | 2007-302767 A | 11/2007 |
| JP | 4170062 | 10/2008 |
| WO | 96/003513 A2 | 2/1996 |
| WO | 2005/096839 A1 | 10/2005 |
| WO | 2006/065579 A2 | 6/2006 |
| WO | 2008/059992 A1 | 5/2008 |

OTHER PUBLICATIONS

Maschine translation of Kobori JP 59-196-072.*
Maschine translation of shoichi et al JP 06-2692901.*
Palacios et al. J. Agr Food Chem. 2004, 52 pp. 5987-5994.*

(Continued)

*Primary Examiner* — Tekchand Saidha
*Assistant Examiner* — Mohammad Y Meah
(74) *Attorney, Agent, or Firm* — Renner, Otto, Boisselle & Sklar, LLP

(57) ABSTRACT

Here is provided a method of producing a starch gel-containing food, the method comprising the steps of: treating starch granules with an enzyme at a temperature of about 10° C. or higher and about 70° C. or lower to obtain an enzyme-treated starch; mixing a food material, the enzyme-treated starch and water to obtain a mixture; heating the mixture thereby gelatinizing the enzyme-treated starch in the mixture; and cooling the mixture containing the gelatinized enzyme-treated starch thereby gelling the starch to obtain a starch gel-containing food, wherein the enzyme is selected from the group consisting of amyloglucosidase, isoamylase, α-glucosidase, α-amylase having a characteristic capable of improving a gel forming ability of a starch, and cyclodextrin glucanotransferase.

36 Claims, 3 Drawing Sheets

(56) References Cited

OTHER PUBLICATIONS

Chinese Office Action for corresponding Chinese Application No. 201080036978.3 dated Oct. 11, 2013 and English translation.
Co-pending U.S. Appl. No. 13/383,060, filed Jan. 9, 2012. (application provided).
International Search Report and Written Opinion for corresponding International Application No. PCT/JP2010/005046 dated Nov. 30, 2010.
Form PCT/ISA/237 for corresponding International Application No. PCT/JP2010/005046 dated Nov. 30, 2010.
Japanese Office Action for corresponding Japanese Application No. 2011-508150 dated Apr. 20, 2011 and English translation.
Fukai et al., "Koso Shori ni yoru Kakushu Denpunryu no Tokusei Kaihen (the 1st report) Characteristic Change of Rice Starch Granules by Enzymatic Treatment", Journal of starch and its related carbohydrates and enzymes, 1993, vol. 40, No. 3, pp. 263-269.
Fukai et al., "Changes in Three Kinds of Starch Granules after Enzymatic Treatment, part II", Journal of the Agricultural Chemical Society of Japan, 1994, vol. 68, No. 4, p. 793-800.
Absar et al., Enzymatic hydrolysis of potato starches containing different amounts of phosphorus, Food Chem., Jan. 1, 2009, Vo. 112, No. 1, p. 57-62.
Karim et al., "Dual Modification of Starch via Partial Enzymatic Hydrolysis in the Granular State and Subsequent Hydroxypropylation", J. Agric Food Chem, 2008, Vo. 56, No. 22, p. 10901-10907.
Machida et al, "Genome sequencing and analysis of *Aspergillus oryzae*", Nature (Lond), 2005, vol. 438, No. 7071, p. 1157-1161.
Nunberg et al., Molecular cloning and characterization of the glucoamylase gene of *Aspergillus awamori*, Mol Cell Biol. 1984, vol. 4, No. 11, p. 2306-15.
Krohn et al., "An isoamylase with neutral pH optimum from a *Flavobacterium* species: cloning, characterization and expression of the *iam* gene", Mol Gen Genet, 1997, vol. 254, No. 5, p. 469-478.
Pel et al., "Genome sequencing and analysis of the versatile cell factory Aspergillus niger CBS 513.88", Nat Biotechnol, 2007, vol. 25, No. 2, p. 221-231.
Chinese Office Action for corresponding Chinese Application No. 201080036978.3 dated Jan. 15, 2013 and English translation.
"Study on physic-chemical characteristics of potato gelatin starch", China Academic Journal Electronic Publishing House. vol. 23, No. 8 77, Dec. 31, 2002 and English translation.
Chinese Office Action for corresponding Chinese Application No. 201080036978.3 dated Jul. 2, 2014 and English translation.
Chinese Office Action for corresponding Chinese Application No. 201080036978.3 dated Jan. 4, 2015 and partial English translation.
Decision of the Rejection for corresponding Chinese Application No. 201080036978.3 dated Jul. 15, 2015 and partial English translation.
Vietnamese Office Action for corresponding Vietnamese Application No. 1-2012-00384 dated Jun. 29, 2015 and English translation.

\* cited by examiner

SEQUENCE LISTING

```
<160> NUMBER OF SEQ ID NOS: 12

<210> SEQ ID NO 1
<211> LENGTH: 1848
<212> TYPE: DNA
<213> ORGANISM: Aspergillus oryzae
<220> FEATURE:
<221> NAME/KEY: CDS
<222> LOCATION: (1)..(1848)

<400> SEQUENCE: 1 atg cct tcc aag gtc aca cag tat ctg acc ggt gtt cca cac acc gac      48
Met Pro Ser Lys Val Thr Gln Tyr Leu Thr Gly Val Pro His Thr Asp
1               5                   10                  15 tgc ttg ggt acc gaa gca gtt gat acg tct att gaa gta gaa cgg cgc      96
Cys Leu Gly Thr Glu Ala Val Asp Thr Ser Ile Glu Val Glu Arg Arg
            20                  25                  30 atg atg acg cat ccg tcc tat att tgg cta tac ctg tca gaa aat cag     144
Met Met Thr His Pro Ser Tyr Ile Trp Leu Tyr Leu Ser Glu Asn Gln
        35                  40                  45 ctt ttt ctt gtt ggg tat ttt cat cag ttt cac ttc gta gcc tct cat     192
Leu Phe Leu Val Gly Tyr Phe His Gln Phe His Phe Val Ala Ser His
    50                  55                  60 agc ggc ttt ctt tct att caa gcc atc aat gtt acc cat tcc atc ctg     240
Ser Gly Phe Leu Ser Ile Gln Ala Ile Asn Val Thr His Ser Ile Leu
65                  70                  75                  80
```

| | | |
|---|---|---|
| gtt tct ctt act tct cta ttc aca agc ggt cgg tct gtg gat act aaa<br>Val Ser Leu Thr Ser Leu Phe Thr Ser Gly Arg Ser Val Asp Thr Lys<br>                  85                          90                          95 | 288 |
| tac gtg gtt aaa ata gaa gag gca cag cat ctt act aaa ctc cca tca<br>Tyr Val Val Lys Ile Glu Glu Ala Gln His Leu Thr Lys Leu Pro Ser<br>                100                        105                        110 | 336 |
| tgg gat acc cct gac aat tcg ctc atg cta caa ggt ttt gaa tgg cat<br>Trp Asp Thr Pro Asp Asn Ser Leu Met Leu Gln Gly Phe Glu Trp His<br>            115                        120                        125 | 384 |
| gtt cca gat gat caa ggg cat tgg aaa cgt ctt caa cgc tca cta gtg<br>Val Pro Asp Asp Gln Gly His Trp Lys Arg Leu Gln Arg Ser Leu Val<br>130                        135                        140 | 432 |
| agt cta aaa tcg att ggt gtc gac agt att tgg att cca ccg gga tgt<br>Ser Leu Lys Ser Ile Gly Val Asp Ser Ile Trp Ile Pro Pro Gly Cys<br>145                      150                        155                        160 | 480 |
| aaa gca atg aac cct tcc ggt aat ggc tat gac atc tat gat cta tac<br>Lys Ala Met Asn Pro Ser Gly Asn Gly Tyr Asp Ile Tyr Asp Leu Tyr<br>                165                        170                        175 | 528 |
| gac cta gga gaa ttc gac cag aag gga tca cga tct aca aaa tgg ggc<br>Asp Leu Gly Glu Phe Asp Gln Lys Gly Ser Arg Ser Thr Lys Trp Gly<br>                  180                        185                        190 | 576 |
| agc aag aca gaa ctc caa tca cta gct tgc tct gcg cgg aat ctc ggg<br>Ser Lys Thr Glu Leu Gln Ser Leu Ala Cys Ser Ala Arg Asn Leu Gly<br>                195                        200                        205 | 624 |
| att ggc att tgc tgg gat gca gtt ctt aac cac aaa gct ggt gcg gat<br>Ile Gly Ile Cys Trp Asp Ala Val Leu Asn His Lys Ala Gly Ala Asp<br>        210                        215                        220 | 672 |
| tat aca gaa cgg ttt tcg gct gta aaa gtg gac cca aaa gac cgc agt<br>Tyr Thr Glu Arg Phe Ser Ala Val Lys Val Asp Pro Lys Asp Arg Ser<br>225                      230                        235                        240 | 720 |
| gtt gaa atc ttc gct gca agg gag att gaa ggc tgg gtt gga ttc agt<br>Val Glu Ile Phe Ala Ala Arg Glu Ile Glu Gly Trp Val Gly Phe Ser<br>                          245                        250                        255 | 768 |
| ttc ccg ggc cgt ggc ggc ata tat agt tct atg aaa tat agc tgg cat<br>Phe Pro Gly Arg Gly Gly Ile Tyr Ser Ser Met Lys Tyr Ser Trp His<br>                        260                        265                        270 | 816 |
| cat ttc agc ggc gtt gac tgg gat gaa gct cgg aag aaa aat gcg ata<br>His Phe Ser Gly Val Asp Trp Asp Glu Ala Arg Lys Lys Asn Ala Ile<br>                275                        280                        285 | 864 |
| tac aga gtt gct agc aaa cga tgg tct gat gat gtg gcc cac gag aag<br>Tyr Arg Val Ala Ser Lys Arg Trp Ser Asp Asp Val Ala His Glu Lys<br>        290                        295                        300 | 912 |
| gga aac tat gac tat ctt atg ttc gcc gac cta gat tat tcc aac cta<br>Gly Asn Tyr Asp Tyr Leu Met Phe Ala Asp Leu Asp Tyr Ser Asn Leu<br>305                      310                        315                        320 | 960 |
| gaa gtt cag aag gac gtt ctc cga tgg gga gaa tgg ata gga agc caa<br>Glu Val Gln Lys Asp Val Leu Arg Trp Gly Glu Trp Ile Gly Ser Gln<br>                        325                        330                        335 | 1008 |
| tta cct ctc tgg ggt atg agg tta gat gca agc aaa cac tac tcg gct<br>Leu Pro Leu Trp Gly Met Arg Leu Asp Ala Ser Lys His Tyr Ser Ala<br>                340                        345                        350 | 1056 |
| gat ttc cag aag aaa ttt gtc aat cac gtt cga gca act gtc ggg ccg<br>Asp Phe Gln Lys Lys Phe Val Asn His Val Arg Ala Thr Val Gly Pro<br>                355                        360                        365 | 1104 |
| cag att ttc ttc gtt gca gag tat tgg agc ggc gat gtc agg gtt ctt<br>Gln Ile Phe Phe Val Ala Glu Tyr Trp Ser Gly Asp Val Arg Val Leu<br>        370                        375                        380 | 1152 |
| atg cat tac cta cag aag atg gat tac cag ctg tct ctg ttc gat gca<br>Met His Tyr Leu Gln Lys Met Asp Tyr Gln Leu Ser Leu Phe Asp Ala<br>385                      390                        395                        400 | 1200 |

| | | | | | | | | | | | | | | | | |
|---|---|---|---|---|---|---|---|---|---|---|---|---|---|---|---|---|
| ccc | tta | gtc | ggg | cgc | ttc | tcg | agg | atc | tcg | cgc | acg | gga | gaa | gat | ctt | 1248 |
| Pro | Leu | Val | Gly | Arg | Phe | Ser | Arg | Ile | Ser | Arg | Thr | Gly | Glu | Asp | Leu | |
| | | | 405 | | | | 410 | | | | | 415 | | | | |
| cgc | gag | atc | ttc | gat | gat | acg | ctg | gta | ggg | aac | aag | cct | gca | cac | gca | 1296 |
| Arg | Glu | Ile | Phe | Asp | Asp | Thr | Leu | Val | Gly | Asn | Lys | Pro | Ala | His | Ala | |
| | | 420 | | | | | 425 | | | | | 430 | | | | |
| att | act | cta | gtt | atg | aat | cat | gac | acg | gta | aga | gag | aga | cag | tcc | cta | 1344 |
| Ile | Thr | Leu | Val | Met | Asn | His | Asp | Thr | Val | Arg | Glu | Arg | Gln | Ser | Leu | |
| | 435 | | | | | 440 | | | | | 445 | | | | | |
| gag | gct | cca | att | gca | tca | ttc | ttc | aag | cca | ctc | gcc | tat | gca | tta | att | 1392 |
| Glu | Ala | Pro | Ile | Ala | Ser | Phe | Phe | Lys | Pro | Leu | Ala | Tyr | Ala | Leu | Ile | |
| 450 | | | | | 455 | | | | | 460 | | | | | | |
| cta | ctc | cga | gac | aag | ggg | cag | ccg | tgt | ata | ttt | tat | gga | gac | ctt | tac | 1440 |
| Leu | Leu | Arg | Asp | Lys | Gly | Gln | Pro | Cys | Ile | Phe | Tyr | Gly | Asp | Leu | Tyr | |
| 465 | | | | | 470 | | | | | 475 | | | | | 480 | |
| ggt | atc | aga | cgc | ggc | gtc | aaa | aat | ccc | atg | act | cca | tcc | tgt | ggc | gga | 1488 |
| Gly | Ile | Arg | Arg | Gly | Val | Lys | Asn | Pro | Met | Thr | Pro | Ser | Cys | Gly | Gly | |
| | | | 485 | | | | | 490 | | | | | 495 | | | |
| aag | ctt | cca | gtt | ctt | gca | cgg | gct | cgt | aag | ctt | tat | gct | tac | ggc | gaa | 1536 |
| Lys | Leu | Pro | Val | Leu | Ala | Arg | Ala | Arg | Lys | Leu | Tyr | Ala | Tyr | Gly | Glu | |
| | | | 500 | | | | | 505 | | | | | 510 | | | |
| caa | tgc | gac | tat | ttt | gat | caa | gcc | aat | tgc | atc | gga | ttc | gtc | cgt | tat | 1584 |
| Gln | Cys | Asp | Tyr | Phe | Asp | Gln | Ala | Asn | Cys | Ile | Gly | Phe | Val | Arg | Tyr | |
| | | 515 | | | | | 520 | | | | | 525 | | | | |
| ggc | aac | ttg | cat | cac | ccg | tcc | ggt | cta | gca | tgc | atc | atg | agc | aac | ggg | 1632 |
| Gly | Asn | Leu | His | His | Pro | Ser | Gly | Leu | Ala | Cys | Ile | Met | Ser | Asn | Gly | |
| | 530 | | | | | 535 | | | | | 540 | | | | | |
| ggt | gcg | tct | cag | aaa | cgt | atg | tac | gtc | gga | cgg | agc | cat | gcc | aag | gag | 1680 |
| Gly | Ala | Ser | Gln | Lys | Arg | Met | Tyr | Val | Gly | Arg | Ser | His | Ala | Lys | Glu | |
| 545 | | | | | 550 | | | | | 555 | | | | | 560 | |
| cga | tgg | aca | gac | att | ttg | ggg | tgg | cat | cca | aag | aca | gtt | atc | atc | gat | 1728 |
| Arg | Trp | Thr | Asp | Ile | Leu | Gly | Trp | His | Pro | Lys | Thr | Val | Ile | Ile | Asp | |
| | | | 565 | | | | | 570 | | | | | 575 | | | |
| aag | aaa | ggt | tat | ggg | ata | ttt | cct | gtt | tct | gca | atg | cag | gtt | agt | gtc | 1776 |
| Lys | Lys | Gly | Tyr | Gly | Ile | Phe | Pro | Val | Ser | Ala | Met | Gln | Val | Ser | Val | |
| | | | 580 | | | | | 585 | | | | | 590 | | | |
| tgg | gtg | aac | tcg | gcc | gca | gaa | gcg | aga | gaa | agt | ctt | caa | gag | cct | ttc | 1824 |
| Trp | Val | Asn | Ser | Ala | Ala | Glu | Ala | Arg | Glu | Ser | Leu | Gln | Glu | Pro | Phe | |
| | | | 595 | | | | | 600 | | | | | 605 | | | |
| gag | gag | aag | att | tac | gag | aat | tga | | | | | | | | | 1848 |
| Glu | Glu | Lys | Ile | Tyr | Glu | Asn | | | | | | | | | | |
| | 610 | | | | | 615 | | | | | | | | | | |

```
<210> SEQ ID NO 2
<211> LENGTH: 615
<212> TYPE: PRT
<213> ORGANISM: Aspergillus oryzae

<400> SEQUENCE: 2
```

| | | | | | | | | | | | | | | | |
|---|---|---|---|---|---|---|---|---|---|---|---|---|---|---|---|
| Met | Pro | Ser | Lys | Val | Thr | Gln | Tyr | Leu | Thr | Gly | Val | Pro | His | Thr | Asp |
| 1 | | | | 5 | | | | | 10 | | | | | 15 | |
| Cys | Leu | Gly | Thr | Glu | Ala | Val | Asp | Thr | Ser | Ile | Glu | Val | Glu | Arg | Arg |
| | | | 20 | | | | | 25 | | | | | 30 | | |
| Met | Met | Thr | His | Pro | Ser | Tyr | Ile | Trp | Leu | Tyr | Leu | Ser | Glu | Asn | Gln |
| | | 35 | | | | | 40 | | | | | 45 | | | |
| Leu | Phe | Leu | Val | Gly | Tyr | Phe | His | Gln | Phe | His | Phe | Val | Ala | Ser | His |
| | 50 | | | | | 55 | | | | | 60 | | | | |
| Ser | Gly | Phe | Leu | Ser | Ile | Gln | Ala | Ile | Asn | Val | Thr | His | Ser | Ile | Leu |
| 65 | | | | | 70 | | | | | 75 | | | | | 80 |

-continued

```
Val Ser Leu Thr Ser Leu Phe Thr Ser Gly Arg Ser Val Asp Thr Lys
             85                  90                  95

Tyr Val Val Lys Ile Glu Glu Ala Gln His Leu Thr Lys Leu Pro Ser
            100                 105                 110

Trp Asp Thr Pro Asp Asn Ser Leu Met Leu Gln Gly Phe Glu Trp His
            115                 120                 125

Val Pro Asp Asp Gln Gly His Trp Lys Arg Leu Gln Arg Ser Leu Val
130                 135                 140

Ser Leu Lys Ser Ile Gly Val Asp Ser Ile Trp Ile Pro Pro Gly Cys
145                 150                 155                 160

Lys Ala Met Asn Pro Ser Gly Asn Gly Tyr Asp Ile Tyr Asp Leu Tyr
                165                 170                 175

Asp Leu Gly Glu Phe Asp Gln Lys Gly Ser Arg Ser Thr Lys Trp Gly
            180                 185                 190

Ser Lys Thr Glu Leu Gln Ser Leu Ala Cys Ser Ala Arg Asn Leu Gly
            195                 200                 205

Ile Gly Ile Cys Trp Asp Ala Val Leu Asn His Lys Ala Gly Ala Asp
            210                 215                 220

Tyr Thr Glu Arg Phe Ser Ala Val Lys Val Asp Pro Lys Asp Arg Ser
225                 230                 235                 240

Val Glu Ile Phe Ala Ala Arg Glu Ile Glu Gly Trp Val Gly Phe Ser
                245                 250                 255

Phe Pro Gly Arg Gly Gly Ile Tyr Ser Ser Met Lys Tyr Ser Trp His
                260                 265                 270

His Phe Ser Gly Val Asp Trp Asp Glu Ala Arg Lys Lys Asn Ala Ile
            275                 280                 285

Tyr Arg Val Ala Ser Lys Arg Trp Ser Asp Asp Val Ala His Glu Lys
            290                 295                 300

Gly Asn Tyr Asp Tyr Leu Met Phe Ala Asp Leu Asp Tyr Ser Asn Leu
305                 310                 315                 320

Glu Val Gln Lys Asp Val Leu Arg Trp Gly Glu Trp Ile Gly Ser Gln
                325                 330                 335

Leu Pro Leu Trp Gly Met Arg Leu Asp Ala Ser Lys His Tyr Ser Ala
                340                 345                 350

Asp Phe Gln Lys Lys Phe Val Asn His Val Arg Ala Thr Val Gly Pro
            355                 360                 365

Gln Ile Phe Phe Val Ala Glu Tyr Trp Ser Gly Asp Val Arg Val Leu
            370                 375                 380

Met His Tyr Leu Gln Lys Met Asp Tyr Gln Leu Ser Leu Phe Asp Ala
385                 390                 395                 400

Pro Leu Val Gly Arg Phe Ser Arg Ile Ser Arg Thr Gly Glu Asp Leu
                405                 410                 415

Arg Glu Ile Phe Asp Asp Thr Leu Val Gly Asn Lys Pro Ala His Ala
            420                 425                 430

Ile Thr Leu Val Met Asn His Asp Thr Val Arg Glu Arg Gln Ser Leu
            435                 440                 445

Glu Ala Pro Ile Ala Ser Phe Phe Lys Pro Leu Ala Tyr Ala Leu Ile
            450                 455                 460

Leu Leu Arg Asp Lys Gly Gln Pro Cys Ile Phe Tyr Gly Asp Leu Tyr
465                 470                 475                 480

Gly Ile Arg Arg Gly Val Lys Asn Pro Met Thr Pro Ser Cys Gly Gly
                485                 490                 495
```

```
                        Lys Leu Pro Val Leu Ala Arg Ala Arg Lys Leu Tyr Ala Tyr Gly Glu
                                        500                 505                 510

Gln Cys Asp Tyr Phe Asp Gln Ala Asn Cys Ile Gly Phe Val Arg Tyr
                                    515                 520                 525

Gly Asn Leu His His Pro Ser Gly Leu Ala Cys Ile Met Ser Asn Gly
                                530                 535                 540

Gly Ala Ser Gln Lys Arg Met Tyr Val Gly Arg Ser His Ala Lys Glu
                        545                 550                 555                 560

Arg Trp Thr Asp Ile Leu Gly Trp His Pro Lys Thr Val Ile Ile Asp
                                        565                 570                 575

Lys Lys Gly Tyr Gly Ile Phe Pro Val Ser Ala Met Gln Val Ser Val
                                    580                 585                 590

Trp Val Asn Ser Ala Ala Glu Ala Arg Glu Ser Leu Gln Glu Pro Phe
                                595                 600                 605

Glu Glu Lys Ile Tyr Glu Asn
                            610                 615

<210> SEQ ID NO 3
<211> LENGTH: 1497
<212> TYPE: DNA
<213> ORGANISM: Aspergillus niger
<220> FEATURE:
<221> NAME/KEY: CDS
<222> LOCATION: (1)..(1497)

<400> SEQUENCE: 3 atg gtc gcg tgg tgg tct cta ttt ctg tac ggc ctt cag gtc gcg gca        48
Met Val Ala Trp Trp Ser Leu Phe Leu Tyr Gly Leu Gln Val Ala Ala
1               5                   10                  15 cct gct ttg gct gca acg cct gcg gac tgg cga tcg caa tcc att tat        96
Pro Ala Leu Ala Ala Thr Pro Ala Asp Trp Arg Ser Gln Ser Ile Tyr
                20                  25                  30 ttc ctc acg gat cga ttt gca agg acg gat ggg tcg acg act gcg              144
Phe Leu Leu Thr Asp Arg Phe Ala Arg Thr Asp Gly Ser Thr Thr Ala
            35                  40                  45 act tgt aat act gcg gat cag aaa tac tgt ggt gga aca tgg cag ggc          192
Thr Cys Asn Thr Ala Asp Gln Lys Tyr Cys Gly Gly Thr Trp Gln Gly
        50                  55                  60 atc atc gac aag ttg gac tat atc cag gga atg ggc ttc aca gcc atc          240
Ile Ile Asp Lys Leu Asp Tyr Ile Gln Gly Met Gly Phe Thr Ala Ile
65                  70                  75                  80 tgg atc acc ccc gtt aca gcc cag ctg ccc cag acc acc gca tat gga          288
Trp Ile Thr Pro Val Thr Ala Gln Leu Pro Gln Thr Thr Ala Tyr Gly
                85                  90                  95 gat gcc tac cat ggc tac tgg cag cag gat ata tac tct ctg aac gaa          336
Asp Ala Tyr His Gly Tyr Trp Gln Gln Asp Ile Tyr Ser Leu Asn Glu
                100                 105                 110 aac tac ggc act gca gat gac ttg aag gcg ctc tct tcg gcc ctt cat          384
Asn Tyr Gly Thr Ala Asp Asp Leu Lys Ala Leu Ser Ser Ala Leu His
            115                 120                 125 gag agg ggg atg tat ctt atg gtc gat gtg gtt gct aac cat atg ggc          432
Glu Arg Gly Met Tyr Leu Met Val Asp Val Val Ala Asn His Met Gly
        130                 135                 140 tat gat gga gcg ggt agc tca gtc gat tac agt gtg ttt aaa ccg ttc          480
Tyr Asp Gly Ala Gly Ser Ser Val Asp Tyr Ser Val Phe Lys Pro Phe
145                 150                 155                 160 agt tcc caa gac tac ttc cac ccg ttc tgt ttc att caa aac tat gaa          528
Ser Ser Gln Asp Tyr Phe His Pro Phe Cys Phe Ile Gln Asn Tyr Glu
                165                 170                 175
```

```
gat cag act cag gtt gag gat tgc tgg cta gga gat aac act gtc tcc      576
Asp Gln Thr Gln Val Glu Asp Cys Trp Leu Gly Asp Asn Thr Val Ser
            180                 185                 190 ttg cct gat ctc gat acc acc aag gat gtg gtc aag aat gaa tgg tac      624
Leu Pro Asp Leu Asp Thr Thr Lys Asp Val Val Lys Asn Glu Trp Tyr
        195                 200                 205 gac tgg gtg gga tca ttg gta tcg aac tac tcc att gac ggc ctc cgt      672
Asp Trp Val Gly Ser Leu Val Ser Asn Tyr Ser Ile Asp Gly Leu Arg
    210                 215                 220 atc gac aca gta aaa cac gtc cag aag gac ttc tgg ccc ggg tac aac      720
Ile Asp Thr Val Lys His Val Gln Lys Asp Phe Trp Pro Gly Tyr Asn
225                 230                 235                 240 aaa gcc gca ggc gtg tac tgt atc ggc gag gtg ctc gac ggt gat ccg      768
Lys Ala Ala Gly Val Tyr Cys Ile Gly Glu Val Leu Asp Gly Asp Pro
            245                 250                 255 gcc tac act tgt ccc tac cag aac gtc atg gac ggc gta ctg aac tat      816
Ala Tyr Thr Cys Pro Tyr Gln Asn Val Met Asp Gly Val Leu Asn Tyr
        260                 265                 270 ccc att tac tat cca ctc ctc aac gcc ttc aag tca acc tcc ggc agc      864
Pro Ile Tyr Tyr Pro Leu Leu Asn Ala Phe Lys Ser Thr Ser Gly Ser
    275                 280                 285 atg gac gac ctc tac aac atg atc aac acc gtc aaa tcc gac tgt cca      912
Met Asp Asp Leu Tyr Asn Met Ile Asn Thr Val Lys Ser Asp Cys Pro
290                 295                 300 gac tca aca ctc ctg ggc aca ttc gtc gag aac cac gac aac cca cgg      960
Asp Ser Thr Leu Leu Gly Thr Phe Val Glu Asn His Asp Asn Pro Arg
305                 310                 315                 320 ttc gct tct tac acc aac gac ata gcc ctc gcc aag aac gtc gca gca     1008
Phe Ala Ser Tyr Thr Asn Asp Ile Ala Leu Ala Lys Asn Val Ala Ala
            325                 330                 335 ttc atc atc ctc aac gac gga atc ccc atc atc tac gcc ggc caa gaa     1056
Phe Ile Ile Leu Asn Asp Gly Ile Pro Ile Ile Tyr Ala Gly Gln Glu
        340                 345                 350 cag cac tac gcc ggc gga aac gac ccc gcg aac cgc gaa gca acc tgg     1104
Gln His Tyr Ala Gly Gly Asn Asp Pro Ala Asn Arg Glu Ala Thr Trp
    355                 360                 365 ctc tcg ggc tac ccg acc gac agc gag ctg tac aag tta att gcc tcc     1152
Leu Ser Gly Tyr Pro Thr Asp Ser Glu Leu Tyr Lys Leu Ile Ala Ser
370                 375                 380 gcg aac gca atc cgg aac tat gcc att agc aaa gat aca gga ttc gtg     1200
Ala Asn Ala Ile Arg Asn Tyr Ala Ile Ser Lys Asp Thr Gly Phe Val
385                 390                 395                 400 acc tac aag aac tgg ccc atc tac aaa gac gac aca acg atc gcc atg     1248
Thr Tyr Lys Asn Trp Pro Ile Tyr Lys Asp Asp Thr Thr Ile Ala Met
            405                 410                 415 cgc aag ggc aca gat ggg tcg cag atc gtg act atc ttg tcc aac aag     1296
Arg Lys Gly Thr Asp Gly Ser Gln Ile Val Thr Ile Leu Ser Asn Lys
        420                 425                 430 ggt gct tcg ggt gat tcg tat acc ctc tcc ttg agt ggt gcg ggt tac     1344
Gly Ala Ser Gly Asp Ser Tyr Thr Leu Ser Leu Ser Gly Ala Gly Tyr
    435                 440                 445 aca gcc ggc cag caa ttg acg gag gtc att ggc tgc acg acc gtg acg     1392
Thr Ala Gly Gln Gln Leu Thr Glu Val Ile Gly Cys Thr Thr Val Thr
450                 455                 460 gtt ggt tcg gat gga aat gtg cct gtt cct atg gca ggt ggg cta cct     1440
Val Gly Ser Asp Gly Asn Val Pro Val Pro Met Ala Gly Gly Leu Pro
465                 470                 475                 480 agg gta ttg tat ccg act gag aag ttg gca ggt agc aag atc tgt agt     1488
Arg Val Leu Tyr Pro Thr Glu Lys Leu Ala Gly Ser Lys Ile Cys Ser
            485                 490                 495
```

```
agc tcg tga                                                    1497
Ser Ser

<210> SEQ ID NO 4
<211> LENGTH: 498
<212> TYPE: PRT
<213> ORGANISM: Aspergillus niger

<400> SEQUENCE: 4
```

Met Val Ala Trp Trp Ser Leu Phe Leu Tyr Gly Leu Gln Val Ala Ala
1               5                   10                  15

Pro Ala Leu Ala Ala Thr Pro Asp Trp Arg Ser Gln Ser Ile Tyr
            20                  25                  30

Phe Leu Leu Thr Asp Arg Phe Ala Arg Thr Asp Gly Ser Thr Thr Ala
            35                  40                  45

Thr Cys Asn Thr Ala Asp Gln Lys Tyr Cys Gly Gly Thr Trp Gln Gly
    50                  55                  60

Ile Ile Asp Lys Leu Asp Tyr Ile Gln Gly Met Gly Phe Thr Ala Ile
65                  70                  75                  80

Trp Ile Thr Pro Val Thr Ala Gln Leu Pro Gln Thr Thr Ala Tyr Gly
                85                  90                  95

Asp Ala Tyr His Gly Tyr Trp Gln Gln Asp Ile Tyr Ser Leu Asn Glu
            100                 105                 110

Asn Tyr Gly Thr Ala Asp Asp Leu Lys Ala Leu Ser Ser Ala Leu His
        115                 120                 125

Glu Arg Gly Met Tyr Leu Met Val Asp Val Val Ala Asn His Met Gly
130                 135                 140

Tyr Asp Gly Ala Gly Ser Ser Val Asp Tyr Ser Val Phe Lys Pro Phe
145                 150                 155                 160

Ser Ser Gln Asp Tyr Phe His Pro Phe Cys Phe Ile Gln Asn Tyr Glu
                165                 170                 175

Asp Gln Thr Gln Val Glu Asp Cys Trp Leu Gly Asp Asn Thr Val Ser
            180                 185                 190

Leu Pro Asp Leu Asp Thr Thr Lys Asp Val Val Lys Asn Glu Trp Tyr
        195                 200                 205

Asp Trp Val Gly Ser Leu Val Ser Asn Tyr Ser Ile Asp Gly Leu Arg
210                 215                 220

Ile Asp Thr Val Lys His Val Gln Lys Asp Phe Trp Pro Gly Tyr Asn
225                 230                 235                 240

Lys Ala Ala Gly Val Tyr Cys Ile Gly Glu Val Leu Asp Gly Asp Pro
                245                 250                 255

Ala Tyr Thr Cys Pro Tyr Gln Asn Val Met Asp Gly Val Leu Asn Tyr
            260                 265                 270

Pro Ile Tyr Tyr Pro Leu Leu Asn Ala Phe Lys Ser Thr Ser Gly Ser
        275                 280                 285

Met Asp Asp Leu Tyr Asn Met Ile Asn Thr Val Lys Ser Asp Cys Pro
290                 295                 300

Asp Ser Thr Leu Leu Gly Thr Phe Val Glu Asn His Asp Asn Pro Arg
305                 310                 315                 320

Phe Ala Ser Tyr Thr Asn Asp Ile Ala Leu Ala Lys Asn Val Ala Ala
                325                 330                 335

Phe Ile Ile Leu Asn Asp Gly Ile Pro Ile Ile Tyr Ala Gly Gln Glu
            340                 345                 350

Gln His Tyr Ala Gly Gly Asn Asp Pro Ala Asn Arg Glu Ala Thr Trp

```
                355                 360                 365
Leu Ser Gly Tyr Pro Thr Asp Ser Glu Leu Tyr Lys Leu Ile Ala Ser
    370                 375                 380

Ala Asn Ala Ile Arg Asn Tyr Ala Ile Ser Lys Asp Thr Gly Phe Val
385                 390                 395                 400

Thr Tyr Lys Asn Trp Pro Ile Tyr Lys Asp Thr Thr Ile Ala Met
                405                 410                 415

Arg Lys Gly Thr Asp Gly Ser Gln Ile Val Thr Ile Leu Ser Asn Lys
                420                 425                 430

Gly Ala Ser Gly Asp Ser Tyr Thr Leu Ser Leu Ser Gly Ala Gly Tyr
                435                 440                 445

Thr Ala Gly Gln Gln Leu Thr Glu Val Ile Gly Cys Thr Thr Val Thr
    450                 455                 460

Val Gly Ser Asp Gly Asn Val Pro Val Pro Met Ala Gly Gly Leu Pro
465                 470                 475                 480

Arg Val Leu Tyr Pro Thr Glu Lys Leu Ala Gly Ser Lys Ile Cys Ser
                485                 490                 495

Ser Ser

<210> SEQ ID NO 5
<211> LENGTH: 1923
<212> TYPE: DNA
<213> ORGANISM: Aspergillus niger
<220> FEATURE:
<221> NAME/KEY: CDS
<222> LOCATION: (1)..(1923)

<400> SEQUENCE: 5 atg tcg ttc cga tct cta ctc gcc ctg agc ggc ctc gtc tgc aca ggg     48
Met Ser Phe Arg Ser Leu Leu Ala Leu Ser Gly Leu Val Cys Thr Gly
1               5                   10                  15 ttg gca aat gtg att tcc aag cgc gcg acc ttg gat tca tgg ttg agc     96
Leu Ala Asn Val Ile Ser Lys Arg Ala Thr Leu Asp Ser Trp Leu Ser
            20                  25                  30 aac gaa gcg acc gtg gct cgt act gcc atc ctg aat aac atc ggg gcg    144
Asn Glu Ala Thr Val Ala Arg Thr Ala Ile Leu Asn Asn Ile Gly Ala
        35                  40                  45 gac ggt gct tgg gtg tcg ggc gcg gac tct ggc att gtc gtt gct agt    192
Asp Gly Ala Trp Val Ser Gly Ala Asp Ser Gly Ile Val Val Ala Ser
    50                  55                  60 ccc agc acg gat aac ccg gac tac ttc tac acc tgg act cgc gac tct    240
Pro Ser Thr Asp Asn Pro Asp Tyr Phe Tyr Thr Trp Thr Arg Asp Ser
65                  70                  75                  80 ggt ctc gtc ctc aag acc ctc gtc gat ctc ttc cga aat gga gat acc    288
Gly Leu Val Leu Lys Thr Leu Val Asp Leu Phe Arg Asn Gly Asp Thr
                85                  90                  95 agt ctc ctc tcc acc att gag aac tac atc tcc gcc cag gca att gtc    336
Ser Leu Leu Ser Thr Ile Glu Asn Tyr Ile Ser Ala Gln Ala Ile Val
            100                 105                 110 cag ggt atc agt aac ccc tct ggt gat ctg tcc agc ggc gct ggt ctc    384
Gln Gly Ile Ser Asn Pro Ser Gly Asp Leu Ser Ser Gly Ala Gly Leu
        115                 120                 125 ggt gaa ccc aag ttc aat gtc gat gag act gcc tac act ggt tct tgg    432
Gly Glu Pro Lys Phe Asn Val Asp Glu Thr Ala Tyr Thr Gly Ser Trp
    130                 135                 140 gga cgg ccg cag cga gat ggt ccg gct ctg aga gca act gct atg atc    480
Gly Arg Pro Gln Arg Asp Gly Pro Ala Leu Arg Ala Thr Ala Met Ile
145                 150                 155                 160
```

```
ggc ttc ggg cag tgg ctg ctt gac aat ggc tac acc agc acc gca acg      528
Gly Phe Gly Gln Trp Leu Leu Asp Asn Gly Tyr Thr Ser Thr Ala Thr
            165                 170                 175 gac att gtt tgg ccc ctc gtt agg aac gac ctg tcg tat gtg gct caa      576
Asp Ile Val Trp Pro Leu Val Arg Asn Asp Leu Ser Tyr Val Ala Gln
            180                 185                 190 tac tgg aac cag aca gga tat gat ctc tgg gaa gaa gtc aat ggc tcg      624
Tyr Trp Asn Gln Thr Gly Tyr Asp Leu Trp Glu Glu Val Asn Gly Ser
            195                 200                 205 tct ttc ttt acg att gct gtg caa cac cgc gcc ctt gtc gaa ggt agt      672
Ser Phe Phe Thr Ile Ala Val Gln His Arg Ala Leu Val Glu Gly Ser
            210                 215                 220 gcc ttc gcg acg gcc gtc ggc tcg tcc tgc tcc tgg tgt gat tct cag      720
Ala Phe Ala Thr Ala Val Gly Ser Ser Cys Ser Trp Cys Asp Ser Gln
225                 230                 235                 240 gca ccc gaa att ctc tgc tac ctg cag tcc ttc tgg acc ggc agc ttc      768
Ala Pro Glu Ile Leu Cys Tyr Leu Gln Ser Phe Trp Thr Gly Ser Phe
                245                 250                 255 att ctg gcc aac ttc gat agc agc cgt tcc ggc aag gac gca aac acc      816
Ile Leu Ala Asn Phe Asp Ser Ser Arg Ser Gly Lys Asp Ala Asn Thr
            260                 265                 270 ctc ctg gga agc atc cac acc ttt gat cct gag gcc gca tgc gac gac      864
Leu Leu Gly Ser Ile His Thr Phe Asp Pro Glu Ala Ala Cys Asp Asp
            275                 280                 285 tcc acc ttc cag ccc tgc tcc ccg cgc gcg ctc gcc aac cac aag gag      912
Ser Thr Phe Gln Pro Cys Ser Pro Arg Ala Leu Ala Asn His Lys Glu
            290                 295                 300 gtt gta gac tct ttc cgc tca atc tat acc ctc aac gat ggt ctc agt      960
Val Val Asp Ser Phe Arg Ser Ile Tyr Thr Leu Asn Asp Gly Leu Ser
305                 310                 315                 320 gac agc gag gct gtt gcg gtg ggt cgg tac cct gag gac acg tac tac     1008
Asp Ser Glu Ala Val Ala Val Gly Arg Tyr Pro Glu Asp Thr Tyr Tyr
                325                 330                 335 aac ggc aac ccg tgg ttc ctg tgc acc ttg gct gcc gca gag cag ttg     1056
Asn Gly Asn Pro Trp Phe Leu Cys Thr Leu Ala Ala Ala Glu Gln Leu
            340                 345                 350 tac gat gct cta tac cag tgg gac aag cag ggg tcg ttg gag gtc aca     1104
Tyr Asp Ala Leu Tyr Gln Trp Asp Lys Gln Gly Ser Leu Glu Val Thr
            355                 360                 365 gat gtg tcg ctg gac ttc ttc aag gca ctg tac agc gat gct gct act     1152
Asp Val Ser Leu Asp Phe Phe Lys Ala Leu Tyr Ser Asp Ala Ala Thr
            370                 375                 380 ggc acc tac tct tcg tcc agt tcg act tat agt agc att gta gat gcc     1200
Gly Thr Tyr Ser Ser Ser Ser Thr Tyr Ser Ser Ile Val Asp Ala
385                 390                 395                 400 gtg aag act ttc gcc gat ggc ttc gtc tct att gtg gaa act cac gcc     1248
Val Lys Thr Phe Ala Asp Gly Phe Val Ser Ile Val Glu Thr His Ala
                405                 410                 415 gca agc aac ggc tcc atg tcc gag caa tac gac aag tct gat ggc gag     1296
Ala Ser Asn Gly Ser Met Ser Glu Gln Tyr Asp Lys Ser Asp Gly Glu
            420                 425                 430 cag ctt tcc gct cgc gac ctg acc tgg tct tat gct gct ctg ctg acc     1344
Gln Leu Ser Ala Arg Asp Leu Thr Trp Ser Tyr Ala Ala Leu Leu Thr
            435                 440                 445 gcc aac aac cgt cgt aac tcc gtc gtg cct gct tct tgg ggc gag acc     1392
Ala Asn Asn Arg Arg Asn Ser Val Val Pro Ala Ser Trp Gly Glu Thr
            450                 455                 460 tct gcc agc agc gtg ccc ggc acc tgt gcg gcc aca tct gcc att ggt     1440
Ser Ala Ser Ser Val Pro Gly Thr Cys Ala Ala Thr Ser Ala Ile Gly
465                 470                 475                 480
```

```
acc tac agc agt gtg act gtc acc tcg tgg ccg agt atc gtg gct act      1488
Thr Tyr Ser Ser Val Thr Val Thr Ser Trp Pro Ser Ile Val Ala Thr
            485                 490                 495 ggc ggc acc act acg acg gct acc ccc act gga tcc ggc agc gtg acc      1536
Gly Gly Thr Thr Thr Thr Ala Thr Pro Thr Gly Ser Gly Ser Val Thr
        500                 505                 510 tcg acc agc aag acc acc gcg act gct agc aag acc agc acc agt acg      1584
Ser Thr Ser Lys Thr Thr Ala Thr Ala Ser Lys Thr Ser Thr Ser Thr
        515                 520                 525 tca tca acc tcc tgt acc act ccc acc gcc gtg gct gtg act ttc gat      1632
Ser Ser Thr Ser Cys Thr Thr Pro Thr Ala Val Ala Val Thr Phe Asp
        530                 535                 540 ctg aca gct acc acc acc tac ggc gag aac atc tac ctg gtc gga tcg      1680
Leu Thr Ala Thr Thr Thr Tyr Gly Glu Asn Ile Tyr Leu Val Gly Ser
545                 550                 555                 560 atc tct cag ctg ggt gac tgg gaa acc agc gac ggc ata gct ctg agt      1728
Ile Ser Gln Leu Gly Asp Trp Glu Thr Ser Asp Gly Ile Ala Leu Ser
                565                 570                 575 gct gac aag tac act tcc agc gac ccg ctc tgg tat gtc act gtg act      1776
Ala Asp Lys Tyr Thr Ser Ser Asp Pro Leu Trp Tyr Val Thr Val Thr
            580                 585                 590 ctg ccg gct ggt gag tcg ttt gag tac aag ttt atc cgc att gag agc      1824
Leu Pro Ala Gly Glu Ser Phe Glu Tyr Lys Phe Ile Arg Ile Glu Ser
        595                 600                 605 gat gac tcc gtg gag tgg gag agt gat ccc aac cga gaa tac acc gtt      1872
Asp Asp Ser Val Glu Trp Glu Ser Asp Pro Asn Arg Glu Tyr Thr Val
610                 615                 620 cct cag gcg tgc gga acg tcg acc gcg acg gtg act gac acc tgg cgg      1920
Pro Gln Ala Cys Gly Thr Ser Thr Ala Thr Val Thr Asp Thr Trp Arg
625                 630                 635                 640 tag                                                                   1923

<210> SEQ ID NO 6
<211> LENGTH: 640
<212> TYPE: PRT
<213> ORGANISM: Aspergillus niger

<400> SEQUENCE: 6

Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
```

```
            145                 150                 155                 160
        Gly Phe Gly Gln Trp Leu Leu Asp Asn Gly Tyr Thr Ser Thr Ala Thr
                        165                 170                 175

Asp Ile Val Trp Pro Leu Val Arg Asn Asp Leu Ser Tyr Val Ala Gln
                        180                 185                 190

Tyr Trp Asn Gln Thr Gly Tyr Asp Leu Trp Glu Glu Val Asn Gly Ser
                        195                 200                 205

Ser Phe Phe Thr Ile Ala Val Gln His Arg Ala Leu Val Glu Gly Ser
                210                 215                 220

Ala Phe Ala Thr Ala Val Gly Ser Ser Cys Ser Trp Cys Asp Ser Gln
        225                 230                 235                 240

Ala Pro Glu Ile Leu Cys Tyr Leu Gln Ser Phe Trp Thr Gly Ser Phe
                        245                 250                 255

Ile Leu Ala Asn Phe Asp Ser Ser Arg Ser Gly Lys Asp Ala Asn Thr
                        260                 265                 270

Leu Leu Gly Ser Ile His Thr Phe Asp Pro Glu Ala Ala Cys Asp Asp
                        275                 280                 285

Ser Thr Phe Gln Pro Cys Ser Pro Arg Ala Leu Ala Asn His Lys Glu
                        290                 295                 300

Val Val Asp Ser Phe Arg Ser Ile Tyr Thr Leu Asn Asp Gly Leu Ser
        305                 310                 315                 320

Asp Ser Glu Ala Val Ala Val Gly Arg Tyr Pro Glu Asp Thr Tyr Tyr
                        325                 330                 335

Asn Gly Asn Pro Trp Phe Leu Cys Thr Leu Ala Ala Ala Glu Gln Leu
                        340                 345                 350

Tyr Asp Ala Leu Tyr Gln Trp Asp Lys Gln Gly Ser Leu Glu Val Thr
                        355                 360                 365

Asp Val Ser Leu Asp Phe Phe Lys Ala Leu Tyr Ser Asp Ala Ala Thr
                        370                 375                 380

Gly Thr Tyr Ser Ser Ser Ser Thr Tyr Ser Ser Ile Val Asp Ala
        385                 390                 395                 400

Val Lys Thr Phe Ala Asp Gly Phe Val Ser Ile Val Glu Thr His Ala
                        405                 410                 415

Ala Ser Asn Gly Ser Met Ser Glu Gln Tyr Asp Lys Ser Asp Gly Glu
                        420                 425                 430

Gln Leu Ser Ala Arg Asp Leu Thr Trp Ser Tyr Ala Ala Leu Leu Thr
                        435                 440                 445

Ala Asn Asn Arg Arg Asn Ser Val Val Pro Ala Ser Trp Gly Glu Thr
                450                 455                 460

Ser Ala Ser Ser Val Pro Gly Thr Cys Ala Ala Thr Ser Ala Ile Gly
        465                 470                 475                 480

Thr Tyr Ser Ser Val Thr Val Thr Ser Trp Pro Ser Ile Val Ala Thr
                        485                 490                 495

Gly Gly Thr Thr Thr Thr Ala Thr Pro Thr Gly Ser Gly Ser Val Thr
                        500                 505                 510

Ser Thr Ser Lys Thr Thr Ala Thr Ala Ser Lys Thr Ser Thr Ser Thr
                        515                 520                 525

Ser Ser Thr Ser Cys Thr Thr Pro Thr Ala Val Ala Val Thr Phe Asp
                        530                 535                 540

Leu Thr Ala Thr Thr Thr Tyr Gly Glu Asn Ile Tyr Leu Val Gly Ser
        545                 550                 555                 560

Ile Ser Gln Leu Gly Asp Trp Glu Thr Ser Asp Gly Ile Ala Leu Ser
                        565                 570                 575
```

| Ala | Asp | Lys | Tyr | Thr | Ser | Ser | Asp | Pro | Leu | Trp | Tyr | Val | Thr | Val | Thr |
|---|---|---|---|---|---|---|---|---|---|---|---|---|---|---|---|
| | | | 580 | | | | | 585 | | | | 590 | | | |

| Leu | Pro | Ala | Gly | Glu | Ser | Phe | Glu | Tyr | Lys | Phe | Ile | Arg | Ile | Glu | Ser |
|---|---|---|---|---|---|---|---|---|---|---|---|---|---|---|---|
| | | 595 | | | | | 600 | | | | | 605 | | | |

| Asp | Asp | Ser | Val | Glu | Trp | Glu | Ser | Asp | Pro | Asn | Arg | Glu | Tyr | Thr | Val |
|---|---|---|---|---|---|---|---|---|---|---|---|---|---|---|---|
| | 610 | | | | | 615 | | | | | 620 | | | | |

| Pro | Gln | Ala | Cys | Gly | Thr | Ser | Thr | Ala | Thr | Val | Thr | Asp | Thr | Trp | Arg |
|---|---|---|---|---|---|---|---|---|---|---|---|---|---|---|---|
| 625 | | | | | 630 | | | | | 635 | | | | | 640 |

<210> SEQ ID NO 7
<211> LENGTH: 2334
<212> TYPE: DNA
<213> ORGANISM: Flavobacterium sp.
<220> FEATURE:
<221> NAME/KEY: CDS
<222> LOCATION: (1)..(2334)

<400> SEQUENCE: 7

```
atg gac cca cac gcc ccg cag cgg caa cga agc ggg cag cgc ttg cgc      48
Met Asp Pro His Ala Pro Gln Arg Gln Arg Ser Gly Gln Arg Leu Arg
1               5                   10                  15 gcc ctc gcc ctg gcc gcg ctg gcc tgc gcg ctg agc ccg gcc cac gcc      96
Ala Leu Ala Leu Ala Ala Leu Ala Cys Ala Leu Ser Pro Ala His Ala
            20                  25                  30 gcc atc gat gcg cag cag ctc ggc gcg cgc tac gac gcc gcc cag gcc     144
Ala Ile Asp Ala Gln Gln Leu Gly Ala Arg Tyr Asp Ala Ala Gln Ala
        35                  40                  45 aac ctc gcg ttc cgg gtc tat tcc tcg cgc gcg acc cgc gtc gag gtg     192
Asn Leu Ala Phe Arg Val Tyr Ser Ser Arg Ala Thr Arg Val Glu Val
50                  55                  60 ttc ctg tac aag aac ccg acc ggc tcg cag gaa gtc gcg cgg ctg gcg     240
Phe Leu Tyr Lys Asn Pro Thr Gly Ser Gln Glu Val Ala Arg Leu Ala
65                  70                  75                  80 ctg agc aag gac ccg gcg acc cag gtg tgg tcg ctg tcg ctg ccg acc     288
Leu Ser Lys Asp Pro Ala Thr Gln Val Trp Ser Leu Ser Leu Pro Thr
                85                  90                  95 agc acg atc aag aac acc tac ggc atc acc ggc gcc gtc tac tac ggt     336
Ser Thr Ile Lys Asn Thr Tyr Gly Ile Thr Gly Ala Val Tyr Tyr Gly
            100                 105                 110 tac cgc gcc tgg ggc ccg aac tgg ccc tac gat gcg gcc tgg acc aag     384
Tyr Arg Ala Trp Gly Pro Asn Trp Pro Tyr Asp Ala Ala Trp Thr Lys
        115                 120                 125 ggc agc gcc acc ggc ttc gtc agc gac gtc gac aac gcc ggc aac cgt     432
Gly Ser Ala Thr Gly Phe Val Ser Asp Val Asp Asn Ala Gly Asn Arg
    130                 135                 140 ttc aat ccg aac aag ctg ctc gac ccc tac gcg cgc gag atc agc        480
Phe Asn Pro Asn Lys Leu Leu Leu Asp Pro Tyr Ala Arg Glu Ile Ser
145                 150                 155                 160 cag gac ccg aac acc gcg acc tgc gcc gac ggc acc atc tac gcc acc     528
Gln Asp Pro Asn Thr Ala Thr Cys Ala Asp Gly Thr Ile Tyr Ala Thr
                165                 170                 175 ggc gcc gcg cac cgc aac aag gac agc ggc ctg tgc gcg agc aag ggc     576
Gly Ala Ala His Arg Asn Lys Asp Ser Gly Leu Cys Ala Ser Lys Gly
            180                 185                 190 atc gcg ctg gcc gcg gac gcg acc tcg gtc ggc agc aag ccg acc cgc     624
Ile Ala Leu Ala Ala Asp Ala Thr Ser Val Gly Ser Lys Pro Thr Arg
        195                 200                 205 gcg ctc aag gac gag gtg atc tac gaa gtg cac gtg cgc ggc ctg acc     672
Ala Leu Lys Asp Glu Val Ile Tyr Glu Val His Val Arg Gly Leu Thr
    210                 215                 220
```

-continued

| | |
|---|---|
| cgc aac gac gac agc gtg ccc gcg gcc gaa cgc ggc acc tac aag ggc<br>Arg Asn Asp Asp Ser Val Pro Ala Ala Glu Arg Gly Thr Tyr Lys Gly<br>225                      230                   235                240 | 720 |
| gcc gcg cgc aag gcc gcc gcg ttg gcc gcg ctc ggc gtc acc gcg gtc<br>Ala Ala Arg Lys Ala Ala Ala Leu Ala Ala Leu Gly Val Thr Ala Val<br>                   245                   250                   255 | 768 |
| gag ttc ctg ccg gtg cag gaa acc cag aac gac cag aac gat gtc gat<br>Glu Phe Leu Pro Val Gln Glu Thr Gln Asn Asp Gln Asn Asp Val Asp<br>                260                   265                 270 | 816 |
| ccc aat tcc acc gcg ggc gac aac tac tgg ggc tac atg acc ctc aac<br>Pro Asn Ser Thr Ala Gly Asp Asn Tyr Trp Gly Tyr Met Thr Leu Asn<br>275                      280                   285 | 864 |
| tac ttc gcc ccg gac cgc cgc tac gcc tac gac aag tcg gcc ggc ggg<br>Tyr Phe Ala Pro Asp Arg Arg Tyr Ala Tyr Asp Lys Ser Ala Gly Gly<br>         290                   295                   300 | 912 |
| ccg acc cgc gaa tgg aag gcg atg gtc aag gcc ttc cac gac gcc ggc<br>Pro Thr Arg Glu Trp Lys Ala Met Val Lys Ala Phe His Asp Ala Gly<br>305                      310                   315                320 | 960 |
| atc aag gtc tac atc gac gtg gtc tac aac cac acc ggc gaa ggc ggc<br>Ile Lys Val Tyr Ile Asp Val Val Tyr Asn His Thr Gly Glu Gly Gly<br>                   325                   330                 335 | 1008 |
| ccg tgg agc ggc acc gac ggg ctc agc gtc tac aac ctg ctc tcg ttc<br>Pro Trp Ser Gly Thr Asp Gly Leu Ser Val Tyr Asn Leu Leu Ser Phe<br>                   340                   345                 350 | 1056 |
| cgc ggc ctc gac aac ccg gcc tac tac tcg ctg agc agc gat tac aag<br>Arg Gly Leu Asp Asn Pro Ala Tyr Tyr Ser Leu Ser Ser Asp Tyr Lys<br>               355                   360                 365 | 1104 |
| tat ccg tgg gac aac acc ggc gtc ggc ggc aac tac aac acc cgc cat<br>Tyr Pro Trp Asp Asn Thr Gly Val Gly Gly Asn Tyr Asn Thr Arg His<br>370                      375                   380 | 1152 |
| ccc atc gcc cag aac ctg atc gtc gac tcg ctg gcg tac tgg cgc gac<br>Pro Ile Ala Gln Asn Leu Ile Val Asp Ser Leu Ala Tyr Trp Arg Asp<br>385                      390                   395                400 | 1200 |
| gcg ctc ggc gta gac ggt ttc cgc ttc gat ctg gcc tcg gtg ctc ggc<br>Ala Leu Gly Val Asp Gly Phe Arg Phe Asp Leu Ala Ser Val Leu Gly<br>                   405                   410                 415 | 1248 |
| aac agc tgc cag cac ggc tgc ttc aac ttc gac aag aac gac tcg ggc<br>Asn Ser Cys Gln His Gly Cys Phe Asn Phe Asp Lys Asn Asp Ser Gly<br>               420                   425                 430 | 1296 |
| aac gcg ctc aac cgc atc gtc gcc gag ctg ccg ccg cgc ccg gcc gcg<br>Asn Ala Leu Asn Arg Ile Val Ala Glu Leu Pro Pro Arg Pro Ala Ala<br>               435                   440                 445 | 1344 |
| ggc ggc gcc ggc gcg gac ctg atc gcc gaa ccc tgg gcg atc ggc ggc<br>Gly Gly Ala Gly Ala Asp Leu Ile Ala Glu Pro Trp Ala Ile Gly Gly<br>450                      455                   460 | 1392 |
| aac tcc tac cag gtc ggc ggc ttc ccg gcc ggc tgg gcc gag tgg aac<br>Asn Ser Tyr Gln Val Gly Gly Phe Pro Ala Gly Trp Ala Glu Trp Asn<br>465                      470                   475                480 | 1440 |
| ggc ctc tac cgc gac gcg ctg cgc aag aag cag aac aag ctc ggc gtg<br>Gly Leu Tyr Arg Asp Ala Leu Arg Lys Lys Gln Asn Lys Leu Gly Val<br>                   485                   490                 495 | 1488 |
| gaa acg gtc acc ccc ggc acc ctg gcc acg cgc ttc gcc ggc tcc aac<br>Glu Thr Val Thr Pro Gly Thr Leu Ala Thr Arg Phe Ala Gly Ser Asn<br>                   500                   505                 510 | 1536 |
| gac ctg tac ggc gac gac ggc cgc aag ccg tgg cat tcg atc aac ttc<br>Asp Leu Tyr Gly Asp Asp Gly Arg Lys Pro Trp His Ser Ile Asn Phe<br>               515                   520                 525 | 1584 |
| gtg gtc gcc cac gac ggc ttc acc ctc aac gac ctg tac gcc tac aac<br>Val Val Ala His Asp Gly Phe Thr Leu Asn Asp Leu Tyr Ala Tyr Asn | 1632 |

```
                  530                 535                 540
gac aag cag aac aac cag ccg tgg ccg tac ggg ccg tcc gac ggc ggc          1680
Asp Lys Gln Asn Asn Gln Pro Trp Pro Tyr Gly Pro Ser Asp Gly Gly
545                 550                 555                 560 gag gac cac aac ctg agc tgg aac cag ggc ggc atc gtc gcc gag cag          1728
Glu Asp His Asn Leu Ser Trp Asn Gln Gly Gly Ile Val Ala Glu Gln
                565                 570                 575 cgc aag gcc gcg cgc acc gga ctg gcg ttg ctg atg ctc agc gcc ggc          1776
Arg Lys Ala Ala Arg Thr Gly Leu Ala Leu Leu Met Leu Ser Ala Gly
            580                 585                 590 gtg ccg atg atc acc ggc ggc gac gag gcg ctg cgc acc cag ttc ggc          1824
Val Pro Met Ile Thr Gly Gly Asp Glu Ala Leu Arg Thr Gln Phe Gly
        595                 600                 605 aac aac aac acc tac aac ctg gat tcg gcg gcc aac tgg ctg tac tgg          1872
Asn Asn Asn Thr Tyr Asn Leu Asp Ser Ala Ala Asn Trp Leu Tyr Trp
    610                 615                 620 agc cgc agc gcg ctc gag gcc gac cac gag acc tac acc aag cgc ctg          1920
Ser Arg Ser Ala Leu Glu Ala Asp His Glu Thr Tyr Thr Lys Arg Leu
625                 630                 635                 640 atc gcg ttc cgc aag gcg cac ccg gcg ctg cgc ccg gcg aac ttc tat          1968
Ile Ala Phe Arg Lys Ala His Pro Ala Leu Arg Pro Ala Asn Phe Tyr
                645                 650                 655 tcg gcc agc gac acc aac ggc aac gtg atg gag cag ttg cgc tgg ttc          2016
Ser Ala Ser Asp Thr Asn Gly Asn Val Met Glu Gln Leu Arg Trp Phe
            660                 665                 670 aag ccc gac ggc gcg cag gcc gac agc gcc tac ttc aac ggc gcc gac          2064
Lys Pro Asp Gly Ala Gln Ala Asp Ser Ala Tyr Phe Asn Gly Ala Asp
        675                 680                 685 aac cac gcc ctg gcc tgg cgc atc gac ggc agc gag ttc ggc gac agc          2112
Asn His Ala Leu Ala Trp Arg Ile Asp Gly Ser Glu Phe Gly Asp Ser
    690                 695                 700 gcc agc gcg atc tac gtc gcc tac aac ggc tgg tcc ggc gcg gtc gac          2160
Ala Ser Ala Ile Tyr Val Ala Tyr Asn Gly Trp Ser Gly Ala Val Asp
705                 710                 715                 720 ttc aag ctg ccg tgg ccg ggc acc ggc aag cag tgg tac cgg gtc acc          2208
Phe Lys Leu Pro Trp Pro Gly Thr Gly Lys Gln Trp Tyr Arg Val Thr
                725                 730                 735 gat acc gcg acc tgg aac gaa ggc ccc aac gcg gtg gcg ctg ccc ggc          2256
Asp Thr Ala Thr Trp Asn Glu Gly Pro Asn Ala Val Ala Leu Pro Gly
            740                 745                 750 agc gag acc ctg atc ggc ggc gag aac acc gtc tac ggc atg cag gcg          2304
Ser Glu Thr Leu Ile Gly Gly Glu Asn Thr Val Tyr Gly Met Gln Ala
        755                 760                 765 cgc tcg ctg ctg ttg ctg atc gcg aag tga                                  2334
Arg Ser Leu Leu Leu Leu Ile Ala Lys
    770                 775
```

<210> SEQ ID NO 8
<211> LENGTH: 777
<212> TYPE: PRT
<213> ORGANISM: Flavobacterium sp.

<400> SEQUENCE: 8

```
Met Asp Pro His Ala Pro Gln Arg Gln Arg Ser Gly Gln Arg Leu Arg
1               5                   10                  15

Ala Leu Ala Leu Ala Ala Leu Ala Cys Ala Leu Ser Pro Ala His Ala
            20                  25                  30

Ala Ile Asp Ala Gln Gln Leu Gly Ala Arg Tyr Asp Ala Ala Gln Ala
        35                  40                  45
```

```
Asn Leu Ala Phe Arg Val Tyr Ser Ser Arg Ala Thr Arg Val Glu Val
 50                  55                  60

Phe Leu Tyr Lys Asn Pro Thr Gly Ser Gln Glu Val Ala Arg Leu Ala
 65                  70                  75                  80

Leu Ser Lys Asp Pro Ala Thr Gln Val Trp Ser Leu Ser Leu Pro Thr
                 85                  90                  95

Ser Thr Ile Lys Asn Thr Tyr Gly Ile Thr Gly Ala Val Tyr Tyr Gly
                100                 105                 110

Tyr Arg Ala Trp Gly Pro Asn Trp Pro Tyr Asp Ala Ala Trp Thr Lys
            115                 120                 125

Gly Ser Ala Thr Gly Phe Val Ser Asp Val Asp Asn Ala Gly Asn Arg
130                 135                 140

Phe Asn Pro Asn Lys Leu Leu Leu Asp Pro Tyr Ala Arg Glu Ile Ser
145                 150                 155                 160

Gln Asp Pro Asn Thr Ala Thr Cys Ala Asp Gly Thr Ile Tyr Ala Thr
                165                 170                 175

Gly Ala Ala His Arg Asn Lys Asp Ser Gly Leu Cys Ala Ser Lys Gly
            180                 185                 190

Ile Ala Leu Ala Ala Asp Ala Thr Ser Val Gly Ser Lys Pro Thr Arg
            195                 200                 205

Ala Leu Lys Asp Glu Val Ile Tyr Glu Val His Val Arg Gly Leu Thr
210                 215                 220

Arg Asn Asp Asp Ser Val Pro Ala Ala Glu Arg Gly Thr Tyr Lys Gly
225                 230                 235                 240

Ala Ala Arg Lys Ala Ala Ala Leu Ala Ala Leu Gly Val Thr Ala Val
                245                 250                 255

Glu Phe Leu Pro Val Gln Glu Thr Gln Asn Asp Gln Asn Asp Val Asp
            260                 265                 270

Pro Asn Ser Thr Ala Gly Asp Asn Tyr Trp Gly Tyr Met Thr Leu Asn
275                 280                 285

Tyr Phe Ala Pro Asp Arg Arg Tyr Ala Tyr Asp Lys Ser Ala Gly Gly
            290                 295                 300

Pro Thr Arg Glu Trp Lys Ala Met Val Lys Ala Phe His Asp Ala Gly
305                 310                 315                 320

Ile Lys Val Tyr Ile Asp Val Val Tyr Asn His Thr Gly Glu Gly Gly
                325                 330                 335

Pro Trp Ser Gly Thr Asp Gly Leu Ser Val Tyr Asn Leu Leu Ser Phe
            340                 345                 350

Arg Gly Leu Asp Asn Pro Ala Tyr Tyr Ser Leu Ser Ser Asp Tyr Lys
            355                 360                 365

Tyr Pro Trp Asp Asn Thr Gly Val Gly Gly Asn Tyr Asn Thr Arg His
370                 375                 380

Pro Ile Ala Gln Asn Leu Ile Val Asp Ser Leu Ala Tyr Trp Arg Asp
385                 390                 395                 400

Ala Leu Gly Val Asp Gly Phe Arg Phe Asp Leu Ala Ser Val Leu Gly
                405                 410                 415

Asn Ser Cys Gln His Gly Cys Phe Asn Phe Asp Lys Asn Asp Ser Gly
            420                 425                 430

Asn Ala Leu Asn Arg Ile Val Ala Glu Leu Pro Arg Pro Ala Ala
            435                 440                 445

Gly Gly Ala Gly Ala Asp Leu Ile Ala Glu Pro Trp Ala Ile Gly Gly
450                 455                 460

Asn Ser Tyr Gln Val Gly Gly Phe Pro Ala Gly Trp Ala Glu Trp Asn
```

```
                465                 470                 475                 480
Gly Leu Tyr Arg Asp Ala Leu Arg Lys Lys Gln Asn Lys Leu Gly Val
                    485                 490                 495
Glu Thr Val Thr Pro Gly Thr Leu Ala Thr Arg Phe Ala Gly Ser Asn
            500                 505                 510
Asp Leu Tyr Gly Asp Gly Arg Lys Pro Trp His Ser Ile Asn Phe
        515                 520                 525
Val Val Ala His Asp Gly Phe Thr Leu Asn Asp Leu Tyr Ala Tyr Asn
530                 535                 540
Asp Lys Gln Asn Asn Gln Pro Trp Pro Tyr Gly Pro Ser Asp Gly Gly
545                 550                 555                 560
Glu Asp His Asn Leu Ser Trp Asn Gln Gly Gly Ile Val Ala Glu Gln
                565                 570                 575
Arg Lys Ala Ala Arg Thr Gly Leu Ala Leu Leu Met Leu Ser Ala Gly
                580                 585                 590
Val Pro Met Ile Thr Gly Gly Asp Glu Ala Leu Arg Thr Gln Phe Gly
            595                 600                 605
Asn Asn Asn Thr Tyr Asn Leu Asp Ser Ala Ala Asn Trp Leu Tyr Trp
610                 615                 620
Ser Arg Ser Ala Leu Glu Ala Asp His Glu Thr Tyr Thr Lys Arg Leu
625                 630                 635                 640
Ile Ala Phe Arg Lys Ala His Pro Ala Leu Arg Pro Ala Asn Phe Tyr
                645                 650                 655
Ser Ala Ser Asp Thr Asn Gly Asn Val Met Glu Gln Leu Arg Trp Phe
            660                 665                 670
Lys Pro Asp Gly Ala Gln Ala Asp Ser Ala Tyr Phe Asn Gly Ala Asp
        675                 680                 685
Asn His Ala Leu Ala Trp Arg Ile Asp Gly Ser Glu Phe Gly Asp Ser
    690                 695                 700
Ala Ser Ala Ile Tyr Val Ala Tyr Asn Gly Trp Ser Gly Ala Val Asp
705                 710                 715                 720
Phe Lys Leu Pro Trp Pro Gly Thr Gly Lys Gln Trp Tyr Arg Val Thr
                725                 730                 735
Asp Thr Ala Thr Trp Asn Glu Gly Pro Asn Ala Val Ala Leu Pro Gly
            740                 745                 750
Ser Glu Thr Leu Ile Gly Gly Glu Asn Thr Val Tyr Gly Met Gln Ala
        755                 760                 765
Arg Ser Leu Leu Leu Leu Ile Ala Lys
    770                 775

<210> SEQ ID NO 9
<211> LENGTH: 2316
<212> TYPE: DNA
<213> ORGANISM: Pseudomonas amyloderamosa
<220> FEATURE:
<221> NAME/KEY: CDS
<222> LOCATION: (1)..(2316)

<400> SEQUENCE: 9 atg aag tgc cca aag att ctc ggc gcg ctg ctt ggc tgc gcg gtg ctc      48
Met Lys Cys Pro Lys Ile Leu Gly Ala Leu Leu Gly Cys Ala Val Leu
1               5                   10                  15 gct ggt gtg ccc gca atg ccg gcg cat gcg gcc atc aac agc atg agc      96
Ala Gly Val Pro Ala Met Pro Ala His Ala Ala Ile Asn Ser Met Ser
            20                  25                  30 ctg ggc gcg agc tac gac gcg caa cag gcc aac atc acc ttt cgc gtt     144
```

```
Leu Gly Ala Ser Tyr Asp Ala Gln Gln Ala Asn Ile Thr Phe Arg Val
            35                  40                  45 tac tcc tcg cag gcc acg cgc atc gtg ctg tac ctc tat tcg gca ggt      192
Tyr Ser Ser Gln Ala Thr Arg Ile Val Leu Tyr Leu Tyr Ser Ala Gly
        50                  55                  60 tac ggt gtg cag gag tcg gcc acc tac acg ctg agc cca gcg ggc agt      240
Tyr Gly Val Gln Glu Ser Ala Thr Tyr Thr Leu Ser Pro Ala Gly Ser
65                  70                  75                  80 ggt gta tgg gcg gtg acg gtg ccg gtg tcg tcg atc aag gcg gcc ggc      288
Gly Val Trp Ala Val Thr Val Pro Val Ser Ser Ile Lys Ala Ala Gly
                85                  90                  95 atc acg ggg gcg gtg tac tac ggg tat cgc gcc tgg ggg ccg aat tgg      336
Ile Thr Gly Ala Val Tyr Tyr Gly Tyr Arg Ala Trp Gly Pro Asn Trp
            100                 105                 110 cct tat gcc agc aac tgg ggc aag ggt tcg cag gcg ggc tgt gtt tcc      384
Pro Tyr Ala Ser Asn Trp Gly Lys Gly Ser Gln Ala Gly Cys Val Ser
        115                 120                 125 gac gtc gac gcc aac ggc gac cgc ttc aat ccc aac aaa ctg ttg ttg      432
Asp Val Asp Ala Asn Gly Asp Arg Phe Asn Pro Asn Lys Leu Leu Leu
130                 135                 140 gac ccc tac gcg cag gaa gtg agc cag gat ccg ctg aac ccg tcc aac      480
Asp Pro Tyr Ala Gln Glu Val Ser Gln Asp Pro Leu Asn Pro Ser Asn
145                 150                 155                 160 cag aac ggc aac gtg ttc gcc tct gcg cac tat cgc acc acc gac agt      528
Gln Asn Gly Asn Val Phe Ala Ser Ala His Tyr Arg Thr Thr Asp Ser
                165                 170                 175 ggc atc tat gca ccc aag ggt gtc gtg ctg gtg ccc agt acg caa agt      576
Gly Ile Tyr Ala Pro Lys Gly Val Val Leu Val Pro Ser Thr Gln Ser
            180                 185                 190 acc ggc acc aaa ccc aca cgc gcg cag aag gat gat gtg atc tac gag      624
Thr Gly Thr Lys Pro Thr Arg Ala Gln Lys Asp Asp Val Ile Tyr Glu
        195                 200                 205 gtg cat gtg cgc ggc ttc acc gag cag gac acc tct atc cct gcg cag      672
Val His Val Arg Gly Phe Thr Glu Gln Asp Thr Ser Ile Pro Ala Gln
210                 215                 220 tat cgc ggc acc tat tac ggt gca ggg ctc aag gcc agt tac ctc gcc      720
Tyr Arg Gly Thr Tyr Tyr Gly Ala Gly Leu Lys Ala Ser Tyr Leu Ala
225                 230                 235                 240 agc ctg ggc gtg acc gcg gtg gaa ttc ctg ccg gtg cag gaa acg cag      768
Ser Leu Gly Val Thr Ala Val Glu Phe Leu Pro Val Gln Glu Thr Gln
                245                 250                 255 aat gat gcg aac gat gtg gtt ccc aat tca gat gcc aac cag aac tac      816
Asn Asp Ala Asn Asp Val Val Pro Asn Ser Asp Ala Asn Gln Asn Tyr
            260                 265                 270 tgg ggc tac atg acc gag aac tac ttc tcg ccg gat cgc cgc tat gcc      864
Trp Gly Tyr Met Thr Glu Asn Tyr Phe Ser Pro Asp Arg Arg Tyr Ala
        275                 280                 285 tac aac aag gcg gct ggc ggt ccc acg gcg gag ttc cag gcg atg gtg      912
Tyr Asn Lys Ala Ala Gly Gly Pro Thr Ala Glu Phe Gln Ala Met Val
290                 295                 300 cag gcg ttt cac aac gca ggc atc aag gtc tac atg gat gtg gtc tac      960
Gln Ala Phe His Asn Ala Gly Ile Lys Val Tyr Met Asp Val Val Tyr
305                 310                 315                 320 aac cac acc gcc gaa ggc ggc acc tgg acc agc agt gat ccc acc acg     1008
Asn His Thr Ala Glu Gly Gly Thr Trp Thr Ser Ser Asp Pro Thr Thr
                325                 330                 335 gcc acc att tat tcg tgg cgc ggc ttg gac aat gcc acg tac tac gag     1056
Ala Thr Ile Tyr Ser Trp Arg Gly Leu Asp Asn Ala Thr Tyr Tyr Glu
            340                 345                 350
```

-continued

```
ctg acc tcg ggc aac caa tac ttc tac gac aac acg ggc att ggc gcg   1104
Leu Thr Ser Gly Asn Gln Tyr Phe Tyr Asp Asn Thr Gly Ile Gly Ala
        355                 360                 365 aac ttc aat acg tac aac acg gtg gcg cag aac ctt atc gtc gac tcg   1152
Asn Phe Asn Thr Tyr Asn Thr Val Ala Gln Asn Leu Ile Val Asp Ser
370                 375                 380 gtg gcg tat tgg gcg aac acg atg ggc gtg gat ggc ttt cgc ttc gac   1200
Val Ala Tyr Trp Ala Asn Thr Met Gly Val Asp Gly Phe Arg Phe Asp
385                 390                 395                 400 ctt gct tcc gtg ctc ggc aac agt tgc ctc aat gcc gta cac gcg tcc   1248
Leu Ala Ser Val Leu Gly Asn Ser Cys Leu Asn Ala Val His Ala Ser
            405                 410                 415 gcg ccc aat tgc ccg aac ggt ggt tat aac ttc gac gcg gcg gat agc   1296
Ala Pro Asn Cys Pro Asn Gly Gly Tyr Asn Phe Asp Ala Ala Asp Ser
        420                 425                 430 aac gta gcg atc aac cgc atc cta cgc gag ttc acg gtg cgc ccg gcg   1344
Asn Val Ala Ile Asn Arg Ile Leu Arg Glu Phe Thr Val Arg Pro Ala
    435                 440                 445 gcg ggc ggc acg gtc tgg atc tgt ttg cgg aac ctt ggg cca tcg gcg   1392
Ala Gly Gly Thr Val Trp Ile Cys Leu Arg Asn Leu Gly Pro Ser Ala
450                 455                 460 gca act cgt acc agc tgg gtg gat tcc cgc agg gtg gtc cga gtg gaa   1440
Ala Thr Arg Thr Ser Trp Val Asp Ser Arg Arg Val Val Arg Val Glu
465                 470                 475                 480 tgg tct gtt ccg cga cag ctg cgg cag gcg cag aac gag ctg ggt agc   1488
Trp Ser Val Pro Arg Gln Leu Arg Gln Ala Gln Asn Glu Leu Gly Ser
            485                 490                 495 atg acc atc tat gtg acg cag gat gcg aat gat ttc tcc ggt tcg tcc   1536
Met Thr Ile Tyr Val Thr Gln Asp Ala Asn Asp Phe Ser Gly Ser Ser
        500                 505                 510 aat ctg ttc cag tcc agt ggg cgg tcg ccg tgg aac tcg atc aac ttt   1584
Asn Leu Phe Gln Ser Ser Gly Arg Ser Pro Trp Asn Ser Ile Asn Phe
    515                 520                 525 atc gac gtg cat gac ggc atg acg ttg aag gac gtg tac tcc tgc aac   1632
Ile Asp Val His Asp Gly Met Thr Leu Lys Asp Val Tyr Ser Cys Asn
530                 535                 540 ggc gcc aac aac agt cag gcg tcg tac ggg ccg tcg gat ggc ggc acg   1680
Gly Ala Asn Asn Ser Gln Ala Ser Tyr Gly Pro Ser Asp Gly Gly Thr
545                 550                 555                 560 agc acc aat tac agt tgg gat cag ggc atg tcg gcg gga acg ggt gcc   1728
Ser Thr Asn Tyr Ser Trp Asp Gln Gly Met Ser Ala Gly Thr Gly Ala
            565                 570                 575 gcg gtc gac cag cgt cga gcg gca cga acg ggc atg gcc ttc gag atg   1776
Ala Val Asp Gln Arg Arg Ala Ala Arg Thr Gly Met Ala Phe Glu Met
        580                 585                 590 ttg tcc gcg ggc acg ccg ttg atg cag ggc ggc gac gaa tac ctg cgc   1824
Leu Ser Ala Gly Thr Pro Leu Met Gln Gly Gly Asp Glu Tyr Leu Arg
    595                 600                 605 acg ctc cag tgc aac aac aat gcc tac aac ctc gac tcc agc gcc aac   1872
Thr Leu Gln Cys Asn Asn Asn Ala Tyr Asn Leu Asp Ser Ser Ala Asn
610                 615                 620 tgg ctt acc tat agc tgg acc acc gat caa tcg aac ttc tac acc ttc   1920
Trp Leu Thr Tyr Ser Trp Thr Thr Asp Gln Ser Asn Phe Tyr Thr Phe
625                 630                 635                 640 gcg caa cgc ctc att cgt tcc gca agg cac atc ccg ctt cgc ccg tcg   1968
Ala Gln Arg Leu Ile Arg Ser Ala Arg His Ile Pro Leu Arg Pro Ser
            645                 650                 655 agc tgg tac agc ggc agc cag ttg acg tgg tat cag ccc agt gga gcc   2016
Ser Trp Tyr Ser Gly Ser Gln Leu Thr Trp Tyr Gln Pro Ser Gly Ala
        660                 665                 670
```

```
gtg gcg gac agc aac tac tgg aac aac acc agc aac tac gcc att gcc    2064
Val Ala Asp Ser Asn Tyr Trp Asn Asn Thr Ser Asn Tyr Ala Ile Ala
        675                 680                 685 tac gcc atc aat ggg cct tcg ctg ggc gac agc aat tcc atc tat gtc    2112
Tyr Ala Ile Asn Gly Pro Ser Leu Gly Asp Ser Asn Ser Ile Tyr Val
690                 695                 700 gct tac aac ggt tgg tcg agc agc gtg act ttc acc ttg cct gcg cca    2160
Ala Tyr Asn Gly Trp Ser Ser Ser Val Thr Phe Thr Leu Pro Ala Pro
705                 710                 715                 720 ccg tca ggc acg cag tgg tat cgc gtc acg gat acc tgc gac tgg aac    2208
Pro Ser Gly Thr Gln Trp Tyr Arg Val Thr Asp Thr Cys Asp Trp Asn
        725                 730                 735 gat ggc gcc agt acg ttt gtt gca ccg ggc agc gag aca ttg atc ggc    2256
Asp Gly Ala Ser Thr Phe Val Ala Pro Gly Ser Glu Thr Leu Ile Gly
        740                 745                 750 ggc gcg ggc acc acc tat ggg caa tgc ggt caa tcg ctg ctg ctg ttg    2304
Gly Ala Gly Thr Thr Tyr Gly Gln Cys Gly Gln Ser Leu Leu Leu Leu
        755                 760                 765 atc tcc aag tag                                                    2316
Ile Ser Lys
        770

<210> SEQ ID NO 10
<211> LENGTH: 771
<212> TYPE: PRT
<213> ORGANISM: Pseudomonas amyloderamosa

<400> SEQUENCE: 10

Met Lys Cys Pro Lys Ile Leu Gly Ala Leu Leu Gly Cys Ala Val Leu
1               5                   10                  15

Ala Gly Val Pro Ala Met Pro Ala His Ala Ala Ile Asn Ser Met Ser
            20                  25                  30

Leu Gly Ala Ser Tyr Asp Ala Gln Gln Ala Asn Ile Thr Phe Arg Val
        35                  40                  45

Tyr Ser Ser Gln Ala Thr Arg Ile Val Leu Tyr Leu Tyr Ser Ala Gly
    50                  55                  60

Tyr Gly Val Gln Glu Ser Ala Thr Tyr Thr Leu Ser Pro Ala Gly Ser
65                  70                  75                  80

Gly Val Trp Ala Val Thr Val Pro Val Ser Ser Ile Lys Ala Ala Gly
            85                  90                  95

Ile Thr Gly Ala Val Tyr Tyr Gly Tyr Arg Ala Trp Gly Pro Asn Trp
            100                 105                 110

Pro Tyr Ala Ser Asn Trp Gly Lys Gly Ser Gln Ala Gly Cys Val Ser
        115                 120                 125

Asp Val Asp Ala Asn Gly Asp Arg Phe Asn Pro Asn Lys Leu Leu Leu
    130                 135                 140

Asp Pro Tyr Ala Gln Glu Val Ser Gln Asp Pro Leu Asn Pro Ser Asn
145                 150                 155                 160

Gln Asn Gly Asn Val Phe Ala Ser Ala His Tyr Arg Thr Thr Asp Ser
            165                 170                 175

Gly Ile Tyr Ala Pro Lys Gly Val Val Leu Val Pro Ser Thr Gln Ser
        180                 185                 190

Thr Gly Thr Lys Pro Thr Arg Ala Gln Lys Asp Asp Val Ile Tyr Glu
    195                 200                 205

Val His Val Arg Gly Phe Thr Glu Gln Asp Thr Ser Ile Pro Ala Gln
    210                 215                 220
```

-continued

```
Tyr Arg Gly Thr Tyr Tyr Gly Ala Gly Leu Lys Ala Ser Tyr Leu Ala
225                 230                 235                 240

Ser Leu Gly Val Thr Ala Val Glu Phe Leu Pro Val Gln Glu Thr Gln
            245                 250                 255

Asn Asp Ala Asn Asp Val Val Pro Asn Ser Asp Ala Asn Gln Asn Tyr
        260                 265                 270

Trp Gly Tyr Met Thr Glu Asn Tyr Phe Ser Pro Asp Arg Arg Tyr Ala
    275                 280                 285

Tyr Asn Lys Ala Ala Gly Gly Pro Thr Ala Glu Phe Gln Ala Met Val
290                 295                 300

Gln Ala Phe His Asn Ala Gly Ile Lys Val Tyr Met Asp Val Val Tyr
305                 310                 315                 320

Asn His Thr Ala Glu Gly Gly Thr Trp Thr Ser Ser Asp Pro Thr Thr
                325                 330                 335

Ala Thr Ile Tyr Ser Trp Arg Gly Leu Asp Asn Ala Thr Tyr Tyr Glu
            340                 345                 350

Leu Thr Ser Gly Asn Gln Tyr Phe Tyr Asp Asn Thr Gly Ile Gly Ala
        355                 360                 365

Asn Phe Asn Thr Tyr Asn Thr Val Ala Gln Asn Leu Ile Val Asp Ser
370                 375                 380

Val Ala Tyr Trp Ala Asn Thr Met Gly Val Asp Gly Phe Arg Phe Asp
385                 390                 395                 400

Leu Ala Ser Val Leu Gly Asn Ser Cys Leu Asn Ala Val His Ala Ser
                405                 410                 415

Ala Pro Asn Cys Pro Asn Gly Gly Tyr Asn Phe Asp Ala Ala Asp Ser
            420                 425                 430

Asn Val Ala Ile Asn Arg Ile Leu Arg Glu Phe Thr Val Arg Pro Ala
        435                 440                 445

Ala Gly Gly Thr Val Trp Ile Cys Leu Arg Asn Leu Gly Pro Ser Ala
    450                 455                 460

Ala Thr Arg Thr Ser Trp Val Asp Ser Arg Arg Val Val Arg Val Glu
465                 470                 475                 480

Trp Ser Val Pro Arg Gln Leu Arg Gln Ala Gln Asn Glu Leu Gly Ser
                485                 490                 495

Met Thr Ile Tyr Val Thr Gln Asp Ala Asn Asp Phe Ser Gly Ser Ser
            500                 505                 510

Asn Leu Phe Gln Ser Ser Gly Arg Ser Pro Trp Asn Ser Ile Asn Phe
        515                 520                 525

Ile Asp Val His Asp Gly Met Thr Leu Lys Asp Val Tyr Ser Cys Asn
530                 535                 540

Gly Ala Asn Asn Ser Gln Ala Ser Tyr Gly Pro Ser Asp Gly Gly Thr
545                 550                 555                 560

Ser Thr Asn Tyr Ser Trp Asp Gln Gly Met Ser Ala Gly Thr Gly Ala
                565                 570                 575

Ala Val Asp Gln Arg Arg Ala Arg Thr Gly Met Ala Phe Glu Met
            580                 585                 590

Leu Ser Ala Gly Thr Pro Leu Met Gln Gly Gly Asp Glu Tyr Leu Arg
        595                 600                 605

Thr Leu Gln Cys Asn Asn Ala Tyr Asn Leu Asp Ser Ser Ala Asn
    610                 615                 620

Trp Leu Thr Tyr Ser Trp Thr Thr Asp Gln Ser Asn Phe Tyr Thr Phe
625                 630                 635                 640

Ala Gln Arg Leu Ile Arg Ser Ala Arg His Ile Pro Leu Arg Pro Ser
```

```
                        645                 650                 655
Ser Trp Tyr Ser Gly Ser Gln Leu Thr Trp Tyr Gln Pro Ser Gly Ala
            660                 665                 670

Val Ala Asp Ser Asn Tyr Trp Asn Asn Thr Ser Asn Tyr Ala Ile Ala
            675                 680                 685

Tyr Ala Ile Asn Gly Pro Ser Leu Gly Asp Ser Asn Ser Ile Tyr Val
            690                 695                 700

Ala Tyr Asn Gly Trp Ser Ser Val Thr Phe Thr Leu Pro Ala Pro
705                 710                 715                 720

Pro Ser Gly Thr Gln Trp Tyr Arg Val Thr Asp Thr Cys Asp Trp Asn
            725                 730                 735

Asp Gly Ala Ser Thr Phe Val Ala Pro Gly Ser Glu Thr Leu Ile Gly
            740                 745                 750

Gly Ala Gly Thr Thr Tyr Gly Gln Cys Gly Gln Ser Leu Leu Leu Leu
            755                 760                 765

Ile Ser Lys
    770

<210> SEQ ID NO 11
<211> LENGTH: 2598
<212> TYPE: DNA
<213> ORGANISM: Aspergillus niger
<220> FEATURE:
<221> NAME/KEY: CDS
<222> LOCATION: (1)..(2598)

<400> SEQUENCE: 11 atg ttg ggg tct ttg ctt tta ctc tta ccc ctt gtg ggc gct gct gtc      48
Met Leu Gly Ser Leu Leu Leu Leu Leu Pro Leu Val Gly Ala Ala Val
1               5                   10                  15 att gga ccc agg gca aac agt cag agt tgc cca ggg tat aag gcg tcc      96
Ile Gly Pro Arg Ala Asn Ser Gln Ser Cys Pro Gly Tyr Lys Ala Ser
                20                  25                  30 aac gtc caa aag cag gct agg tca ctg act gcg gat ctg act cta gct     144
Asn Val Gln Lys Gln Ala Arg Ser Leu Thr Ala Asp Leu Thr Leu Ala
            35                  40                  45 ggt acg cct tgt aat agc tat ggc aag gat ttg gaa gac ctc aag ctg     192
Gly Thr Pro Cys Asn Ser Tyr Gly Lys Asp Leu Glu Asp Leu Lys Leu
50                  55                  60 ctt gtg gaa tat cag act gat gaa cgg tta cat gtt atg atc tac gat     240
Leu Val Glu Tyr Gln Thr Asp Glu Arg Leu His Val Met Ile Tyr Asp
65                  70                  75                  80 gcc gac gag gaa gtc tat caa gtt cct gaa tca gtc ctt cct cgc gtg     288
Ala Asp Glu Glu Val Tyr Gln Val Pro Glu Ser Val Leu Pro Arg Val
                85                  90                  95 ggt agt gac gag gac tct gag gac agt gtt ttg gaa ttt gac tat gtg     336
Gly Ser Asp Glu Asp Ser Glu Asp Ser Val Leu Glu Phe Asp Tyr Val
                100                 105                 110 gaa gaa ccg ttt tca ttc acc atc tcc aag gga gat gag gtc ctg ttt     384
Glu Glu Pro Phe Ser Phe Thr Ile Ser Lys Gly Asp Glu Val Leu Phe
            115                 120                 125 gac tct tcg gca tca cca cta gtt ttt cag tcg caa tat gtg aac ctt     432
Asp Ser Ser Ala Ser Pro Leu Val Phe Gln Ser Gln Tyr Val Asn Leu
        130                 135                 140 cgc acc tgg ttg ccc gat gat ccc tat gtg tat ggt ctc gga gag cat     480
Arg Thr Trp Leu Pro Asp Asp Pro Tyr Val Tyr Gly Leu Gly Glu His
145                 150                 155                 160 tct gac cct atg cgc ttg cca aca tac aat tac acg cgg acc ctt tgg     528
Ser Asp Pro Met Arg Leu Pro Thr Tyr Asn Tyr Thr Arg Thr Leu Trp
```

```
                    165                 170                 175
aac cgc gac gcg tat ggc act cca aac aac acc aac ttg tac ggt agt      576
Asn Arg Asp Ala Tyr Gly Thr Pro Asn Asn Thr Asn Leu Tyr Gly Ser
            180                 185                 190 cat cct gtc tac tat gat cac cgt gga aag tcc gga act tat gga gtc      624
His Pro Val Tyr Tyr Asp His Arg Gly Lys Ser Gly Thr Tyr Gly Val
            195                 200                 205 ttc ctg ctg aac tct aat ggt atg gac atc aag atc aac caa acg aca      672
Phe Leu Leu Asn Ser Asn Gly Met Asp Ile Lys Ile Asn Gln Thr Thr
210                 215                 220 gat gga aag cag tac ttg gaa tac aat ctt ctc ggc ggt gtt ctg gac      720
Asp Gly Lys Gln Tyr Leu Glu Tyr Asn Leu Leu Gly Gly Val Leu Asp
225                 230                 235                 240 ttc tac ttc ttc tac gga gaa gat cct aag caa gcg agc atg gaa tac      768
Phe Tyr Phe Phe Tyr Gly Glu Asp Pro Lys Gln Ala Ser Met Glu Tyr
                245                 250                 255 tca aag att gtc ggt ctc ccg gca atg cag agt tac tgg act ttc ggc      816
Ser Lys Ile Val Gly Leu Pro Ala Met Gln Ser Tyr Trp Thr Phe Gly
            260                 265                 270 gta tgc ccc cca ccc cct aat ccc ata aca gtc cga gtt gtg gtc tac      864
Val Cys Pro Pro Pro Pro Asn Pro Ile Thr Val Arg Val Val Val Tyr
            275                 280                 285 aac tac agc cag gca aag att cct ctg gag acg atg tgg aca gat atc      912
Asn Tyr Ser Gln Ala Lys Ile Pro Leu Glu Thr Met Trp Thr Asp Ile
            290                 295                 300 gac tac atg gac aag aga agg gtg ttt acc ctt gat cct cag agg ttc      960
Asp Tyr Met Asp Lys Arg Arg Val Phe Thr Leu Asp Pro Gln Arg Phe
305                 310                 315                 320 ccg ctc gaa aag atg cgg gag ttg gta acc tac ctg cac aat cat gat      1008
Pro Leu Glu Lys Met Arg Glu Leu Val Thr Tyr Leu His Asn His Asp
                325                 330                 335 cag cat tac att gtc atg gtt gac ccg gct gtg agc gta agc aat aac      1056
Gln His Tyr Ile Val Met Val Asp Pro Ala Val Ser Val Ser Asn Asn
            340                 345                 350 acg gca tat atc acc ggc gtg aga gac gat gtt ttc ctt cac aat cag      1104
Thr Ala Tyr Ile Thr Gly Val Arg Asp Asp Val Phe Leu His Asn Gln
            355                 360                 365 aac ggt agc cta tac gag ggt gct gtt tgg cct ggt gtc act gtt ttc      1152
Asn Gly Ser Leu Tyr Glu Gly Ala Val Trp Pro Gly Val Thr Val Phe
370                 375                 380 cca gac tgg ttc aat gag ggt act cag gat tac tgg act gcg caa ttt      1200
Pro Asp Trp Phe Asn Glu Gly Thr Gln Asp Tyr Trp Thr Ala Gln Phe
385                 390                 395                 400 caa cag ttc ttt gat ccc aag tcc gga gtc gat att gac gcc ctg tgg      1248
Gln Gln Phe Phe Asp Pro Lys Ser Gly Val Asp Ile Asp Ala Leu Trp
                405                 410                 415 att gac atg aac gaa gcc tcc aat ttc tgc cct tat cct tgt ctg gac      1296
Ile Asp Met Asn Glu Ala Ser Asn Phe Cys Pro Tyr Pro Cys Leu Asp
            420                 425                 430 cca gcg gca tac gcg atc tcc gcc gac ctc cca ccg gca gca cca cct      1344
Pro Ala Ala Tyr Ala Ile Ser Ala Asp Leu Pro Pro Ala Ala Pro Pro
            435                 440                 445 gtt cgg cca agc agc ccg atc cca ctg ccc gga ttc ccc gcg gac ttt      1392
Val Arg Pro Ser Ser Pro Ile Pro Leu Pro Gly Phe Pro Ala Asp Phe
450                 455                 460 cag cct tcg tct aag cga tct gtt aaa aga gcg caa gga gat aaa ggg      1440
Gln Pro Ser Ser Lys Arg Ser Val Lys Arg Ala Gln Gly Asp Lys Gly
465                 470                 475                 480 aag aag gtt ggg ttg ccc aat cgc aac ctc act gac ccg ccc tac acc      1488
```

```
Lys Lys Val Gly Leu Pro Asn Arg Asn Leu Thr Asp Pro Pro Tyr Thr
            485                 490                 495 att cgg aat gcc gca ggt gtc ctt agt atg agc act atc gag acg gat    1536
Ile Arg Asn Ala Ala Gly Val Leu Ser Met Ser Thr Ile Glu Thr Asp
                500                 505                 510 ctc att cat gcg ggt gaa ggg tat gcc gag tat gat act cac aat ctc    1584
Leu Ile His Ala Gly Glu Gly Tyr Ala Glu Tyr Asp Thr His Asn Leu
                515                 520                 525 tat gga aca agg tta gtg atg agc tct gct tcc cgc acg gct atg cag    1632
Tyr Gly Thr Arg Leu Val Met Ser Ser Ala Ser Arg Thr Ala Met Gln
        530                 535                 540 gcc cgc cgt ccc gat gtg agg cct ttg gtc atc act cgc agt acg ttt    1680
Ala Arg Arg Pro Asp Val Arg Pro Leu Val Ile Thr Arg Ser Thr Phe
545                 550                 555                 560 gca ggc gct gga gca cac gta gga cac tgg ctg ggc gac aac ttt agc    1728
Ala Gly Ala Gly Ala His Val Gly His Trp Leu Gly Asp Asn Phe Ser
                565                 570                 575 gat tgg gtt cac tac cgg atc tcc atc gcg cag atc ctc tcc ttc gcg    1776
Asp Trp Val His Tyr Arg Ile Ser Ile Ala Gln Ile Leu Ser Phe Ala
                580                 585                 590 tcc atg ttc cag att cca atg gtc ggg gct gac gtg tgt ggg ttt ggt    1824
Ser Met Phe Gln Ile Pro Met Val Gly Ala Asp Val Cys Gly Phe Gly
            595                 600                 605 agc aac acg acg gag gaa ttg tgt gcc cga tgg gcg tca ctt ggt gcc    1872
Ser Asn Thr Thr Glu Glu Leu Cys Ala Arg Trp Ala Ser Leu Gly Ala
        610                 615                 620 ttc tat acg ttc tac cgc aat cat aac gag ctg ggc gac ata tcg caa    1920
Phe Tyr Thr Phe Tyr Arg Asn His Asn Glu Leu Gly Asp Ile Ser Gln
625                 630                 635                 640 gag ttc tac cgc tgg cct acg gtt gcc gag tcc gcg cgt aag gcc att    1968
Glu Phe Tyr Arg Trp Pro Thr Val Ala Glu Ser Ala Arg Lys Ala Ile
                645                 650                 655 gac atc cgg tac aag ctc ctc gat tat atc tac act gct ctt cac cgg    2016
Asp Ile Arg Tyr Lys Leu Leu Asp Tyr Ile Tyr Thr Ala Leu His Arg
                660                 665                 670 caa agc cag acc ggc gag cca ttc ctg cag cct caa ttc tac ctg tac    2064
Gln Ser Gln Thr Gly Glu Pro Phe Leu Gln Pro Gln Phe Tyr Leu Tyr
            675                 680                 685 cct gag gat tcg aac acc ttt gcg aac gac cgg cag ttc ttc tat ggt    2112
Pro Glu Asp Ser Asn Thr Phe Ala Asn Asp Arg Gln Phe Phe Tyr Gly
        690                 695                 700 gac gcc ctt ctt gtc agc ccc gtg ttg aat gag gga tcc acc tca gtc    2160
Asp Ala Leu Leu Val Ser Pro Val Leu Asn Glu Gly Ser Thr Ser Val
705                 710                 715                 720 gac gca tac ttc ccg gac gac atc ttc tac gat tgg tac aca ggg gca    2208
Asp Ala Tyr Phe Pro Asp Asp Ile Phe Tyr Asp Trp Tyr Thr Gly Ala
                725                 730                 735 gtg gtg cgt ggg cac gga gaa aac atc acg ctc agc aac atc aac atc    2256
Val Val Arg Gly His Gly Glu Asn Ile Thr Leu Ser Asn Ile Asn Ile
                740                 745                 750 acc cac atc cct ctg cac atc cgc ggt gga aat atc ata cct gtc agg    2304
Thr His Ile Pro Leu His Ile Arg Gly Gly Asn Ile Ile Pro Val Arg
            755                 760                 765 aca tcc agc ggc atg aca acc act gag gtt cgt aag cag ggc ttc gag    2352
Thr Ser Ser Gly Met Thr Thr Thr Glu Val Arg Lys Gln Gly Phe Glu
        770                 775                 780 ctg atc atc gcg cca gac ttg gat gac acc gca tcg ggc agt cta tat    2400
Leu Ile Ile Ala Pro Asp Leu Asp Asp Thr Ala Ser Gly Ser Leu Tyr
785                 790                 795                 800
```

| | | | |
|---|---|---|---|
| ttg gat gat gga gac tcg ttg aac ccg tca tct gtg aca gag ctc gag<br>Leu Asp Asp Gly Asp Ser Leu Asn Pro Ser Ser Val Thr Glu Leu Glu<br>805 810 815 | | | 2448 |
| ttc acg tac agc aaa ggg gag ttg cac gtg aag ggt aca ttc gga cag<br>Phe Thr Tyr Ser Lys Gly Glu Leu His Val Lys Gly Thr Phe Gly Gln<br>820 825 830 | | | 2496 |
| aag gcc gtc ccc aag gtg gag aaa tgt acc ttg ctg ggg aag tca gca<br>Lys Ala Val Pro Lys Val Glu Lys Cys Thr Leu Leu Gly Lys Ser Ala<br>835 840 845 | | | 2544 |
| cgg acg ttc aag ggc ttt gca ctc gat gcg ccg gtg aac ttt aag ctg<br>Arg Thr Phe Lys Gly Phe Ala Leu Asp Ala Pro Val Asn Phe Lys Leu<br>850 855 860 | | | 2592 |
| aag tag<br>Lys<br>865 | | | 2598 |

<210> SEQ ID NO 12
<211> LENGTH: 865
<212> TYPE: PRT
<213> ORGANISM: Aspergillus niger

<400> SEQUENCE: 12

Met Leu Gly Ser Leu Leu Leu Leu Pro Leu Val Gly Ala Ala Val
1               5                   10                  15

Ile Gly Pro Arg Ala Asn Ser Gln Ser Cys Pro Gly Tyr Lys Ala Ser
            20                  25                  30

Asn Val Gln Lys Gln Ala Arg Ser Leu Thr Ala Asp Leu Thr Leu Ala
        35                  40                  45

Gly Thr Pro Cys Asn Ser Tyr Gly Lys Asp Leu Glu Asp Leu Lys Leu
    50                  55                  60

Leu Val Glu Tyr Gln Thr Asp Glu Arg Leu His Val Met Ile Tyr Asp
65                  70                  75                  80

Ala Asp Glu Glu Val Tyr Gln Val Pro Glu Ser Val Leu Pro Arg Val
                85                  90                  95

Gly Ser Asp Glu Asp Ser Glu Asp Ser Val Leu Glu Phe Asp Tyr Val
            100                 105                 110

Glu Glu Pro Phe Ser Phe Thr Ile Ser Lys Gly Asp Glu Val Leu Phe
        115                 120                 125

Asp Ser Ser Ala Ser Pro Leu Val Phe Gln Ser Gln Tyr Val Asn Leu
    130                 135                 140

Arg Thr Trp Leu Pro Asp Asp Pro Tyr Val Tyr Gly Leu Gly Glu His
145                 150                 155                 160

Ser Asp Pro Met Arg Leu Pro Thr Tyr Asn Tyr Thr Arg Thr Leu Trp
                165                 170                 175

Asn Arg Asp Ala Tyr Gly Thr Pro Asn Asn Thr Asn Leu Tyr Gly Ser
            180                 185                 190

His Pro Val Tyr Tyr Asp His Arg Gly Lys Ser Gly Thr Tyr Gly Val
        195                 200                 205

Phe Leu Leu Asn Ser Asn Gly Met Asp Ile Lys Ile Asn Gln Thr Thr
    210                 215                 220

Asp Gly Lys Gln Tyr Leu Glu Tyr Asn Leu Leu Gly Val Leu Asp
225                 230                 235                 240

Phe Tyr Phe Phe Tyr Gly Glu Asp Pro Lys Gln Ala Ser Met Glu Tyr
                245                 250                 255

Ser Lys Ile Val Gly Leu Pro Ala Met Gln Ser Tyr Trp Thr Phe Gly
            260                 265                 270

```
Val Cys Pro Pro Pro Asn Pro Ile Thr Val Arg Val Val Tyr
        275                 280                 285

Asn Tyr Ser Gln Ala Lys Ile Pro Leu Glu Thr Met Trp Thr Asp Ile
    290                 295                 300

Asp Tyr Met Asp Lys Arg Arg Val Phe Thr Leu Asp Pro Gln Arg Phe
305                 310                 315                 320

Pro Leu Glu Lys Met Arg Glu Leu Val Thr Tyr Leu His Asn His Asp
            325                 330                 335

Gln His Tyr Ile Val Met Val Asp Pro Ala Val Ser Val Ser Asn Asn
                340                 345                 350

Thr Ala Tyr Ile Thr Gly Val Arg Asp Asp Val Phe Leu His Asn Gln
        355                 360                 365

Asn Gly Ser Leu Tyr Glu Gly Ala Val Trp Pro Gly Val Thr Val Phe
    370                 375                 380

Pro Asp Trp Phe Asn Glu Gly Thr Gln Asp Tyr Trp Thr Ala Gln Phe
385                 390                 395                 400

Gln Gln Phe Phe Asp Pro Lys Ser Gly Val Asp Ile Asp Ala Leu Trp
                405                 410                 415

Ile Asp Met Asn Glu Ala Ser Asn Phe Cys Pro Tyr Pro Cys Leu Asp
                420                 425                 430

Pro Ala Ala Tyr Ala Ile Ser Ala Asp Leu Pro Pro Ala Ala Pro Pro
            435                 440                 445

Val Arg Pro Ser Ser Pro Ile Pro Leu Pro Gly Phe Pro Ala Asp Phe
        450                 455                 460

Gln Pro Ser Ser Lys Arg Ser Val Lys Arg Ala Gln Gly Asp Lys Gly
465                 470                 475                 480

Lys Lys Val Gly Leu Pro Asn Arg Asn Leu Thr Asp Pro Pro Tyr Thr
            485                 490                 495

Ile Arg Asn Ala Ala Gly Val Leu Ser Met Ser Thr Ile Glu Thr Asp
                500                 505                 510

Leu Ile His Ala Gly Glu Gly Tyr Ala Glu Tyr Asp Thr His Asn Leu
        515                 520                 525

Tyr Gly Thr Arg Leu Val Met Ser Ser Ala Ser Arg Thr Ala Met Gln
    530                 535                 540

Ala Arg Arg Pro Asp Val Arg Pro Leu Val Ile Thr Arg Ser Thr Phe
545                 550                 555                 560

Ala Gly Ala Gly Ala His Val Gly His Trp Leu Gly Asp Asn Phe Ser
            565                 570                 575

Asp Trp Val His Tyr Arg Ile Ser Ile Ala Gln Ile Leu Ser Phe Ala
            580                 585                 590

Ser Met Phe Gln Ile Pro Met Val Gly Ala Asp Val Cys Gly Phe Gly
            595                 600                 605

Ser Asn Thr Thr Glu Glu Leu Cys Ala Arg Trp Ala Ser Leu Gly Ala
    610                 615                 620

Phe Tyr Thr Phe Tyr Arg Asn His Asn Glu Leu Gly Asp Ile Ser Gln
625                 630                 635                 640

Glu Phe Tyr Arg Trp Pro Thr Val Ala Glu Ser Ala Arg Lys Ala Ile
            645                 650                 655

Asp Ile Arg Tyr Lys Leu Leu Asp Tyr Ile Tyr Thr Ala Leu His Arg
                660                 665                 670

Gln Ser Gln Thr Gly Glu Pro Phe Leu Gln Pro Gln Phe Tyr Leu Tyr
        675                 680                 685

Pro Glu Asp Ser Asn Thr Phe Ala Asn Asp Arg Gln Phe Phe Tyr Gly
```

```
                690                 695                 700
Asp Ala Leu Leu Val Ser Pro Val Leu Asn Glu Gly Ser Thr Ser Val
705                 710                 715                 720

Asp Ala Tyr Phe Pro Asp Asp Ile Phe Tyr Asp Trp Tyr Thr Gly Ala
            725                 730                 735

Val Val Arg Gly His Gly Glu Asn Ile Thr Leu Ser Asn Ile Asn Ile
            740                 745                 750

Thr His Ile Pro Leu His Ile Arg Gly Gly Asn Ile Ile Pro Val Arg
            755                 760                 765

Thr Ser Ser Gly Met Thr Thr Thr Glu Val Arg Lys Gln Gly Phe Glu
            770                 775                 780

Leu Ile Ile Ala Pro Asp Leu Asp Asp Thr Ala Ser Gly Ser Leu Tyr
785                 790                 795                 800

Leu Asp Asp Gly Asp Ser Leu Asn Pro Ser Ser Val Thr Glu Leu Glu
                805                 810                 815

Phe Thr Tyr Ser Lys Gly Glu Leu His Val Lys Gly Thr Phe Gly Gln
                820                 825                 830

Lys Ala Val Pro Lys Val Glu Lys Cys Thr Leu Leu Gly Lys Ser Ala
                835                 840                 845

Arg Thr Phe Lys Gly Phe Ala Leu Asp Ala Pro Val Asn Phe Lys Leu
    850                 855                 860

Lys
865
```

FOOD PRODUCT CONTAINING STARCH GEL, STARCH GRANULE, PRODUCTION METHOD AND USE THEREOF

TECHNICAL FIELD

The present invention relates to a starch gel-containing food, a starch having a high viscosity and a gel forming ability, a food containing the starch, a method of producing thereof and use thereof. More particularly, the present invention relates to a method of producing a starch gel-containing food using an enzyme capable of improving a gel forming ability of a starch.

BACKGROUND ART

With diversification of foods, foods having various shapes, physical properties and textures have been required. Particularly, intense interest has recently been shown towards melt in mouth and texture as important physical properties for the purpose of designing foods. Also in the fields related to deglutition and care toward which intense interest has recently been shown, texture has been studied as important physical properties.

In the case of designing processed foods, utilization of a gelling agent is important so as to improve texture and physical properties, and it is possible to develop various products according to how to use.

For the purpose of altering physical properties of foods, various gelling agents have hitherto been added to food materials in the case of preparing foods.

In food processing, natural macromolecules such as agar, gelatin, gellan gum, xanthan gum, locust bean gum, carrageenan, pectin, sodium alginate, Tamarind seed gum, psyllium seed gum, microcrystal cellulose, curdlan, and starch; or synthetic macromolecules such as carboxymethyl cellulose (CMC) or methyl cellulose are commonly used as gelling agents.

In the case of using these gelling agents, gelling agents may be sometimes used alone, however, in order to form gels having more various characteristics, for example, use of two or more kinds of gelling agents such as native gellan gum and guar gum in combination is studied and utilized (Patent Document 1).

However, there are few combinations which can synergistically chancre the gel strength of foods. Even if it is possible to synergistically chancre the gel strength, the gel obtained thereby does not have nice physical properties. Mixing of two or more kinds of gelling agents is a defect due to being complicated and that many materials are very expensive.

Furthermore, there is such a restriction on use in food processing that, for example, a gelatin is inferior in resistance to an acid and an alkali, and also an agar is inferior in resistance to an acid.

Starches have successfully produced various physical properties by adding not only raw starches but also a processed starch obtained by chemically modifying starches (also referred to as a chemically modified starch) such as starch acetate and monostarch phosphate as a gelling agent to food materials. For example, Patent Documents 2, 3 and 4 indicate examples in which a crosslinked starch is utilized in a white table bread, confectioneries or noodles. However, in the case where a crosslinked starch having a high crosslinking degree is added to a food, the hardness and the viscosity of a gel can be enhanced, but there is such a drawback that a final product has powdery texture and also is inferior in flavor. Also, in the case where a starch having a low crosslinking degree is added to a food, since a large amount of the starch needs to be used so as to obtain the desired hardness, the obtained food has increased powdery texture, thus causing deterioration of quality of a final product. Therefore, there is a limit on the use amount of the starch having a low crosslinking degree. In addition, processing of the starch utilizing a chemical reaction also has such problems that there is a strict legal restriction on a processing method and a processing degree so as to secure safety, and that it is not necessarily suited to needs of consumers who require security and safety.

For the purpose of deigning these processed foods, it is urgently necessary to develop a processing technique to obtain a processed starch which exhibits various physical properties and has high safety.

As a result of intensive studies, we have found that a food with rich elasticity, crispy sensation and the like can be prepared by adopting the steps of treating starch granules with a starch hydrolase or a glycosyltransferase in advance; then mixing the resultant with a food material and water; and heating the mixture.

A starch is a material utilized for various purposes and the most important function thereof is the thickening function and the gel forming function. Particularly in the food industry, the thickening function and the gel forming function of the starch are widely utilized for forming the shape, physical properties and texture of a food. The structure of a starch delicately varies depending on plant from which the starch derived (for example, corn, potato, wheat, and cassava). As a result, the thickening function and gel forming function also vary depending on the plant from which the starch derived. Therefore, those skilled in the art have been selected a native starch to be used for a long time depending on the purpose. For example, a wheat starch has often been used in a fish paste product for a long time. The reason is that the wheat starch is excellent in gel forming function. For example, a cassava starch is commonly utilized in a food which has high transparency and requires sticky texture. However, with the advancement of characteristics required in the current food industry, it becomes impossible to cope with the advancement only by changing a native starch to be used. Therefore, there arises the need to alter the thickening function or the gel forming function of a starch.

Means which are used most commonly to alter the thickening function or the gel forming function of a starch is a chemical modification of a starch. Above all, techniques of applying a chemical treatment, such as a technique of introducing a new crosslinking point between starch molecules using a suitable chemical crosslinking agent and a technique of introducing a suitable functional group have widely been utilized so as to remarkably alter the thickening function or the gel forming function. However, a starch subjected to such a chemical treatment has been specified as a food additive from October, 2008 in Japan, and thus restricted by law. Therefore, there has been required a technique in which the thickening function or the gel forming function of a starch is altered without a chemical treatment.

The technique of altering a starch without a chemical treatment includes a technique of an enzymatic treatment of a starch. Since an enzyme commonly acts on a substrate dissolved in water, an enzymatic treatment is usually carried out after completely dissolving a starch in water. A hydrolytic enzyme or a glycosyltransferase is allowed to act on a starch dissolved in water to cleave the starch, thereby producing molecules having a lower molecular weight such as dextrin, starch syrup, maltooligosaccharide, maltose, and glucose. However, in the enzymatic treatment with a hydrolytic enzyme or a glycosyltransferase, a starch molecule is cleaved to form low-molecular weight molecules. Therefore, it has been commonly considered that the thickening function and the gel forming function of the obtained molecule deteriorate as compared with the thickening function and the gel forming function of the starch, or are lost.

Also, Patent Document 5 discloses, as a method of altering physical properties of a starch, a technique in which an enzyme is allowed to act on a starch in the form of starch granules in water without dissolving them in water. Patent Document 5 discloses that although a starch has conventionally been dissolved in water before an enzymatic treatment in the case of subjecting the starch to the enzymatic treatment, it is not necessarily required to dissolve the starch in water before the enzymatic treatment, and it is possible to subject starch granules, which are not dissolved in water but suspended in water, to the enzymatic treatment. Specifically, it is disclosed that a hydrolytic enzyme such as α-amylase or glucoamylase can act on starch granules, which are not dissolved in water but, suspended in water, and thus a reducing sugar can be produced. Patent Document 5 also discloses as a result of this that the viscosity of the starch subjected to the enzymatic treatment is lower than that of the starch which has not been subjected to the enzymatic treatment. However, Patent Document 5 neither suggests nor discloses that a starch having improved thickening function or gel forming function as compared with the starch, which has not been subjected to the enzymatic treatment, is obtained by allowing a hydrolytic enzyme or a glycosyltransferase to act on starch granules.

Patent Documents 6 to 10 also disclose a technique of allowing a hydrolytic enzyme to act on insoluble starch granules. These inventions disclose a technique in which the action of a hydrolytic enzyme on starch granules opens pores on the surfaces of starch granules to make porous starch granules, and the porous starch granules are utilized as a powdered base material or a porous carrier. However, Patent Documents 6 to 10 neither suggests nor discloses that a starch having improved thickening function and gel forming function is obtained by allowing a hydrolytic enzyme or a glycosyltransferase to act on starch granules. An object of the present invention is not to open pores on the surfaces of enzyme-treated starch granules, and there is not any relationship between an improvement in thickening function and gel forming function, and whether or not pores are opened on the surfaces of enzyme-treated starch granules. If a heated food is produced using the enzyme-treated starch granules of the present invention, the enzyme-treated starch granules form a hard gel in the heated food. The enzyme-treated starch granules of the present invention are usable in the heated food. On the other hand, in the prior art, it is important that pores are present on the surfaces of starch granules. If starch granules after subjected to the enzymatic treatment and water are mixed and then heated, starch granules are collapsed and pore-opened states thereof are lost. Therefore, those skilled in the art did not consider to use a pore-opened starch of the prior art in the heated food. In the present invention, it is possible to adjust the hardness of a gel to be formed using an enzyme-treated starch by adjusting the degree of the enzymatic treatment. The hardness of the gel exerts an influence on texture, chewiness, and the like of the food. Therefore, use of the method of the present invention can exert an influence on texture of the food. As described above, the enzyme-treated starch granules of the prior art and the enzyme-treated starch granules used in the present application quite differ in application and usage.

As described above, it was conventionally impossible to provide starch granules excellent in thickening function or gel forming function without utilizing a chemical modification of a starch.

Also, in the prior art, no attention was paid at all whether or not an enzyme has characteristics capable of improving a gel forming ability of a starch. It was not also found at all whether or not industrial advantages are exerted by characteristics of an enzyme capable of improving a gel forming ability of a starch.

Starch has been used for various applications in addition to food application. Starch has excellent characteristics as follows: (1) it is a polymer material which does not depend on a petroleum raw material, and can be reproduced; (2) administrations of starch not only the oral ingestion as a food, but also in a blood expander to human blood have been performed for a long time and thus, there are actual positive results accumulated for a long period of time concerning its safety to the human body; and (3) it is a biodegradable polymer material which can be degraded in an environment. Therefore, starch has been utilized as biodegradable articles such as hydrogels, powders, films, sheets, threads, fibers, nonwoven fabrics or other shaped articles, in a wide variety of industrial fields in addition to foods. Specifically, starch is utilized in, for example, paints, adhesives, pharmaceutical drugs, pharmaceutical drug additives, quasi-drugs, quasi-drug additives, cosmetics, cosmetic additives, agricultural chemicals, fertilizers, biocompatible medical materials, capsules, biodegradable articles which are hydrogels for hydraulic fracturing used for underground resource digging, biodegradable articles which are compositions for injection to form hydrogel in a human body, or the like. However, the characteristics of the starch granules obtained by the method of the present invention have not been known. Therefore, it could not have been inferred to those skilled in the art at all that the starch granules of the present invention, which were originally intended to be used in food applications, are used as these biodegradable articles.

Esterification and etherification are effective chemical modifications to give retrogradation resistance, transparency, film property and the like to starch, and have been widely employed to improve starch properties. However, there was a problem that, apparent specific gravity of esterified starch granules and etherified starch granules are lower than those of untreated starch granules, therefore, it is difficult with the esterified starch granules and the etherified starch granules to remove an unreacted esterifying nor agent or an unreacted etherifying agent from a product containing esterified starch granules or etherified starch granules (solid-liquid separation) after untreated starch granules having been processed with an esterifying agent or an etherifying agent.

PRIOR ART DOCUMENTS

Patent Documents

Patent Document 1: Japanese Laid-open Patent Publication No. 10-215795
Patent Document 2: Japanese Patent Gazette No. 3,723,860
Patent Document 3: Japanese Patent Gazette No. 3,312,225
Patent Document 4: Japanese Patent Publication for Opposition No. 7-63324

Patent Document 5: Japanese Laid-open Patent Publication No. 6-269291
Patent Document 6: Japanese Laid-open Patent Publication No. 2003-219813
Patent Document 7: Japanese Patent Gazette No. 4,170,062
Patent Document 8: Japanese Laid-open Patent Publication No. 1-159047
Patent Document 9: Japanese Laid-open Patent Publication No. 5-112469
Patent Document 10: Japanese Laid-open Patent Publication No. 8-277230

SUMMARY OF THE INVENTION

Problems to be Solved by the Invention

The present invention is intended to solve the above problems, and it is an object of the invention to provide a food containing a starch gel having the desired degree of hardness and a method of producing the same. In a specific embodiment of the present invention, objects are to provide starch granules excellent, in thickening function or gel forming function without utilizing a chemical modification of a starch; a food prepared from the starch granules; and a method of producing the starch granules and food. In a particular embodiment of the present invention, an object is to provide starch granules that are excellent in a thickening function or a gel-forming function, the production method and various applications thereof.

Means for Solving the Problems

The present inventors have intensively studied so as to solve the above problems and have found that a starch excellent in thickening function and gel forming function is obtained by allowing a specific hydrolytic enzyme or glycosyltransferase having characteristics capable of improving a gel forming ability of a starch to act on starch granules under the condition where a starch is not dissolved, and thus have completed the present invention based on this finding. It is commonly considered that when a hydrolytic enzyme or a glycosyltransferase is allowed to act on a starch, the starch is cleaved to form smaller molecules, and therefore the viscosity and the gel forming ability of the obtained molecules deteriorate as compared with the viscosity and gel forming ability of the starch before being subjected to the enzymatic treatment, or are lost. Actually, when the same hydrolytic enzyme or glycosyltransferase as the hydrolytic enzyme or glycosyltransferase capable of producing such an excellent starch when being allowed to act on starch granules under the condition, where a starch is not dissolved in water is allowed to act on a starch after dissolving the starch in water, the starch viscosity decreases, and thus a starch excellent in thickening function or gel forming function cannot be obtained. As described above, the present invention cannot be conceived from the conventionally general knowledge and technical common sense possessed by those skilled in the art.

The conditions of an enzymatic treatment of starch granules can vary depending on the specificity of the enzyme and the origin of starch granules. For example, first, starch granules are suspended in ion-exchange water or a buffer solution to prepare a starch suspension. In the case where the pH adjustment of the starch suspension is required, the pH is adjusted to the optimum pH of the enzyme. While warming this starch suspension at the temperature at which starch granules are not degraded (preferably from about 10° C. to about 70° C.), the enzyme is added and the reaction can be carried out, for example, within about 24 hours (preferably from about for 1 hour to about 20 hours). Then, the enzyme and a carbohydrate eluted by enzymatic degradation are removed by the washing and dehydration steps which are a conventional method of preparing a starch, followed by the drying step, and thus the objective enzyme-treated starch granules can be obtained.

It was confirmed that the enzyme-treated-chemically modified starch granules of the present invention have very high viscosity and an ability to form harder gel compared to the conventional untreated starch granules, and its viscosity is rapidly increased. Further, it shows high transparency when a gel was formed, and shows physical properties suitable for a biodegradable article.

The enzyme-treated starch granules of the present invention are macromolecules which have a main framework of neutral polysaccharides and are not derived from an animal. Therefore, the enzyme-treated starch granules of the present invention have little concern about the safety with respect to the use in a human body. The starch granules of the present invention are usable without anxiety, in particular, as pharmaceutical drugs, cosmetics and biocompatible medical materials, and further the action to a cell and the skin is mild.

The enzyme-treated starch granules of the present invention are excellent in the film property similarly to the conventional untreated starch granules. Therefore, cosmetics using the starch granules of the present invention are excellent in film formation ability. The starch granules of the present invention are superior in the thickening function in comparison with the conventional untreated starch granules. Therefore, cosmetics using the starch granules of the present invention have higher viscosity than cosmetics using the conventional untreated starch granules. Stability of gel and starch paste made from the starch granules of the present invention is superior in comparison with those made from the conventional untreated starch granules. Therefore, cosmetics using the starch granules of the present invention have higher gel stability in comparison with cosmetics using the conventional untreated starch granules, and are suitable for long-term storage. As described above, the starch granules of the present invention, are quite suitable for the use in cosmetic applications. The cosmetics using the starch granules of the present invention and the cosmetics using the cosmetic additives using the starch granules of the present invention have superior characteristics in comparison with cosmetics using the conventional untreated starch granules, in film forming ability, thickening effect, stability and the like. Therefore, the cosmetics of the present invention have excellent characteristics in the touch at the time of use, the touch at the coated surface at the time of application and after the application, the moisture retention property, the stability and the like.

The starch granules of the present invention can be broken down by bacteria, microorganisms or the like. Therefore, the starch granules of the present invention are unlikely to cause environmental pollution problem. The starch granules of the present invention are suitable for applications in which they are used in a large amount in the environment (for example, they can be preferably used as a thickening agent at the time of the digging of shale gas).

Furthermore, the present inventors found that enzyme-treated esterified starch granules and enzyme-treated etherified starch granules which have high apparent specific gravity (that is, it is easy to perform solid-liquid separation) are obtained by performing an enzyme treatment of the starch granules before esterification and etherification. The present inventors found that the starch granules that have been esterified and etherified after the enzyme treatment have further advantage characteristics such that the viscosity of the starch paste using the starch granules is increased fast, while the granules maintain retrogradation resistance, transparency and film property which are possessed by the conventional esterified starch and etherified starch.

The method for producing enzyme-treated-chemical modified starch granules of the present invention has advantages that the filtration velocity at the time of the separation of an enzyme-treated-chemically modified starch granules and the chemical modification treatment liquid is fast, the precipitation speed of the enzyme-treated-chemically modified starch granules from chemical reaction liquid is fast, and therefore the production efficiency is improved. Furthermore, the enzyme-treated-chemically modified starch granules obtained by the method of the present invention have an excellent effect in that when a starch suspension containing the granules is prepared, they are quickly precipitated.

When wheat starch granules are used as a raw material, there is an effect in that a good result is constantly provided. Therefore, wheat starch granules are very preferred in industrial production. Corn starch granules account for most of the amount of starch produced in the United States of America. Therefore, the corn starch granules are preferable in industrial production.

Cereal-derived starch granules such as wheat starch granules and corn starch granules generally have slow filtration velocity. Therefore, the improvement of the filtration velocity and the improvement, of productivity efficiency by the enzyme-treatment-chemical modification of the present invention are significant.

The present invention is, for example, as follows:

(Item 1) A method of producing a starch gel-containing food, the method comprising the steps of:

treating starch granules with an enzyme at a temperature of about 10° C. or higher and about 70° C. or lower to obtain enzyme-treated starch granules;

mixing a food material, the enzyme-treated starch granules and water to obtain a mixture;

heating the mixture thereby gelatinizing the enzyme-treated starch granules in the mixture; and cooling the mixture containing the gelatinized enzyme-treated starch thereby gelling the starch to obtain a starch gel-containing food, wherein the enzyme is selected from the group consisting of amyloglucosidase, isoamylase, α-glucosidase, α-amylase having a characteristic capable of improving a gel forming ability of a starch, and cyclodextrin glucanotransferase.

(Item 2) The method according to Item 1, wherein the enzyme is selected from the group consisting of amyloglucosidase, isoamylase, α-glucosidase, α-amylase derived from the genus *Aspergillus*, and cyclodextrin glucanotransferase.

(Item 3) The method according to Item 1, wherein the enzyme is selected from the group consisting of amyloglucosidase, isoamylase, α-glucosidase, α-amylase derived from *Aspergillus oryzae*, α-amylase derived from *Aspergillus niger*, and cyclodextrin glucanotransferase.

(Item 3-2) The method according to Item 1, wherein the enzyme is selected from the group consisting of α-amylase derived from *Aspergillus oryzae* or *Aspergillus niger*,
amyloglucosidase derived from *Aspergillus niger*, *Rhizopus niveus*, or *Rhizopus oryzae*,
α-glucosidase derived from *Aspergillus niger*, isoamylase derived from *Flavobacterium* sp. or *Pseudomonas amyloderamosa*, and
cyclodextrin glucanotransferase derived from *Bacillus licheniformis*, or *Paenibacillus macerans* (*Bacillus macerans*).

(Item 4) The method according to Item 1, wherein the enzyme is selected from the group consisting of amyloglucosidase derived from *Aspergillus niger* commercially available from Novozyme as AMG, amyloglucosidase derived from *Aspergillus niger* commercially available from Genencor as OPTIDEX L-400, amyloglucosidase derived from *Aspergillus niger* commercially available from DANISCO as DIAZYME X4NP, amyloglucosidase derived from *Aspergillus niger* commercially available from Amano Enzyme as glucoamylase "Amano" SD, amyloglucosidase derived from *Rhizopus niveus* commercially available from Amano Enzyme as Gluczyme AF6, amyloglucosidase derived from *Rhizopus oryzae* commercially available from SHIN NIHON CHEMICALS Corporation as Sumizyme, α-glucosidase derived from *Aspergillus niger* commercially available from Amano Enzyme as transglucosidase L "Amano", α-glucosidase derived from *Aspergillus niger* commercially available from Genencor as Transglucosidase L-500, α-amylase derived from *Aspergillus oryzae* commercially available from Amano Enzyme as Biozyme A, α-amylase derived from *Aspergillus oryzae* commercially available from SHIN NIHON CHEMICALS Corporation as Sumizyme L, α-amylase derived from *Aspergillus niger* commercially available from Danisco as AMYLEX A3, α-amylase derived from *Aspergillus niger* commercially available from SHIN NIHON CHEMICALS Corporation as Sumizyme AS, isoamylase derived from *Pseudomonas amyloderamosa* commercially available from Sigma as isoamylase, cyclodextrin glucanotransferase derived from *Bacillus licheniformis* commercially available from Novozyme as Toruzyme, and cyclodextrin glucanotransferase derived from *Paenibacillus macerans* (*Bacillus macerans*) commercially available from Amano Enzyme as Cyclodextrin glucanotransferase "Amano".

(Item 5) The method according to Item 1, wherein:
(1) the enzyme is encoded by a nucleic acid molecule which is capable of hybridizing under stringent conditions with a nucleic acid molecule consisting of a base sequence complementary to a base sequence of SEQ ID NO: 1, 3, 5, 7, 9 or 11, and has a starch hydrolysis activity; or
(2) the enzyme is encoded by a nucleic acid molecule which is capable of hybridizing under stringent conditions with a nucleic acid molecule consisting of a base sequence complementary to a base sequence of SEQ ID NO: 13, and has a transglycosylation activity; wherein the stringent conditions are hybridization in a solution containing 50% formamide, 5×SSC (750 mM NaCl, 75 mM trisodium citrate), 50 mM sodium phosphate (pH 7.6), 5×Denhardt's solution (0.2% BSA, 0.2% Ficoll 400 and 0.2% polyvinylpyrrolidone), 10% dextran sulfate and 20 µg/ml denatured sheared salmon sperm DNA at 65° C., and subsequent washing under the condition of 65° C. using an SSC solution having a 0.1 to 2-fold concentration (a composition of an SSC solution having a 1-fold concentration is 150 mM sodium chloride and 15 mM sodium citrate).

(Item 6) The method according to Item 1, wherein:
(1) the enzyme has an amino acid sequence having at least 95% or more of homology with an amino acid sequence of SEQ ID NO: 2, 4, 6, 8, 10 or 12, and has a starch hydrolysis activity; or (2) the enzyme has an amino acid sequence having at least 95% or more of homology with an amino acid sequence of SEQ ID NO: 14, and has a transglycosylation activity.

(Item 7) The method according to any of Items 1 to 6 and 3-2, wherein the starch granules to be enzyme-treated are starch granules of an untreated starch, a physically treated starch or a chemically modified starch.

(Item 8) The method according to any of Items 1 to 7 and 3-2, wherein the starch granules to be enzyme-treated are starch granules of an untreated starch, and the starch granules have been neither chemically modified nor physically treated in any stage until the starch gel-containing food is obtained by the method.

(Item 9) The method according to any of Items 1 to 7 and 3-2, wherein the starch granules to be enzyme-treated are starch granules of an untreated starch or a physically treated starch, the method further comprises the step of chemically modifying the enzyme-treated starch granules, and the chemically modified enzyme-treated starch granules are mixed with the food material and water.

(Item 10) The method according to any of Items 1 to 7 and 3-2, wherein the starch granules to be enzyme-treated are starch granules of an untreated starch or a chemically modified starch, the method further comprises the step of physically treating the enzyme-treated starch granules, and the physically treated enzyme-treated starch granules are mixed with the food material and water.

(Item 10-2) The method according to any of Items 1 to 10 and 3-2, further comprising a step of removing a carbohydrate eluted by enzymatic degradation from the product containing the enzyme-treated starch granules, before the step of mixing the food material, the enzyme-treated starch granules and water to obtain the mixture.

(Item 11) A starch gel-containing food produced by the method according to any of Items 1 to 10, 3-2 and 10-2.

(Item 12) The food according to Item 11, wherein the food is a high moisture content type food and the amount of moisture of the food is more than 40 g and less than 95 g per 100 g of the edible portion.

(Item 13) The food according to Item 11, wherein the food is selected from the group consisting of traditional Japanese-style confectioneries, fat- or oil-containing foods, gelatinous foods, fish meat and animal meat processed foods, salsa and sauces, and noodles.

(Item 14) The food according to Item 11, wherein the food is a low moisture content type food and the amount of moisture of the food is 1 g or more and 40 g or less per 100 g of the edible portion.

(Item 15) The food according to Item 11, wherein the food is selected from the group consisting of bakeries, Western-style confectioneries, and fried foods.

(Item 16) The food according to Item 11, wherein the enzyme is selected from the group consisting of amyloglucosidase, isoamylase, α-glucosidase, α-amylase derived from the genus *Aspergillus*, and cyclodextrin glucanotransferase.

(Item 17) The food according to any of Items 11 to 16, wherein the enzyme is selected from the group consisting of amyloglucosidase, isoamylase, α-glucosidase, α-amylase derived from *Aspergillus oryzae*, α-amylase derived from *Aspergillus niger*, and cyclodextrin glucanotransferase.

(Item 18) The food according to any of Items 11 to 17, wherein the starch granules are derived from cassava, corn or wheat.

In a specific embodiment, the present invention is, for example, as follows:

(Item 1A) A heat-cooked starch-containing food prepared from enzyme-treated starch granules having high viscosity and gel-forming ability, the starch-containing food is a food produced by a method comprising the steps of mixing a food material and the enzyme-treated starch granules and then heating them, the enzyme-treated starch granules are starch granules obtained by treating starch granules of untreated starch with a starch hydrolase under the condition where the starch granules are not dissolved, the enzyme-treated starch granules are not, modified on hydroxyl groups at the positions 2, 3 and 6 of the glucose residues, the enzyme-treated starch granules can form a gel having a Young's modulus higher than that of the starch granules of the untreated starch or a rupture stress higher than that of the starch granules of the untreated starch, when measured by a rheometer.

(Item 2A) The food according to Item 1A, wherein the untreated starch is a untreated wheat starch, the enzyme-treated starch granules are enzyme-treated wheat starch granules, and the enzyme-treated wheat starch granules are capable of forming a gel having a Young's modulus which accounts for 110% or more and 500% or less (110% or more and 330% or less in an embodiment) of the Young's modulus the starch granules of the untreated wheat starch, or a rupture stress which accounts for 110% or more and 300% or less of the rupture stress of the starch granules of the untreated wheat starch, when measured by a rheometer.

(Item 3A) The food according to Item 1A, wherein the untreated starch is a untreated cassava starch, the enzyme-treated starch granules are a enzyme-treated cassava starch granules, and the enzyme-treated cassava starch granules are capable of forming a gel having a Young's modulus which accounts for 110% or more and 500% or less (110% or more and 330% or less in an embodiment) of the Young's modulus of the starch granules of the untreated cassava starch, or a rupture stress which accounts for 110% or more and 300% or less of the rupture stress of the starch granules of the untreated cassava starch, when measured by a rheometer.

(Item 4A) The food according to Item 1A, wherein the untreated starch is a untreated corn starch, the enzyme-treated starch granules are enzyme-treated corn starch granules, and the enzyme-treated corn starch granules are capable of forming a gel having a Young's modulus which accounts for 110% or more and 500% or less (110% or more and 330% or less in an embodiment) of the Young's modulus of the starch granules of the untreated corn starch, or a rupture stress which accounts for 110% or more and 300% or less of the rupture stress of the starch granules of the untreated corn starch, when measured by a rheometer.

(Item 5A) A heat-cooked starch-containing food prepared from enzyme-treated wheat starch granules having high viscosity and gel-forming ability, the starch-containing food is a food produced by a method comprising the steps of mixing a food material and the enzyme-treated wheat starch granules and then heating them, the enzyme-treated wheat starch granules are starch granules obtained by treating starch granules of untreated wheat starch with a starch hydrolase under the condition where the starch granules are not dissolved, the enzyme-treated wheat starch granules are not modified on hydroxyl groups at the positions 2, 3 and 6 of the glucose residues, the enzyme-treated wheat starch granules can form a gel having a Young's modulus of $5.0 \times 10^6$ dyn/cm$^2$ or more and $8.0 \times 10^6$ dyn/cm$^2$ or less, or a rupture stress of 150 g or more and 450 g or less, when measured by a rheometer.

(Item 6A) A heat-cooked starch-containing food prepared from an enzyme-treated cassava starch granules having high viscosity and gel-forming ability, the starch-containing food is a food produced by a method comprising the steps of mixing a food material and the enzyme-treated cassava starch granules and then heating them, the enzyme-treated cassava starch granules are starch granules obtained by treating starch granules of untreated cassava starch with an starch hydrolase under the condition where the starch granules are not dissolved, the enzyme-treated cassava starch granules are not modified on hydroxyl groups at the positions 2, 3 and 6 of the glucose residues, the enzyme-treated cassava starch granules can form a gel having a Young's modulus of $5.2 \times 10^5$ dyn/cm$^2$ or more and $2.7 \times 10^6$ dyn/cm$^2$ or less ($5.2 \times 10^5$ dyn/cm$^2$ or more and $1.6 \times 10^6$ dyn/cm$^2$ or less in one embodiment), or a rupture stress of 55 g or more and 150 g or less, when measured by a rheometer.

(Item 7A) A heat-cooked starch-containing food prepared from an enzyme-treated corn starch granules having high viscosity and gel-forming ability, the starch-containing food is a food produced by a method comprising the steps of mixing a food material and the enzyme-treated corn starch granules and then heating them, the enzyme-treated corn starch granules are starch granules obtained by treating starch granules of untreated corn starch with an starch hydrolase under the condition where the starch granules are not dissolved, the enzyme-treated corn starch granules are not modified on hydroxyl groups at the positions 2, 3 and 6 of the glucose residues, the enzyme-treated corn starch granules can form a gel having a Young's modulus of $6.0 \times 10^6$ dyn/cm$^2$ or more and $9.0 \times 10^6$ dyn/cm$^2$ or less, or a rupture stress of 210 g or more and 450 g or less (220 g or more and 450 g or less in one embodiment), when measured by a rheometer.

(Item 8A) The food according to any one of Items 1A to 7A, wherein the starch is forming a gel in the food.

(Item 9A) The food according to any one of Items 1A to 8A, wherein the food is a high moisture content type food and the amount of moisture of the food is more than 40 g and less than 95 g per 100 g of the edible portion.

(Item 10A) The food according to any one of Items 1A to 9A, wherein the food is selected from the group consisting of traditional Japanese-style confectioneries, fat- or oil-containing foods, gelatinous foods, fish meat and animal meat processed foods, salsa and sauces, and noodles.

(Item 11A) The food according to any one of Items 1A to 8A, wherein the food is a low moisture content type food and the amount of moisture of the food is 1 g or more and 40 g or less per 100 g of the edible portion.

(Item 12A) The food according to any one of Items 1A to 8A and 11A, wherein the food is selected from the group consisting of bakeries, Western-style confectioneries (and fried foods.

(Item 13A) The food according to any one of Items 1A to 12A, wherein the starch hydrolase is selected from the group consisting of amyloglucosidase, isoamylase, α-glucosidase, and α-amylase having characteristics capable of improving a gel-forming ability of a starch.

(Item 14A) The food according to Item 13, wherein the starch hydrolase is selected from the group consisting of amyloglucosidase, isoamylase, α-glucosidase, and α-amylase derived from the genus *Aspergillus*.

(Item 15A) The food according to Item 13A, wherein the starch hydrolase is selected from the group consisting of amyloglucosidase, isoamylase, α-glucosidase, α-amylase derived from *Aspergillus oryzae*, and α-amylase derived from *Aspergillus niger*.

(Item 16A) A method of producing a starch-containing food, the method comprising the steps of:

adding and mixing an enzyme-treated starch granules to a food material; and heat-cooking the mixture;

the enzyme-treated starch granules are starch granules obtained by treating starch granules of untreated starch with a starch hydrolase under the condition where the starch granules are not dissolved;

the enzyme-treated starch granules are not modified on hydroxyl groups at the positions 7, 3 and 6 of the glucose residues, the enzyme-treated starch granules can form a gel having a Young's modulus higher than that of the untreated starch or a rupture stress higher than that of the untreated starch, when measured by a rheometer.

(Item 17A) Enzyme-treated starch granules having high viscosity and gel-forming ability, the enzyme-treated starch granules are starch granules obtained by treating starch granules of untreated starch with an starch hydrolase under the condition where the starch granules are not dissolved, the enzyme-treated starch granules are not modified on hydroxyl groups at the positions 2, 3 and 6 of the glucose residues, the enzyme-treated starch granules can form a gel having a Young's modulus higher than that of the granules of the untreated starch or a rupture stress higher than that of the granules of the untreated starch, when measured by a rheometer.

(Item 18A) The starch granules according to Item 17A, wherein the untreated starch is untreated wheat starch granules, the enzyme-treated starch granules are enzyme-treated wheat starch granules, and the enzyme-treated wheat starch granules are capable of forming a gel having a Young's modulus which accounts for 110% or more and 500% or less (110% or more and 330% or less in an embodiment) of the Young's modulus of the granules of the untreated wheat starch, or a rupture stress which accounts for 110% or more and 300% or less of the rupture stress of the granules of the untreated wheat starch, when measured by a rheometer.

(Item 19A) The starch granules according to Item 17A, wherein the untreated starch is untreated cassava starch, the enzyme-treated starch granules are enzyme-treated cassava starch granules, and the enzyme-treated cassava starch granules are capable of forming a gel having a Young's modulus which accounts for 110% or more and 500% or less (110% or more and 330% or less in an embodiment) of the Young's modulus of granules of the untreated cassava starch, or a rupture stress which accounts for 110% or more and 300% or less of the rupture stress of granules of the untreated cassava starch granules, when measured by a rheometer.

(Item 20A) The starch granules according to Item 17A, wherein the untreated starch is untreated corn starch, the enzyme-treated starch granules are enzyme-treated corn starch granules, and the enzyme-treated corn starch granules are capable of forming a gel having a Young's modulus which accounts for 110% or more and 500% or less (110% or more and 330% or less in an embodiment) of the Young's modulus of granules of the untreated corn starch, or a rupture stress which accounts for 110% or more and 300% or less of the rupture stress of granules of the untreated corn starch, when measured by a rheometer.

(Item 21A) Enzyme-treated wheat starch granules having high viscosity and gel-forming ability, the enzyme-treated wheat starch granules are starch granules obtained by treating starch granules of untreated wheat starch with an starch hydrolase under the condition where the starch granules are not dissolved, the enzyme-treated wheat starch granules are not modified on hydroxyl groups at the positions 2, 3 and 6 of the glucose residues, the enzyme-treated wheat starch granules can form a gel having a Young's modulus of $5.0 \times 10^6$ dyn/cm$^2$ or more and $8.0 \times 10^6$ dyn/cm$^2$ or less, or a rupture stress of 150 g or more and 450 g or less, when measured by a rheometer.

(Item 22A) Enzyme-treated cassava starch granules having high viscosity and gel-forming ability, the enzyme-treated cassava starch granules are starch granules obtained by treating starch granules of untreated cassava starch with an starch hydrolase under the condition where the starch granules are not dissolved, the enzyme-treated cassava starch granules are not modified on hydroxyl groups at the positions 2, 3 and 6 of the glucose residues, the enzyme-treated cassava starch granules can form a gel having a Young's modulus of $5.2 \times 10^5$ dyn/cm$^2$ or more and $2.7 \times 10^6$ dyn/cm$^2$ or less ($5.2 \times 10^5$ dyn/cm$^2$ or more and $1.6 \times 10^6$ dyn/cm$^2$ or less in one embodiment), or a rupture stress of 55 g or more and 150 g or less, when measured by a rheometer.

(Item 23A) Enzyme-treated corn starch granules having high viscosity and gel-forming ability, the enzyme-treated corn starch granules are starch granules obtained by treating starch granules of untreated corn starch with an starch hydrolase under the condition where the starch granules are not dissolved, the enzyme-treated corn starch granules are not modified on hydroxyl groups at the positions 2, 3 and 6 of the glucose residues, the enzyme-treated corn starch granules can form a gel having a Young's modulus of $6.0 \times 10^6$ dyn/cm$^2$ or more and $9.0 \times 10^6$ dyn/cm$^2$ or less, or a rupture stress of 210 g or more and 450 g or less (220 g or more and 450 g or less in one embodiment), when measured by a rheometer.

(Item 24A) The starch granules according to any one of Items 18A to 23A, wherein the starch hydrolase is selected from the group consisting of amyloglucosidase, isoamylase, α-glucosidase, and α-amylase having characteristics capable of improving a gel-forming ability of a starch.

(Item 25A) The starch granules according to Item 24A, wherein the starch hydrolase is selected from the group consisting of amyloglucosidase, isoamylase, α-glucosidase, and α-amylase derived from the genus *Aspergillus*.

(Item 26A) The starch granules according to Item 24A, wherein the starch hydrolase is selected from the group consisting of amyloglucosidase, isoamylase, α-glucosidase, α-amylase derived from *Aspergillus oryzae*, and α-amylase derived from *Aspergillus niger*.

(Item 27A) A method of producing enzyme-treated starch granules having high viscosity and gel-forming ability, the method comprising the step of:

treating starch granules of untreated starch with a starch hydrolase at a temperature of 10° C. or higher and 70° C. or lower;

the starch hydrolase is selected from the group consisting of amyloglucosidase, isoamylase, α-glucosidase, and α-amylase having a characteristic capable of improving a gel forming ability of a starch.

(Item 28A) The method according to Item 27A, wherein the starch hydrolase is selected from the group consisting of amyloglucosidase, isoamylase, α-glucosidase, and α-amylase derived from the genus *Aspergillus*.

(Item 29A) The method according to Item 27A or 28A, wherein the starch hydrolase is selected from the group consisting of amyloglucosidase, isoamylase, α-glucosidase, α-amylase derived from *Aspergillus oryzae*, and α-amylase derived from *Aspergillus niger*.

(Item 30A) The method according to any one of Items 27A to 29A, wherein the starch hydrolase is selected from the group consisting of amyloglucosidase derived from *Aspergillus niger* commercially available from Novozyme as AMG, amyloglucosidase derived from *Aspergillus niger* commercially available from Genencor as OPTIDEX L-400, amyloglucosidase derived from *Aspergillus niger* commercially available from DANISCO as DIAZYME X4NP, amyloglucosidase derived from *Aspergillus niger* commercially available from Amano Enzyme as glucoamylase "Amano" SD, amyloglucosidase derived from *Rhizopus niveus* commercially available from Amano Enzyme as Gluczyme AF6, amyloglucosidase derived from *Rhizopus oryzae* commercially available from SHIN NIHON CHEMICALS Corporation as Sumizyme, α-glucosidase derived from *Aspergillus niger* commercially available from Amano Enzyme as transglucosidase L "Amano", α-glucosidase derived from *Aspergillus niger* commercially available from Genencor as Transglucosidase L-500, α-amylase derived from *Aspergillus oryzae* commercially available from Amano Enzyme as Biozyme A, α-amylase derived from *Aspergillus oryzae* commercially available from SHIN NIHON CHEMICALS Corporation as Sumizyme L, α-amylase derived from *Aspergillus niger* commercially available from Danisco as AMYLEX A3, α-amylase derived from *Aspergillus niger* commercially available from SHIN NIHON CHEMICALS Corporation as Sumizyme AS, and isoamylase derived from *Pseudomonas amyloderamosa* commercially available from Sigma as isoamylase.

(Item 31A) The method according to anyone of Items 27A to 30A, wherein the starch hydrolase is encoded by a nucleic acid molecule which is capable of hybridizing under stringent, conditions with a nucleic acid molecule having a complementary sequence of the base sequence of SEQ ID NO: 1, 3, 5, 7, 9 or 11, and has a starch hydrolysis activity; wherein the stringent conditions are hybridization in a solution containing 50% formamide, 5×SSC (750 mM NaCl, 75 mM trisodium citrate), 50 mM sodium phosphate (pH 7.6), 5×Denhardt's solution (0.2% BSA, 0.2% Ficoll 400 and 0.2% polyvinylpyrrolidone), 10% dextran sulfate and 20 µg/ml denatured sheared salmon sperm DNA at 65° C., and subsequent washing under the condition of 65° C. using an SSC solution having a 0.1 to 2-fold concentration (a composition of an SSC solution having a 1-fold concentration is 150 mM sodium chloride and 15 mM sodium citrate).

(Item 32A) The method according to anyone of Items 27A to 30A, wherein the starch hydrolase has an amino acid sequence having at least 95% or more of homology with an amino acid sequence of SEQ ID NO: 2, 4, 6, 8, 10 or 12, and has a starch hydrolysis activity.

(Item 33A) Enzyme-treated starch granules having high viscosity and gel-forming ability, the enzyme-treated starch granules are starch granules obtained by treating starch granules of untreated starch with a starch hydrolase under the condition where the starch granules are not dissolved;

the enzyme-treated starch granules are not modified on hydroxyl groups at the positions 2, 3 and 6 of the glucose residues, the starch hydrolase is selected from the group consisting of amyloglucosidase derived from *Aspergillus niger* commercially available from Novozyme as AMG, amyloglucosidase derived from *Aspergillus niger* commercially available from Genencor as OPTIDEX L-400, amyloglucosidase derived from *Aspergillus niger* commercially available from DANISCO as DIAZYME X4NP, amyloglucosidase derived from *Aspergillus niger* commercially available from Amano Enzyme as glucoamylase "Amano" SD, amyloglucosidase derived from *Rhizopus niveus* commercially available from Amano Enzyme as Gluczyme AF6, amyloglucosidase derived from *Rhizopus oryzae* commercially available from SHIN NIHON CHEMICALS corporation as Sumizyme, α-glucosidase derived from *Aspergillus niger* commercially available from Amano Enzyme as transglucosidase L "Amano", α-glucosidase derived from *Aspergillus niger* commercially available from Genencor as Transglucosidase L-500, α-amylase derived from *Aspergillus oryzae* commercially available from Amano Enzyme as Biozyme A, α-amylase derived from *Aspergillus oryzae* commercially available from SHIN NIHON CHEMICALS Corporation as Sumizyme L, α-amylase derived from *Aspergillus niger* commercially available from Danisco as AMYLEX A3, α-amylase derived from *Aspergillus niger* commercially available from SHIN NIHON CHEMICALS Corporation as Sumizyme AS, and isoamylase derived from *Pseudomonas amyloderamosa* commercially available from Sigma as isoamylase.

(Item 34A) Enzyme-treated starch granules having high viscosity and gel-forming ability, the enzyme-treated starch granules are starch granules obtained by treating starch granules of untreated starch with a starch hydrolase under the condition where the starch granules are not dissolved;

the enzyme-treated starch granules are not modified on hydroxyl groups at the positions 2, 3 and 6 of the glucose residues, the starch hydrolase is encoded by a nucleic acid molecule which is capable of hybridizing under stringent conditions with a nucleic acid molecule having a complementary sequence of the base sequence of SEQ ID NO: 1, 3, 5, 7, 9 or 11, and has a starch hydrolysis activity; wherein the stringent conditions are hybridization in a solution containing 50% formamide, 5×SSC (750 mM NaCl, 75 mM trisodium citrate), 50 mM sodium phosphate (pH 7.6), 5×Denhardt's solution (0.2% BSA, 0.2% Ficoll 400 and 0.2% polyvinylpyrrolidone), 10% dextran sulfate and 20 µg/ml denatured sheared salmon sperm DNA at 65° C., and subsequent washing under the condition of 65° C. using an SSC solution having a 0.1 to 2-fold concentration (a composition of an SSC solution having a 1-fold concentration is 150 mM sodium chloride and 15 mM sodium citrate).

(Item 35A) Enzyme-treated starch granules having high viscosity and gel-forming ability, the enzyme-treated starch granules are starch granules obtained by treating starch granules of untreated starch with a starch hydrolase under the condition where the starch granules are not dissolved;

the enzyme-treated starch granules are not modified on hydroxyl groups at the positions 2, 3 and 6 of the glucose residues, the starch hydrolase has an amino acid sequence having at least 95% or more of homology with an amino acid sequence of SEQ ID NO: 2, 4, 6, 8, 10 or 12, and has a starch hydrolysis activity.

In another particular embodiment, the present inventions are, for example, as follows:

(Item 21B) A method of producing enzyme-treated starch granules, the method comprising the steps of:

treating starch granules with an enzyme at a temperature of about 10° C. or higher and about 70° C. or lower to obtain enzyme-treated starch granules; and removing a carbohydrate eluted by enzymatic degradation from the enzyme-treated starch granules, wherein the enzyme is selected from the group consisting of α-amylase having a characteristic capable of improving a gel forming ability of a starch, amyloglucosidase, α-glucosidase, isoamylase, and cyclodextrin glucanotransferase.

(Item 22B) The method according to Item 21B, wherein the starch granules are starch granules of an untreated starch, a physically treated starch or a chemically modified starch.

(Item 23B) The method according to Item 21B, wherein the starch granules are starch granules of an untreated starch, and the starch granules have been neither chemically modified nor physically treated in any stage until the final product is obtained by the method.

(Item 24B) The method according to Item 21B, wherein the starch granules are starch granules of an untreated starch or a physically treated starch, and the method further comprises the step of chemically modifying the enzyme-treated starch granules.

(Item 25B) The method according to Item 21B, wherein the starch granules are starch granules of an untreated starch or a chemically modified starch, the method further comprises the step of physically treating the enzyme-treated starch granules.

(Item 26B) A method of producing enzyme-treated-chemically modified starch granules, the method comprising the steps of:

(a) treating starch granules with an enzyme at a temperature of about 10° C. or higher and about 70° C. or lower to obtain an enzyme-treated starch granules; and (b) etherifying or esterifying the enzyme-treated starch granules to obtain an enzyme-treated-chemically modified starch granules, wherein the method further comprises the step of removing a carbohydrate eluted by enzymatic degradation from the product of enzyme-treatment between the steps (a) and (b), or from the product of chemical modification after the step (b), and the enzyme is selected from the group consisting of α-amylase having a characteristic capable of improving a gel forming ability of a starch, amyloglucosidase, α-glucosidase, isoamylase, and cyclodextrin glucanotransferase.

(Item 27B) Enzyme-treated starch granules produced by the method according to Item 21B.

(Item 28B) Enzyme-treated and chemically modified starch granules produced by the method according to Item 26B.

(Item 29B) A biodegradable article which was prepared using the enzyme-treated and chemically modified starch granules according to Item 28B.

(Item 30B) The biodegradable article according to Item 29B, wherein the biodegradable article is a hydrogel, powder, a film, a sheet, a thread, a fiber or a nonwoven fabric.

(Item 31B) The biodegradable article according to Item 29B, wherein the biodegradable article is a paint or adhesive.

(Item 32B) The biodegradable article according to Item 29B, wherein the biodegradable article is a pharmaceutical drug, a pharmaceutical drug additive, a quasi-drug, a quasi-drug additive, a cosmetic, a cosmetic additive, an agricultural chemical or a fertilizer.

(Item 33B) The biodegradable article according to Item 29B, wherein the biodegradable article is a medical material.

(Item 34B) The biodegradable article according to Item 29B wherein the biodegradable article is a capsule.

(Item 35B) The biodegradable article according to Item 29B, wherein the biodegradable article is a thickening agent composition for use in a hydrogel for hydraulic fracturing.

(Item 36B) The biodegradable article according to Item 29B, wherein the biodegradable article is a composition to be injected into a human body to form a hydrogel.

Effects of the Invention

According to the present invention, starch granules "having a strong gel forming ability and a high viscosity" which have never been achieved by a conventional starch has been successfully developed by using an enzyme having characteristics capable of improving a gel forming ability of a starch.

Since a conventional starch having a strong gel forming ability cannot sufficiently undergo swelling and gelatinization in a usual heating temperature zone, powderiness is likely to be left when added to a food. In order to sufficiently swell and gelatinize the conventional starch having a strong gel forming ability, heating at higher temperature than usual heating temperature zone of a food is required. As for a starch subjected to an acid treatment and a starch having enriched in amylose fraction, they are excellent in gel forming ability, however they do not exhibit viscosity or hardly exhibit viscosity, and thus the application of them has been limited. Even in the case of such a starch subjected to an acid treatment, the gel forming ability can be improved as compared to the prior art by the enzymatic treatment according to the method of the present invention while maintaining a certain degree of viscosity.

Furthermore, although a chemically treated starch is often used for a bracken-starch dumpling (Warabimochi), it is necessary to use an acetylation treatment and a phosphate-crosslinking treatment in combination.

The starch granules developed in this time are starch granules in which these defects have been improved. In the case where an untreated starch, a physically treated starch, or a bleached starch is used as a raw material, and the starch granules developed in this time are produced under the condition where a chemical treatment is not applied in any stage of the production process, the addition to a usual food, or the application in a food containing a starch as a main raw material is not limited, and the starch granules can be used in all foods "dealt as a food".

In the case where an untreated starch, a physically treated starch or a bleached starch is used as a raw material and the enzyme-treated starch granules of the present invention are produced under the condition where a chemical treatment is not applied in any stage of the production process, the enzyme-treated starch granules of the present invention prepared by using a starch hydrolase or a glycosyltransferase do not correspond to a processed starch obtained by a chemical modification in a food additive. Therefore, it is possible to prepare a food without the addition of a food additive if the enzyme-treated starch granules of the present invention prepared by using a starch hydrolase or a glycosyltransferase are used.

In the case where an untreated starch granules are used as a raw material and an enzyme-treated starch granules are produced under the condition where neither a chemical treatment nor a physical treatment is applied in any stage of the production process, since the enzyme-treated starch granules used in the present invention have a higher gel forming ability than that of the untreated starch granules and are free from a forcible bond, the starch can sufficiently undergo gelatinization even at usual heating temperature and can exhibit viscosity. Furthermore, the obtained starch paste has less spinnability regardless of being sufficiently gelatinized. The gel obtained by using a high concentration of the starch granules of the present invention is very rich in elasticity. That is, in the case where the starch granules of the present invention are added to a high moisture content type food, a body can be imparted and also natural elasticity can be imparted by a strong gel forming ability. On the other hand, in the case where the starch granules of the present invention are added to a low moisture content type food, texture with nice melt in mouth can be imparted to a food. Furthermore, there is less restriction even in the operation step due from the viewpoint of gelatinization characteristics of them.

Even in the case where a processed starch or a physically treated starch is used as a raw material or a food is produced under the condition where a chemical modification or a physical treatment is applied in any stage of the production process of a food, a food of the present invention has a harder gel and has different texture as compared with the case where a food is produced using a corresponding starch produced without being subjected to an enzymatic treatment. Therefore, according to the present invention, it is possible to provide a food having texture which is different from that of the prior art.

The enzyme-treatment as used in the present invention does not adversely affect a chemical modification used in a conventional starch treatment. Therefore, the chemical modification (such as, gel hardening action, gel transparency improvement, gel softening action, retrogradation resistance or the like) can be introduced into enzyme-treated starch granules and desired effects of the chemical starch treatment can be achieved.

A starch granule is a starch molecule in a crystalline state. The present invention is not restricted by a particular theory. However, from a recent finding, it is considered that crystalline state and binding state of starch of a center part of a natural starch granule is different from those of starch in the surface part of the natural starch granule. It is considered that the starch at the surface part of the natural starch granule is in a condition where the crystallinity is low, and it is relatively easy to dissolve the starch in water and the starch is likely to be easily subjected to chemically modification and enzyme-treatment. It is considered that the starch at the center part of the natural starch granule forms tight crystalline structure.

When a starch granule is treated with an enzyme, starch at the surface part of the starch granule is enzyme-treated to obtain an enzyme-treated starch granule wherein the starch at the surface part has been removed. The obtained enzyme-treated starch granule is a starch granule which mainly consists of starch keeping tight crystalline state (see FIG. 1A). That is the structure of the enzyme-treated starch granule is different from the structure of the starch granule before the enzyme treatment. Therefore, the physical properties of the enzyme-treated starch granule are different from those of the starch granule before the enzyme treatment. The enzyme-treated starch granule exerts high gel forming ability, a feeling of elasticity, crispness and strippness.

The effect of the enzyme treatment becomes further remarkable when an enzyme-treated starch granule is chemically treated. When a starch granule is chemically modified while maintaining the surface part of the starch granule, a chemically modified starch granule in which many chemical modification groups have been introduced in the surface part is obtained. However, when chemical modification is carried out after removing starch of the surface part by an enzyme treatment, a chemically modified starch granule in which the tight crystalline state is maintained and chemical modification groups have been introduced into the starch (see FIG. 1B). That is, the structure of the enzyme-treated-chemically modified starch granule is different from the structure of the conventional chemically modified starch granule. Therefore, the physical properties of the enzyme-treated-chemically modified starch granule are different from the physical properties of the conventional, chemically modified starch granule. For example, when a starch granule whose surface part is not enzymatically treated is chemically modified, a chemically modified starch granule having a relatively small specific gravity is obtained. However, when a chemical modification is carried out after the removal of starch at the surface part, a chemically modified starch granule having a relatively large specific gravity is obtained.

Therefore, if the order of a chemical modification and an enzyme treatment is different, the physical properties (for example, specific gravity) of the obtained modified starch granule are quite different. A chemical modification after the removal of starch at the surface part by enzyme treatment results in an enzyme-treated-chemically modified starch granule having a relatively large specific gravity. Since this enzyme-treated-chemically modified starch granule has a large specific gravity, it can be separated from a reagent for chemical modification (i.e., reagents which are added for chemical modification and still reside in the reaction solution after the chemical modification reaction) easily and is precipitated from an aqueous solution easily.

In the production of the enzyme-treated-chemically modified starch granules of the present invention, it important that a filtration step is carried out after the enzyme treatment and further a filtration step is carried out after the chemical modification. However, the filtration step after the enzyme treatment can be omitted depending on the situation. Furthermore, the filtration step after the chemical modification can be omitted depending on the situation. Furthermore, both of the filtration step after the enzyme treatment and the filtration step after the chemical modification can be omitted depending on the situation.

It should be noted that a filtration (the first filtration) after the enzyme treatment and before the chemical modification can prevent a reaction of starch chains that were cut out by the enzyme treatment and a chemical modification reagent. Thus it is possible to efficiently allow the chemical modification reagent to react with the enzyme-treated starch granules. For example, when the chemical modification is etherification of a high substitution degree, the gelatinization temperature of the resultant chemically modified starch is low. Thus, when the first filtration is not performed, there is a problem that the reaction solution will be gelatinized excessively during the chemical modification reaction. However, when a filtration is carried out before the chemical modification, there would not be such a problem.

MODE FOR CARRYING OUT THE INVENTION

Figure 1A:
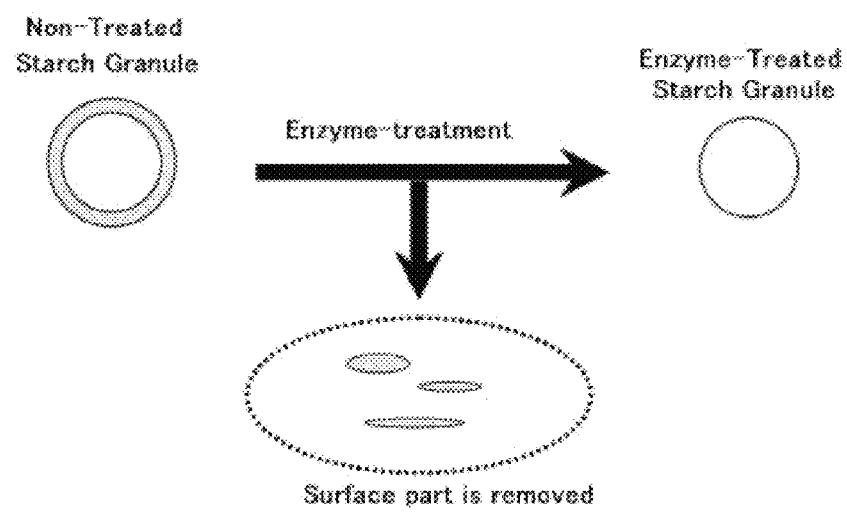
FIG. 1A schematically shows the difference of the structures of a starch granule before an enzyme treatment and an enzyme-treated starch granule. The structure of the enzyme-treated starch granule is different from the structure of the starch granule before the enzyme treatment. Therefore, the enzyme treatment changes the structure of a starch granule, and thus results in the change of the physical properties.
Figure 1B:
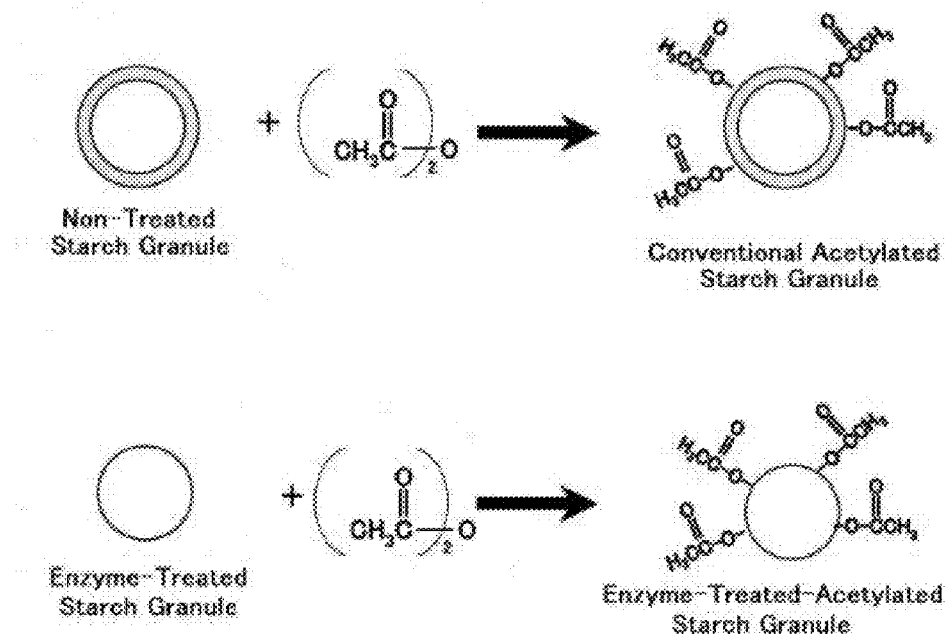
FIG. 1B schematically shows the structures of an acetylated starch granule which has not been enzyme-treated, and an acetylated starch granule that was obtained by acetylating the enzyme-treated starch granule. The structure of the enzyme-treated-acetylated starch granule is different from the structure of the acetylated starch which has not been enzyme-treated. Accordingly, the enzyme treatment changes the structure of a chemically modified starch granule, and thus results in the changes of the physical properties.

Hereinafter, the present invention will be described in detail.

1. Materials 1.1 Starch Granules

In the present description, the term "starch granules" refers to starch molecules in a crystalline state. The starch granules may be untreated starch granules, or may be starch granules obtained by a chemical modification or a physical treatment of untreated starch granules. In the case where an enzyme-treated starch classified as a food is preferably used, starch granules to be used are untreated starch granules obtained from plants. Plants store starch molecules as granules (i.e., as a large crystal) in amyloplasts. The granules are called starch granules. In the starch granules, starch molecules are mutually bonded through a hydrogen bond or the like. Therefore, starch granules are not easily dissolved in water as they are, and are not also easily digested. When the starch granules are heated together with water, they are swollen and molecules are disentangled to form a colloid. This change is called "gelatinization". The size and shape of the starch granules vary depending on plants from which the starch granules are obtained. For example, an average granule size of corn starch granules (corn starch) is from about 12 μm to about 15 μm and is slightly smaller, and the size is relatively uniform, than that of other starch granules. Starch granules of wheat and barley are classified into two kinds in size: large-sized starch granules having a granule size of about 20 μm to about 40 μm, and small-sized starch granules having a granule size of several μm. Rice has a compound starch granule structure in which many small angular starch granules having a diameter of several μm are accumulated in amyloplast. The average granule size of potato starch granules is about 40 μm and is the largest among those which are commonly used as a starch raw material. In the present invention, commercially available various starch granules can be used. Starch granules may be prepared by the method of, for example, purifying starch granules from plants and used in the present invention.

In a state of starch granules, the enzyme hardly acts on starch granules since starch molecules are strongly bonded to each other. In a specific embodiment for obtaining an enzyme-treated starch granules to be treated as a food, the starch granules used in the present invention are isolated or purified from plants, but are not subjected to an acid treatment, a chemical modification treatment and a heat treatment. In the present description, the term "untreated" starch granules refer to starch granules which are naturally produced and are not subjected to a treatment other than treatments required to separate starch granules from other components (for example, protein and lipid) coexisting in a natural state. Accordingly, the respective steps in the method of preparing starch granules, such as the step of removing impurities from plants or the like to purify a starch is not encompassed in a treatment of starch granules in the present description. It is possible to use, as starch granules, any starch granules as long as they are usually commercially available starch granules.

In another specific embodiment, the starch granules used for enzyme treatment in the present invention may be starch granules treated by subjecting untreated starch granules to a chemical modification or a physical treatment. Examples of the chemically modified starch granules that can be used for foods include an acetylated distarch adipate, an acetylated oxidized starch, an acetylated distarch phosphate, a starch sodium octenyl succinate, a starch acetate, an oxidized starch, a bleached starch, a hydroxypropyl distarch phosphate, a hydroxypropyl starch, a distarch phosphate, a monostarch phosphate, and a phosphated distarch phosphate. In the present specification, the term "distarch phosphate" and "phosphate-crosslinking starch" are interchangeably used. In the present specification, the term "hydroxypropyl distarch phosphate" and "hydroxypropylated phosphate-crosslinking starch" are interchangeably used. In the present specification, the term "hydroxypropyl starch" and "hydroxypropylated starch" are interchangeably used. In the present specification, the term "hydroxypropyl starch" and "hydroxypropylated starch" are interchangeably used. The "acetylated distarch adipate" refers to those obtained by esterifying a starch with acetic anhydride and adipic anhydride. The "acetylated oxidized starch" refers to those obtained by treating a starch with sodium hypochlorite and then esterifying it with acetic anhydride. The "acetylated distarch phosphate" refers to those obtained by esterifying a starch with sodium trimetaphosphate or phosphorus oxychloride and acetic anhydride or vinyl acetate. The "starch sodium octenyl succinate" refers to those obtained by esterifying a starch with octenyl succinic anhydride. The "starch acetate" refers to those obtained by esterifying a starch with acetic anhydride or vinyl acetate. The "oxidized starch" refers to those obtained by treating a starch with sodium hypochlorite, wherein the content of carboxyl groups is 1.1% or less when carboxyl groups (also referred to as carboxyl groups) in a sample starch are analyzed in accordance with the method for the purity test described in Ministry of Health and Welfare Notification No. 485. Provided that, even when the amount of a carboxyl group is within the above range, the "bleached starch" is not included in the definition of the "oxidized starch". The "bleached starch" refers to those obtained by treating a starch with sodium hypochlorite, wherein the content of carboxyl groups is 0.1% or less when carboxyl groups in a sample starch are analyzed in accordance with the method for the purity test described in Ministry of Health and Welfare Notification No. 485, and wherein the test results of "Confirmation test (3)" of the oxidized starch described in Ministry of Health and Welfare Notification No. 485 are negative and wherein it can be reasonably explained that a change in properties, such as viscosity, of the starch is not caused by oxidation. Those in which, even if the amount of carboxyl groups is 0.1% or less, properties such as viscosity of the starch change from those of the native starch are classified as the oxidized starch, and are not dealt as a food in Japan but dealt as food additives. The "hydroxypropyl distarch phosphate" refers to those obtained by esterifying a starch with sodium trimetaphosphate or phosphorus oxychloride and etherifying it with propylene oxide. The "hydroxypropyl starch" refers to those obtained by etherifying a starch with propylene oxide. The "distarch phosphate" refers to those obtained by esterifying a starch with sodium trimetaphosphate or phosphorus oxychloride. The "monostarch phosphate" refers to those obtained by esterifying a starch with orthophosphoric acid, a potassium salt or a sodium salt thereof, or sodium tripolyphosphate. The "phosphated distarch phosphate" refers to those obtained by esterifying a starch with orthophosphoric acid, a potassium salt or a sodium salt thereof, or sodium tripolyphosphate, and esterifying it with sodium trimetaphosphate or phosphorus oxychloride. These chemical treatments can be conducted without breaking down the shape of starch granules if it is conducted at appropriate temperature.

Furthermore, examples of industrially usable chemically modified starch granules include aforementioned chemically modified starch granules, without modification ratio limitation; acylated esterification starch granules such as propionic acid ester starch granules; hydroxyethylated starch granules; carboxymethylated starch granules; etherification starch granules treated with alkyl halide or dialkyl sulfate in the presence of an alkaline; grafted starch granules wherein a vinyl monomer such as acrylic acid or methacrylic acid is added in the presence of an iron ion or a cerium ion, or carboxylic acid having a hydroxyl group such as lactic acid is added in a branched form by polycondensation; cationized starch granule; and the like.

Examples of the types of the physically treated starch granules include a heat-moisture-treated starch and a thermally inhibited starch.

The starch granules used for enzyme treatment in the present invention may be either a aboveground starch or a underground starch. Examples of the underground starch include a cassava starch, a potato starch, a sweet potato starch, and a kudzu starch. Examples of the aboveground starch include a wheat starch, a corn starch (for example, a high amylose corn starch, a usual corn starch, and a waxy corn starch), a rice starch (for example, a glutinous rice starch and a nonglutinous rice starch), a bean starch (for example, a green gram starch, a pea starch, an adzuki bean starch, and a fava bean starch), and an Amaranthus starch. The starch granules used in the present invention are preferably starches derived from cassava, corn, or wheat. In the case where the untreated starch is used as the starch granules, an untreated cassava starch, an untreated corn starch or an untreated wheat starch is preferably used. In the case where the chemically modified starch is used as the starch granules, it is preferred to use an acetylated distarch adipate, an acetylated oxidized starch, an acetylated distarch phosphate, a starch sodium octenyl succinate, a starch acetate, an oxidized starch, a bleached starch, a hydroxypropyl distarch phosphate, a hydroxypropyl starch, a distarch phosphate, a monostarch phosphate or a phosphated distarch phosphate of a cassava starch, a corn starch or a wheat starch. In the case where the physically treated starch is used, it is preferred to use a heat-moisture-treated starch or a thermally inhibited, starch of a cassava starch, a corn starch or a wheat starch.

Since the structure of the starch delicately varies depending on the origin, features of physical properties vary depending on the origin. For example, although the untreated wheat starch has a high gel forming ability, the starch paste thereof has a low viscosity and the starch paste is opaque. Although the untreated cassava starch has a low gel forming ability, the starch paste thereof has a high viscosity and the starch paste has high transparency and the degree of retrogradation is a middle degree. Particularly, although the untreated cassava starch is inexpensive, the starch paste thereof is transparent, and it therefore has a merit of being easily added, the application thereof is limited because of their low gel forming ability. Furthermore, the untreated native wheat starch could not be used in the application where viscosity is required because of a low viscosity of the starch paste. Although the untreated corn starch has a high gel forming ability, the starch paste thereof has slightly low viscosity, and the starch paste is opaque and has high retrogradation property.

The chemical modification alters physical properties of the untreated starch granules. Commonly, crosslinking such as phosphate-crosslinking or adipate-crosslinking often makes the gel formed by using the obtained starch granules harder and higher turbidity than the gel formed by using the untreated starch granules. Generally, hydroxypropylation, acetylation and oxidation treatments often improve transparency of and make softer the gel formed by using the obtained starch granules as compared with the gel formed by using the untreated starch granules. Commonly, the treatment with octenyl succinic acid can make it possible for the gel formed using the obtained starch granules to contain oil.

The physical treatment also alters physical properties of the untreated starch granules. For example, commonly, the heat-moisture treatment often makes the gel formed by using the obtained starch granule harder and the viscosity of the starch paste lower than those of the gel formed by using the untreated starch granules. For example, commonly, the thermal inhibition treatment often makes the gel formed by using the obtained starch granules harder than the gel formed by using the untreated starch granules. Also, when the time of the dry heat treatment is long, the obtained starch often exhibits low viscosity of the starch paste like a highly crosslinked starch.

It is preferred that the starch granules used for enzyme treatment in the present invention contain impurities as low as possible. The content of impurities in the starch granules is preferably about 10% by weight or less, more preferably about 5% by weight or less, and still more preferably about 1% by weight or less.

1.2 Enzyme

The enzyme usable in the present invention is a starch hydrolase or a glycosyltransferase. The starch hydrolase is roughly classified into α-amylase, β-amylase, amyloglucosidase, isoamylase, pullulanase, and α-glucosidase. However, even in the enzymes classified as the same enzyme (for example, α-amylase), if the microorganisms producing the enzyme are different, it is considered that features such as reaction specificity and substrate specificity of the enzymes are different. Since these starch hydrolases and glycosyltransferase are very widely distributed in animals, microorganisms and plants, it can be said that there are infinite kinds of starch hydrolases and glycosyltransferases.

The starch hydrolase usable in the production of the starch granules of the present invention is a starch hydrolase selected from the group consisting of amyloglucosidase, isoamylase, α-glucosidase, and α-amylase having characteristics capable of improving a gel forming ability of a starch. In the present description, the "α-amylase having characteristics capable of improving a gel forming ability of a starch" is α-amylase wherein the Young's modulus or rupture stress of the starch granules after the treatment with the enzyme is 10% or more higher than the Young's modulus or rupture stress of the starch granules before the treatment with the enzyme, when measured by the judgment method described below. The starch hydrolase used in the present invention is preferably an enzyme classified as α-amylase, amyloglucosidase, isoamylase, or α-glucosidase. The enzyme classified as β-amylase or pullulanase is not preferable. It is considered that the enzyme classified as amyloglucosidase, isoamylase or α-glucosidase can produce enzyme-treated starch granules having a high viscosity and a gel forming ability if these enzymes are allowed to act on starch granules. However, in the case of the enzyme classified as α-amylase, not all enzymes can be suitably utilized and α-amylase having characteristics capable of improving a gel forming ability of a starch needs to be selected, and the starch granules of the present invention cannot be produced even if an α-amylase not having this activity is used.

It is possible to judge whether or not the enzyme classified as α-amylase is α-amylase having characteristics capable of improving a gel forming ability of a starch, by the following judgment method.

Examples of the glycosyltransferase usable in the production of the starch granules of the present invention include cyclodextrin glucanotransferase.

1.2.1 Method of Judging α-Amylase Having Characteristics Capable of Improving Gel Forming Ability of Starch The α-amylase having characteristics capable of improving a gel forming ability of a starch can be judged by the following method. To 400 g of a wheat starch, 900 g of ion-exchange water is added thereby suspending the wheat starch, and each enzyme is added thereto. The amount of a reducing sugar released in the suspension by the reaction is measured to determine a degradation ratio. When the degradation ratio reaches 15%, starch granules are obtained by filtration, washed with water and then dried. Using the enzyme-treated starch granules thus obtained, a Young's modulus and a rupture stress are determined by rheometer analysis. In the case where the Young's modulus or rupture stress of the starch granules after treatment with the enzyme increases by 10% or more as compared with the Young's modulus or rupture stress of the starch granules before treatment with the enzyme, the enzyme is judged as α-amylase having characteristics capable of improving a gel forming ability of the starch. As an example, the judgment results of various starch hydrolases are shown in Table 1A below.

TABLE 1A

| Name of enzyme group | Origin | Product name (Selling agency) | Rupture stress Measured value (g) | Rupture stress Relative %*1 | Young's modulus Measured value (dyn/cm²) | Young's modulus Relative %*2 | Judgment |
|---|---|---|---|---|---|---|---|
| Before treatment with enzyme | — | — | 141 | 100 | 4,601,665 | 100 | Reference |
| α-amylase | *Aspergillus oryzae* | Biozyme A (Amano Enzyme) | 197 | 140 | 5,518,329 | 120 | Usable |
| α-amylase | *Aspergillus niger* | AMYLEX A3 (DANISCO) | 211 | 150 | 5,465,779 | 119 | Usable |
| α-amylase | *Bacillus subtilis* | Novamyl (Novo) | Not measurable since gel is not formed because of being too soft | | | | Not usable |
| α-amylase | *Bacillus amyloliquefaciens* | α-amylase (Reagent) (Sigma) | Not measurable since gel is not formed because of being too soft | | | | Not usable |
| α-amylase | *Bacillus* sp. | Maltogenase L (Novo) | 25 | 18 | 834,422 | 18 | Not usable |
| α-amylase | *Bacillus licheniformis* | Termamyl 120L (Novo) | 37 | 26 | 1,493,271 | 32 | Not usable |

*[1]Relative rupture stress = {(rupture stress for after treatment with enzyme)/(rupture stress for before treatment with enzyme)} × 100
*[2]Relative Young's modulus = {(Young's modulus for after treatment with enzyme)/(Young's modulus for before treatment with enzyme)} × 100

As described above, it is possible to easily decide whether or not various α-amylases have characteristics capable of improving a gel forming ability of a starch. It is noted that a specific method of rheometer analysis is as described in 1.2.2 below.

1.2.2 Specific Method of Rheometer Analysis

A starch paste is prepared so that the concentration of the starch is 20% by weight on the dry matter basis, and then filled in a Krehalon casing having a folding width of 45 mm. This starch paste filled in the casing is heated to 90° C. at 1° C./min and maintained at 90° C. for 30 minutes. Then the starch paste is left to cool in a constant-temperature water bath at 20° C. for 30 minutes and then cooled to 5° C. an a refrigerator. After cooling, it is refrigeration stored at 5° C. for 16 hours, then it is left at room temperature (about 25° C.) for 4 hours to return the temperature of it to room temperature, and then measurements by a rheometer (RT-2010J-CW) manufactured by Rheotech Inc. is performed. The measurement is carried out under the measurement conditions of the rheometer: a test item: a rupture test; a height of a sample: 25 mm; and a movement rate (rupture rate) of a sample: 6 cm/min, using an adapter of a spherical jig for measurement viscosity φ5 (diameter: 5 mm, area: 19.635 mm²). At the measurement, the hardness of the starch gel is evaluated by a rupture stress (g) and a Young's modulus (dyn/cm²).

1.2.3: Preferred Example Used in Present Application

In order to produce the starch granules of the invention, an enzyme selected from the group consisting of amyloglucosidase, isoamylase, α-glucosidase, α-amylase having characteristics capable of improving a gel forming ability of a starch, and cyclodextrin glucanotransferase is used.

In a specific embodiment, the enzyme is selected from the group consisting of amyloglucosidase, isoamylase, α-glucosidase, α-amylase derived from the genus *Aspergillus*, and cyclodextrin glucanotransferase.

In a specific embodiment the enzyme is selected from the group consisting of amyloglucosidase, isoamylase, α-glucosidase, α-amylase derived from *Aspergillus oryzae*, α-amylase derived from *Aspergillus niger*, and cyclodextrin glucanotransferase.

In a preferred embodiment, the enzyme is selected from the group consisting of amyloglucosidase derived from *Aspergillus niger* commercially available from Novozyme as AMG, amyloglucosidase derived from *Aspergillus niger* commercially available from Genencor as OPTIDEX L-400, amyloglucosidase derived from *Aspergillus niger* commercially available from DANISCO as DIAZYME X4NP, amyloglucosidase derived from *Aspergillus niger* commercially available from Amano Enzyme as glucoamylase "Amano" SD, amyloglucosidase derived from *Rhizopus niveus* commercially available from Amano Enzyme as Gluczyme AF6, amyloglucosidase derived from *Rhizopus oryzae* commercially available from SHIN NIHON CHEMICALS Corporation as Sumizyme, α-glucosidase derived from *Aspergillus niger* commercially available from Amano Enzyme as transglucosidase L "Amano", α-glucosidase derived from *Aspergillus niger* commercially available from Genencor as Transglucosidase L-500, α-amylase derived from *Aspergillus oryzae* commercially available from Amano Enzyme as Biozyme A, α-amylase derived from *Aspergillus oryzae* commercially available from SHIN NIHON CHEMICALS Corporation as Sumizyme L, α-amylase derived from *Aspergillus niger* commercially available from Danisco as AMYLEX A3, α-amylase derived from *Aspergillus niger* commercially available from SHIN NIHON CHEMICALS Corporation as Sumizyme AS, isoamylase derived from *Pseudomonas amyloderamosa* commercially available from Sigma as isoamylase, cyclodextrin glucanotransferase derived from *Bacillus licheniformis* commercially available from Novozyme as Toruzyme, and cyclodextrin (glucanotransferase derived from *Paenibacillus macerans* (*Bacillus macerans*) commercially available from Amano Enzyme as Cyclodextrin glucanotransferase "Amano".

In a specific preferred embodiment, the enzyme is a starch hydrolase, and the starch hydrolase is encoded by a nucleic acid molecule which is capable of hybridizing under stringent conditions with a nucleic acid molecule having a complementary sequence to the base sequence of SEQ ID NO: 1, 3, 5, 7, 9 or 11 and has a starch hydrolysis activity; wherein the stringent conditions are hybridization in a solution containing 50% formamide, 0.5×SSC (750 mM NaCl, 75 mM trisodium citrate), 0.50 mM sodium phosphate (pH 7.6), 5×Denhardt's solution (0.2% BSA, 0.2% Ficoll 400 and 0.2% polyvinylpyrrolidone), 10% dextran sulfate and 20 µg/ml denatured sheared salmon sperm DNA at 65° C., and subsequent washing under the condition of 65° C. using an SSC solution having a 0.1 to 2-fold concentration (a composition of an SSC solution having a 1-fold concentration is 150 mM sodium chloride and 15 mM sodium citrate).

In a preferred embodiment, the starch hydrolase has an amino acid sequence having at least 95% or more of homology with an amino acid sequence of SEQ ID NO: 2, 4, 6, 8, 10 or 12, and has a starch hydrolysis activity

1.2.4. α-amylase

α-Amylases exist in many microorganisms, animals and plants. Examples of microorganisms which produce an α-amylase include those of genus *Aspergillus* (for example, *Aspergillus oryzae, Aspergillus niger, Aspergillus awamori, Aspergillus flavus, Aspergillus kawachii, Aspergillus sclerotiorum* and the like); those of genus *Bacillus* (for example, *Bacillus subtilis, Bacillus acidocaldarius, Bacillus amyloliquefaciens, Bacillus stearothermophilus, Bacillus cereus, Bacillus licheniformis* and the like); those of genus *Geobacillus* (for example, *Geobacillus stearothermophilus, Geobacillus thermodenitrificans, Geobacillus thermodenitrificans* and the like); those of genus *Lactobacillus* (for example, *Lactobacillus amylovorus, Lactobacillus cellobiosus, Lactobacillus manihotivorans* and the like); further more, *Pseudomonas* sp., *Pyrococcus furiosus, Rhizopus microsporus, Thermotoga maritima, Vibrio* sp. and the like. Furthermore, it is confirmed that the α-amylase derived from animals exist in human pancreas, human saliva, human urine, porcine pancreas, bovine pancreas, carp intestinal tract and the like, and that the α-amylase derived from plants exist in barley, rice, wheat, oat, rye, soybean, and fava bean. The organisms that produce an α-amylase are not limited to them.

α-Amylase may be commercially available one or may be prepared from these organisms by a method known in the art, or may be prepared by a genetic recombination method based on an amino acid sequence or a base sequence of α-amylase of these organisms, or may be chemically synthesized. Any α-amylase known in the art can be used as long as it has properties of cleaving an α-1,4-glucoside bond in the end type.

An α-amylase used in the present invention is preferably an α-amylase from genus *Aspergillus*, and most preferably an α-amylase derived from *Aspergillus oryzae* or *Aspergillus niger*.

A nucleotide sequence encoding typical α-amylase derived from *Aspergillus oryzae* is shown in SEQ ID NO: 1, and its amino acid sequence is shown in SEQ ID NO: 2. A nucleotide sequence encoding typical α-amylase derived from *Aspergillus niger* is shown in SEQ ID NO: 3, and its amino acid sequence is shown in SEQ ID NO: 4. It is considered that α-amylases of closely related species have a very high homology and exhibit the similar enzyme activities. Therefore, it is considered that α-amylases derived from *Aspergillus oryzae* have amino acid sequences having a very high homology to SEQ ID NO: 2 and exhibit the similar enzyme activities. Since it is shown that a commercially available α-amylase derived from *Aspergillus oryzae* has characteristics capable of improving a gel forming ability of a starch, it is considered that α-amylase having an amino acid sequence of SEQ ID NO: 2 and α-amylase having an amino acid sequence which has a high homology thereto also have characteristics capable of improving a gel forming ability of a starch. Similarly, since it is shown that a commercially available α-amylase derived from *Aspergillus niger* has characteristics capable of improving a gel forming ability of a starch, it is considered that α-amylase having an amino acid sequence of SEQ ID NO: 2 and α-amylase having an amino acid sequence which have a high homology thereto also have characteristics capable of improving a gel forming ability of a starch.

The α-amylase used in the present invention is not an amylase derived from *Bacillus amyloliquefaciens*. The reason is that the amylase derived from *Bacillus amyloliquefaciens* cannot produce a starch having a high viscosity and a gel forming ability.

A lot of α-amylase is commercially available. Examples of the commercially available α-amylase are described below: Biozyme F1OSD (origin: *Aspergillus oryzae*; Amano Enzyme Inc.), Biozyme A (origin: *Aspergillus oryzae*; Amano Enzyme Inc.), Kokulase (origin: *Aspergillus oryzae*; Mitsubishi-Kagaku Foods Corporation), Sumizyme L (origin: *Aspergillus oryzae*; SHIN NIHON CHEMICALS Corporation), AMYLEX A3 (origin: *Aspergillus niger*; Danisco Japan Ltd.), GRINDAMYLA (origin: *Aspergillus oryzae*; Danisco Japan Ltd.), VERON AX (origin: *Aspergillus oryzae*; HIGUCHI INC.), VERON GX (origin: *Aspergillus oryzae*; HIGUCHI INC.), VERON M4 (origin: *Aspergillus oryzae*; HIGUCHI INC.), VERON ELS (origin: *Aspergillus oryzae*; HIGUCHI INC.), Sumizyme AS (origin: *Aspergillus niger*; SHIN NIHON CHEMICALS Corporation), Bakezyme P500 (origin: *Aspergillus oryzae*; Nihon Siber Hegner K. K.), and α-Amylase (origin: *Aspergillus oryzae*; Sigma-Aldrich Corporation).

Such commercially available α-amylase is subjected to amino acid analysis to determine the amino acid sequence thereof, and a DNA sequence is designed based on the amino acid sequence, and then the DNA sequence is introduced into *E. coli* or the like, and thus α-amylase having the same amino acid sequence as that of the commercially available α-amylase can be produced.

1.2.5 Amyloglucosidase

Amyloglucosidase refers to an enzyme capable of producing β-D-glucose by hydrolyzing a 1,4-α bond at a non-reducing terminal of a carbohydrate chain of a starch or the like. The amyloglucosidase hydrolyzes an α-1,4-glucoside chain from a non-reducing terminal, and also an α-1, 6-glucoside chain, although the degradation rate is low. A systematic name of the amyloglucosidase is glucan 1,4-α-glucosidase. Another name of the amyloglucosidase is exo-1,4-α-D-glucosidase, 1,4-α-D-glucan glucohydrolase, glucoamylase, γ-amylase, lysosomal α-glucosidase, or acidic maltase. The amyloglucosidase is classified as EC 3.2.1.3.

Amyloglucosidases exist in many microorganisms, animals and plants. Examples of microorganisms which produce an amyloglucosidase include those of genus *Aspergillus* (for example, *Aspergillus niger, Aspergillus oryzae, Aspergillus candidus, Aspergillus terreus, Aspergillus awamori, Aspergillus phoenicis, Aspergillus saitoi* and the like); those of genus *Candida* (for example, *Candida antarctica, Candida tsukubaensis* and the like); those of genus *Rhizopus* (for example, *Rhizopus delemar, Rhizopus delmar, Rhizopus javanicus, Rhizopus niveus, Rhizopus niveus, Rhizopus oligosporus, Rhizopus oryzae* and the like); those of genus *Saccharomyces* (for example, *Saccharomyces cerevisiae, Saccharomyces diastaticus, Saccharomyces dia-*

*staticus, Saccharomyces fibuligera*); further more, *Clostridium thermoamylolyticum, Cladosporium resinae, Lentinus edodes, Mucor rouxianus, Magnaporthe grisea, Monascus kaoliang, Paecilomyces varioti, Penicillium oxalicum, Thermomyces lanuginosus, Trichoderma reesei* and the like. Furthermore, it is confirmed that an amyloglucosidase derived from animals exists in mucosa membrane of small intestine of human, rat and mice, and that an amyloglucosidase derived from plants exists in beet and the like. The organisms that produce an amyloglucosidase are not limited to them.

Amyloglucosidase may be commercially available one or may be prepared from these organisms by a method known in the art, or may be prepared by a genetic recombination method based on an amino acid sequence or a base sequence of amyloglucosidase of these organisms, or may be chemically synthesized. Any amyloglucosidase known in the art can be used as long as it has properties of cleaving an α-1,4-glucoside bond and an α-1,6-glucoside bond in an exo type from a non-reducing terminal side in a glucose unit to produce β-glucose.

An amyloglucosidase used in the present invention is preferably an amyloglucosidase from genus *Aspergillus* or an amyloglucosidase from genus *Rizopus*, and most preferably an amyloglucosidase derived from *Aspergillus niger* or an amyloglucosidase derived from *Rizopus niveus*.

A nucleotide sequence encoding typical amyloglucosidase derived from *Aspergillus niger* is shown in SEQ ID NO: 5, and its amino acid sequence is shown in SEQ ID NO: 6. It is considered that amyloglucosidase of closely related species have a very high homology and exhibit the similar enzyme activities. Therefore, it is considered that amyloglucosidase derived from *Aspergillus niger* have amino acid sequences having a very high homology to SEQ ID NO: 6 and exhibit the similar enzyme activities. Since it is shown that a commercially available amyloglucosidase derived from *Aspergillus niger* has starch hydrolysis activity, it is considered that amyloglucosidase having an amino acid sequence of SEQ ID NO: 6 and amyloglucosidase having an amino acid sequence which has a high homology thereto also have starch hydrolysis activity.

The amyloglucosidase used in the present invention is not an amyloglucosidase derived from *Candida tsukubaensis*. The reason is that the amyloglucosidase derived from *Candida tsukubaensis* cannot produce a starch having a high viscosity and a gel forming ability.

A lot of amyloglucosidase is commercially available. Examples of the commercially available amyloglucosidase are described below: GlucS G (origin: *Rhizopus niveus*; Amano Enzyme Inc.), Gluczyme AF6 (origin: *Rhizopus niveus*; Amano Enzyme Inc.), Gluczyme NL4.2 (origin: *Aspergillus niger*; Amano Enzyme Inc.), Brewing glucoamylase "Amano" SD (origin: *Aspergillus niger*; Amano Enzyme Inc.), GODO-ANGH (origin: *Aspergillus niger*; GODO SHUSEI CO., LTD.), OPTIDEX L-400 (origin: *Aspergillus niger*; Genencor Kyowa), OPTIDEX L (origin: *Aspergillus niger*; Genencor Kyowa), Sumizyme (origin: *Rhizopus oryzae*; SHIN NIHON CHEMICALS Corporation), Sumizyme SG (origin: *Rhizopus sp.*; SHIN NIHON CHEMICALS Corporation), Sumizyme HG (origin: *Rhizopus oryzae*; SHIN NIHON CHEMICALS Corporation), GLUCOZYME #20000 (origin: *Rhizopus sp.*; Nagase Chemtex Corporation), AMG (origin: *Aspergillus niger*; Novozymes Japan Ltd.), GLUTASE AN (origin: *Aspergillus niger*; HBI Enzymes Ltd.), UNIASE K, 2K (origin: *Rhizopus sp.*; YAKULT PHARMACEUTICAL INDUSTRY CO., LTD.), UNIASE 30 (origin: *Rhizopus sp.*; YAKULT PHARMACEUTICAL INDUSTRY CO., LTD.), UNIASE 60F (origin *Rhizopus sp.*; YAKULT PHARMACEUTICAL INDUSTRY CO., LTD.), MAGNUX JW-201 (origin: *Rhizopus sp.*; Rakuto Kasei Industrial CO., Ltd.), GRINDAMYL AG (origin *Aspergillus sp.*; Danisco Japan Ltd.), DIAZYME X4NP (origin; *Aspergillus niger*; Danisco Japan Ltd.), Bakezyme AG800 (origin *Aspergillus niger*; Nihon Siber Hegner K. K.), Amyloglucosidase (origin: *Aspergillus niger*; Sigma-Aldrich Corporation), Amyloglucosidase (origin: *Rhizopus sp.*; Sigma-Aldrich Corporation), and Glucoamylase (origin: *Rhizopus sp.*; Toyobo Co., Ltd.).

Such commercially available amyloglucosidase is subjected to amino acid analysis to determine the amino acid sequence thereof, and a DNA sequence is designed based on the amino acid sequence, and then the DNA sequence is introduced into *E. coli* or the like, and thus amyloglucosidase having the same amino acid sequence as that of the commercially available amyloglucosidase can be produced.

1.2.6 Isoamylase

Isoamylase refers to an enzyme which cleaves an α-1,6-glucoside bond of at a branched point of amylopectin, glycogen, or the like to produce amylose-like linear polysaccharides. Another name of the isoamylase is glycogen 6-glucanohydrolase. The isoamylase is classified as EC3.2.1.68. The isoamylase can be derived from any organism capable of producing isoamylase.

Isoamylases exist in many microorganisms, animals and plants. Examples of microorganisms which produce an isoamylase include *Flavobacterium* sp.; *Bacillus* sp.; furthermore, *Pseudomonas amyloderamosa, Sulfolobus solfataricus* and the like. Furthermore, it is confirmed that an isoamylase derived from animals exists in human pancreas and the like, and that an isoamylase derived from plants exists in *Oryza sativa*, potato (*Solanum tuberosum*) tuber, *Arahidopsis thaliana* and the like. The organisms that produce an isoamylase are not limited to them.

Isoamylase may be commercially available or may be prepared from these organisms by a method known in the art, or may be prepared by a genetic recombination method based on an amino acid sequence or a base sequence of isoamylase of these organisms, or may be chemically synthesized. Any isoamylase known in the art can be used as long as it has properties of cleaving an α-1,6-glucoside bond of amylopectin in the end type.

An isoamylase used in the present invention is preferably an isoamylase from genus *Flavobacterium* or genus *Pseudomonas*, and more preferably an isoamylase derived from *Flavobacterium* sp. or an isoamylase derived from *Pseudomonas amyloderamosa*.

A nucleotide sequence encoding typical isoamylase derived from *Flavobacterium* sp. is shown in SEQ ID NO: 7, and its amino acid sequence is shown in SEQ ID NO: 8. A nucleotide sequence encoding typical isoamylase derived from *Pseudomonas amyloderamosa* is shown in SEQ ID NO: 9, and its amino acid sequence is shown in SEQ ID NO: 10. It is considered that isoamylase of closely related species have a very high homology and exhibit the similar enzyme activities. Therefore, it is considered that isoamylase derived from *Flavobacterium* sp. have amino acid sequences having a very high homology to SEQ ID NO: 8 and exhibit the similar enzyme activities. Since it is shown that a commercially available isoamylase derived from *Flavobacterium* sp. has starch hydrolysis activity, it is considered that isoamylase having an amino acid sequence of SEQ ID NO: 8 and isoamylase having an amino acid sequence which has a high homology thereto also have starch hydrolysis activity. Similarly, since it is shown that a commercially available isoamylase derived from *Pseudomonas amyloderamosa* has starch hydrolysis activity, it is considered that isoamylase having an amino acid sequence of SEQ ID NO: 10 and isoamylase having an amino acid sequence which has a high homology thereto also have starch hydrolysis activity.

A lot of isoamylase is commercially available. Examples of the commercially available isoamylase are described below: GODO-FIA (origin: *Flavobacterium odoratum*; GODO SHUSEI CO., LTD.), and Isoamylase (origin: *Pseudomonas* sp.; Sigma-Aldrich Corporation).

Such commercially available isoamylase is subjected to amino acid analysis to determine an amino acid sequence thereof, and a DNA sequence is designed based on the amino acid sequence, and then the DNA sequence is introduced into *E. coli* or the like, and thus isoamylase having the same amino acid sequence as that of the commercially available isoamylase can be produced.

1.2.7 α-glucosidase

α-Glucosidase refers to an enzyme which hydrolyzes an α-1,4-glucoside bond at a non-reducing terminal to produce α-glucose. Systematic name of the α-glucosidase is α-D-glucoside glucohydrolase. Another name of the α-glucosidase is maltase, glucoinvertase, or glucoside sucrase. The α-D-glucosidase is classified as EC 3.2.1.20.

α-Glucosidases exist in many microorganisms, animals and plants. Examples of microorganisms which produce an α-glucosidase include those of genus *Aspergillus* (for example, *Aspergillus oryzae, Aspergillus niger, Aspergillus awamori, Aspergillus fumigatus, Aspergillus nidulans* and the like); those of genus *Bacillus* (for example, *Bacillus amyloliquefaciens, Bacillus amyiolyticus, Bacillus caldovelox, Bacillus cereus, Bacillus licheniformis, Bacillus thermoglucosidius, Bacillus* sp., *Bacillus subtilis, Bacillus brevis, Bacillus stearothermophilus*; those of genus *Lactobacillus* (*Lactobacillus acidophilus, Lactobacillus brevis* and the like); those of genus *Penicillium* (*Penicillium brevicompactum, Penicillium citrinum, Penicillium oxalicum, Penicillium purpurogenum*); those of genus *Pyroccus* (*Pyrococcus furiosus, Pyrococcus woesei* and the like), those of genus *Saccharomyces* (*Saccharomyces carlsbergensis, Saccharomyces cerevisiae, Saccharomyces fibuligera, Saccharomyces oviformis, Saccharomyces carlsbergensis, Saccharomyces logos* and the like); furthermore, *Candida tropicalis, Schizosaccharomyces pombe, Sulfolobus solfataricus, Thermotoga maritima, Escherichia coli* and the like. It is confirmed that the α-glucosidase derived from animals widely exist within a range from invertebrate animals such as mollusks, crustaceans, and insects to vertebrate animals such as fishes, amphibians, reptiles, birds, and mammalians, and the α-glucosidase derived from plants exist in beans, rice, buckwheat, corn, beet seeds and the like. It is noted that organisms capable of producing α-glucosidase are not limited to them.

α-Glucosidase may be commercially available one or may be prepared from these organisms by a method known in the art, or may be prepared by a genetic recombination method based on an amino acid sequence or a base sequence of α-glucosidase of these organisms, or may be chemically synthesized. Any α-glucosidase known in the art can be used as long as it has properties of cleaving an α-1,4-glucoside bond and an α-1,6-glucoside bond in an exo type from a non-reducing terminal side in a glucose unit to produce α-glucose.

An α-glucosidase used in the present invention is preferably an α-glucosidase from genus *Aspergillus*, and more preferably an α-glucosidase derived from *Aspergillus niger*.

A nucleotide sequence encoding typical α-glucosidase derived from *Aspergillus niger* is shown in SEQ ID NO: 11, and its amino acid sequence is shown in SEQ ID NO: 12. It is considered that α-glucosidase of closely related species have a very high homology and exhibit the similar enzyme activities. Therefore, it is considered that α-glucosidase derived from *Aspergillus niger* have amino acid sequences having a very high homology to SEQ ID NO: 12 and exhibit the similar enzyme activities. Since it is shown that a commercially available α-glucosidase derived from *Aspergillus niger* has starch hydrolysis activity, it is considered that α-glucosidase having an amino acid sequence of SEQ ID NO: 12 and α-glucosidase having an amino acid sequence which has a high homology thereto also have starch hydrolysis activity.

A lot of α-glucosidase is commercially available. Examples of the commercially available α-glucosidase are described below: Transglucosidase L 500 (origin: *Aspergillus*; Genencor Kyowa), Transglucosidase L "Amano" (origin: *Aspergillus niger*; Amano Enzyme Inc.), α-Glucosidase (origin: *Bacillus stearothermophilus*; Sigma-Aldrich Corporation), α-Glucosidase (origin: rice; Sigma-Aldrich Corporation), α-Glucosidase (origin: *Saccharomyces cerevisiae*; Sigma-Aldrich Corporation), α-Glucosidase (origin: *Aspergillus niger*; Sigma-Aldrich Corporation), and α-Glucosidase (origin: Microorganism; Toyobo Co., Ltd.).

Such commercially available α-glucosidase is subjected to amino acid analysis to determine the amino acid sequence thereof, and a DNA sequence is designed based on the amino acid sequence, and then the DNA sequence is introduced into *E. coli* or the like, and thus α-glucosidase having the same amino acid sequence as that of the commercially available α-glucosidase can be produced.

1.2.8 Cyclodextrin Glucanotransferase

Cyclodextrin glucanotransferase is also called CGTase and is classified as EC2.4.1.19. CGTase is an enzyme capable of catalyzing a transglycosylation reaction (i.e., disproportionation reaction) of maltooliaosaccharide. CGTase is an enzyme which performs a transfer reaction so as to recognize 6 to 8 glucose-chain at a non-reducing terminal of donor molecules thereby cyclizing this portion to produce cyclodextrin having a degree of polymerization of 6 to 8 and noncyclic limit dextrin. As an example of CGTase usable in the present invention, CGTase derived from well-known microorganisms or a commercially available CGTase can be used. CGTase is preferably selected from the group consisting of cyclodextrin glucanotransferase derived from *Bacillus licheniformis* commercially available from Novozyme as Toruzyme, and cyclodextrin glucanotransferase (optimum pH 6.0) derived from *Paenibacillus macerans* (also classified as *Bacillus macerans*) commercially available from Amano Enzyme as Cyclodextrin glucanotransferase "Amano".

CGTase may be commercially available or may be prepared from CGTase producing organisms by a method known in the art, or may be prepared by a genetic recombination method based on an amino acid sequence or a base sequence of CGTase of CGTase producing organisms, or may be chemically synthesized. Any CGTase known in the art can be used as long as it has a transglycosylation activity, and an activity capable of improving a gel forming ability of a starch.

1.2.9 Use of Enzymes in Combination

In the case of producing the starch granules of the present invention, multiple kinds of starch hydrolases or glycosyltransferases may be allowed to act on in combination. Particularly, since α-glucosidase alone does not easily react with starch granules, it is preferred to use in combination with α-amylase.

1.2.10 Common Explanation about Enzymes

In the present description, the fact that the enzyme is "derived" from certain organisms means not only the fact that the enzyme is directly isolated from the organisms, but also the fact that an enzyme having the same amino acid sequence is produced from another organisms based on an amino acid sequence of the enzyme possessed by the organisms, or a base sequence encoding the amino acid sequence. For example, also in the case of introducing a gene encoding the enzyme obtained from the organisms into *E. coli* and isolating the enzyme from the *E. coli*, it is said that the enzyme is "derived" from the organisms.

In the present description, a large excess amount of the enzyme is added to starch granules. Therefore, the amount of the enzyme is represented by % by weight. It is not necessary to represent it by the unit (U).

Many α-amylases, amyloglucosidases, isoamylases, α-glucosidases and cyclodextrin glucanotransferases are known, and, therefore, many natural base sequences and amino acid sequences of these enzymes are known. It is known that variants (so-called allele variants) having a slightly different sequence from the natural sequences can occur naturally. Such naturally occurring variants and variants created by artificially mutating the natural enzymes, in addition to the enzymes exemplified above, can be used in the method of the present invention insofar as they have a desired activity. Variant enzymes preferably have activity equal to, or higher than, that of the enzyme before modification. For example, the amino acid sequence of a starch hydrolase used in the present invention, in a certain embodiment, may be identical with (that is, 100% identical with) an amino acid sequence (that is, a reference amino acid sequence) of the starch hydrolase used in the Examples of the present application, or the amino acid sequence of SEQ ID NO: 2, SEQ ID NO: 4, SEQ ID NO: 6, SEQ ID NO: 8, SEQ ID NO: 10, or SEQ ID NO: 12; or this amino acid sequence may, in another embodiment, be altered in up to a certain number of amino acids compared with a reference amino acid sequence. Such alterations can be selected from the group consisting of a deletion, a substitution (including conservative and non-conservative substitution), or an insertion of at least 1 (preferably 1 or several; there is no specific upper limit, for example, about 50 or less, about 40 or less, about 30 or less, about 20 or less, about 10 or less, or the like) amino acids. This alteration may occur at a position of an amino terminus or a carboxyl terminus of a reference amino acid sequence, or may occur at any position other than these termini. Alteration of an amino acid residue may be interspersed, with one residue, or a few residues may be contiguous. Those skilled in the art can easily select an objective enzyme having a desired property. Alternatively, a gene encoding the objective enzyme may be directly chemically synthesized. Methods for such chemical synthesis are well-known in the art.

Modification to enzyme can be carried out using a method well-known in the art, for example, by carrying out site-directed mutagenesis, mutagenesis with a mutagen (treatment of a subject gene with a mutagenic agent such as nitrite, or treatment with UV rays), or error-prone PCR. It is preferable to use site-directed mutagenesis from the viewpoint that the objective mutation is easily obtained, because the objective modification can be introduced at an objective site when site-directed mutagenesis is used. Alternatively, a nucleic acid molecule having an objective sequence may be directly synthesized. Such chemical synthesis methods are well-known in the art. Techniques of site-directed mutagenesis are described in, for example, Nucl. Acid Research, Vol. 10, pp. 6487-6500 (1982).

Upon design of the aforementioned modification, the hydrophobicity index of an amino acid can be considered. Significance of a hydrophobic amino acid index upon impartation interacting biological function to a protein is generally recognized in the art (Kyte. J and Doolittle, R. F., J. Mol. Biol. 157 (1): 105-132, 1982). The hydrophobic nature of an amino acid contributes to the secondary structure of a produced protein and, then, defines interaction between the protein and other molecule (e.g. starch hydrolase or glycosyltransferase, substrate, receptor, DNA, antibody, antigen and the like). An amino acid is assigned a hydrophobicity index based on hydrophobicity and a nature of a charge thereof. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamic acid (−3.5); glutamine (−3.5); aspartic acid (−3.5); asparagine (−3.5); lysine (−3.9); and arginine (−4.5).

It is well-known in the art to substitute a certain amino acid with another amino acid having a similar hydrophobicity index, thereby, a protein still having substantially similar biological functions (e.g. protein substantially equivalent in enzyme activity) can be produced. In such an amino acid substitution, a hydrophobicity index is preferably within ±2, more preferably within ±1, further preferably within ±0.5. It is understood in the art that such the substitution of an amino acid based on hydrophobicity is efficient. As described in U.S. Pat. No. 4,554,101, the following hydrophilicity index is assigned to amino acid residues: arginine (+3.0); lysine (+3.0); aspartic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid can be substituted with another amino acid which has a similar hydrophilicity index, and can still provide a biological equivalent. In such the amino acid substitution, the hydrophilicity index is preferably within ±2, more preferably within ±1, and further preferably within ±0.5.

In the present invention, "conservative substitution" refers to substitution in which a hydrophilicity index or/and a hydrophobicity index are similar, as described above, between the original amino acid and an amino acid to be substituted, in amino acid substitution. Examples of conservative substitution are well-known to those skilled in the art, and include, but are not limited to, substitution among the following each group, for example: arginine and lysine;

glutamic acid and aspartic acid; serine and threonine; glutamine and asparagines; and valine, leucine, and isoleucine.

The enzyme used in the method of the present invention may be isolated from naturally occurring microorganisms producing the above-mentioned enzyme of interest. For example, firstly, a microorganism producing the enzyme of interest is inoculated into a suitable medium (for example, L broth (1% Bacto-Tryptone (Difco Laboratories, Detroit, Mich., USA), 0.5% Bacto-Yeast Extract (Difco), 0.5% NaCl, pH 7.3) and cultured at appropriate temperature (for example, about 30° C. to about 40° C.) overnight with shaking. Then, this culture is centrifuged to precipitate the microbial cells and then obtained a culture supernatant. The obtained culture supernatant is concentrated with UF membrane to obtain an enzyme liquid of interest. When further purification is necessary, a solution containing a purified enzyme of interest can be obtained by combining fractionation with ion-exchange chromatography on O-Sepharose or the like, fractionation with gel filtration chromatography on Sephacryl S-200HR (manufactured by Pharmacia) or the like and fractionation with hydrophobic chromatography on Phenyl-TOYOPEARL 650M (manufactured by Tosoh Corporation) or the like, if necessary.

Alternatively, the enzyme used in the method of the present invention can be obtained by introducing a nucleic acid molecule containing a base sequence encoding enzyme of interest into a suitable host cell, to express the enzyme, and purifying the expressed enzyme from the host cell or its culture liquid.

Purified enzyme obtained resultingly is treated with trypsin, the resulting trypsin treated fragment is separated by HPLC, and the amino acid sequence of the N-terminus of any of the separated peptide fragments is determined using a peptide sequencer. Then, using synthetic oligonucleotide probes prepared based on the identified amino acid sequence, a suitable genome library or a cDNA library is screened, thereby, a nucleic acid molecule (also referred to as a gene) comprising a base sequence encoding natural enzyme can be obtained. Fundamental strategies for preparing the oligonucleotide probes and DNA libraries, and screening them by hybridization of nucleic acids, are well-known to those skilled in the art. For example, see Sambrook et al., *Molecular Cloning: A Laboratory Manual* (1989); *DNA Cloning*, Volumes I and II (edited by D. N. Glover, 1985); *Oligonucleotide Synthesis* (edited by M. J. Gait, 1984); and *Nucleic Acid Hybridization* (edited by B. D. Hames & S. J. Higgins, 1984).

Alternatively, based on homology to a base sequence of a certain enzyme gene for which a base sequence encoding enzyme is known, screening can be conducted by hybridization using nucleic acid probes containing at least a part of this base sequence, thereby, a nucleic acid molecule containing another kind of the enzyme gene may be acquired. Such methods are known in the art.

Alternatively, degenerate primers corresponding to a region which is conserved in the amino acid sequence of various enzymes are prepared, and PCR is performed, and the base sequence of the enzyme may be acquired. Such methods are known in the art.

When a genome library is screened, the resulting nucleic acid molecule can be subcloned using methods well-known to those skilled in the art. For example, by mixing λ phage containing an objective gene, suitable *Escherichia coli* and suitable helper phage, a plasmid containing an objective gene can be easily obtained. Thereafter, by transforming suitable *Escherichia coli* using a solution containing the plasmid, an objective gene can be subcloned. By culturing the resulting transformant, a plasmid DNA may be obtained, for example, by an alkaline SDS method, and the base sequence of the objective gene can be determined. A method of determining a base sequence is well-known to those skilled in the art. Further, using primers synthesized based on a base sequence of a DNA fragment, and using a polymerase chain reaction (PCR) employing, for example, the genomic DNA of *Aquifex aeolicus, Rhodothermus obamensis, Bacillus stearothermophilus, Bacillus caldovelox, Bacillus thermocatenulatus, Bacillus caldolyticus* or the like as a template, an enzyme gene may be directly amplified.

Alternatively, the enzyme gene can be chemically synthesized based on a known base sequence.

A base sequence encoding an amino acid sequence of the enzyme used in the method of the present invention may be altered in up to certain number of nucleotides as compared with the nucleotide sequence (that is, the reference nucleotide sequence) encoding the reference amino acid sequence described above. Such alterations can be selected from the group consisting of a deletion of at least one nucleotide, substitution with at least one nucleotide, including transition and transversion, or an insertion of at least one nucleotide. This alteration may occur at a position of the 5' terminus or the 3' terminus of a reference nucleotide sequence, or may occur at any position other than these termini. Alteration of a base may be interspersed with one base, or a few bases may be contiguous.

A nucleotide alteration can generate a nonsense, missense or frame shift mutation in a code sequence, and thus alteration of the enzyme encoded by such a altered base sequence can be effected.

In the case where the enzyme used in the present invention is a starch hydrolase, it is preferred that this enzyme has at least about 20%, preferably at least about 30%, more preferably at least about 40%, still more preferably at least about 50%, and particularly preferably at least about 60%, at least about 70%, at least about 80%, at least about 90%, at least about 95%, at least about 96%, at least about 97%, at least about 98% or at least about 99% of identity against an amino acid, sequence of a starch hydrolase used in Examples, or an amino acid sequence of SEQ ID NO: 2, 4, 6, 8, 10 or 12, and has a starch hydrolysis activity (characteristics capable of improving a gel forming ability of a starch in a specific case).

In the case where the enzyme used in the present invention is a glycosyltransferase, it is preferred that this enzyme has at least about 20%, preferably at least about 30%, more preferably at least about 40%, still more preferably at least about 50%, and particularly preferably at least about 60%, at least about 70%, at least about 80%, at least about 90%, at least about 9.5%, at least about 96%, at least about 97%, at least about 98% or at least about 99% of identity against an amino acid sequence of a glycosyltransferase used in Examples, or an amino acid sequence of SEQ ID NO: 14, and has a transglycosylation activity (characteristics capable of improving a gel forming ability of a starch in a specific case).

In the present specification, the identity of sequences is calculated using maximum matching of GENETYX-WIN Ver. 4.0 (Genetics Co., Ltd.). This program aligns sequence data to be analyzed, and sequence data to be compared so that amino acid pairs matched between sequences become greatest while substitution and deletion are considered, and thereupon, gives a score to each of Matches, Mismatches, and Gaps, calculates a sum, outputs alignment at the smallest sum, and calculates identity thereupon (Reference:

Takashi, K., and Gotoh, O. 1984. Sequence Relationships among Various 4.5 S RNA Species J. Biochem. 92:1173-1177). In the present specification, the percentage identity of sequences is calculated using maximum matching of GENE-TYX-WIN Ver. 4.0 under the condition of Matches=−1; Mismatches=1; Gaps=1; *N+=2.

As a natural enzyme or nucleic acid molecule, an enzyme or nucleic acid molecule having a sequence that is not identical with, but is homologous to, the amino acid sequence of the enzyme or the base sequence encoding the amino acid sequence of the enzyme can also be used. Such an enzyme or nucleic acid molecule having homology with the natural enzyme or nucleic acid molecule includes, but are not limited to, in the case of a nucleic acid, nucleic acid molecules containing a base sequence having at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% identity with a comparison subject sequence, and, in the case of an enzyme, includes, but are not limited to, enzymes having an amino acid sequence having at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% identity with a comparison subject sequence, when compared in maximum matching in for example GENETYX-WIN Ver. 4.0 under the conditions described above.

A starch hydrolase, which is encoded by a nucleic acid molecule which is capable of hybridizing under stringent conditions with a nucleic acid molecule having a complementary sequence of a base sequence (for example, SEQ ID NO: 1, 3, 5, 7, 9 or 11) encoding a natural known starch hydrolase, can be used in the method of the present invention as long as it has a starch hydrolysis activity (characteristics of improving a gel forming ability of a starch in a specific case). A starch hydrolase, which is encoded by a nucleic acid, molecule containing an altered base sequence obtained by altering a nucleic acid molecule which is capable of hybridizing under stringent conditions with a nucleic acid molecule having a complementary sequence of a base sequence encoding a natural known starch hydrolase can also be used in the method of the present invention as long as it has an ability capable of producing a high viscosity starch having a gel forming ability. Those skilled in the art can easily select a desired starch hydrolase gene.

A transglycosylase, which is encoded by a nucleic acid molecule which is capable of hybridizing under stringent conditions with a nucleic acid molecule having a complementary sequence of a base sequence (for example, SEQ ID NO: 13) encoding a natural known transglycosylase, can be used in the method of the present invention as long as it has a transglycosylase activity (characteristics of improving a gel forming ability of a starch in a specific case). A transglycosylase, which is encoded by a nucleic acid molecule containing an altered base sequence obtained by altering a nucleic acid molecule which is capable of hybridizing under stringent conditions with a nucleic acid molecule having a complementary sequence of a base sequence encoding a natural known transglycosylase can also be used in the method of the present invention as long as it has an ability to produce a high viscosity starch having a gel forming ability. Those skilled in the art can easily select a desired transglycosylase gene.

As used in the present description, the term "stringent conditions" refers to conditions under which a sequence hybridizes with a specific sequence, but not with a non-specific sequence. Selection of appropriate stringent, conditions is well-known to those skilled in the art, and is described, for example, in Molecular Cloning (Sambrook, et al., supra). For example, "stringent conditions" are hybridization in a solution containing 50% formamide, 5×SSC (750 mM NaCl, 7.5 mM trisodium citrate), 50 mM sodium phosphate (pH 7.6), 0.5×Denhardt's solution (0.2% BSA, 0.2% Ficoll 400 and 0.2% polyvinylpyrrolidone), 10% dextran sulfate and 20 µg/ml denatured sheared salmon sperm DNA at 65° C., and subsequent washing under the condition of 65° C. using an SSC (saline-sodium citrate) solution having a 0.1 to 2-fold concentration (a composition of an SSC solution having a 1-fold concentration is 150 mM sodium chloride and 15 mM sodium citrate). Therefore, for example, a polynucleotide being capable to hybridize under stringent conditions means, specifically, a polynucleotide which can be identified using the conditions under which hybridization is performed at 65° C. in a solution containing 50% formamide, 5×SSC (750 mM MaCl, 75 mM trisodium citrate), 50 mM sodium phosphate (pH 7.6), 5×Denhardt's solution (0.2% BSA, 0.2% Ficoll 400 and 0.2% polyvinyl pyrrolidone), 10% dextran sulfate, and 20 µg/ml denatured sheared salmon sperm DNA using a filter on which a DNA derived from a colony or a plaque has been immobilized, and a filter is washed under the condition of 65° C. lasing an SSC (saline-sodium citrate) solution having a 0.1 to 2-fold concentration (a composition of an SSC solution having a 1-fold concentration is 150 mM sodium chloride, 15 mM sodium citrate).

Specifically, the conditions mean, for example, that

A nucleic acid molecule used for producing an enzyme used in the present method may be a nucleic acid molecule which was conservatively modified relative to a nucleic acid molecule comprising a base sequence encoding a natural enzyme. The "nucleic acid molecule which was conservatively modified relative to a nucleic acid molecule comprising a base sequence encoding natural enzyme" refers to a nucleic acid molecule comprising a base sequence encoding an amino acid sequence which is the same or essentially the same as an amino acid sequence of the natural enzyme. The "amino acid sequence which is essentially the same as an amino acid sequence of the natural enzyme" refers to an amino acid sequence having essentially the same enzyme activity as that of the natural enzyme. Due to the degeneracy of the genetic code, many functionally equivalent base sequences encode any prescribed amino acid sequence. For example, codons GCA, GCC, CCC and GCU all encode the amino acid alanine. Therefore, at all positions where alanine is specified by a GCA codon, the codon can be changed to GCC, CCC or GCU without changing the encoded alanine. Similarly, regarding an amino acid which can be encoded by a plurality of codons, at all positions where the amino acid is specified by a codon, the codon can be changed to any another codon encoding the amino acid without changing the particular amino acid coded. Such a variation in a base sequence is a "silent mutation" which is one kind of conservatively modified mutation. All base sequences in the present specification which encode a polypeptide also include all possible silent mutations of the nucleic acid. Silent mutation includes "silent substitution" in which a coded amino acid is not changed, and the case where a nucleic acid does not originally encode an amino acid (for example, a mutation at an intron portion, a mutation at other untranslated region and the like). When a certain nucleic acid encodes an amino acid, silent mutation has the same meaning as that of silent substitution. In the present specification, "silent substitution" refers to substitution of a base sequence encoding a certain amino acid with another base sequence encoding the same amino acid, in a base sequence. Based on the phenomenon of degeneracy in the genetic code, in the case where there are a plurality of base sequences encoding a certain amino acid (for example, glycine and the like), such silent substitution is possible. Therefore, a polypeptide having an amino acid sequence encoded by a base sequence produced by silent substitution has the same amino acid sequence as that of the original polypeptide. In the art, it is understood that each codon in a nucleic acid (except for AUG which is the only codon usually encoding methionine, and TGG which is the only codon usually encoding tryptophan) can be modified in order to produce functionally the same molecule. Therefore, each silent mutation of a nucleic acid encoding a polypeptide is implicitly included in each described sequence. Preferably, such a modification can be performed so that substitution of cysteine, which is an amino acid that greatly influences the conformation of a polypeptide, is avoided.

A base sequence encoding enzyme used in the present invention can be changed in conformity with a codon usage in an organism into which the sequence is introduced for expression. Codon usage reflects the usage in a gene which is highly expressed in the organism. For example, when expression is intended in *Escherichia coli*, the sequence can be made to be optimal for expression in *Escherichia coli* according to the published codon usage table (for example, Sharp, et al., Nucleic Acids Research 16, No. 17, p. 8207 (1988)).

An expression vector can be made using a nucleic acid molecule comprising the base sequence modified as described above. A method for preparing an expression vector using a particular nucleic acid sequence is well-known to those skilled in the art.

When a nucleic acid molecule is referred to in the present specification, a "vector" refers to a nucleic acid molecule which can transfer an objective base sequence into an objective cell. Examples of such vectors include a vector which can autonomously replicate in an objective cell, or can be incorporated into a chromosome of an objective cell, and has a promoter at a position suitable for transcribing a modified base sequence. In the present specification, the vector may be a plasmid.

As used in the present description, an "expression vector" refers to a vector which can express a modified base sequence (i.e. base sequence encoding modified enzyme) in an objective cell. An expression vector contains, in addition to a modified base sequence, various regulation elements such as a promoter regulating expression thereof and, if necessary, factors necessary for replication in an objective cell and selection of a recombinant (e.g. origin of replication (ori), and a selectable marker such as a drug resistant gene). In an expression vector, a modified base sequence is operably linked so that it is transcribed and translated. Regulation elements include a promoter, a terminator and an enhancer. In addition, when secretion of an expressed enzyme outside a cell is intended, a base sequence encoding a secretion signal peptide is linked upstream of a modified base sequence in the correct reading frame. It is well-known to those skilled in the art that both the type of an expression vector used for introduction into a particular organism (e.g. bacterium), and the kind of a regulation element and other factors used in the expression vector, can vary depending on an objective cell.

As used in the present description, a "terminator" is a sequence which is situated downstream of a protein coding region, and is involved in termination of transcription upon transcription of a base sequence into an mRNA, and in the addition of a poly A sequence. It is known that a terminator influences the expression level of a gene by involving the stability of an mRNA.

As used in the present description, a "promoter" refers to a region on a DNA which determines a transcription initiation site of a gene, and directly regulates the transcription frequency, and is a base sequence to which a RNA polymerase binds, thereby, initiating transcription. Since the region of a promoter is usually a region about 2 kbp or less upstream of a first exon of a putative protein coding region in many cases, when a protein coding region in a genome base sequence is predicted using a DNA analyzing software, a promoter region can be putative. A putative promoter region varies with every structural gene, and is usually upstream of a structural gene without limitation, and may be downstream of a structural gene. Preferably, a putative promoter region is present about 2 kbp or less upstream of a first exon translation initiation point.

As used in the present description, an "enhancer" can be used for enhancing the expression efficiency of an objective gene. Such an enhancer is well-known in the art. A plurality of enhancers can be used, or only one may be used, or may not be used at all.

As used in the present description, "operably linked" refers to when a desired base sequence is placed under the control of a transcription and translation regulating sequence (e.g. promoter, enhancer and the like) or a translation regulating sequence which effect expression (i.e. operation). In order that a promoter is operably linked to a gene, usually, a promoter is disposed immediately upstream of the gene, but it is not necessary that the promoter is disposed adjacent to the gene.

In order to operably link a modified nucleic acid sequence to the aforementioned regulation element, an enzyme gene should be processed in some cases. Examples include the case where the distance between a promoter and a coding region is too long, and reduction in a transcription efficiency is predicted, the case where the distance between a ribosome binding site and a translation initiation codon is not suitable, and the like. Examples of processing mean include digestion with a restriction enzyme, digestion with an exonuclease such as Bal31 and ExoIII, or introduction of site-directed mutation using a single-stranded DNA such as M13 or PCR.

Then, the expression vector prepared as described above is introduced into a cell, thereby, the objective enzyme is expressed.

As used in the present description, "expression" of an enzyme refers to in vivo or in vitro transcription and translation of a base sequence encoding the enzyme, and production of the encoded enzyme.

A cell into which an expression vector is introduced (also referred to as a host) includes prokaryotes and eukaryotes. A cell into which an expression vector is introduced can be easily selected, taking various conditions such as ease of expression of objective enzyme, ease of culturing, growth rate, and safety into consideration. Examples of such cells include microorganisms such as bacteria and fungi. Examples of more preferable cells include mesophilic microorganisms (e.g. yeast, mold, *Escherichia coli, Bacillus subtilis*). A cell may be a microorganism cell, or may be a plant or animal cell. Depending on the cell to be used, a starch hydrolase can be an enzyme which has undergone post-translational processing.

In the method of the present invention, the technique of introducing an expression vector into a cell may be any technique known in the art. Examples of such techniques include, for example, transformation, transduction, and transfection. Such techniques of introducing a nucleic acid molecule are well-known in the art, and are conventional, and are described, for example, in Ausubel F. A., et al. ed. (1988), Current Protocols in Molecular Biology, Wiley, New York, N.Y.; Sambrook J, et al. (1987) Molecular Cloning: A Laboratory Manual, 2nd Ed., Cold Spring Harbor Laboratory Press, Cold Spring Harbor, N.Y., and Bessatsu Jikkenigaku "Idenshidounyu & Hatsugen kaiseki jikkenhou", Yodosha, 1997.

1.3 Other Materials

In the production of enzyme-treated starch granules, any material used usually in an enzymatic treatment can be used as long as it does not obstruct an action of the enzyme. Examples of such other material include salts and buffer agents. Since it is commonly known that a rate of an enzyme reaction can be drastically improved by adding a specific salt suitable to each enzyme, it is preferred to add such a specific salt. It is possible to shorten the treatment time by adding such a suitable salt to each enzyme. Examples of the combination of the enzyme and the salt include a combination of amyloglucosidase and a metal ion (for example, sodium ion, potassium ion, calcium ion, or magnesium ion). As a result of a test by the present inventors, for example, in the case of treating an untreated native cassava starch with amyloglucosidase (for example, "OPTIDEX L-400" derived from *Aspergillus niger*, manufactured by Genencor), a degradation rate of the starch in the system, in which 100 ppm (in terms of a metal ion) of sodium chloride, or sodium sulfate, or potassium chloride, or calcium chloride, or magnesium chloride is added, increased by 1.5 to 2 times as compared with the system in which no metal ion is added.

2. Method for Producing Enzyme-Treated Starch Granule

Enzyme-treated starch granules are produced by treating starch granules with a starch hydrolase or a glycosyltransferase. Details of each step will be described below.

2.1 Preparation of Suspension

In the production method of the present invention, for example, starch granules, a starch hydrolase or a glycosyltransferase, a buffer agent, and a solvent dissolving them are used as main materials. Although all of these materials are usually added at the time of initiation of a reaction, any material among these materials may be further added during the reaction. The solvent used in the production method of the present invention can be any solvent as long as it is a solvent which does not impair an enzyme activity of the enzyme to be used. The typical solvent is water (for example, ion-exchange water, purified water, and tap water). The solvent may be moisture of a crushed cell liquid obtained in association with the enzyme upon preparing the enzyme.

In the production method of the present invention, first, a reaction solution is prepared. The reaction solution can be obtained, for example, by adding starch granules and a starch hydrolase or a glycosyltransferase to a suitable solvent. For example, the enzyme may be added after preparing a starch suspension by suspending starch granules in the solvent (for example, water or buffer solution). Alternatively, the reaction solution may be prepared by mixing a suspension containing starch granules with a solution containing an enzyme. To this reaction solution, any buffer agent may be optionally added for the purpose of adjusting the pH as long as it does not inhibit the enzyme reaction. It is noted that although starch granules are not dissolved but suspended in the reaction solution, it is called as reaction solution, since other components such as an enzyme are dissolved therein.

The pH of the reaction solution can be arbitrarily set as long as it is the pH at which the enzyme to be used can exert an activity. The pH of the reaction solution is preferably around the optimum pH of the enzyme to be used. The pH of the reaction solution is typically about 2 or more, preferably about 3 or more, still more preferably about 4 or more, particularly preferably about 5 or more, particularly preferably about 6 or more, and most, preferably about 7 or more. The pH of the reaction solution is typically about 13 or less, preferably about 12 or less, still more preferably about 11 or less, particularly preferably about 10 or less, particularly preferably about 9 or less, and most preferably about 8 or less. In an embodiment, the pH of the reaction solution is typically within the optimum pH±3, preferably within the optimum pH±2, still more preferably within the optimum pH±1, and most preferably within the optimum pH±0.5, of the enzyme to be used.

The amount of the starch granules in the reaction solution can be arbitrarily set as long as it is the amount which enables the enzyme reaction. The amount of the starch granules in the reaction solution is preferably about 5% by weight or more, more preferably about 10% by weight or more still more preferably about 20% by weight or more, and most preferably about 30% by weight or more. The amount of the starch granules in the reaction solution is preferably about 60% by weight or less, more preferably about 50% by weight or less, still more preferably about 40% by weight or less, and most preferably about 35% by weight or less.

The amount of the enzyme in the reaction solution can be arbitrarily set as long as it is the amount which enables the enzyme reaction. The amount of the enzyme is preferably the amount enough to carry out the reaction within a reasonable time. As the amount of the enzyme increases, the time required to the reaction becomes shorter. As the amount of the enzyme decreases, the time required to the reaction becomes longer. When the amount of the enzyme is too large, the cost increases too much and the enzyme may be sometimes aggregated to form a precipitate. Therefore, it is preferred to appropriately set the amount of the enzyme.

The amount of the enzyme in the reaction solution is preferably about 0.01% by weight or more, more preferably about 0.05% by weight or more, and still more preferably about 0.1% by weight or more, based on the dry weight of the starch granules. The amount of the enzyme in the reaction solution is preferably about 10% by weight or less, more preferably about 5% by weight or less, and still more preferably about 1% by weight or less, based on the dry weight of the starch granules. The amount of the enzyme in the reaction solution may be the amount enough to enable proceeding of the enzyme reaction. Therefore, it is not necessary to examine in detail about an activity (number of units) of the enzyme.

2.2 Enzyme Reaction

Next, the reaction solution is reacted optionally by heating using a method known in the art. The solution temperature in the reaction step can be any temperature as long as it is the temperature at which the starch granules are not substantially collapsed. The reaction temperature is preferably the temperature at which an enzyme to be used can sufficiently exert an activity and sufficiently retain an activity (that is, less likely to be inactivated). The temperature of the solution in this reaction step is preferably the temperature at which about 50% or more, and more preferably about 80% or more of the activity of the enzyme contained in this solution before the reaction remains after a predetermined reaction time. For example, this temperature can be an optimum temperature±10° C., more preferably an optimum temperature±5, still more preferably an optimum temperature±1° C., and most preferably an optimum pH±0.5° C., of the enzyme to be used. The reaction temperature is preferably about 10° C. or higher, more preferably about 10° C. or higher, still more preferably about 15° C. or higher, further more preferably about 20° C. or higher, particularly preferably about 30° C. or higher, and most preferably 40° C. or higher. The reaction temperature is preferably about 70° C. or lower, more preferably about 65° C. or lower, particularly preferably about 60° C. or lower, and most preferably 55° C. or lower.

The reaction time can be arbitrarily set taking the reaction temperature, the amount of the enzyme to starch granules into consideration. The reaction time can be preferably for about 1 hour or more, for example, about 2 hours or more, about 3 hours or more, about 6 hours or more, and about 12 hours or more. Although there is no particular upper limit of the reaction time, the reaction time is preferably about 72 hours or less, more preferably about 48 hours or less, still more preferably about 35 hours or less, particularly preferably about 24 hours or less, and most preferably about 20 hours or less.

2.3 Post-Treatment

The starch granules subjected to the enzymatic treatment can be used as they are depending on the application. However, it is preferred that the enzyme used and glucide eluted by enzymatic degradation are removed by washing the starch granules subjected to the enzymatic treatment, and followed by dehydration. Washing and dehydration of the starch granules subjected to the enzymatic treatment can be carried out by any method known in the art. Washing and dehydration of the starch granules are conventional methods used for preparation of a starch, and are commonly carried out. For example, solid-liquid separation can be carried out by filtration, centrifugal filtration or the like to obtain the starch granules. Furthermore, it is preferred to obtain the desired enzyme-treated starch granules by drying the starch granules after dehydration. Drying of the starch granules after dehydration can be carried out by any method known in the art.

When starch granules are chemically modified, the chemical modification may be conducted before the enzyme treatment, and the chemical modification may be conducted after the enzyme treatment. However, it is preferred to perform an enzyme treatment before the chemical modification. When the enzyme treatment is performed before the chemical modification, it is preferred to remove the enzymes used for the enzyme treatment and carbohydrates eluted by enzymatic degradation from the product of the enzyme-treatment by performing filtration (for example, centrifugal filtration), washing, dehydration or the like of the reaction solution after the enzyme treatment. However, the steps of filtration, washing, dehydration or the like can be omitted depending one situation.

2.4 Chemical Modification

The starch granules subjected to the enzymatic treatment can be subjected to a chemical modification, if desired. Not only in the case where the starch granules used in the enzymatic treatment are untreated starch granules or starch granules subjected to a physical treatment, but also in the case where starch granules of some chemically modified starch are used, it is possible to be subjected to a chemical modification which is different from various chemical modifications applied to the chemically modified starch. Examples of the chemical modification include acetylation, adipate-crosslinking, oxidation, bleaching, phosphate-crosslinking, treatment with octenyl succinic acid, hydroxypropylation, phosphorylation, and phosphoric acid monoesterification. These chemical modification methods are well known in the art. These chemical modifications can be carried out to any degree as long as they are within the scope permitted by the Food Sanitation Law of Japan, in the case where the chemically modified starch granules are intended to be utilized as a food in Japan. In Japan, in order that the chemically modified starch is approved as a food additive, it is essential that various chemical substances in a sample starch are analyzed in accordance with a method for a purity test described in Ministry of Health and Welfare Notification No. 485 and the obtained analytical results meet the following standards:

(a) Acetylated distarch adipate: the content of adipic acid groups shall be 0.135% or less and the content of acetyl groups shall be 2.5% or less;
(b) Acetylated oxidized starch: the content of acetyl groups shall be 2.5% or less and the content of carboxyl groups shall be 1.3% or less;
(c) Acetylated distarch phosphate: the content of acetyl groups shall cc 2.5% or less and the content of phosphorus shall be 0.14% or less in terms of P;
(d) Starch sodium octenyl succinate: the content of octenyl succinic acid groups shall be 3.0% or less;
(e) Starch acetate: the content of acetyl groups shall be 2.5% or less;
(f) Oxidized starch: the content of carboxyl groups shall be 1.1% or less;
(g) Hydroxypropyl distarch phosphate: the content of hydroxypropyl groups shall be 7.0% or less and the content of phosphorus shall be 0.14% or less in terms of P;
(h) Hydroxypropyl starch: the content of hydroxypropyl groups shall be 7.0% or less;
(i) Distarch phosphate: the content of phosphorus shall be 0.5% or less in terms of P;
(j) Monostarch phosphate: the content of phosphorus shall be 0.5% or less in terms of P;
(k) Phosphated distarch phosphate: the content of phosphorus shall be 0.5% or less in terms of P;
(l) Bleached starch; the content of carboxyl groups shall be 0.1% or less, the test results of "Confirmatory test (3)" of the oxidized starch described in Ministry of Health and Welfare Notification No. 485 shall be negative, and it shall be reasonably explained that a change in properties, such as viscosity, of the starch is not caused by oxidation. Regarding the countries other than Japan, any degree of a chemical treatment can be carried out as long as it is within the scope permitted in that country. Some kinds of chemical modifications can be used in combination.

In the case where starch granules are used for purposes other than foods, types and levels of chemical modifications those which are not permitted in the case of starch used in a food can be conducted. Examples of industrially usable chemically modified starch granules include the afore mentioned chemically modified starch granules; acylated esterification starch granules such as propionic acid ester starch granules; hydroxyethylated starch granules; carboxymethylated starch granules; etherification starch granules treated with alkyl halide or dialkyl sulfate in the presence of an alkaline; grafted starch granules wherein a vinyl monomer such as acrylic acid or methacrylic acid is added in the presence of an iron ion or a cerium ion, or carboxylic acid having a hydroxyl group such as lactic acid is added in branched form by polycondensation; cationized starch granules; and the like. In the case of the industrial uses other than foods, there is no restriction of modification ratios like those described above.

After the chemical modification is carried out, it is preferred to perform post-treatment to remove a reagent used for the chemical modification from the product containing the starch granules. It is preferred to remove a used chemical modification reagent by washing the chemically modified starch granules and followed by dehydration. Washing and dehydration of the chemically modified starch granules can be carried out by any method known in the art. Washing and dehydration of the starch granules are conventional methods used for preparation of a starch, and are commonly carried out. For example, solid-liquid separation can be carried out by filtration, centrifugal filtration or the like to collect the starch granules. Furthermore, it is preferred to obtain the desired enzyme-treated-chemically modified starch granules by drying the starch granules after dehydration. Drying of the starch granules after dehydration can be carried out by any method known in the art.

Chemical modification to be carried out after enzyme treatment is preferably etherification or esterification. Preferable examples of etherification include hydroxypropylation, hydroxyethylation, carboxymethylation and the like. Preferable examples of esterification include acetylation, phosphorylation, propionic acid esterification and the like. Enzyme-treated-chemically modified starch granules having the following characteristics are obtained by removing a part on the surface of the starch granules by enzyme treatment, removing the resultant carbohydrates and carrying out an etherification modification or an esterification modification:

(1) In comparison with chemically modified starch granules which have not been enzyme-treated, the enzyme-treated-chemically modified starch granules have faster filtration velocity in filtration performed during the separation of starch granules from the chemical modification treatment liquid. Specifically, in comparison with etherified starch granules which have not been enzyme-treated, the enzyme-treated-etherified starch granules have faster filtration velocity in filtration performed during the separation of starch granules from the etherification treatment liquid. Further, in comparison with esterified starch granules which have not been enzyme-treated, the enzyme-treated-esterified starch granules have faster filtration velocity in filtration performed during the separation of starch granules from the esterification treatment liquid.

(2) when the reaction liquid immediately after the chemical modification reaction is left stand at room temperature, the enzyme-treated-etherified starch granules and the enzyme-treated-esterified starch granules precipitate quickly, and there are fewer clouds of the supernatant compared with the starch granules which have not been enzyme-treated.

(3) When the enzyme-treated-etherified starch granules are allowed to be gelatinized, velocities of increasing viscosity of these starch granules are faster than those of the starch granules which have not been enzyme-treated. When the enzyme-treated-esterified starch granules are allowed to be gelatinized, velocities of increasing viscosity of these starch granules are faster than those of the starch granules which have not been enzyme-treated.

(4) After drying the enzyme-treated-etherified starch granules, when starch suspension is prepared again with water, these starch granules are precipitated more quickly than starch granules which have not been enzyme-treated. After drying the enzyme-treated-esterified starch granules, when starch suspension is prepared again with water, these starch granules are precipitated more quickly than starch granules which have not been enzyme-treated.

2.5 Physical Treatment

The starch granules subjected to the enzymatic treatment can be subjected to a physical treatment, if desired. Not only in the case where the starch granules used in the enzymatic treatment are untreated starch granules or a chemically modified starch, but also in the case where the starch granules subjected to some physical treatment are used, it is possible to be subjected to a physical treatment which is different from the physical treatment. Examples of the physical treatment include a heat-moisture treatment and a thermal inhibition treatment.

The "heat-moisture treatment" refers to heating to a temperature of about 95 to about 125° C. in a low moisture state where a starch is not gelatinized in a closed container under the condition of a relative humidity of about 100%. The "low moisture state where a starch is not gelatinized" indicates, for example, the moisture content of about 50% or less. The low moisture state where a starch is not gelatinized may be, for example, the moisture content of about 35% or less, about 30% or less, about 25% or less, or about 20% or less. The heating time of the heat-moisture treatment can vary depending on the method of the heat-moisture treatment. For example, a heat-moisture treatment is carried out in accordance with the method described in Japanese Laid-oven Patent Publication No. 6-145203, a heat treatment is carried out by first decompressing to a pressure of about 0 to 500 torr (about 0 to 66.661 kPa) and then introducing pressurized steam, followed by retention at about 100° C. to about 150° C. for about 2 minutes to about 120 minutes. The heat-moisture treatment is described in various documents and can be carried out in accordance with any heat-moisture treatment method known in the art. The heat-moisture treatment is described, for example, in Japanese Laid-open Patent Publication No. 6-145203, Japanese Laid-open Patent Publication No. 4-130102, A Technical Journal on Food Chemistry & Chemicals 2010-2 (P. 37-42) and the like. The temperature, time and the like of the heat-moisture treatment can be appropriately set depending on the objective starch and physical properties thereof.

The "thermal inhibition treatment" refers to the fact that a crystal structure of starch granules is reinforced by subjecting starch granules dried to extremely low water content to a dry heat treatment. The "starch granules dried to extremely low water content" refers to starch granules whose moisture content is less than about 1%. The moisture content of the starch granules subjected to a thermal inhibition treatment is preferably about 0%. The method of drying starch granules to extremely low water content is described, for example, in JP-A-2008-223032 and can be, for example, a method in which the pH of starch granules is adjusted to the pH of 7.0 or more and then dehydration is carried out until, the moisture content reaches less than about 1%. In the case of drying to low water content, the pH is preferably 7 or more, more preferably more than 8, still more preferably from 7.5 to 10.5, and further more preferably from 8 to 9.5. The dehydration may be either thermal dehydration or nonthermal dehydration. In the case of a dry heat treatment, a heat treatment is carried out at a sufficient temperature for the time enough to inhibit a starch. Preferably, a heat treatment is carried out at a sufficient temperature for the time enough to make a starch non-aggregative. The heating temperature for a thermal inhibition treatment is preferably higher than about 100° C. The heat treatment temperature is preferably about 200° C. or lower. The heating temperature for a thermal inhibition treatment is more preferably from about 120° C. to about 180° C., particularly preferably from about 140° C. to about 160° C., and most preferably from about 160° C. The level of inhibition depends on the pH, heating temperature and heating time. As the pH becomes higher, a more highly inhibited starch is obtained. As the temperature of the heat treatment becomes higher, a more highly inhibited starch is obtained. As the time of the heat treatment becomes longer, a more highly inhibited starch is obtained. The thermal treatment time for a thermal inhibition treatment can be, for example, about 3 hours or more, and preferably about 20 hours or less. The thermal inhibition treatment is described in various documents and can be carried out in accordance with any thermal inhibition treatment method known in the art. The thermal inhibition treatment is described, for example, in U.S. Pat. No. 6,221,420, Pamphlet of International Publication No. WO 95/04082, and Japanese Laid-open Patent Publication No. 2008-223032. The temperature, time, and the like of the thermal inhibition treatment can be appropriately set depending on the objective starch and physical properties thereof. The physical treatment can be carried out in accordance with the method well known in the art.

Examples of the heat-moisture-treated starch include, for example, "Delicastar series", "Naturastar series", and "AMYLOGEL" manufactured by SANWA CORNSTARCH CO., LTD.; and "ROADSTER" manufactured by Nihon Shokuhin Kako Co., Ltd. Examples of the thermally inhibited starch include "NOVATION series" manufactured by National Starch Corp.

3. Characteristics of Enzyme-Treated Starch Granules of the Present Invention In a specific embodiment, the enzyme-treated starch granules of the present invention are enzyme-treated starch granules having a high viscosity and a gel forming ability, and the enzyme-treated starch granules are enzyme-treated starch granules obtained by treating starch granules with an enzyme at a temperature of about 10° C. or higher and about 70° C. or lower. In the present specification, the term "high viscosity" with regard to the starch granules means that by dispersing the enzyme-treated starch granules into water and by heating, a high viscosity of the suspension liquid is obtained. For example, it refers to an enzyme-treated starch granule showing a high value of the highest viscosity when the viscosity is analyzed with an amylograph.

In another specific embodiment, the enzyme-treated starch granules of the present invention are enzyme-treated starch granules having a high viscosity and a gel forming ability; the enzyme-treated starch granules are starch granules obtained by treating starch granules of an untreated starch with a starch hydrolase under the condition where the starch granules are not dissolved; the enzyme-treated starch granules are not modified on hydroxyl groups at the positions 2, 3 and 6 of the glucose residues; and the enzyme-treated starch granules can form a gel having a Young's modulus higher than that of the untreated starch granules or a rupture stress higher than that of the untreated starch granules, when measured by a rheometer.

In the present specification, the starch granule obtained by performing an enzyme treatment to a starch granule is referred to as "an enzyme-treated starch granule." In some cases, paying attention to starch constituting the starch granule, it may be referred to as "enzyme-treated starch." In the present specification, a starch granule obtained by performing a chemical modification after an enzyme treatment to a starch granule is referred to as "an enzyme-treated-chemically modified starch granule". In some cases, paying attention to starch constituting the starch granule, it may be referred to as "enzyme-treated-chemically modified starch". An enzyme-treated-chemically modified starch granule is a kind of enzyme-treated starch granules. The chemical modification is preferably an etherification or an esterification. Therefore, in the particular embodiment, enzyme-treated-chemically modified starch granules of the present invention are preferably enzyme-treated-etherified starch granules or enzyme-treated-esterified starch granules.

3.1 Viscosity

It is well known that when a starch is heated together with a predetermined amount or more of water, starch granules generally cause a gelatinization phenomenon such as swelling, an increase in transparency, and an increase in viscosity. The starch granules are collapsed by further heating. In order to measure a change in viscosity associated with a series of these events, an amylograph manufactured by Brabender Inc. is practical and is widely used, although there are some methods. The amylograph is that in which the object is heated at a predetermined rate and a relationship between the temperature and the viscosity of the object is recorded. That is, starch granules undergo swelling with heating, while manifestation of viscosity and an increase in viscosity arise in the amylograph. Then, when the swelling of the starch granules becomes to maximum, the viscosity also reaches a peak. This viscosity is called maximum viscosity. Further heating causes collapse of the starch granules and simultaneously causes a decrease in viscosity. This degree of the decrease in viscosity is called breakdown. A viscosity curve obtained by this amylograph varies depending on the origin and production method of the starch, and is a measuring method showing features of the starch.

For example, the measurement by the amylograph is carried out as follows. A starch suspension is prepared in 450 ml of water so as to obtain a predetermined amount of enzyme-treated starch granules (for example, the concentration of a wheat starch is 8.5% by weight, the concentration of a corn starch is 7.0% by weight, and the concentration of a cassava starch is 6.0% by weight, on the dry matter basis), put in a sample container, and then warmed to 50° C. while rotating them. Then the suspension is heated to 95° C. at 1.5° C./min and maintained at 95° C. for 15 minutes, followed by cooling at 1.5° C./min. The measurement is carried out using an amylograph VISCOGRAPH-E manufactured by Brabender Inc. under the conditions of a rotation number of a sample container of 75 rpm and a measuring cartridge of 700 cmg. Wherein, the viscosity reached to a peak is regarded as a maximum viscosity, and a difference between this maximum viscosity and a viscosity at the point after maintaining at 9.5° C. for 15 minutes is regarded as breakdown. This difference is also called as a breakdown viscosity. When the difference between the maximum viscosity and the viscosity at the point after maintaining at 95° C. for 15 minutes is less than 100 BU, it is said that the starch has no "breakdown".

In the case where the enzyme-treated starch granules of the present invention are prepared from the granules of an untreated starch and have not been subjected to either a chemical modification or a physical treatment, it is preferred that the enzyme-treated starch granules of the present invention have a maximum viscosity which accounts for about 50% or more (more preferably about 60% or more, particularly preferably about 70% or more, and most preferably about 80% or more, about 90% or more, or about 100% or more) of the maximum viscosity of the granules of the untreated starch, when measured by an amylograph under the above conditions. There is no particular upper limit of the maximum viscosity of the enzyme-treated starch granules of the present invention. For example, the maximum viscosity of the enzyme-treated starch granules of the present invention can be about 300% or less, about 250% or less, about 200% or less, about 150% or less, about 110% or less, and about 100% or less of the maximum viscosity of the granules of the untreated starch, when measured by an amylograph under the above conditions. For example, it is preferred that the enzyme-treated wheat starch granules can form a gel having a viscosity which accounts for 70% or more and 200% or less (more preferably 80% or more and 200% or less) of the viscosity of the granules of the untreated wheat starch.

For example, regarding the wheat starch, a maximum viscosity of the native wheat starch when measured by an amylograph under the above conditions is from about 550 BU to about 650 BU. On the other hand, in the case where the enzyme-treated starch granules of the present invention are prepared from the granules of an untreated wheat starch and have not been subjected to either a chemical modification or a physical treatment, a maximum viscosity of the enzyme-treated wheat starch granules of the present invention when measured by an amylograph under the above conditions may be preferably about 400 BU or more, more preferably about 420 BU or more, particularly preferably about 450 BU or more, most preferably about 500 BU or more, for example, about 550 BU or more, about 570 BU or more, about 600 BU or more, or about 650 BU or more. In a specific embodiment, it is possible to make the maximum viscosity of the enzyme-treated wheat starch granules of the present invention when measured by an amylograph under the above conditions to about 660 BU or more, about 670 BU or more, or about 700 BU or more. The maximum viscosity of the enzyme-treated wheat starch granules of the present invention when measured by an amylograph under the above conditions can be for example, about 900 BU or less, about 850 BU or less, about 800 BU or less, or about 750 BU or less.

For example, regarding the corn starch, a maximum viscosity of the granules of the native corn starch when measured by an amylograph under the above conditions is from about 400 BU to about 500 BU. On the other hand, in the case where the enzyme-treated starch granules of the present invention are prepared from an untreated corn starch and have not been subjected to either a chemical modification a physical treatment, a maximum viscosity of the enzyme-treated corn starch granules of the present invention when measured by an amylograph under the above conditions may be preferably about 250 BU or more, more preferably about 270 BU or more, particularly preferably about 300 BU or more, most preferably about 350 BU or more, for example, about 400 BU or more, about 420 BU or more, about 440 BU or more, or about 450 BU or more. The maximum viscosity of the enzyme-treated corn starch granules of the present invention when measured by an amylograph under the above conditions can be, for example, about 600 BU or less, about 550 BU or less, about 520 BU or less, or about 500 BU or less.

For example, regarding the cassava starch, a maximum viscosity of the granules of the native cassava starch when measured by an amylograph under the above conditions is from about 700 BU to about 800 BU. On the other hand, in the case where the enzyme-treated starch granules of the present invention are prepared from the granules of an untreated cassava starch and have not been subjected to either a chemical modification or a physical treatment, a maximum viscosity of the enzyme-treated cassava starch granules of the present invention when measured by an amylograph under the above conditions may be preferably about 500 BU or more, more preferably about 520 BU or more, particularly preferably about 530 BU or more, most preferably about 550 BU or more, for example, about 600 BU or more, about 620 BU or more, about 630 BU or more, or about 650 BU or more. The maximum viscosity of the enzyme-treated cassava starch granules of the present invention when measured by an amylograph under the above conditions can be, for example, about 900 BU or less, about 850 BU or less, about 800 BU or less, or about 770 BU or less.

In case where the enzyme-treated starch granules of the present invention are prepared from the granules of an untreated starch and have not been subjected to either a chemical modification or a physical treatment, the enzyme-treated starch granules of the present invention have breakdown when measured by an amylograph. Some conventional starches have no breakdown, whereas, the enzyme-treated starch granules of the present invention have breakdown.

For example, in the case where the untreated starch granules are wheat starch granules, corn starch granules or cassava starch granules and neither a chemical modification nor a physical treatment is carried out, the obtained enzyme-treated starch granules have a breakdown viscosity of about 100 BU or more.

In the case where the untreated starch is a wheat starch and neither a chemical modification nor a physical treatment is carried out, the breakdown viscosity of the obtained enzyme-treated starch granules is preferably about 100 BU or more, more preferably about 120 BU or more, still more preferably about 130 BU or more, and most preferably about 150 BU or more. In the case where the untreated starch is a wheat starch and neither a chemical modification nor a physical treatment is carried out, although there is no particular upper limit of the breakdown viscosity of the obtained enzyme-treated starch granules, the breakdown viscosity of the obtained enzyme-treated starch granules can be, for example, about 500 BU or less, about 450 BU or less, about 400 BU or less, about 350 BU or less, or about 300 BU or less.

In the case were the untreated starch is a corn starch and neither a chemical modification nor a physical treatment is carried out, the breakdown viscosity of the obtained enzyme-treated starch granules is preferably about 100 BU or more, more preferably about 110 BU or more, still more preferably about 120 BU or more, and most preferably about 150 BU or more. In the case where the untreated starch is a corn starch and neither a chemical modification nor a physical treatment is carried out, although there is no particular upper limit of the breakdown viscosity of the obtained enzyme-treated starch granules, the breakdown viscosity of the obtained enzyme-treated starch granules can be, for example, about 300 BU or less, about 290 BU or less, about 280 BU or less, 200 BU or less, about 190 BU or less, or about 180 BU or less.

In the case where the untreated starch is a cassava starch and neither a chemical modification nor a physical treatment is carried out, the breakdown viscosity of the obtained enzyme-treated starch granules is preferably about 300 BU or more, more preferably about 320 BU or more, still more preferably about 330 BU or more, and most preferably about 350 BU or more. In the case where the untreated starch is a cassava starch and neither a chemical modification nor a physical treatment is carried out, although there is no particular upper limit of the breakdown viscosity of the obtained enzyme-treated starch granules, the breakdown viscosity of the obtained enzyme-treated starch granules can be, for example, about 550 BU or less, about 540 BU or less, about 530 BU or less, about 500 BU or less, about 480 BU or less, or about 470 BU or less.

3.2 Gel Forming Ability

It is well known that when the concentration of a starch of a starch paste reaches a predetermined concentration or more, a starch gel is formed by cooling it. Similarly to the viscosity, physical properties of this starch gel vary depending on the origin and production method of the starch, and the starch is used in various foods taking features of this gelling physical properties into consideration. Some methods of measuring physical properties of the gel are practically used, and one of them is a method of measuring using a rheometer. The gel forming ability can be measured by the following method using a rheometer. For example, a starch paste is filled in a casing, heated, and then refrigerated for 16 hours or 21 days (for example, at about 5° C.) and, after returning to room temperature (for example, at about 25° C.), physical properties of the gel are measured by a rheometer.

The specific measuring method using a rheometer is as described in the aforementioned 1.2.2. In the case where the enzyme-treated starch granules of the present invention are prepared from an untreated wheat starch and have not been subjected to either a chemical modification or a physical treatment, it is preferred that the enzyme-treated wheat starch granules have a rupture stress which accounts for 110% or more and 300% or less of the rupture stress of the granules of the untreated wheat starch, or has a Young's modulus which accounts for 110% or more and 500% or less (110% or more and 330% or less in an embodiment) of the Young's modulus of the untreated wheat starch.

In the case were the enzyme-treated starch granules of the present invention are prepared from an untreated corn starch and have not been subjected to either a chemical modification or a physical treatment, it is preferred that the enzyme-treated corn starch granules have a rupture stress which accounts for 110% or more and 300% or less of the rupture stress of the granules of the untreated corn starch, or has a Young's modulus which accounts for 110% or more and 500% or less (330% or less in an embodiment) of the Young's modulus of the granules of the untreated corn starch.

In the case where the enzyme-treated starch granules of the present invention are prepared from an untreated cassava starch and have not been subjected to either a chemical modification or a physical treatment, it is preferred that the enzyme-treated cassava starch granules have a rupture stress which accounts for 110% or more and 300% or less of the rupture stress of the granules of the untreated cassava starch, or has a Young's modulus which accounts for 110% or more and 500% or less (330% or less in an embodiment) of the granules of the untreated cassava starch.

In the case where the enzyme-treated starch granules of the present invention are prepared from an untreated wheat starch and have not been subjected to either a chemical modification or a physical treatment, and the untreated starch is a wheat starch, the rupture stress of the obtained enzyme-treated starch granules is preferably about 150 g or more, more preferably about 160 g or more, still more preferably about 170 g or more particularly preferably about 180 g or more, and most preferably about 200 g or more. In the case where the untreated starch is a wheat starch, although there is no particular upper limit of the rupture stress of the obtained enzyme-treated starch granules, the rupture stress of the obtained enzyme-treated starch granules can be, for example, about 450 g or less, about 440 g or less, about 430 g or less, about 420 g or less, about 410 g or less, or about 400 g or less.

In the case where the untreated starch is a corn starch and neither a chemical modification nor a physical treatment is carried out, the rupture stress of the obtained enzyme-treated starch granules is preferably about 210 g or more, more preferably about 220 g or more, still more preferably about 230 g or more, and most preferably about 240 g or more, and, in one embodiment, is 250 g or more. In the case where the untreated starch is a corn starch and neither a chemical modification nor a physical treatment is carried out, although there is no particular upper limit of the rupture stress of the obtained enzyme-treated starch granules, the rupture stress of the obtained enzyme-treated starch granules can be, for example, about 450 g or less, about 440 g or less, about 430 g or less, about 420 g or less, about 410 g or less, or about 400 g or less.

In the case where the untreated starch is a cassava starch and neither a chemical modification nor a physical treatment is carried out, the rupture stress of the obtained enzyme-treated starch granules is preferably about 55 g or more, more preferably about 60 g or more, still more preferably about 65 g or more, and most preferably about 70 g or more. In the case where the untreated starch is a cassava starch and neither a chemical modification nor a physical treatment is carried out, although there is no particular upper limit of the rupture stress of the obtained enzyme-treated starch granules, the rupture stress of the obtained enzyme-treated starch granules can be, for example, about 150 g or less, about 140 g or less, about 130 g or less, about 120 g or less, about 110 g or less, or about 100 g or less.

In the case where the untreated starch is a wheat starch and neither a chemical modification nor a physical treatment is carried out, the Young's modulus of the obtained enzyme-treated starch granules is preferably about $5.0 \times 10^6$ dyn/cm$^2$ or more, more preferably about $5.2 \times 10^6$ dyn/cm$^2$ or more, still more preferably about $5.4 \times 10^6$ dyn/cm$^2$ or more, and most preferably about $5.6 \times 10^6$ dyn/cm$^2$ or more. In the case where the untreated starch is a wheat starch and neither a chemical modification nor a physical treatment is carried out, although there is no particular upper limit of the Young's modulus of the obtained enzyme-treated starch granules, the Young's modulus of the obtained enzyme-treated starch granules can be, for example, about $8.0 \times 10^6$ dyn/cm$^2$ or less, about $7.5 \times 10^6$ dyn/cm$^2$ or less, about $7.0 \times 10^6$ dyn/cm$^2$ or less, about $6.9 \times 10^6$ dyn/cm$^2$ or less, about $6.8 \times 10^6$ dyn/cm$^2$ or less, or about $6.7 \times 10^6$ dyn/cm$^2$ or less.

In the case where the untreated starch is a corn starch and neither a chemical modification nor a physical treatment is carried out, the Young's modulus of the obtained enzyme-treated starch granules is preferably about $6.0 \times 10^6$ dyn/cm$^2$ or more, more preferably about $6.2 \times 10^6$ dyn/cm$^2$ or more, still more preferably about $6.3 \times 10^6$ dyn/cm$^2$ or more, and most preferably about $6.5 \times 10^6$ dyn/cm$^2$ or more. In the case where the untreated starch is a corn starch and neither a chemical modification nor a physical treatment is carried out, although there is no particular upper limit of the Young's modulus of the obtained, enzyme-treated starch granules, the Young's modulus of the obtained, enzyme-treated starch granules can be, for example, about $9.0 \times 10^6$ dyn/cm$^2$ or less, about $8.9 \times 10^6$ dyn/cm$^2$ or less, about $8.8 \times 10^6$ dyn/cm$^2$ or less, about $8.7 \times 10^6$ dyn/cm$^2$ or less, about $8.6 \times 10^6$ dyn/cm$^2$ or less, or about $8.5 \times 10^6$ dyn/cm$^2$ or less.

In the case where the untreated starch is a cassava starch and neither a chemical modification nor a physical treatment is carried out, the Young's modulus of the obtained enzyme-treated starch granules is preferably about $5.2 \times 10^5$ dyn/cm$^2$ or more, more preferably about $5.4 \times 10^5$ dyn/cm$^2$ or more still more preferably about $5.6 \times 10^5$ dyn/cm$^2$ or more, and most preferably about $5.8 \times 10^5$ dyn/cm$^2$ or more. In the case where the untreated starch is a cassava starch and neither a chemical modification nor a physical treatment is carried out, although there is no particular upper limit of the Young's modulus of the obtained enzyme-treated starch granules, the Young's modulus of the obtained enzyme-treated starch granules can be, for example, about $2.7 \times 10^6$ dyn/cm$^2$ or less, about $2.5 \times 10^6$ dyn/cm$^2$ or less, about $2.4 \times 10^6$ dyn/cm$^2$ or less, about $2.3 \times 10^6$ dyn/cm$^2$ or less, about $2.2 \times 10^6$ dyn/cm$^2$ or less, about $2.0 \times 10^6$ dyn/cm$^2$ or less, about $1.8 \times 10^6$ dyn/cm$^2$ or less, about $1.6 \times 10^6$ dyn/cm$^2$ or less, about $1.5 \times 10^6$ dyn/cm$^2$ or less, about $1.4 \times 10^6$ dyn/cm$^2$ or less, about $1.3 \times 10^6$ dyn/cm$^2$ or less, about $1.2 \times 10^6$ dyn/cm$^2$ or less, or about $1.1 \times 10^6$ dyn/cm$^2$ or less.

In a specific embodiment, in the case where the untreated starch is a wheat starch and neither a chemical modification nor a physical treatment is carried out, the obtained enzyme-treated starch granules have breakdown (about 100 BU or more), and a rupture stress of about 150 to about 450 (g) or a Young's modulus of about 5,000,000 to about 8,000,000 (dyn/cm$^2$).

In a specific embodiment, in the case where the untreated starch is a corn starch and neither a chemical modification nor a physical treatment is carried out, the obtained enzyme-treated starch granules have breakdown (about 100 BU or more), and a rupture stress of about 210 to about 450 (g) (about 220 to about 450 (g) in one embodiment) or a Young's modulus of about 6,000,000 to about 9,000,000 (dyn/cm$^2$).

In a specific embodiment, in the case where the untreated starch is a cassava starch and neither a chemical modification nor a physical treatment is carried out, the obtained enzyme-treated starch granules have breakdown (about 100 BU or more), and a rupture stress of about 55 to about 150 (g) or a Young's modulus of about 520,000 to about 2,700,000 (dyn/cm$^2$) (about 520,000 to about 1,600,000 (dyn/cm$^2$) in one embodiment).

Also, in the case where a chemically modified starch or a physically treated starch is used as starch granules, or in the case where a chemical modification or a physical treatment is carried out after an enzymatic treatment, an improvement in gel forming ability can be obtained similarly to the above.

3.3 Enzyme-Treated Starch Granules in which Hydroxyl Groups at Positions 2, 3 and 6 of Glucose Residues are not Modified In the case where the enzyme-treated starch granules of the present invention are prepared from an untreated starch, a physically treated starch or a bleached starch and have not been subjected to chemical modification, since the enzyme-treated starch granules of the present invention have not been subjected to an artificial chemical treatment, hydroxyl groups at the positions 2, 3 and 6 of glucose residues are not modified as compared with a native starch (i.e., untreated starch). A starch, in which hydroxyl groups at the positions 2, 3 and 6 of glucose residues are modified, refers to a modified starch (also referred to as a chemically modified starch) subjected to so-called chemical modification by an industrial process. According to the ministerial ordinance to revise a part of the Ordinance For Enforcement of the Food Sanitation Act notified in Ministry of Health and Welfare Notification No. 485 dated Oct. 1, 2008, the following 11 items of modified starches will be dealt as an additive:
acetylated distarch adipate;
acetylated oxidized starch;
acetylated distarch phosphate;
starch sodium octenyl succinate;
starch acetate;
oxidized starch;
hydroxypropyl distarch phosphate;
hydroxypropyl starch;
distarch phosphate;
monostarch phosphate; and
phosphated distarch phosphate. In Ministry of Health and Welfare Notification No. 485, a method for a purity test of these starches is described. Therefore, it is possible to judge that a sample starch is not a starch subjected to a chemical modification, for example, by analyzing various chemical substances in the sample starch, such as adipic acid groups, acetyl groups, and carboxyl groups in accordance with a method for a purity test of the above various modified starches described in Ministry of Health and Welfare Notification No. 485 dated Oct. 1, 2008, comparing with the results of analysis of a raw material native starch carried out for comparison reference, and confirming there is no increase in the content of corresponding various chemical substances. Particularly, it is possible to judge that a sample starch is not a starch subjected to a chemical modification, by measuring the content of adipic acid groups, the content of acetyl groups, the content of carboxyl groups, the content of vinyl acetate, the content of octenyl succinic acid groups, the content of hydroxypropyl groups, and the content of propylene chlorohydrins, and confirming that the contents of them do not increase as compared with those of the raw material native starch. It is preferred to use the content of adipic acid groups, the content of acetyl groups, the content of carboxyl groups, the content of octenyl succinic acid groups, the content of hydroxypropyl groups, and the content of propylene chlorohydrins as evaluation criteria. It is recognized that a bleached starch subjected to a bleaching treatment using sodium hypochlorite is distributed as a food. It is also possible to judge this bleached starch by measuring the content of carboxyl groups using a method for a purity test similar to that in the above oxidized starch. The chemical modified starch other than the above modified starches of 11 items cannot be used in a food since it is not recognized by the Food Sanitation Law of JAPAN. Therefore, the chemically modified starch other than the above 11 items are not basically used in JAPAN and are not distributed. Accordingly, practically, in the case of confirming whether or not hydroxyl groups at the 2-, 3- and 6-positions of a glucose residue of the starch of the invention of the present application are modified, it is not necessary to confirm whether or not a chemical modification other than the above chemical modification has been subjected.

In the present description, in the case where "hydroxyl groups at the positions 2, 3 and 6 of glucose residues are not modified", it is preferred that all hydroxyl groups at the positions 2, 3 and 6 of glucose residues are not modified. However, in the case where hydroxyl groups are subjected to some modification in a natural state, some modifications may be contained. In this case, based on the total number of hydroxyl groups at the positions 2, 3 and 6 of glucose residues, preferably about 70% or more, more preferably about 80% or more, still more preferably about 90% or more, particularly preferably about 95% or more, about 96% or more, about 97% or more, about 98% or more, about 99% or more, or about 99.5%, and most preferably about 100% of hydroxyl groups are not modified.

3.4 Filtration Velocity

The enzyme-treated-etherified starch granules which are obtained by performing an enzyme treatment, removing the enzyme and the eluted carbohydrate by filtration or the like, and etherifying the enzyme-treated starch granules have faster filtration velocity at the time of filtration and a larger apparent specific gravity, compared with etherified starch granules which have not been enzyme-treated. The enzyme-treated-esterified starch granules which are obtained by performing an enzyme treatment, removing the enzyme and the eluted carbohydrate by filtration or the like, and esterifying the enzyme-treated starch granules have faster filtration velocity at the time of filtration and a larger apparent specific gravity, compared with an esterified starch granules which have not been enzyme-treated. That is, solid-liquid separation of the reaction liquid used for the chemical modification can be performed more easily than starch granules which have not been enzyme-treated. Filtration velocity can be measured with any of methods which are conventionally known in the art. The relationship between the degree of the enzyme-treatment and the filtration velocity is not necessarily linear. However, there is a tendency that the filtration velocity becomes faster when the degradation ratio of the starch granule by the enzyme-treatment (i.e., starch removal ratio) is higher. An effect to make filtration velocity faster is seen in the case even when the degradation ratio of the starch granule is about 2% by weight. The degradation ratio of the starch by the enzyme-treatment can be suitably selected. When it is intended to conduct a chemical modification after enzyme treatment, the lower limit of the starch degradation ratio is preferably about 2% by weight or more, more preferably about 3% by weight or more, and particularly preferably about 5% by weight or more; and the upper limit of the starch degradation ratio is preferably about 20% by weight or less, more preferably about 17% by weight or less, and particularly preferably about 15% by weight or less. When the degradation ratio is too low, the effect of the enzyme-treatment (improvement of the filtration velocity or the like) may not be achieved. When the degradation ratio is too high, a yield may be too low, and cost may be too high.

3.5 Precipitation Properties

The enzyme-treated-etherified starch granules are precipitated faster than etherified starch granules which have not been enzyme-treated, and the interface of the supernatant and thick suspension part of their suspension liquid is easily lowered. This is a characteristic obtained not only when it is precipitated from the reaction solution after the chemical modification but also when it is resuspended into water. The enzyme-treated-esterified starch granules are precipitated faster than esterified starch granules which have not been enzyme-treated, and the interface of the supernatant and thick suspension part of their suspension liquid is easily lowered. This is a characteristic obtained not only when it is precipitated from the reaction solution after the chemical modification but also when it is resuspended into water. Precipitation properties can be confirmed by a method conventionally known in the art.

3.6 Velocity of Increasing Viscosity

When heated in water, the enzyme-treated-etherified starch granules have higher velocity of increasing viscosity than etherified starch granules which have not been enzyme-treated, and therefore, a sufficiently gelatinized starch paste can be obtained in a shorter time period. When heated in water, the enzyme-treated-esterified starch granules have higher velocity of increasing viscosity than esterified starch granules which have not been enzyme-treated, and therefore, a sufficiently gelatinized starch paste can be obtained in a shorter time period. Velocity of increasing viscosity can be confirmed by a method conventionally known in the art.

Figure 2:
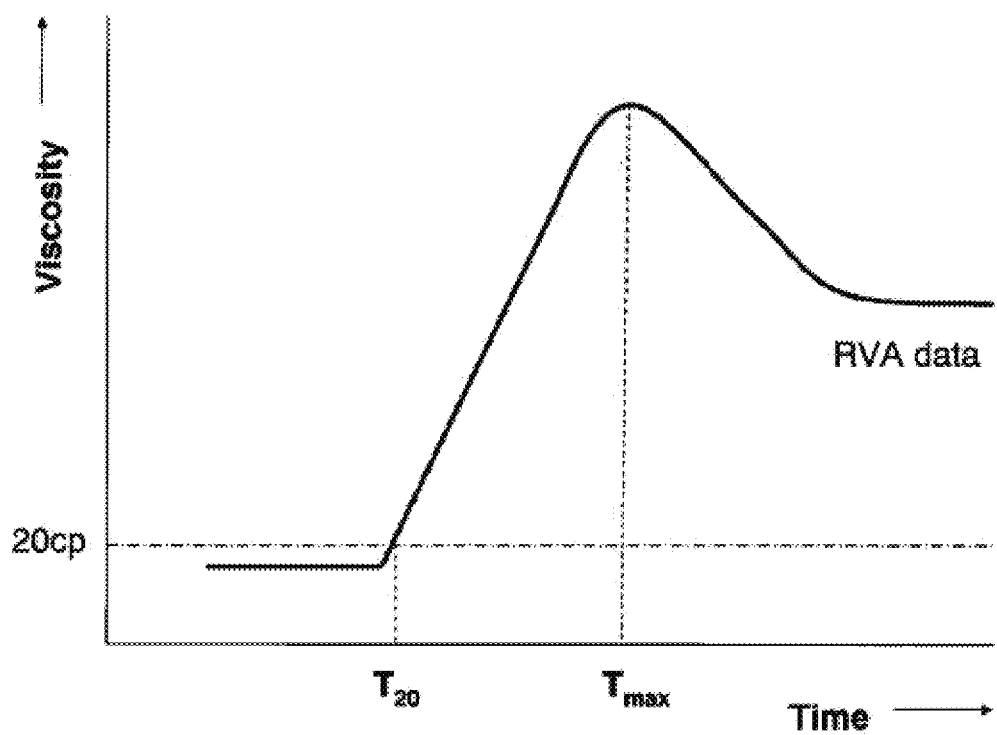
FIG. 2 is a graph schematically showing an example of RVA data and a viscosity increment measuring interval. A viscosity increment was measured every four seconds between $T_{20}$ (the time of reaching 20 cp) and $T_{max}$ (the time of reaching the highest viscosity). The maximum value of them was deemed as a "maximum viscosity increase".

An example of an indicator for the velocity of increasing viscosity is a maximum viscosity increase. A maximum viscosity increase can be measured as follows. A maximum viscosity increase is analyzed with RVA (Rapid visco analyzer "TEC MASTER", Perten) using 7.5% by weight starch suspension. Just after initiation of the measurement, it is heated to 50° C. and thereafter, the temperature is raised to 95° C. in 4.5° C./min with rotating at 120 rpm. Meanwhile, the starch is gelatinized and viscosity is increased. The amount of increase of viscosity were measured every four seconds from a time point when the viscosity arrived at 20 cp until a time point when the viscosity arrived at the highest viscosity, and the maximum value of them was considered as the "maximum viscosity increase". An example of RVA data and a viscosity increment measuring interval were schematically showed in FIG. 2.

3.7 Retrogradation Resistance

The enzyme-treated-etherified starch granules can form a gel which is excellent in retrogradation resistance and transparency, similarly to an etherified starch granule. The enzyme-treated-esterified starch granules can form a gel which is excellent in retrogradation resistance and transparency, similarly to an esterified starch granule.

The retrogradation resistance can be confirmed, for example, by the following method. A starch paste is prepared so that the concentration of the starch is 20% by weight on the dry matter basis, and then the starch paste is filled in a Krehalon casing having a folding width of 45 mm. This starch paste filled in the casing is heated to 90° C. at 1°

C./min and maintained at 90° C. for 30 minutes. Then the starch paste is left to cool in a constant-temperature water bath at 20° C. for 30 minutes and then cooled to 5° C. in a refrigerator. After cooling, it is refrigeration stored at 5° C. for 21 days, then it is left at room temperature (about 25° C.) for 4 hours to return the temperature of it to room temperature, and then it is assessed by a skilled person to determine the presence and absence of retrogradation resistance by the state of cloudiness and touch feeling when touched with a hand. Gel which maintains the transparency and elasticity is considered as having retrogradation resistance, and gel which became clouded or has poor elasticity or feeling of fragility is considered as having no retrogradation resistance. This method for confirming retrogradation resistance is a method conventionally known before the filing of the original application from which the present application claims priority.

3.8 Transparency

The enzyme-treated-etherified starch granules can form a gel which is excellent in retrogradation resistance and transparency similarly to an etherified starch granule. The enzyme-treated-esterified starch granules can form a gel which is excellent in retrogradation resistance and transparency similarly to an esterified starch granule.

The transparency can be confirmed, for example, by the following method. A starch paste is prepared so that the concentration of the starch is 20% by weight on the dry matter basis, and the paste is heated to 90° C. at 1° C./min and maintained at 90° C. for 30 minutes. Then the starch paste is poured into a 100 ml beaker, left at room temperature for 10 minutes, and then assessed by a skilled person to determine the transparency visually. Gel having transparency is considered as having transparency, and gel which slightly lacks transparency is considered as being slightly opaque, and opaque in white is considered as being opaque. This method for confirming transparency is a method conventionally known before the filing of the original application from which the present application claims priority.

3.9 Film Property

The enzyme-treated-etherified starch granules and the enzyme-treated-esterified starch granules are excellent in film property. The enzyme treatment performed in advance does not adversely affect etherification treatment and esterification treatment.

The film property can be confirmed, for example, by the following method. A starch paste is prepared so that the concentration of the starch is 15% by weight on the dry matter basis, and the paste is heated to 90° C. at 1° C./min and maintained at 90° C. for 30 minutes. 15 g of the starch paste is placed in a petri dish, the paste is spread as thinly as possible, and left in a dryer at 50° C. for 24 hours. 24 hours later, it is confirmed that it is sufficiently dried, and the transparency and the feeling of touch when touched with a hand are confirmed by skilled persons. Films which have transparency and which can be felt having elongation when touched with a hand is considered as having film property, and films which became to be clouded in white, or had a feeling of fragility when touched with a hand is considered as having no film property. This method for confirming film property is a method to confirm that a starch particle has a property capable of forming transparent and flexible film, and is a method conventionally known before the filing of the original application from which the present application claims priority.

4. Food of the Present Invention

In a specific embodiment, the food of the present invention is a food produced by a method including the steps of treating starch granules with an enzyme at a temperature of about 10° C. or higher and about 70° C. or lower to obtain an enzyme-treated starch granules; mixing a food material, the enzyme-treated starch granules and water to obtain a mixture; heating the mixture thereby gelatinizing the enzyme-treated starch granules in the mixture; and cooling the mixture containing the gelatinized enzyme-treated starch thereby gelling the starch to obtain a starch gel-containing food.

In another specific embodiment, the food of the present invention is a heat cooked starch-containing food prepared from enzyme-treated starch granules having a high viscosity and a gel forming ability. In another specific embodiment, the starch-containing food of the present invention is a food produced by a method including mixing a food material with the enzyme-treated starch granules, and then heating the mixture.

In the present description, the starch gel-containing food refers to a food containing a starch gel. If the food contains the starch gel, it is not necessary for the food to be entirely in a gel form. For example, in the case of gelatinous foods such as custard pudding; and gel-like traditional Japanese-style confectioneries such as kudzu starch cake and Uiro, entire foods form a gel. In the case of fat or oil-containing foods such as whipping cream and ice cream; and sauces such as meat sauce, foods are not entirely in a gel form but contain a micro starch gel, and are therefore included in the starch gel-containing food of the present invention. Also, bakeries and Western-style confectioneries are included in the starch gel-containing food of the present invention since they contain a starch gel with the decreased water content which was obtained by once forming a gel during the production process, and baking the gel.

In a specific embodiment, the food of the present invention can be prepared by using enzyme-treated starch granules. The starch produced by the method of the present invention can be utilized in the same application as in a conventional starch. By utilizing the enzyme-treated starch granules of the present invention in a food, physical properties and texture of the food are altered. The enzyme-treated starch granules of the present invention can be used in almost all of compositions for eating and drinking or compositions for food additives prepared by utilizing a conventional starch. In the food of the present invention, any material used usually in the objective composition and food can be used as long as an excellent effect obtained by the enzyme-treated starch granules is not impaired. In a preferred embodiment, the starch of the present invention forms a gel in the food of the present invention.

In the case where the enzyme-treated starch granules of the present invention is utilized in a high moisture content type food, it imparts a body, imparts natural elasticity by a strong gel forming ability, and also imparts appropriate smooth texture in mouth. The high moisture content type food refers to a food in which the amount of moisture per 100 g of the edible portion is more than 40 g in a state at the time of eating. Examples of the high moisture content type food include, for example, traditional Japanese-style confectioneries, fat or oil-containing foods, gelatinous foods, fish meat and animal meat processed foods, salsa and sauces, and noodles.

In the case where the enzyme-treated starch granules of the present invention are utilized in a low moisture content type food, it is possible to impart smooth texture with nice melt in mouth. The low moisture content type food refers to a food in which the amount of moisture per 100 g of the edible portion is 40 g or less in a state at the time of eating. Examples of the low moisture content type food include, for example, bakeries, Western-style confectioneries, fried foods, and jelly candies.

As described above, the high moisture content type food and the low moisture content type food are classified by the amount of moisture, per 100 g of the edible portion, which is more than 40 g, or 40 g or less. Provided that the food in which the amount of moisture per 100 g of the edible portion is around 40 g (35 to 50 g) may sometimes exhibit contradicting physical properties depending on the form, even in the case of the same amount of moisture. Also, in the case of the fried food, it is judged by the amount of moisture for the coating part in which core food materials have been removed.

The amounts of water per 100 g of the edible portion of various foods are exemplified below (extract from Standard Tables of Food Composition in Japan (Fifth Revised and Enlarged Edition); the number in parenthesis denotes the amount of moisture):
(1) Bakeries: white table bread (38.0 g), hard biscuit (2.6 g), pie pastry (32.0 g), Eisei-boro (4.5 g);
(2) Traditional Japanese-style confectioneries: Uiro (54.5 g), Kudzu-manju (45.0 g), Daifuku-mochi (41.5 g);
(3) Western-style confectioneries: sponge cake (32.0 g), Kasutera (25.6 g), hot cake (40.0 g);
(4) Fat- or oil-containing foods: whipping cream (milk fat type, 42.1 g), whipping cream (vegetable fat type, 41.2 g), ice creams (ice milk: 65.6 g, lactic ice: 60.4 g);
(5) Gelatinous foods: custard pudding (74.1 g);
(6) Fish meat and animal meat processed foods: Sumaki-kamaboko (75.8 g), Yakinuki-kanaboko (72.8 g), Vienna sausage (53.0 g);
(7) Salsa and sauces: worcester sauce (61.7 g), meat sauce (78.8 g), Thousand Island dressing (44.1 g); and
(8) Jelly candies: jelly candy (16 g), jelly beans (9.5 g).

By using the enzyme-treated starch granules of the present invention in these foods, the following physical properties, for example, are improved as compared with the case of using a conventional starch:
(1) In bakeries, textures with softness and nice melt in mouth is imparted. Examples of bakeries include breads, cookies, biscuits, pizza crusts, pie pastries, corn cups for ice creams, pastries of Monaka, and puff of cream puff.
(2) In traditional Japanese-style confectioneries, appropriate hardness, brittleness, and appropriate viscoelasticity and sticky textures are imparted. Examples of traditional Japanese-style confectioneries include kudzu starch cake, Uiro, and Manju.
(3) In Western-style confectioneries, improvement of volumes by nice puffing after baking as well as soft and nice textures are imparted. Examples of Western-style confectioneries include sponge cake, chiffon cake, Kasutera, Madeleine, financier, pound cake, and Swiss roll.
(4) In fat- or oil-containing foods, while maintaining appropriate body and shape retention, nice melt in mouth and smooth texture is imparted. Examples of the fat- or oil-containing food include custard cream, flour paste, filling, whipping cream, and ice creams (for example, ice milk, lactic ice).
(5) In gelatinous foods, while maintaining sticky and chewy, nice melt in mouth and smooth texture is imparted. Examples of the gelatinous food include jelly, pudding, mousse, yogurt, and goma-dofu.
(6) In fish meat and animal meat processed foods, while having elasticity with nice chewiness, the effect of small change with time is imparted. Examples of fish meat and meat processed foods include kamaboko and sausage.
(7) In salsa and sauces, while having nice body and shape retention, properties of being less likely to cause dropping because of nice adhesion onto a food as well as less stickiness and thread-forming sensation, and smooth textures are imparted. Examples of salsa and sauces include salsa for split and broiled fish, glaze for mitarashi dango, fruit sauce, white sauce, and dressing.
(8) In fried foods, crispy light texture is imparted. Examples of fried foods include tempura and fried prawn.
(9) In noodles, sticky texture rich in chewiness is imparted. Examples of noodles include udon, somen, hiyamugi, Chinese noodles, buckwheat noodles, macaroni, and spaghetti.
(10) In jelly candies, while having appropriate elasticity, nice melt in mouth and smooth texture is imparted. Examples of jelly candies include jelly candy and jelly beans.

In the food of the present invention, the enzyme-treated starch granules of the present invention can be used in the same amount as that of the starch which has been conventionally used in the food. A conventional starch may be used as a part and the remainder may be replaced by the enzyme-treated starch granules of the present invention. The enzyme-treated starch granules of the present invention preferably accounts for about 50% by weight or more, more preferably about 60% by weight or more, still more preferably about 70% by weight or more, further preferably about 80% by weight or more, particularly preferably about 90% by weight or more, and most preferably 100% by weight, of a usual use amount of the starch. In other word, most preferably, the entire amount of a conventional starch is replaced by the enzyme-treated starch of the present invention.

5. Method for Producing Starch Gel-Containing Food

In a specific embodiment, the method for producing a starch gel-containing food of the present invention includes the steps of treating starch granules with an enzyme at a temperature of about 10° C. or higher and about 70° C. or lower to obtain enzyme-treated starch granules; mixing a food material, the enzyme-treated starch granules and water to obtain a mixture; heating the mixture thereby gelatinizing the enzyme-treated starch granules in the mixture; and cooling the mixture containing the gelatinized enzyme-treated starch thereby gelling the starch to obtain a starch gel-containing food. In the production of a conventional food, starch granules are not subjected to an enzymatic treatment during the food production process.

The step of treating starch granules with an enzyme at a temperature of about 10° C. or higher and about 70° C. or lower to obtain enzyme-treated starch granules can be carried out as described in detail in the aforementioned "2.2 Enzyme Reaction". As described above, the starch granules can be starch granules of an untreated starch, a physically treated starch or a chemically modified starch. In the case where it is preferable to obtain enzyme-treated starch granules which is dealt as a food, starch granules are starch granules of an untreated starch, a physically treated starch or a bleached starch, and the starch granules are not subjected to a chemical modification in any stage until a starch gel-containing food is obtained using the starch granules. In a specific embodiment, the starch granule is a starch granule of an untreated starch or a physically treated starch, the step of chemically modifying the enzyme-treated starch granules is further included, and the chemically modified enzyme-treated starch granules are mixed with the food material and water. In another specific embodiment, the starch granules are starch granules of an untreated starch or a chemically modified starch, the step of physically treating the enzyme-treated starch granules is further included, and the physically treated enzyme-treated starch granules are mixed with the food material and water.

Next, a mixture is obtained by mixing a food material, the enzyme-treated starch granules and water. A mixing method and a mixing ratio of the food material, the enzyme-treated starch granules and water can be a mixing method and a mixing ratio in accordance with a usual method for producing the objective food.

Next, the mixture is heated thereby gelatinizing the enzyme-treated starch in the mixture. The heating can be heat cooking. Heating can be carried out under the same conditions as those of heat cooking in a usual method for producing the objective food.

Next, the mixture containing the gelatinized enzyme-treated starch is cooled, thereby gelling the starch to obtain a starch gel-containing food. Cooling may be carried out by leaving the mixture after heating at room temperature, or carried out in a refrigerator or the like.

In the embodiment in which the enzyme-treated starch granules of the present invention is used the food of the present invention can be produced in the same method as in the case of a usual starch, except that the enzyme-treated starch granules are used. The method for producing the starch-containing food of the present invention includes the steps of adding enzyme-treated starch granules to a food material and mixing them; and heat cooking the mixture.

The enzyme-treated starch granules of the present invention have excellent viscosity and gel forming ability as compared with a conventional untreated starch. Therefore, by adding the enzyme-treated starch granules of the present invention to the food material, mixing them and heat cooking the mixture, this enzyme-treated starch granules are gelatinized and then cooled to form a gel. Accordingly, the obtained heat cooked material is provided with excellent physical properties (for example, excellent body, natural elasticity, nice melt in mouth, smooth texture, sticky texture, and soft texture) as compared with the heat cooked material in which a conventional untreated starch is used. In the present description, the food may also be a beverage.

In the present description, "heat cooking" refers to heating of a mixture of a food material and a starch. Preferably, heat cooking can be heating at a collapse temperature or higher of starch granules. For example, the mixture of a food material and a starch can be heated at about 70° C. or higher, about 80° C. or higher, about 90° C. or higher or about 95° C. or higher. Preferably, heat cooking is carried out at a temperature at which excess denaturation of the food material and the starch does not arise. For example, the mixture of a food material and a starch can be heated at about 200° C. or lower, about 150° C. or lower, about 130° C. or lower or about 110° C. or lower. Heat cooking is carried out for a usual heat cooking time of the objective food.

Heat cooking is preferably carried out in the presence of some degree of moisture. Usually, when starch granules are heated in the presence of a predetermined amount or more of water, swelling arises, transparency increases and viscosity increases. When the food material contains too much moisture, it is not necessary to add water to the mixture of a food material and a starch. However, when the food material contains small amount of moisture, it is preferred to add water to the mixture of a food material and a starch. It is noted that in the case of a food which does not contain food materials other than water and a starch, like a sugar-free kuzuyu, water is considered as the food material.

Heat cooking can be a part of the method for producing the objective food. For example, in the case of a gelatinous food such as jelly, it, can be heat cooled after cooking at a temperature of, for example, about 5 to 10° C.

6. Explanation of Sequence

SEQ. ID NO: 1 is a nucleotide sequence encoding α-amylase derived from *Aspergillus oryzae*;
SEQ ID NO: 2 is an amino acid sequence of α-amylase derived from *Aspergillus oryzae*;
SEQ ID NO: 3 is a nucleotide sequence encoding α-amylase derived from *Aspergillus niger*;
SEQ ID NO: 4 is an amino acid sequence of α-amylase derived from *Aspergillus niger*;
SEQ ID NO: 5 is a nucleotide sequence encoding amyloglucosidase derived from *Aspergillus niger*;
SEQ ID NO: 6 is an amino acid sequence of amyloglucosidase derived from *Aspergillus niger*;
SEQ ID NO: 7 is a nucleotide sequence encoding isoamylase derived from *Flavobacterium* sp.;
SEQ ID NO: 8 is an amino acid sequence of isoamylase derived from *Flavobacterium* sp.;
SEQ ID NO: 9 is a nucleotide sequence encoding isoamylase derived from *Pseudomonas amyloderamosa*;
SEQ ID NO: 10 is an amino acid sequence of isoamylase derived from *Pseudomonas amyloderamosa*;
SEQ ID NO: 11 is a nucleotide sequence encoding α-glucosidase derived from *Aspergillus niger*;
SEQ ID NO: 12 is an amino acid sequence of α-glucosidase derived from *Aspergillus niger*;
SEQ ID NO: 13 is a nucleotide sequence encoding cyclodextrin glucanotransferase derived from *Paenibacillus macerans* (also classified as *Bacillus macerans*).
SEQ ID NO: 14 is an amino acid sequence of cyclodextrin glucanotransferase derived from *Paenibacillus macerans* (also classified as *Bacillus macerans*).

7. Industrial Applications Except for Foods

As used in the present specification, the term "article" refers to a corporeal matter. That is, the term "article" refers to a matter which is corporeal and physically occupies a part of a space. The term "article" is used for a wide general concept encompassing not only matters having a constant form which is generally conceivable but also formless matters which do not have a constant form. The starch granules of the present invention can be used for the article for which a conventional synthetic macromolecule is widely used. The starch granules of the present invention may be used in the form of a granule, as it is, for various applications and also may be used in the form of a gel, after the granules are gelatinized and gelled, for various applications. Furthermore, the starch granules of the present invention may be used for an article, in the conditions where the form of the starch granules has been completely broken. When an article is prepared using the starch granules of the present invention, even if the form of the starch granule are completely broken, an article having various advantages such as high transparency of the article, high hardness, high viscosity or the like compared with the case where a conventional starch is used. In the article, the starch granules of the present invention are preferably comprised in the form of a starch granule. Examples of articles comprising the starch granules of the present invention in the form of a granule include a gel, a liquid and a solid. Examples of the applications wherein the starch granules are gelatinized and gelled, and used in the form of a gel include hydrogels, starch pastes, gel adhesives and the like. Examples of liquid applications include liquid coatings, liquid adhesives, and the like. Examples of solid applications include powders, films, sheets, molded article and the like. The term "film" refers to an article having smaller thickness compared with other dimensions and having thickness that is less than 0.25 mm. The term "sheet" refers to an article having smaller thickness compared with other dimensions and having thickness that is 0.25 mm or more. A solid application may also be a solid paint or a solid adhesive. The molded article may be a container, packaging material or the like. The article may also be used in an application which is the same as the application in which a starch, protein or the like, that is a natural macromolecule, is conventionally used, for example, a pharmaceutical drug, a quasi-drug, an agricultural chemical, a cosmetic or a fertilizer. The article of the present invention is preferably a biodegradable article. However, in the present specification, in a particular embodiment, the article is an article except for foods.

The enzyme-treated starch granules of the present invention can be preferably used for any applications in which a conventional starch granule is used. Particularly, the enzyme-treated-chemically modified starch granules of the present invention exert a particularly excellent effect in applications that are related to the filtration velocity, the precipitation speed or a viscosity increase of the starch granules. Particularly, the enzyme-treated-chemically modified starch granules of the present invention can be used for a hydrogel for hydraulic fracturing. For this purpose, it is required to prepare a large amount of hydrogel in a simple facility. In this regard, the enzyme-treated-chemically modified starch granules of the present invention have rapid filtration velocity and precipitation speed. Therefore, the enzyme-treated-chemically modified starch granules of the present invention are suitable for this purpose.

The term "pharmaceutical drug" refers to a substance which is intended to be used in diagnosis, treatment or prevention of a disease of a human or an animal, and which is neither an equipment, an instrument, a dental material, a medical material nor a sanitary material; or a substance which is intended to affect on a structure or function of the body of a human or an animal, and which is neither an equipment, an instrument, a dental material, a medical material nor a sanitary material. The definition of the pharmaceutical drug does not encompass quasi-drugs and the cosmetics.

A composition, production method and method for use of a pharmaceutical drug are known to those skilled in the art. The enzyme-treated starch granules of the present invention may be formulated as an additive in a pharmaceutical drug. When it is used as an additive in a pharmaceutical drug, it can be used in various applications such as an excipient, a gelling agent, a thickening agent, a binder, a lubricant and the like. Particularly, when the enzyme-treated-chemically modified starch granules of the present invention are used as a gelling agent, it provides such an advantage that it is gelatinized quickly, and a gel having a high viscosity is obtained. When the enzyme-treated-chemically modified starch granules of the present invention are used as a thickening agent, it provides such an advantage that the viscosity of the gel is high. When the enzyme-treated-chemically modified starch granules of the present invention are used as an excipient of a tablet or powder, an advantage that after it is administered it collapses quickly and it does not remain in the mouth.

Therefore, additive compositions for a pharmaceutical drug (for example, excipient compositions, gelling agent compositions, thickening agent compositions, binder compositions, and lubricant compositions) comprising the enzyme-treated starch granules (particularly the enzyme-treated-chemically modified starch granules) of the present invention has particularly remarkable advantages.

The term "quasi-drugs" refers to a substance whose purpose is prevention of nausea or other unpleasantness, or prevention of halitosis or body odor; prevention of a heat rash, erosion or the like; alopecia prevention, hair growth or hair removal; alternatively, control or prevention of a mouse, a fly, a mosquito, a flea or the like which is performed for the health of a human or an animal; and which is mild in their action to a human; and which is neither an equipment, an instrument, dental material, medical material nor sanitary material.

Compositions, production methods and methods for use of the quasi-drugs are known to those skilled in the art. The enzyme-treated starch granules of the present invention may be formulated as an additive for the quasi-drugs. When it is used as an additive in quasi-drugs, it can be used in various applications such as an excipient, a gelling agent, a thickening agent, a binder, a lubricant and the like. Particularly, when the enzyme-treated-chemically modified starch granules of the present invention are used as a gelling agent, it provides such an advantages that it is gelatinized quickly, and a gel is obtained. When the enzyme-treated-chemically modified starch granules of the present invention are used as a thickening agent, provides such an advantage that the viscosity of the gel is high. When the enzyme-treated-chemically modified starch granules of the present invention are used as an excipient of a tablet or powder, it provides such an advantage that it collapses quickly after taken and not remain in the mouth.

Therefore, additive compositions for quasi-drugs (for example, excipient compositions, gelling agent compositions, thickening agent compositions, binder compositions, and lubricant compositions) comprising the enzyme-treated starch granules (particularly the enzyme-treated-chemically modified starch granules) of the present invention has particularly remarkable advantages.

The biodegradable article of the present invention can be provided as biocompatible medical materials and medical devices comprising them.

In the present specification, the term "medical material" refers to a substance that can be applied to a human body directly for a purpose of treatment, and which is neither a pharmaceutical drug, a quasi-drug nor a medical device. Examples of the medical material include a material for implant, hemostatic agent, surgical adhesives, and coatings for artificial blood vessel. In Japan, the term "implant" sometimes refers to a dental implant. However, in the present specification, the term "implant" is not limited to a dental implant, but encompasses any implants which can be implanted in a body. In the present specification, the term "biocompatible" means that there is no toxicity and immunological rejection ability, and there is no adverse effect on the body. The biodegradable article of the present invention is preferably a biocompatible medical material. Compositions, production methods and methods for use of the medical material are known to those skilled in the art. When the enzyme-treated starch granules of the present invention are used as a medical material, their thickening property is high, and therefore, it is particularly effective.

In the present specification, the term "medical device" refers to a device that is applicable to various affected parts such as skin, muscle tissues and viscus tissues, for the purpose of treatment similarly to a medical material, and which was manufactured by combining the medical material and a separately prepared substrate, solvent, part or device. Examples of the medical device include, for example, artificial blood vessels, artificial organs, artificial skins and the like.

In both of the medical materials or medical devices of the present invention, the amount of the medical material applied to an affected part can be selected from a range that can coat the affected part depending on the region and the area of the affected part, the time period or term when gel-forming is required, or the like. In this context, the term "gel-forming" means that the medical material absorbs an effusion (i.e., a body fluid or blood) from an affected part and holds it such that the medical material is gelled at a surface contacting with the affected part. Due to the gel formation, it is possible to maintain the affected part a wet environment, and to promote skin formation, and at the same time, it is possible to give an environment wherein it is hard for a bacterium or the like to pass through. The enzyme-treated-chemically modified starch granules of the present invention are gelatinized more easily than conventional starch. Therefore, it is easy to absorb and hold an effusion from the affected part and thus the enzyme-treated-chemically modified starch granules of the present invention are particularly suitable for this application.

In the present invention, a medical material or a medical device comprising it may be prepared in a conventional method. For example, a medical material or a medical device comprising it may be prepared by: mixing the ingredients which are described in relation to the biodegradable article (i.e., (a) starch granules of the present invention, and (b) other macromolecule(s) and, if desired, various additives such as a plasticizer); performing sterilization treatment if necessary; filling in a predetermined container; and performing sterilization treatment. The medical material may be filled in an injectable container (such as syringe type container) or filled in a spray bottle with a propellant, if necessary, and may be applied to an affected part by injection or spray. In this case, an injectable container or a spray bottle comprising the medical material is a medical device of the present invention. Alternatively, the medical material may be applied to the substrate of a poultice or sealing agent to form an applied layer. In this case, the medical device comprising the medical material is the poultice (for example, a cataplasm or a plaster) or sealing agent. In one embodiment, an applied layer is laminated on the substrate, and further the applied layer is coated with a peelable protective sheet. At the time of use, the protective sheet is pealed and the applied layer is applied to an affected part.

The biodegradable article of the present invention may be a pharmaceutical drug additive consisting of materials containing the starch granules of the present invention. In recent years, a solid preparation which collapses or dissolves rapidly in oral cavity is developed as a dosage form which is easily taken by an elderly person, an infant or a patient having dysphagia, or a dosage form which can be taken without water. The starch granules used for the biodegradable article of the present invention have high swellability and nice melt in mouth. Therefore, the starch granules may be used in a collapse improvement agent in the tablets such as a pharmaceutical drug, supplement or the like, and the starch granules may be used for the purpose of improvement of melt in mouth. Furthermore, the enzyme-treated-chemically modified starch granules of the present invention are more easily gelatinized than conventional starches. Therefore, it is particularly suitable for this application. For example, the starch granules of the present invention may be utilized for an intraoral disintegratable tablet.

The biodegradable article of the present invention may be a composition for injection to form a hydrogel comprising a material wherein the material comprises the starch granules of the present invention or the material is prepared from the starch granules of the present invention. Treatment in which a water-soluble macromolecule is injected into a living body for the purpose of lubricating action of ligament, joint or the like, or improving resilience or softness of the skin, or for the purpose of prevention of adherence after the surgical operation is conventionally performed. The starch granules utilized in the biodegradable article of the present invention have high viscosity and high gelling ability and their biocompatibility is high. Therefore, it can be used as a material that will be gelled to become a hydrogel in a living body. The phrase "composition for injection to form a hydrogel" refers to a composition to be injected into a human or an animal to form a hydrogel in a living body. The term "hydrogel" refers to a colloid in which a dispersion phase (colloid) is bound to a continuous phase (water) to form a viscous jelly-like product. The hydrogel can be used for the purpose of lubricating action for ligament, joint or the like, improvement, of resilience or softness of the skin, prevention of adherence after a surgical operation, or the like. The enzyme-treated starch granules (particularly enzyme-treated-chemically modified starch granules) of the present invention are gelatinized more quickly than conventional starch. Therefore, it has an advantage that it is easy to prepare a composition for injection to form a hydrogel at the medical site immediately. Therefore, the composition for injection comprising the enzyme-treated starch granules of the present invention is particularly useful. The composition for injection of the present invention is: for example, mixed with water and other additives, if necessary; heated to make the starch gelatinized; and then injected into the body to form a hydrogel in the body. Alternatively, when the composition for injection of the present invention is injected into the body in a powdery state, it absorbs neighboring liquids to form a hydrogel. As described here, the composition for injection of the present invention comprising the starch granules of the present invention may be in a powder state or a suspension liquid state. The stability of the starch granules of the present invention is high not only in the state of powder but also in the state of suspension liquid. Therefore, there is no problem even if it is stored as a composition for injection for a long period of time. Formulations, production methods and methods for use of the compositions for injection may be easily understood by those skilled in the art.

The medical materials, medical devices and the pharmaceutical drug additives of the present invention are made from raw materials which are the starch granules of the present invention. Therefore, it is safe in human body and is excellent in biocompatibility and mechanical properties. The medical materials, medical devices and the pharmaceutical drug additives of the present invention can be provided in the form of a thread, a cloth, a nonwoven fabric, a film, a sheet, a tube, a capsule, a tablet or other molded article, paste, cream or a form of combination thereof.

The medical materials, medical devices and pharmaceutical drug additives of the present invention can be applied to various kinds of mammalian, for example, a domestic animal, a pet and the like in addition to human, and can be used effectively, particularly in the field of their health maintenance or internal medicinal medical care and surgical operation. The biodegradable article of the present invention can be biocompatible.

The biodegradable article of the present invention may be cosmetics or cosmetics additives, produced from materials containing the starch granules of the present invention.

The term "cosmetic" refers to a substance by which a skin or the like is treated with (for example, the substance is applied to the skin or the like) for the purpose of making a body clean, or making an appearance beautiful, and it does not correspond to a pharmaceutical drug or a quasi-drug.

The cosmetics and the cosmetic additives using the starch granules of the present invention are those obtained by making the starch granules of the present invention be comprised in water or a mixture of a cosmetically acceptable medium and water. The kind of the cosmetically acceptable medium is not particularly limited. The mixing ratio can be selected appropriately. Furthermore, in addition to the starch granules of the present invention and medium, an ingredient, an additive or the like which can be formulated in conventional cosmetics can be formulated appropriately to the cosmetics and cosmetic additives of the present invention. The starch granules of the present invention may be comprised in a state of a starch granule, in a gelatinized state, or in a suspended state, in the cosmetics or cosmetic additives.

Starch has been used as a cosmetic raw material conventionally. The enzyme-treated starch granules of the present invention can be used in cosmetics similarly to conventional starch.

The amount of the starch granules of the present invention formulated in cosmetics and cosmetic additives is preferably about 0.2% by weight to about 50% by weight, and more preferably about 0.5% by weight to about 30% by weight, on the basis of the total amount of the cosmetics and the cosmetic additives.

Furthermore, the starch granules of the present invention are excellent in a thickening effect, solution stability, and hydrophilicity improvement, and particularly the enzyme-treated-chemically modified starch granules of the present invention are further excellent in transparency and film property. Therefore, by adding the starch granules of the present invention to the cosmetics and cosmetic additives of the present invention, cosmetics and cosmetic additives having excellent properties in film formation ability, thickening effect, stability, moisture retention property and the like are obtained. The enzyme-treated starch granules of the present invention are based on starch which has been used for foods conventionally, and has high safety and high biocompatibility. Therefore, the resultant cosmetics and cosmetic additives have an excellent skin compatibility. Furthermore, the enzyme-treated-chemically modified starch granules of the present invention absorb the water of the circumstances and quickly increase viscosity. Therefore, it has a remarkable action as a cosmetic additive. Furthermore, the enzyme-treated-chemically modified starch granules of the present invention help improvement of the skin feeling of the cosmetic and moisture retention action of the cosmetic.

The cosmetics and the cosmetic additives of the present invention can be produced according to a conventional method. The form of the cosmetics and cosmetic additives of the present invention is not particularly limited, and can be, for example, a solution, emulsion, cream, gel, mousse, paste, solid, powder, or multilayer. The starch granules of the present invention which are a component of the cosmetics and cosmetic additives of the present invention can be used in a state of a gel or a sol by heating them to be gelatinized. Furthermore, it can be used in a dry state by further vaporizing moisture from the state of an aqueous solution, a gel, or a sol.

The kinds of the cosmetics of the present invention are not particularly limited. Examples of the cosmetics of the present invention include, for example, lotions, skin lotions, emulsions, creams, pack agent, cosmetic nutrient lotions, anti-sunburn cosmetics, face washes, makeup cosmetics, hair care products, body soaps, bath agents and fragrances.

Examples of the makeup cosmetics include, for example, foundation cosmetics, face powders, rouge for cheek, lipsticks, eye shadows, eyeliners, eyebrows, mascaras, manicures and the like.

Examples of the hair care products include, for example, shampoos, rinses, conditioners, hair treatments, hair growth stimulators, hair liquids, hair gels, hair coloring agents, hair creams, agents for permanent wave or color, bleaching agents and the like.

The kinds of the cosmetic additives of the present invention are not particularly limited. The starch granules of the present invention can be used as, for example, a thickening agent, a moisturizer, a disintegrating agent or the like, in a form of liquid, cream, powder, paste or the like.

Other additive ingredients which are used for cosmetics, quasi-drugs for external application or the like can be formulated, as needed, in the cosmetics and the cosmetic additives of the present invention, appropriately. Examples of other additive ingredients include, for example, oily raw materials (oils and fats, waxes, hydrocarbons, higher fatty acids, higher alcohols, esters, silicone-based oil, fluorinated oil and the like); powders (organic or inorganic natural powders, semisynthetic powders, synthetic powder, spherical microparticles and the like); coloring materials (organic synthetic dyes, inorganic pigments, natural colors, nacreous pigments, functional pigments, macromolecule powders, dyes, dye intermediates, and the like); moisturizers (polyethylene glycol, propylene glycol, 1,3-butylene glycol, hexylene glycol, glycerin, diglycerol, xylitol, maltitol, maltose, D-mannite, starch syrup, glucose, fructose, lactose, sodium chondroitin sulfate, sodium hyaluronate, sodium adenosine phosphate, sodium lactate, bile salt, pyrrolidone carboxylic acid, glucosamine polyhydric alcohol, acid mucopolysaccharide, collagen, sericin, fibroin, glycogen and the like); macromolecular compound (natural, semisynthetic or synthetic polymers); ultraviolet absorber (organic low molecular-based, organic macromolecular-based and inorganic-based ultraviolet absorption insulation agents); surfactants (nonionic, anionic, cationic, amphoteric, macromolecule-based or natural-based surfactants); antioxidants, sequestering agents, preservatives, organic solvents (ethanol, methanol and the like), flavoring agents (natural or synthetic perfumes, perfume oils and the like), deodorants, oxidizing agents, antioxidants, thickening agents, gelation accelerating agents, pH adjusting agents and the like.

Examples of the drug ingredients includes drugs for whitening (β-arbutin, α-arbutin, vitamin C derivatives, vitamin C and the like); drugs for hair growth (vasodilators, nutritional agents, female hormones, hair root activator and the like); anti-skin roughness drugs (anti-inflammatory drugs, astringents, cooling agent, vitamins, hormones, antihistamines and the like); drug for pimples (sebum suppressers, cuticle abrasion/solubilizing agents, antimicrobial agents and the like); drugs for dandruff/itch (cuticle abrasion/solubilizing agents, antiseborrheic drugs, antimicrobial agents, antiinflammatory agents, antipruritic agents, and the like); drugs for prevention of hircismus (antiperspirants, antimicrobial agents, deodorants, and the like); vitamins; proteins (collagen, sericin, fibroin or the like); hormone drugs; amino acids; blood circulation accelerating agents; cold sensation agents; antiperspirant; antimicrobial agents; skin activating agents; various extracted materials and extracts having a variety of pharmaceutical efficacy. These optional components can be formulated in the qualitative and quantitative range which would not adversely affect the objective and effect of the present invention. Furthermore, the above described ingredients are merely examples of the representative ingredients which can be used to obtain external preparation of the present invention. The ingredient(s) which can be formulated in the external preparation for skin of the present invention is not limited to these ingredients.

The biodegradable articles of the present invention can be prepared using the starch granules of the present invention alone, or using the combination of (a) the starch granules of the present invention and (b) other macromolecular materials.

Other macromolecular material (b) which can be used for the production of the biodegradable article of the present invention do not always need to have biodegradability. When a macromolecular material which does not have biodegradability is used, only the starch of the present invention degrades, and other parts remain without degradation. Examples of other macromolecular materials (b) having biodegradability include polylactide, polyglycolic acid, poly(β-hydroxybutyrate), poly(β-hydroxy valerate) and other poly(β-hydroxy alkanoate) as well as aliphatic biodegradable polyester.

The biodegradability under the natural environments of the starch of the present invention is rapid, and further, the degradation intermediates are safe. Therefore, the starch granules of the present invention are materials which are friendly to a human and natural environment. When the starch of the present invention (a) and other macromolecular materials (b) are used in combination, the weight ratio of (a) to (b) (a/b) is preferably about 99/1 to about 1/99, more preferably about 95/5 to about 5/95, particularly preferably about 90/10 to about 10/90. The lower limit of the weight ratio of (a) to (b) may also be, for example, about 80/20, about 70/30, about 60/40, about 50/50, about 40/50 or the like. The upper limit of the weight ratio of (a) to (b) may also be, for example, about 20/80, about 30/70, about 40/60, about 50/50, about 60/40 or the like.

A plasticizer can be added to the biodegradable article of the present invention as needed to achieve further high material processability and the improvement of strength property. A plasticizer selected from urea, natural oils and fats such as soybean oil and castor oil, various alkyl esters of an acid having biodegradability which are known in the chemical field may be formulated as a plasticizer to control processability or strength property, in the biodegradable article of the present invention. Examples of the alkyl esters of acids having biodegradability include, for example, mono- or di-alkyl esters of phthalic acid, alkyl esters of succinic acid, alkyl esters of lactic acid, alkyl esters of citric acid, alkyl esters of adipic acid, alkyl esters of stearic acid, alkyl esters of oleic acid, alkyl esters of ricinoleic acid and alkyl esters of erucic acid. Examples of the alkyl groups include methyl group, ethyl group, propyl group, hexyl group, heptyl group, octyl group and the like. Esters of glycerin, for example, glycerin triacetate, glycerin, mono- and di-acetate, glycerin, mono-, di- and tri-propionate, glycerin mono- and di-butanoate, glycerin mono-, di- and tri-stearate can be used. Among others, a reduction of the flow temperature of the biodegradable article and an improvement of elongation can be expected by formulating urea or glycerin as a plasticizer in the biodegradable article of the present invention. The biodegradable article in this case may be a final product such as a plastic film and may be pre-shaping raw material before shaping into a final product.

The biodegradable article of the present invention may further comprise an inorganic and/or organic filler in order to broaden the scope of the characteristics of the product. Examples of the inorganic filler include talc, titanium dioxide, calcium carbonate, clay, sand, chalk, limestone, diatomaceous earth, silicate, mica, glass, quartz, ceramics and the like. Examples of the organic filler include starches, cellulose, wood powders, fibers and the like.

The biodegradable article of the present invention can be shaped into a shaped article, for example, a film or sheet, by a conventional plastic shaping machine. The shaping method is not specifically limited, and, for example, extrusion molding, injection molding and a film shaping method can be applied. The biodegradable article of the present invention has an advantage that facilities used for the production of a conventional product can be used as it is in the production of a molded article and a product other than the above.

The shaped form may be, for example, a film, a sheet, a thread, a fiber, a nonwoven fabric or other shaped articles. Examples of other shaped articles include, for example, non-edible containers for food (for example, for hamburgers, for hot dogs, for French fries, for takoyaki (octopus dumplings), for rice cakes, for cooked white rice, for ice cream, for Lamian, for curry, for vegetables, for fruits, for meats, for fish, for juices, for coffee, for beer, for milk and the like), an edible container (for example, an ice cream cone) and the like. Examples of containers other than those for food include wide variety of shaped articles such as flowerpots, tee for golf, packing materials for wrapping, daily necessities and the like.

The biodegradable articles of the present invention have excellent characteristics of plastic. For example, the biodegradable articles of the present invention produced using the enzyme-treated-chemically modified starch granules of the present invention are remarkably superior in the point of transparency and glossiness in comparison with general-purpose plastic film and a film produced from the conventional starch. Therefore, when the biodegradable article of the present invention is used as a packaging material for wrapping, it is advantage that a color, pattern or the like of the wrapped contents can be seen clearly from the outside. Furthermore, the biodegradable articles of the present invention have little electrostatic ability. Therefore, a problem of dirt adsorption does not occur during use or storage, particularly at the time of printing. Furthermore, when the biodegradable articles of the present invention are shaped into a film, there is an advantage that heat seal and wet adhesion are possible.

The biodegradable article obtained from the starch granules of the present invention is also excellent, in workability and strength characteristics. Therefore, the biodegradable article of the present invention can be used in the field in which a water-soluble synthetic macromolecule was used, for example, in application fields such as paints or adhesives in which starch and polyvinyl alcohol (PVA) have been conventionally used. Particularly, when the starch granules of the present invention are the enzyme-treated-chemically modified starch granules, there is an advantage that gelatinization is quite quicker and the viscosity is higher in comparison with the conventional starch. Therefore, the enzyme-treated-chemically modified starch granules of the present invention are useful in powdery paints and adhesives which are the paints and adhesives of the types wherein they are mixed with liquid such as water at the time of application to prepare a liquid paint or adhesive. The enzyme-treated-chemically modified starch granules of the present invention are preferably used as a suspension paint or adhesive comprising the enzyme-treated-chemically modified starch granules of the present invention in the state of the starch granules. There is an advantage that such suspension paint and adhesive are heated at the time of use and immediately they are gelatinized to form a paint film/adhesive layer. Examples of application such as paint or adhesive, includes sizing agents for fiber processing such as paste for warp, textile finishing paste, textile printing paste and the like; denaturing agents for textile resin processing; adhesives for felt, nonwoven fabric or the like; pigment binders for paper processing; surface sizing agents; adhesives for general paper, such as paper bags, paper boxes, corrugated fiberboard, paper tubes, bookbinding, business use and office use; water-soluble adhesives for a packing tape, a postage stamp, a label and the like; and plywood adhesives.

The enzyme-treated-chemically modified starch granules of the present invention have quick precipitation speed. Therefore, it can be effectively used, for example, as adsorption remover to adsorb and remove a toxic substance (for example, an organic compound, metal, or the like) in a solution.

The starch granules of the present invention can be also used as matrix material for medical material, agricultural material, fertilizer and the like, for which a water-soluble synthetic macromolecule, a native starch, a protein or the like has been used. When the starch granules of the present invention are used as a matrix material, there is an advantage that the granules easily absorb moisture to become gel than the case where a conventional starch is used.

When the biodegradable article of the present invention are buried in a soil, it is degraded by bacteria, microorganisms or the like. Therefore, the biodegradable article of the present invention would not cause an environmental pollution problem by their waste product, contrary to a container made by general-purpose synthetic plastic. A period of time required for decomposition may vary depending on the composition of the product, environmental condition, and the like. However, it would be in the range of several weeks to several months. Furthermore, depending on the type of a product, it can be used as a feed or fertilizer instead of burying it in the soil.

The biodegradable article of the present invention may be a capsule produced from a material containing the starch granules of the present invention. In the present invention, the capsule is applicable to a quite wide variety of fields by changing the contents. The configuration, form and dimensions of the capsule are not particularly limited. The production method for producing the above described capsules is not particularly limited. Known production methods can be used. For example, as for soft capsule production method, a rotary method wherein filling liquid is wrapped with two pieces of cover sheets and is tableted with a punching mold, chemical method such as in-air and in-liquid curing covering methods, and hard capsule production methods wherein male and female capsule components which are molded with a mold are combined, or the like can be appropriately employed. The capsule can be used as at least one kind of article selected from, for example, industrial products, medicinal-agricultural pharmaceutical products, medical products, feeds, fertilizers, daily use miscellaneous goods and cosmetics. Contents encapsulated in a capsule can be varied widely, as desired, from powdery solid, hydrophobic liquid, hydrophilic liquid to a solution. Furthermore, when it is applied to an article administered orally, a capsule can be produced such that the capsule itself is digested in the body; or when a capsule is applied to a medical care medicine or a medical care product, a capsule can be produced so that it is degraded and/or absorbed in a living body after healing of the affected part.

The term "capsule" is generally used for the meanings of a container including a drug which is difficult to be taken. However, as used in the present specification, it is used as a term which means such a container itself and a matter enclosing the contents such as a drug is referred to as a "capsule agent".

When the enzyme-treated starch granules of the present invention are used for a capsule, effects of appropriate elastic feeling and excellent, shape retention property are especially obtained.

The starch granules of the present invention can be used similarly to general-purpose plastics in the field of film, sheet, and shaped articles that are required to be waterproof. Furthermore, the starch granules of the present invention are easily processed into a form of an aqueous solution, a paste or a cream. Furthermore, the starch granules of the present invention can be filled in a container (for example, a bottle, a tube or the like) to be stored stably for a long period of time.

In recent years, exhaustion of petroleum resources has been concerned, and a shale gas has attracted attention as a resource whose amount of deposit is vast. A shale gas is a natural gas that exists in a thin sedimentary rock layer (shale layer) which is present in deep underground and is easily cracked, and its $CO_2$ emission amount is less than petroleum and coal. Thus, the shale gass is recognized as an environmentally friendly clean energy.

A technique referred to as "hydraulic fracturing" is usually used for the digging of shale gas. This is a technique to make a gap in a stratum by the water pressure artificially and gas is extracted. In this technique, at first a chute is dug deeply in the ground, a large quantity of water is poured by high pressure to produce an artificial crack, and then a supporting agent which is mixed with a high viscosity material is injected with pressure in the crack to prevent the crack from closing naturally. This supporting agent is buried in the underground. Therefore, it is concerned about leading to a destruction of nature when a chemical compound is used as the supporting agent. As described above, the biodegradable article of the present invention is unlikely to cause a problem of environmental pollution. Furthermore, the starch granules (particularly the enzyme-treated-chemically modified starch granules) used for the biodegradable article of the present invention increase its viscosity rapidly and provide adequate viscosity. Therefore, they can be utilized as a supporting agent sufficiently. Therefore, the thickening agent composition for hydraulic fracturing comprising the enzyme-treated starch granules (particularly the enzyme-treated-chemically modified starch granules) of the present invention and the hydrogel for hydraulic fracturing made from the composition are quite effective for the digging of the shale gas. The formulation, production method and method for use of the thickening agent composition for hydraulic fracturing can be easily understood by those skilled in the art. It is considered that, in a hydrogel for hydraulic fracturing, the form of the starch granule of the enzyme-treated starch granules of the present invention is broken, and a form of gel is formed.

EXAMPLES

Next, the present invention will be described in more detail by way of Examples, but the present invention is not limited to these Examples. It is noted that in the Examples, a viscosity was measured by an amylograph from Brabender Inc., and physical properties of a gel were measured by a rheometer from Rheotech Inc.

(1. Method for Measurement of Viscosity)

A viscosity was measured by the following method. A starch suspension was adjusted in 450 ml of water so that the concentration of a wheat starch was 8.5% by weight, the concentration of a corn starch was 7.0% by weight and the concentration of a cassava starch was 6.0% by weight, on the dry matter basis and, put in a sample container, and then warmed to 50° C. while rotating them. Then the suspension was heated to 95° C. at 1.5° C./min, and maintained at 95° C. for 15 minute, followed by cooling at 1.5° C./min. The measurement was carried out using an amylograph VISCO-GRAPH-E manufactured by Brabender Inc. under the conditions of a rotation number of the sample container of 75 rpm and a measuring cartridge of 700 cmg. Wherein, the viscosity reached to a peak was regarded as a maximum viscosity, and a difference between this maximum viscosity and a viscosity soon after maintaining at 95° C. for 15 minutes was regarded as breakdown.

(2. Method for Measurement of Physical Properties of a Gel)

Physical properties of a gel were measured by the following method. A starch paste was prepared so that the concentration of the starch was 20% by weight on the dry matter basis, and then filled in a Krehalon casing having a folding width of 45 mm. This starch paste filled in the casing was heated to 90° C. at 1° C./min and maintained at 90° C. for 30 minutes. Then, the starch paste was left to cool in a constant-temperature water bath at 20° C. for 30 minutes and then cooled to 5° C. in a refrigerator. After cooling, it was refrigeration storaged at 5° C. for 16 hours, then it was left at room temperature (about 25° C.) for 4 hours to return the temperature of it to room temperature, and then physical properties of the gel were measured rheometer (RT-2010J-CW) manufactured by Rheotech Inc. The measurement was carried out under the measurement conditions of the rheometer: a test item: a rupture test; a height of a sample: 25 mm; and a movement rate (rupture rate) of a sample: 6 cm/min, using an adapter of a spherical jig for measurement viscosity φ5 (diameter: 5 mm, area: 19.635 mm$^2$). At the measurement, the hardness of the starch gel was evaluated by a rupture stress (g) and Young's modulus (dyn/cm$^2$).

(3. Method for Measurement of Degradation Ratio of Starch Granules)

A degradation ratio of starch granules was measured by the following method. The amount (g) of released reducing sugars contained in the supernatant obtained by centrifugation (at 3,000 rpm for 5 minutes) of a starch degraded suspension after subjecting to an enzyme reaction was measured by a phenol-sulfuric acid method. The percentage of the amount of the released reducing sugars to total amount of the starch (g) before subjecting to an enzyme reaction was determined.

Degradation ratio (%) of starch granules={(amount (g) of released reducing sugars)×100}/{(total amount (g) of starch before enzymatic reaction)}   [Equation 1]

Test Example 1: Comparison Between Liquid Reaction and Solid Reaction

1. Liquid Reaction

To 15 g (dry weight) of an untreated native wheat starch (starch granules), 250 g of ion-exchange water was added and, after adjusting the pH of the mixture to 5.0, the mixture was warmed in a boiled water bath to prepare a starch paste in which a starch was completely dissolved. To this starch paste, 0.1% by weight (based on starch solid content) of α-amylase (origin: *Aspergillus oryzae*) was added to make the total weight to 300 g, and stirred at 50° C. to carry out an enzyme reaction. After 30 minutes, this was left in a boiled water bath for 10 minutes to deactivate the enzyme and thereby obtained a sample 1. Using the obtained sample 1, physical properties of the gel were measured and evaluated by a rupture stress and a Young's modulus.

2. Solid Reaction

To 400 g (dry weight) of an untreated native wheat starch (starch granules), 900 g of ion-exchange water was added to prepare a starch suspension. After adjusting the pH of the suspension to 5.0, 1% by weight (based on starch solid content) of α-amylase (origin: *Aspergillus oryzae*) was added and stirred it 50° C. for 18 hours to carry out an enzyme reaction. After completion of the reaction, an enzyme-treated starch granules was obtained by centrifugal filtration and blow drying. To 15 g (dry weight) of this enzyme-treated starch granules, ion-exchange water was added to make the total weight to 300 g. This was warmed in a boiled water bath to prepare a starch paste in which the starch was completely dissolved, as a sample 2. Using the obtained sample 2, physical properties of the gel were measured and evaluated by a rupture stress and a Young's modulus.

TABLE 1

| Physical properties of Gel | Sample 1 (those reacted in a form of liquid) | Sample 2 (those reacted in a form of solid) | Untreated wheat starch |
|---|---|---|---|
| Rupture stress | Not measurable since gel is not formed because of being too soft | 206 g | 141 g |
| Young's modulus | | 5,533,540 dyn/cm$^2$ | 4,601,665 dyn/cm$^2$ |

When an enzyme was allowed to act on the starch after gelling, a remarkable decrease in viscosity was confirmed in the obtained sample 1, and the sample did not retain viscosity physical properties of the starch anymore and thus a gel was not formed. On the other hand, when the enzyme is reacted keeping the starch granules as it is, it was confirmed that the obtained sample 2 retained viscosity physical properties of the starch and a hard gel was formed.

Comparative Example 1

Viscosity characteristics were analyzed by the amylograph and the rheometer without subjecting an untreated native wheat starch (starch granules) to an enzymatic treatment. The results are shown in Table 2-2.

Examples 1-1 and 1-2

To 400 g of an untreated native wheat starch of the same lot as what was used in Comparative Example 1, 900 g of ion-exchange water was added to prepare a starch suspension. After adjusting the pH of the suspension to 5.0, 0.1% by weight (based on starch solid content) of α-amylase ("Biozyme A" derived from *Aspergillus oryzae*, manufactured by Amano Enzyme Inc.; optimum pH of 5.0) was added and stirred at 50° C. for 1 hour to carry out an enzyme reaction and resulted in preparation of a sample having a degradation ratio of about 5% by weight (Example 1-1). Using a similar amount of the enzyme, stirring was carried out at 50° C. for 3 hours to prepare a sample having a degradation ratio of about 10% by weight (Example 1-2). After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 2-2.

Example 1-3

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of α-amylase ("Biozyme A" derived from *Aspergillus oryzae*, manufactured by Amano Enzyme Inc.; optimum pH of 5.0) was added and stirred at 50° C. for 18 hours to carry out an enzyme reaction. After completion of the reaction, enzyme-treated starch granules were obtained y centrifugal filtration and blow drying. Viscosity characteristics of the obtained enzyme-treated starch granules were analyzed by the amylograph and the rheometer. Also, after completion of the reaction, a degradation ratio was determined using a part of the reaction solution. The results are shown in Table 2-2.

Example 2A

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using apart of the reaction solution. The results are shown in Table 2-2.

Example 2B

To 400 g of an untreated native wheat starch of the same lot as what was used in Comparative Example 1, 900 g or ion-exchange water was added to prepare a starch suspension. After adjusting the pH of the suspension to 5.0, 1% by weight (based on starch solid content) of α-amylase ("Sumizyme AS" derived from *Aspergillus niger*, manufactured by SHIN NIHON CHEMICALS Corporation; optimum pH of 4.5) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 2-2.

Comparative Examples 2, 3, 4-3, and 5 to 6

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of α-amylase ("α-amylase 3A" derived from *Bacillus subtilis*, manufactured by HBI, Inc.; optimum pH of 5.9; Comparative Example 2), α-amylase ("Novamyl" derived from *Bacillus subtilis*, manufactured by Novo; optimum pH of 5.0; Comparative Example 3), α-amylase ("α-amylase" derived from *Bacillus amyloliquefaciens*, manufactured by Sigma-Aldrich Corporation; optimum pH of 6.0; Comparative Example 4-3), α-amylase ("TERMAMYL 120 L" derived from *Bacillus licheniformis*, manufactured by Novo; optimum pH of 6.0; Comparative Example 5), or α-amylase ("Maltogenase L" derived from *Bacillus* sp., manufactured by Novo; optimum pH of 5.0; Comparative Example 6) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined by a part of the reaction solution. The results are shown in Table 2-2.

Comparative Examples 4-1 and 4-2

To 400 g of an untreated native wheat starch of the same lot as what was used in Comparative Example 1, 900 g of ion-exchange water was added to prepare a starch suspension. After adjusting the pH of the suspension to 5.0, 0.01% by weight (based on starch solid content) of α-amylase ("α-amylase" derived from *Bacillus amyloliquefaciens*, manufactured by Sigma-Aldrich Corporation; optimum pH of 6.0) was added and stirred at 50° C. for 30 minutes to prepare a sample having a degradation ratio of about 5% by weight. Also, using a similar amount of the enzyme, stirring was carried out at 50° C. for 1.5 hours to prepare a sample having a degradation ratio of about 10% by weight. After completion of the reaction, enzyme-treated starch granules were obtained by centrifugal filtration and blow drying. Viscosity characteristics of the obtained enzyme-treated starch granules were analyzed by the amylograph and the rheometer. The results are shown in Table 2-2.

Examples 3A-1 and 3A-2

To 400 g of an untreated native wheat starch of the same lot as what was used in Comparative Example 1, 900 g of ion-exchange water was added to prepare a starch suspension. After adjusting the pH of the suspension to 5.0, 0.1% by weight (based on starch solid content) of amyloglucosidase ("AMG" derived from *Aspergillus niger*, manufactured by Novozymes; optimum pH of 4.5) was added and stirred at 50° C. for 2 hours to prepare a sample having a degradation ratio of about 5% by weight (Example 3A-1). Also, 0.5% by weight (based on starch solid content) of the similar enzyme was added and stirred at 50° C. for 3 hours to prepare a sample having a degradation ratio of about 10% by weight (Example 3A-2). After completion of the reaction, enzyme-treated starch granules were obtained by centrifugal filtration and blow drying. Viscosity characteristics of the obtained enzyme-treated starch granules were analyzed by the amylograph and the rheometer.

Example 3A-3

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of amyloglucosidase ("AMG" derived from *Aspergillus niger*, manufactured by Novozymes; optimum pH of 4.5) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using apart of the reaction solution. The results are shown in Table 2-2.

Example 3B

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 2-2.

Example 3C

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of amyloglucosidase ("DIAZYME X4NP" derived from *Aspergillus niger*, manufactured by DANISCO; optimum pH of 4.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 2-2.

Example 3D

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of amyloglucosidase ("glucoamylase 'Amano' SD" derived from *Aspergillus niger*, manufactured by Amano Enzyme Inc.; optimum pH of 4.5) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 2-2.

Example 3E

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of amyloglucosidase ("Gluczyme AF6" derived from *Rhizopus niveus*, manufactured by Amano Enzyme Inc.; optimum pH of 4.5) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 2-2.

Example 3F

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of amyloglucosidase ("Sumizyme" derived from *Rhizopus oryzae*, manufactured by SHIN NIHON CHEMICALS Corporation; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 2-2.

Comparative Example 8

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of amyloglucosidase ("Reagent" derived from *Candida tsukubaensis*, manufactured by Sigma-Aldrich Corporation; optimum pH of 2.5) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 2-2.

Example 4

To 400 g of an untreated native wheat starch of the same lot as what was used in Comparative Example 1, 900 g of ion-exchange water was added to prepare a starch suspension. After adjusting the pH of the suspension to 5.0, 0.1% by weight (based on starch solid content) of isoamylase ("Reagent" derived from *Pseudomonas amyloderamosa*, manufactured by Sigma-Aldrich Corporation; optimum pH of 3.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 2-2.

Example 5A

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of α-glucosidase ("Transglucosidase L 'Amano'" derived from *Aspergillus niger*, manufactured by Amano Enzyme Inc.; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 2-2.

Example 5B

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of α-glucosidase ("Transglucosidase L-500" derived from *Aspergillus niger*, manufactured by Genencor; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 2-2.

Comparative Examples 10 and 11

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of β-amylase ("OPTI-MALT BBA" derived from barley, manufactured by Genencor; optimum pH of 5.0) or pullulanase ("Pullulanase" derived from *Klebsiella pneumoniae*, manufactured by Amano Enzyme Inc.; optimum pH of 6.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 2-2.

Comparative Example 12

Viscosity characteristics were analyzed by the amylograph and the rheometer without subjecting a corn starch to an enzymatic treatment. The results are shown in Table 3-2.

Example 6

To 400 g of an untreated native corn starch of the same lot as what was used in Comparative Example 12, 900 g of ion-exchange water was added to prepare a starch suspension. After adjusting the pH of the suspension to 5.0, 1% by weight (based on starch solid content) of α-amylase ("Biozyme A" derived from *Aspergillus oryzae*, manufactured by Amano Enzyme Inc.; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined using a part of the reaction solution. The results are shown in Table 3-2.

Comparative Examples 13-1 and 13-2

To 400 g of an untreated native corn starch of the same lot as what was used in Comparative Example 12, 900 g of ion-exchange water was added to prepare a starch suspension. After adjusting the pH of the suspension to 5.0, 0.01% by weight (based on starch solid content) (Comparative Example 13-1) of α-amylase ("Reagent" derived from *Bacillus amyloliquefaciens*, manufactured by Sigma-Aldrich Corporation; optimum pH of 6.0) was added and stirred at 50° C. for 30 minutes, or 1% by weight (based on starch solid content) (Comparative Example 13-2) of the α-amylase was added and stirred at 50° C. for 18 hours, to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined by a part of the reaction solution. The results are shown in Table 3-2.

Examples 7-1 and 7-2

To 400 g of an untreated native corn starch of the same lot as what was used in Comparative Example 12, 900 g of ion-exchange water was added to prepare a starch suspension. After adjusting the pH of the suspension to 5.0, 0.5% by weight (based on starch solid content) (Example 7-1) of amyloglucosidase ("AMG" derived from *Aspergillus niger*, manufactured by Novozymes; optimum pH of 4.5) was added and stirred at 50° C. for 3 hours, or 1% by weight (based on starch solid content) (Example 7-2) of the amyloglucosidase was added and stirred at 50° C. for 18 hours, to carry out an enzyme reaction. After completion of the reaction, enzyme-treated starch granules were was obtained by centrifugal filtration and blow drying. Viscosity characteristics of the obtained enzyme-treated starch granules were analyzed by the amylograph and the rheometer. Also, after completion of the reaction, a degradation ratio was determined by a part of the reaction solution. The results are shown in Table 3-2.

Comparative Example 14

To 400 g of an untreated native corn starch of the same lot as what was used in Comparative Example 12, 900 g of ion-exchange water was added to prepare a starch suspension. After adjusting the pH of the suspension to 5.0, 1% by weight (based on starch solid content) of β-amylase ("OPTI-MALT BBA" derived from barley, manufactured by Genencor; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 3-2.

Example 8A

To 400 g of an untreated native corn starch of the same lot as what was used in Comparative Example 12, 900 g of ion-exchange water was added to prepare a starch suspension. After adjusting the pH of the suspension to 5.0, 0.1% by weight (based on starch solid content) of isoamylase ("Reagent" derived from *Pseudomonas amyloderamosa*, manufactured by Sigma-Aldrich Corporation; optimum pH of 3.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 3-2.

Example 8B

To 400 g of an untreated native corn starch of the same lot as what was used in Comparative Example 12, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 3-2.

Example 8C

To 400 g of an untreated native corn starch of the same lot as what was used in Comparative Example 12, 900 g of ion-exchange water was added to prepare a starch suspension. After adjusting the pH of the suspension to 5.0, 1% by weight (based on starch solid content) of α-glucosidase ("Transglucosidase L 'Amano'" derived from *Aspergillus niger*, manufactured by Amano Enzyme Inc.; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 3-2.

Comparative Example 15

Viscosity characteristics were analyzed by the amylograph and the rheometer without subjecting an untreated native cassava starch to an enzymatic treatment. The results are shown in Table 4-2.

Example 9

To 400 g of an untreated native cassava starch of the same lot as what was used in Comparative Example 15, 900 g of ion-exchange water was added to prepare a starch suspension. After adjusting the pH of the suspension to 5.0, 1% by weight (based on starch solid content) of α-amylase ("Biozyme A" derived from *Aspergillus oryzae*, manufactured by Amano Enzyme Inc.; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 4-2.

Comparative Examples 16-1 and 16-2

To 400 g of an untreated native cassava starch of the same lot as what was used in Comparative Example 15, 900 g of ion-exchange water was added to prepare a starch suspension. After adjusting the pH of the suspension to 5.0, 0.01% by weight (based on starch solid content) (Comparative Example 16-1) of α-amylase ("Reagent" derived from *Bacillus amyloliquefaciens*, manufactured by Sigma-Aldrich Corporation; optimum pH of 6.0) was added and stirred at 50° C. for 30 minutes, or 1.0% by weight (based on starch solid content) (Comparative Example 16-2) of the α-amylase was added and stirred at 50° C. for 18 hours, to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined by a part of the reaction solution. The results are shown in Table 4-2.

Examples 10-1 and 10-2

To 400 g of an untreated native cassava starch of the same lot as what was used in Comparative Example 15, 900 g of ion-exchange water was added to prepare a starch suspension. After adjusting the pH of the suspension to 5.0, 0.5% by weight (based on starch solid content) (Example 10-1) of amyloglucosidase ("AMG" derived from *Aspergillus niger*, manufactured by Novozymes; optimum pH of 4.5) was added and stirred at 50° C. for 3 hours, or 1% by weight (based on starch solid content) (Example 10-2) of the amyloglucosidase was added and stirred at 50° C. for 18 hours, to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined by a part of the reaction solution. The results are shown in Table 4-2.

Comparative Example 17

To 400 g of an untreated native cassava starch of the same lot as what was used in Comparative Example 15, 900 g of ion-exchange water was added to prepare a starch suspension. After adjusting the pH of the suspension to 5.0, 1% by weight (based on starch solid content) of β-amylase ("OPTIMALT BBA" derived from barley, manufactured by Genencor; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 4-2.

Example 11A

To 400 g of an untreated native cassava starch of the same lot as what was used in Comparative Example 15, 900 g of ion-exchange water was added to prepare a starch suspension. After adjusting the pH of the suspension to 5.0, 0.1% by weight (based on starch solid content) of isoamylase ("Reagent" derived from *Pseudomonas amyloderamosa*, manufactured by Sigma-Aldrich Corporation; optimum pH of 3.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 4-2.

Example 11B

To 400 g of an untreated native cassava starch of the same lot as what was used in Comparative Example 15, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 4-2.

Example 11C

To 400 g of an untreated native cassava starch of the same lot as what was used in Comparative Example 15, 900 g of ion-exchange water was added to prepare a starch suspension. After adjusting the pH of the suspension to 5.0, 1% by weight (based on starch solid content) of α-glucosidase ("Transglucosidase L 'Amano'" derived from *Aspergillus niger*, manufactured by Amano Enzyme Inc.; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 4-2.

As a result, in Examples 1 to 11C, it was confirmed that a novel starch having both a high viscosity and strong gel characteristics can be prepared by subjecting to an enzymatic treatment. Further, using α-amylase derived from *Bacillus amyloliquefaciens* used in Comparative Examples 4-1 and 4-2, 13-1, 13-2, 16-1, 16-2 at a degradation ratio of 40% by weight or less, it was impossible to prepare a starch having both a high viscosity and strong gel characteristics, which is the object of the present inventors. Therefore, it has been proved that the starch developed by the present inventors is a substance which is different from the starch prepared by Japanese Patent Gazette No. 2,615,398.

Example 12A (Method for Preparation of α-Amylase Derived from *Aspergillus oryzae*)

A double stranded DNA was chemically synthesized by adding an EcoRI recognition site (GAATTC) to both terminals of a base sequence of SEQ ID NO: 1 in the sequence listing. This synthetic DNA was completely cleaved by a restriction enzyme EcoRI, mixed with pYCDE1 (Method in Enzymology, 101, pp. 192-201 (1983)) which was previously completely cleaved by EcoRI, and then ligation was carried out. *E. coli* TG1 was transformed with the ligation reaction solution and a transformant into which a synthetic gene was properly introduced was selected. Plasmid pYAMY1 held by this transformant was prepared.

In accordance with the method of Ito et al. (J. bacteriol., Vol. 153, 163-168 (1983)), pYAMY1 was introduced into a yeast host DBY746, and obtained a transformant capable of growing in a tryptophan-free culture medium by complementation of the tryptophan requirement. This transformant was inoculated in 100 ml of a synthetic culture medium consisting of 2% by weight glucose, 0.67% by weight yeast nitrogen base, 24 mg/l L-uracil, 24 mg/l L-histidine and 36 mg/l L-leucine at pH 5.7 and then cultured with shaking at 30° C. for 120 hours.

The supernatant obtained by centrifugation (at 5,000 rpm for 10 minutes) of the culture was concentrated using a hollow fiber type UF membrane module having a molecular weight cut-off of 10,000 to prepare α-amylase derived from *Aspergillus oryzae*. This α-amylase has an amino acid sequence of SEQ ID NO: 2.

Example 12B (Method for Preparation of α-Amylase Derived From *Aspergillus niger*)

A double stranded DNA was chemically synthesized by adding an EcoRI recognition site (GAATTC) to both terminals of a base sequence of SEQ ID NO: 3 in the sequence listing. This synthetic DNA was completely cleaved by a restriction enzyme EcoRI, mixed with pYCDE1 (Method in Enzymology, 101, pp. 192-201 (1983)) which was previously completely cleaved by EcoRI, and then ligation was carried out. *E. coli* TG1 was transformed with the ligation reaction solution and a transformant into which a synthetic gene was properly introduced was selected. Plasmid pYAMY2 held by this transformant was prepared.

In accordance with the method of Ito et al. (J. bacteriol., Vol. 153, 163-168 (1983)), pYAMY2 was introduced into a yeast host DBY746, and obtained a transformant capable of growing in a tryptophan-free culture medium by complementation of the tryptophan requirement. This transformant was inoculated in 100 ml of a synthetic culture medium consisting of 2% by weight glucose, 0.67% by weight yeast nitrogen base, 24 mg/l L-uracil, 24 mg/l L-histidine and 36 mg/l L-leucine at pH 5.7 and then cultured with shaking at 30° C. for 120 hours.

The supernatant obtained by centrifugation (at 5,000 rpm for 10 minutes) of the culture was concentrated using a hollow fiber type UF membrane module having a molecular weight cut-off of 10,000 to prepare α-amylase derived from *Aspergillus niger*. This α-amylase has an amino acid sequence of SEQ ID NO: 4.

Example 12C (Method for Preparation of Amyloglucosidase Derived from *Aspergillus niger*)

A double stranded DNA was chemically synthesized by adding an EcoRI recognition site (GAATTC) to both terminals of a base sequence of SEQ ID NO: 5 in the sequence listing. This synthetic DNA was completely cleaved by a restriction enzyme EcoRI, mixed with pYCDE1 (Method in Enzymology, 101, pp. 192-201 (1983)) which was previously completely cleaved by EcoRI, and then ligation was carried out. *E. coli* TG1 was transformed with the ligation reaction solution and a transformant into which a synthetic gene was properly introduced was selected. Plasmid pYGLU1 held by this transformant was prepared.

In accordance with the method of Ito et al. (J. bacteriol., Vol. 153, 163-168 (1983)), pYGLU1 was introduced into a yeast host DBY746, and obtained a transformant capable of growing in a tryptophan-free culture medium by complementation of the tryptophan requirement. This transformant was inoculated in 100 ml of a synthetic culture medium consisting of 2% by weight glucose, 0.67% by weight yeast nitrogen base, 24 mg/l L-uracil, 24 mg/l L-histidine and 36 mg/l L-leucine at pH 5.7 and then cultured with shaking at 30° C. for 120 hours.

The supernatant obtained by centrifugation (at 5,000 rpm for 10 minutes) of the culture was concentrated using a hollow fiber type UF membrane module having a molecular weight cut-off of 10,000 to prepare amyloglucosidase derived from *Aspergillus niger*. This amyloglucosidase has an amino acid sequence of SEQ ID NO: 6.

Example 12D (Method for Preparation of Isoamylase Derived from *Flavobacterium* sp.)

A double stranded DNA was chemically synthesized by adding an EcoRI recognition site (GAATTC) to both terminals of a base sequence of SEQ ID NO: 7 in the sequence listing. This synthetic DNA was completely cleaved by a restriction enzyme EcoRI, mixed with pYCDE1 (Method in Enzymology, 101, pp. 192-201 (1983)) which was previously completely cleaved by EcoRI, and then ligation was carried out. *E. coli* TG1 was transformed with the ligation reaction solution and a transformant into which a synthetic gene was properly introduced was selected. Plasmid pYISO1 held by this transformant was prepared.

In accordance with the method of Ito et al. (J. bacteriol., Vol. 153, 163-168 (1983)), pYISO1 was introduced into a yeast host DBY746, and obtained a transformant capable of growing in a tryptophan-free culture medium by complementation of the tryptophan requirement. This transformant was inoculated in 100 ml of a synthetic culture medium consisting of 2% by weight glucose, 0.67% by weight yeast nitrogen base, 24 mg/l L-uracil, 24 mg/l L-histidine and 36 mg/l L-leucine at pH 5.7 and then cultured with shaking at 30° C. for 120 hours.

The supernatant obtained by centrifugation (at 5,000 rpm for 10 minutes) of the culture was concentrated using a hollow fiber type UF membrane module having a molecular weight cut-off of 10,000 to prepare isoamylase derived from *Flavobacterium* sp. This isoamylase has an amino acid sequence of SEQ ID NO: 8.

Example 12E (Method for Preparation of Isoamylase Derived from *Pseudomonas amyloderamosa*)

A double stranded DNA was chemically synthesized by adding an EcoRI recognition site (GAATTC) to both terminals of a base sequence of SEQ ID NO: 9 in the sequence listing. This synthetic DNA was completely cleaved by a restriction enzyme EcoRI, mixed with pYCDE1 (Method in Enzymology, 101, pp. 192-201 (1983)) which was previously completely cleaved by EcoRI, and then ligation was carried out. *E. coli* TG1 was transformed with the ligation reaction solution and a transformant into which a synthetic gene was properly introduced was selected. Plasmid pYISO2 held by this transformant was prepared.

In accordance with the method of Ito et al. (J. bacteriol., Vol. 153, 163-168 (1983)), pYISO2 was introduced into a yeast host DBY746, and obtained a transformant capable of growing in a tryptophan-free culture medium by complementation of the tryptophan requirement. This transformant was inoculated in 100 ml of a synthetic culture medium consisting of 2% by weight glucose, 0.67% by weight yeast nitrogen base, 24 mg/l L-uracil, 24 mg/l L-histidine and 36 mg/l L-leucine at pH 5.7 and then cultured with shaking at 30° C. for 120 hours.

The supernatant obtained by centrifugation (at 5,000 rpm for 10 minutes) of the culture was concentrated using a hollow fiber type UF membrane module having a molecular weight cut-off of 10,000 to prepare isoamylase derived from *Pseudomonas amyloderamosa*. This isoamylase has an amino acid sequence of SEQ ID NO: 10.

Example 12A-1

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of α-amylase (derived from *Aspergillus oryzae*) prepared in Example 12A was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 5-2 below.

Example 12B-1

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of α-amylase (derived from *Aspergillus niger*) prepared in Example 12B was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 5-2 below.

Example 12C-1

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of amyloglucosidase (derived from *Aspergillus niger*) prepared in Example 12C was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 5-2 below.

Example 12D-1

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of isoamylase (derived from *Flavobacterium* sp.) prepared in Example 12D was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 5-2 below.

Example 12E-1

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of isoamylase (derived from *Pseudomonas amyloderamosa*) prepared in Example 12E was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution. The results are shown in Table 5-2 below.

TABLE 2-1

Summary of Names, Origins and Product Names of Enzymes used for Wheat Starch

| Example | Name | Origins | Product name (Manufacturer) |
|---|---|---|---|
| Comp. Ex. 1 | — | — | Untreated wheat starch |
| Example 1-1 | α-amylase | *Aspergillus oryzae* | Biozyme A (Amano Enzyme) |
| Example 1-2 | α-amylase | *Aspergillus oryzae* | Biozyme A (Amano Enzyme) |
| Example 1-3 | α-amylase | *Aspergillus oryzae* | Biozyme A (Amano Enzyme) |
| Example 2A | α-amylase | *Aspergillus niger* | AMYLEX A3 (DANISCO) |
| Example 2B | α-amylase | *Aspergillus niger* | Sumizyme AS (SHIN NIHON CHEMICALS Corporation) |
| Comp. Ex. 2 | α-amylase | *Bacillus subtilis* | α-amylase 3A (HBI) |
| Comp. Ex. 3 | α-amylase | *Bacillus subtilis* | Novamyl (Novo) |
| Comp. Ex. 4-1 | α-amylase | *Bacillus amyloliquefaciens* | Reagent (Sigma-Aldrich Corporation) |
| Comp. Ex. 4-2 | α-amylase | *Bacillus amyloliquefaciens* | Reagent (Sigma-Aldrich Corporation) |
| Comp. Ex. 4-3 | α-amylase | *Bacillus amyloliquefaciens* | Reagent (Sigma-Aldrich Corporation) |
| Comp. Ex. 5 | α-amylase | *Bacillus licheniformis* | TERMAMYL 120L (Novo) |
| Comp. Ex. 6 | α-amylase | *Bacillus* sp. | Maltogenase L (Novo) |
| Example 3A-1 | amyloglucosidase | *Aspergillus niger* | AMG (Novo) |
| Example 3A-2 | amyloglucosidase | *Aspergillus niger* | AMG (Novo) |
| Example 3A-3 | amyloglucosidase | *Aspergillus niger* | AMG (Novo) |
| Example 3B | amyloglucosidase | *Aspergillus niger* | OPTIDEX L-400 (Genencor) |
| Example 3C | amyloglucosidase | *Aspergillus niger* | DIAZYME X4NP (DANISCO) |
| Example 3D | amyloglucosidase | *Aspergillus niger* | Glucoamylase "Amano" SD (Amano Enzyme) |
| Example 3E | amyloglucosidase | *Rhizopus niveus* | Gluczyme AF6 (Amano Enzyme) |

TABLE 2-1-continued

Summary of Names, Origins and Product Names of Enzymes used for Wheat Starch

| Example | Name | Origins | Product name (Manufacturer) |
|---|---|---|---|
| Example 3F | amyloglucosidase | *Rhizopus oryzae* | Sumizyme (SHINNIHON CHEMICALS Corporation) |
| Comp. Ex. 8 | amyloglucosidase | *Candida tsukubaensis* | Reagent (Sigma-Aldrich Corporation) |
| Example 4 | isoamylase | *Pseudamonas amyloderamosa* | Reagent (Sigma-Aldrich Corporation) |
| Example 5A | α-glucosidase | *Aspergillus niger* | Transglucosidase L "Amano" (Amano Enzyme) |
| Example 5B | α-glucosidase | *Aspergillus niger* | Transglucosidase L-500 (Genencor) |
| Comp. Ex. 10 | β-amylase | Barley | OPTIMALT BBA (Genencor) |
| Comp. Ex. 11 | pullulanase | *Klebsiella pneumoniae* | Pullulanase (Amano Enzyme) |
| Example 13-1 | CGTase | *Bacillus licheniformis* | Toruzyme 3.0L (Novo) |
| Example 13-2 | CGTase | *Paenibacillus macerans* (*Bacillus macerans*) | Cyclodextrin glucanotransferase "Amano" (Amano Enzyme) |

Comp. Ex. = Comparative Example

TABLE 2-2

Summary of Results of Wheat Starch (Starch Concentration for Amylograph: 8.5%)

| Example | Degradation ratio (%) | Maximum viscosity Measured value (BU) | Maximum viscosity Relative % (%) | Breakdown viscosity (BU) | Rupture stress Measured value (g) | Rupture stress Relative % (%) | Young's modulus Measured value (dyn/cm$^2$) | Young's modulus Relative % (%) | Evaluation results |
|---|---|---|---|---|---|---|---|---|---|
| Comp. Ex. 1 | — | 621 | 100 | 126 | 141 | 100 | 4,601,665 | 100 | — |
| Example 1-1 | 5 | 672 | 108 | 188 | 167 | 118 | 5,188,263 | 113 | Usable |
| Example 1-2 | 8 | 707 | 114 | 221 | 185 | 131 | 5,490,949 | 119 | Usable |
| Example 1-3 | 19 | 738 | 119 | 279 | 206 | 146 | 5,533,540 | 120 | Usable |
| Example 2A | 15 | 880 | 142 | 365 | 211 | 150 | 5,465,779 | 119 | Usable |
| Example 2B | 14 | 839 | 135 | 374 | 165 | 117 | 5,484,457 | 119 | Usable |
| Comp. Ex. 2 | 33 | 398 | 64 | 241 | 15 | 11 | 637,600 | 14 | Not usable |
| Comp. Ex. 3 | 24 | 14 | 2 | 8 | Not measurable since gel is not formed because of being too soft | | | | Not usable |
| Comp. Ex. 4-1 | 5 | 148 | 24 | 118 | Not measurable since gel is not formed because of being too soft | | | | Not usable |
| Comp. Ex. 4-2 | 13 | 172 | 28 | 142 | Not measurable since gel is not formed because of being too soft | | | | Not usable |
| Comp. Ex. 4-3 | 46 | 658 | 106 | 302 | 34 | 24 | 1,260,110 | 27 | Not usable |
| Comp. Ex. 5 | 29 | 535 | 86 | 271 | 37 | 26 | 1,493,271 | 32 | Not usable |
| Comp. Ex. 6 | 20 | 70 | 11 | 33 | 25 | 18 | 834,422 | 18 | Not usable |
| Example 3A-1 | 4 | 641 | 103 | 165 | 218 | 155 | 5,520,234 | 120 | Usable |
| Example 3A-2 | 15 | 719 | 116 | 229 | 263 | 187 | 5,890,552 | 128 | Usable |
| Example 3A-3 | 29 | 727 | 117 | 267 | 311 | 221 | 6,356,475 | 138 | Usable |
| Example 3B | 20 | 858 | 138 | 385 | 307 | 218 | 6,731,469 | 146 | Usable |
| Example 3C | 26 | 873 | 141 | 394 | 313 | 222 | 6,489,069 | 141 | Usable |
| Example 3D | 20 | 867 | 140 | 369 | 242 | 172 | 5,998,440 | 130 | Usable |
| Example 3E | 42 | 806 | 130 | 407 | 283 | 201 | 5,581,328 | 121 | Usable |
| Example 3F | 43 | 808 | 130 | 403 | 286 | 203 | 5,941,241 | 129 | Usable |
| Comp. Ex. 8 | 5 | 736 | 119 | 263 | 119 | 84 | 4,096,046 | 89 | Not usable |
| Example 4 | 6 | 828 | 133 | 300 | 297 | 211 | 6,987,728 | 152 | Usable |
| Example 5A | 4 | 746 | 120 | 291 | 166 | 118 | 5,142,993 | 112 | Usable |
| Example 5B | 5 | 554 | 89 | 274 | 180 | 128 | 6,418,528 | 139 | Usable |
| Comp. Ex. 10 | 7 | 757 | 122 | 256 | 145 | 103 | 4,385,924 | 95 | Not usable |
| Comp. Ex. 11 | 4 | 601 | 97 | 245 | 140 | 99 | 4,534,673 | 99 | Not usable |
| Example 13-1 | 14 | 444 | 71 | 422 | 161 | 114 | 5,136,339 | 112 | Usable |
| Example 13-2 | 12 | 475 | 76 | 460 | 159 | 113 | 5,291,915 | 115 | Usable |

Comp. Ex. = Comparative Example

TABLE 3-1

Summary of Names, Origins and Product Names of Enzymes used for Corn Starch

| Example | Name | Origins | Product name (Manufacturer) |
|---|---|---|---|
| Comp. Ex. 12 | — | — | Untreated corn starch |
| Example 6 | α-amylase | *Aspergillus oryzae* | Biozyme A (Amano Enzyme) |
| Comp. Ex. 13-1 | α-amylase | *Bacillus amyloliquefaciens* | Reagent (Sigma-Aldrich Corporation) |
| Comp. Ex. 13-2 | α-amylase | *Bacillus amyloliquefaciens* | Reagent (Sigma-Aldrich Corporation) |
| Example 7-1 | amyloglucosidase | *Aspergillus niger* | AMG (Novo) |

TABLE 3-1-continued

Summary of Names, Origins and Product Names of Enzymes used for Corn Starch

| Example | Name | Origins | Product name (Manufacturer) |
|---|---|---|---|
| Example 7-2 | amyloglucosidase | *Aspergillus niger* | AMG (Novo) |
| Comp. Ex. 14 | β-amylase | Barley | OPTIMALT BBA (Genencor) |
| Example 8A | isoamylase | *Pseudomonas amyloderamosa* | Reagent (Sigma-Aldrich Corporation) |
| Example 8B | α-amylase | *Aspergillus niger* | AMYLEX A3 (DANISCO) |
| Example 8C | α-glucosidase | *Aspergillus niger* | Transglucosidase L "Amano" (Amano Enzyme) |
| Example 14 | CGTase | *Bacillus licheniformis* | Toruzyme 3.0L (Novo) |

Comp. Ex. = Comparative Example

TABLE 3-2

Summary of Results of Corn Starch (Starch Concentration for Amylograph: 7.0%)

| Example | Degradation ratio (%) | Maximum viscosity Measured value (BU) | Maximum viscosity Relative % (%) | Breakdown viscosity (BU) | Rupture stress Measured value (g) | Rupture stress Relative % (%) | Young's modulus Measured value (dyn/cm$^2$) | Young's modulus Relative % (%) | Evaluation results |
|---|---|---|---|---|---|---|---|---|---|
| Comp. Ex. 12 | — | 476 | 100 | 182 | 171 | 100 | 5,603,029 | 100 | — |
| Example 6 | 8 | 425 | 89 | 161 | 230 | 135 | 6,054,798 | 108 | Usable |
| Comp. Ex. 13-1 | 11 | 414 | 87 | 162 | 56 | 33 | 2,434,858 | 43 | Not usable |
| Comp. Ex. 13-2 | 40 | 383 | 80 | 141 | 153 | 90 | 4,318,913 | 77 | Not usable |
| Example 7-1 | 11 | 455 | 96 | 153 | 381 | 223 | 7,805,888 | 139 | Usable |
| Example 7-2 | 33 | 432 | 91 | 170 | 348 | 204 | 6,219,387 | 111 | Usable |
| Comp. Ex. 14 | 1 | 477 | 100 | 152 | 183 | 107 | 5,582,293 | 100 | Not usable |
| Example 8A | 1 | 445 | 93 | 163 | 216 | 126 | 6,304,730 | 113 | Usable |
| Example 8B | 23 | 414 | 87 | 176 | 297 | 174 | 5,910,873 | 105 | Usable |
| Example 8C | 1 | 451 | 95 | 163 | 220 | 129 | 6,731,402 | 120 | Usable |
| Example 14 | 7 | 285 | 60 | 273 | 222 | 130 | 6,546,236 | 117 | Usable |

Comp. Ex. = Comparative Example

TABLE 4-1

Summary of Names, Origins and Product Names of Enzymes used for Cassava Starch

| Example | Name | Origins | Product name (Manufacturer) |
|---|---|---|---|
| Comp. Ex. 15 | — | — | Untreated cassava starch |
| Example 9 | α-amylase | *Aspergillus oryzae* | Biozyme A (Amano Enzyme) |
| Comp. Ex. 16-1 | α-amylase | *Bacillus amyloliquefaciens* | Reagent (Sigma-Aldrich Corporation) |
| Comp. Ex. 16-2 | α-amylase | *Bacillus amyloliquefaciens* | Reagent (Sigma-Aldrich Corporation) |
| Example 10-1 | amyloglucosidase | *Aspergillus niger* | AMG (Novo) |
| Example 10-2 | amyloglucosidase | *Aspergillus niger* | AMG (Novo) |
| Comp. Ex. 17 | β-amylase | Barley | OPTIMALT BBA (Genencor) |
| Example 11A | isoamylase | *Pseudomonas amyloderamosa* | Reagent (Sigma-Aldrich Corporation) |
| Example 11B | α-amylase | *Aspergillus niger* | AMYLEX A3(DANISCO) |
| Example 11C | α-glucosidase | *Aspergillus niger* | Transglucosidase L "Amano" (Amano Enzyme) |
| Example 15 | CGTase | *Bacillus licheniformis* | Toruzyme 3.0L(Novo) |

Comp. Ex. = Comparative Example

TABLE 4-2

Summary of Results of Cassava Starch (Starch Concentration for Amylograph: 6.0%)

| Example | Degradation ratio (%) | Maximum viscosity Measured value (BU) | Maximum viscosity Relative % (%) | Breakdown viscosity (BU) | Rupture stress Measured value (g) | Rupture stress Relative % (%) | Young's modulus Measured value (dyn/cm$^2$) | Young's modulus Relative % (%) | Evaluation results |
|---|---|---|---|---|---|---|---|---|---|
| Comp. Ex. 15 | — | 757 | 100 | 509 | 51 | 100 | 472,273 | 100 | — |
| Example 9 | 6 | 737 | 97 | 434 | 60 | 118 | 567,949 | 120 | Usable |
| Comp. Ex. 16-1 | 11 | 271 | 36 | 256 | 21 | 41 | 225,310 | 48 | Not usable |

TABLE 4-2-continued

Summary of Results of Cassava Starch (Starch Concentration for Amylograph: 6.0%)

| | | Maximum viscosity | | | Rupture stress | | Young's modulus | | |
|---|---|---|---|---|---|---|---|---|---|
| Example | Degradation ratio (%) | Measured value (BU) | Relative % (%) | Breakdown viscosity (BU) | Measured value (g) | Relative % (%) | Measured value (dyn/cm²) | Relative % (%) | Evaluation results |
| Comp. Ex. 16-2 | 34 | 112 | 15 | 109 | Not measurable since gel is not formed because of being too soft | | | | Not usable |
| Example 10-1 | 11 | 704 | 93 | 419 | 71 | 139 | 715,243 | 151 | Usable |
| Example 10-2 | 28 | 660 | 87 | 388 | 115 | 225 | 1,390,964 | 295 | Usable |
| Comp. Ex. 17 | 2 | 755 | 100 | 440 | 52 | 102 | 494,672 | 105 | Not usable |
| Example 11A | 2 | 642 | 85 | 377 | 75 | 147 | 701,944 | 149 | Usable |
| Example 11B | 16 | 561 | 74 | 328 | 89 | 175 | 969,841 | 205 | Usable |
| Example 11C | 2 | 638 | 84 | 374 | 70 | 137 | 663,407 | 140 | Usable |
| Example 15 | 7 | 533 | 70 | 529 | 92 | 180 | 2,342,930 | 496 | Usable |

Comp. Ex. = Comparative Example

TABLE 5-1

Summary of Names, Origins and Product Names of Enzymes used when Enzyme prepared by Genetic Recombination is reacted with Wheat Starch

| Example | Name | Origins | Product name (Manufacturer) |
|---|---|---|---|
| Comparative Example 1 | — | — | Untreated wheat starch |
| Example 12A-1 | α-amylase | *Aspergillus oryzae* | SEQ ID NO: 2 |
| Example 12B-1 | α-amylase | *Aspergillus niger* | SEQ ID NO: 4 |
| Example 12C-1 | amyloglucosidase | *Aspergillus niger* | SEQ ID NO: 6 |
| Example 12D-1 | isoamylase | *Flavobacterium* sp. | SEQ ID NO: 8 |
| Example 12E-1 | isoamylase | *Pseudomonas amyloderamosa* | SEQ ID NO: 10 |

TABLE 5-2

Summary of Results when Enzyme prepared by Genetic Recombination is reacted with Wheat Starch (Starch Concentration for Amylograph: 8.5%)

| | | Maximum viscosity | | | Rupture stress | | Young's modulus | | |
|---|---|---|---|---|---|---|---|---|---|
| Example | Degradation ratio (%) | Measured value (BU) | Relative % (%) | Breakdown viscosity (BU) | Measured value (g) | Relative % (%) | Measured value (dyn/cm²) | Relative % (%) | Evaluation results |
| Comparatve Example 1 | — | 621 | 100 | 81 | 141 | 100 | 4,601,665 | 100 | — |
| Example 12A-1 | 25 | 785 | 126 | 403 | 252 | 179 | 5,785,782 | 126 | Usable |
| Example 12B-1 | 15 | 797 | 128 | 309 | 281 | 199 | 6,712,299 | 146 | Usable |
| Example 12C-1 | 26 | 806 | 130 | 407 | 378 | 268 | 6,973,739 | 152 | Usable |
| Example 12D-1 | 6 | 781 | 126 | 306 | 285 | 202 | 6,425,189 | 140 | Usable |
| Example 12E-1 | 6 | 775 | 125 | 297 | 263 | 187 | 6,483,006 | 141 | Usable |

Retrogradation resistance, transparency and film property were assessed for starches of Comparative examples 1 to 17 and Examples 1-1 to 15.

Retrogradation resistance was evaluated according to the following method. A starch paste was prepared so that the concentration of the starch was 20% by weight on the dry matter basis, and then filled in a Krehalon casing having a folding width of 45 mm. This starch paste filled in the casing was heated to 90° C. at 1° C./min and maintained at 90° C. for 30 minutes. Then the starch paste was left to cool in a constant-temperature water bath at 20° C. for 30 minutes and then cooled to 5° C. in a refrigerator. After cooling, it was refrigeration stored at 5° C. for 21 days, then it was left at room temperature (about 25° C.) for 4 hours to return the temperature of it to room temperature, and then assessed by a skilled person to determine the presence and absence of retrogradation resistance by the state of cloudiness and touch feeling when touched with a hand. Gel which maintained the transparency and elasticity was considered as having retrogradation resistance, and gel which became clouded, has poor elasticity, or feeling of fragility was considered as having no retrogradation resistance.

Transparency was evaluated by the following method. A starch paste was prepared so that the concentration of the starch was 20% by weight on the dry matter basis, and the paste was heated to 90° C. at 1° C./min and maintained at 90° C. for 30 minutes. Then the starch paste was poured into a 100 ml beaker, left at room temperature for 10 minutes, and then assessed by a skilled person to determine the transparency visually. Gel having transparency was considered as having transparency, and gel which slightly lacked transparency was considered as being slightly opaque, and gel which is opaque in white was considered as being opaque.

Film property was evaluated according to the following method. A starch paste was prepared so that the concentration of the starch was 15% by weight on the dry matter basis, and the paste was heated to 90° C. at 1° C./min and maintained at 90° C. for 30 minutes. 15 g of the starch paste was placed in a petri dish, the paste was spread as thinly as possible, and left in a dryer at 50° C. for 24 hours. After 24 hours, it was confirmed that it was sufficiently dried, and the transparency and the feeling of touch when touched with a hand were confirmed by a skilled person. Films which have transparency and which can be felt having elongation when touched with a hand was considered as having film property, and the film which became clouded in white, or had a feeling of fragility when touched with a hand was considered as having no film property.

As a result, it was confirmed that the starch granules of Comparative examples 1 to 17 and Examples 1-1 to 15 have no retrogradation resistance, no transparency and no film property. Each enzyme-treated starch granule has an evaluation at the same level as that of a natural starch granule which has not been treated with the enzyme about all of retrogradation resistance, transparency and film property, and these characteristics did not become worse.

Trial Production Examples

Next, the present invention will be described in more detail by way of Trial Production Examples, but the present invention is not limited to the following Trial Production Example. Unless otherwise specified, "parts" means "parts by mass".

Trial Production Example 1: Preparation of Cookie

Among the formulations shown in Table 10 below, salt-free butter and shortening were put in a mixer and then well mixed. Furthermore, white soft sugar and common salt were added, well mixed, and then ammonium hydrogen carbonate previously dissolved in water was added and well mixed. Finally, a powder sample obtained by previously mixing soft wheat flour, a starch and baking soda (sodium hydrogen carbonate) was added, followed by well mixing until a mass of a dough was formed. The mass of the dough was spread thinly using a rolling pin, cut using a mold and then baked in an oven (at 200° C. for 15 minutes) to prepare cookies.

The obtained cookies showed the following results. That is, both the cookies of Trial Production Examples 1-1 and 1-2, in which any one of the starches prepared in Examples 9 and 10-2 was added, were soft and had texture with nice melt in mouth as compared with the cookies of Comparative Trial Production Examples 1 to 4, which were hard and crunchy, and also had texture with poor melt in mouth. In particular, the cookies of Trial Production Examples 1-1 and 1-2 had very light texture and were readily edible. Regarding the dough at the time of shaping, both the doughs of Trial Production Examples 1-1 and 1-2 were very dry and non-sticky as compared with the doughs of Comparative Trial Production Examples 1-1 to 1-4, and did not stick to hands, rolling pin and the like, and also showed very nice operability.

Trial Production Example 2: Preparation of Sponge Cake

Among the formulations shown in Table 11 below, whole egg and granulated sugar were warmed to around a body temperature while mixing using a hand mixer. Furthermore, the mixture was stirred by a hand mixer until the mixture become to a mixture that has a viscosity, fine bubbles and wholly whitish state. To the mixture, a powder sample obtained by previously mixing soft wheat flour, a starch and wheat gluten was added through sieving, followed by mixing using a spatula. Finally, a mixture of melted butter and milk was added and mixed. The obtained mixture was poured into a mold and then baked in an oven (at 200° C. for 15 minutes, then at 190° C. for 18 minutes) to prepare a sponge cake.

TABLE 10

| Formulation (Parts) | Comparative Trial Production Example 1-1 | Comparative Trial Production Example 1-2 | Comparative Trial Production Example 1-3 | Comparative Trial Production Example 1-4 | Trial Production Example 1-1 | Trial Production Example 1-2 |
|---|---|---|---|---|---|---|
| Soft wheat flour | 150 | 150 | 150 | 150 | 150 | 150 |
| Chemically unmodified cassava starch [Note (4)] | 150 | — | — | — | — | — |
| Chemically modified cassava starch 1 [Note (1)] | — | 150 | — | — | — | — |
| Chemically modified cassava starch 2 [Note (2)] | — | — | 150 | — | — | — |
| Chemically modified cassava starch 3 [Note (3)] | — | — | — | 150 | — | — |
| Starch prepared in Example 9 | — | — | — | — | 150 | — |
| Starch prepared in Example 10-2 | — | — | — | — | — | 150 |
| White soft sugar | 120 | 120 | 120 | 120 | 120 | 120 |
| Salt-free butter | 60 | 60 | 60 | 60 | 60 | 60 |
| Shortening | 60 | 60 | 60 | 60 | 60 | 60 |
| Ammonium hydrogen carbonate | 3 | 3 | 3 | 3 | 3 | 3 |
| Baking soda | 3 | 3 | 3 | 3 | 3 | 3 |
| Common salt | 1 | 1 | 1 | 1 | 1 | 1 |
| Water | 34 | 34 | 34 | 34 | 34 | 34 |

Note (1)
Chemically modified cassava starch 1: "RK-08", manufactured by GLICO FOODS CO., LTD.

Note (2)
Chemically modified cassava starch 2: "CHEMISTAR 280", manufactured by GLICO FOODS CO., LTD. "CHEMISTAR" is a registered trademark of GLICO FOODS CO., LTD.

Note (3)
Chemically modified cassava starch 3: "CHEMISTAR 300S", manufactured by GLICO FOODS CO., LTD. "CHEMISTAR" is a registered trademark of GLICO FOODS CO., LTD.

Note (4)
Chemically unmodified cassava starch: untreated native cassava starch.

TABLE 11

| Formulation (Parts) | Comparative Trial Production Example 2-1 | Comparative Trial Production Example 2-2 | Trial Production Example 2-1 | Trial Production Example 2-2 | Trial Production Example 2-3 | Trial Production Example 2-4 |
|---|---|---|---|---|---|---|
| Soft wheat flour | 50 | 50 | 50 | 50 | 50 | 50 |
| Chemically unmodified wheat starch Note (3) | 40 | — | — | — | — | — |
| Chemically unmodified wheat starch Note (1) | — | 40 | — | — | — | — |
| Starch prepared in Example 1-3 | — | — | 40 | — | — | — |
| Starch prepared in Example 2A | — | — | — | 40 | — | — |
| Starch prepared in Example 3A-3 | — | — | — | — | 40 | — |
| Starch prepared in Example 5A | — | — | — | — | — | 40 |
| Wheat gluten Note (2) | 4.5 | 4.5 | 4.5 | 4.5 | 4.5 | 4.5 |
| Whole egg | 170 | 170 | 170 | 170 | 170 | 170 |
| Granulated sugar | 100 | 100 | 100 | 100 | 100 | 100 |
| Salt-free butter | 35 | 35 | 35 | 35 | 35 | 35 |
| Milk | 25 | 25 | 25 | 25 | 25 | 25 |

Note (1)
Chemically modified wheat starch: "MIDSOL 1020", manufactured by GLICO FOODS CO., LTD.

Note (2)
Wheat gluten: "FinegluVP", manufactured by GLICO FOODS CO., LTD. "Fineglu" is a registered trademark of GLICO FOODS CO., LTD.

Note (3)
Chemically unmodified wheat starch: untreated native wheat starch.

The obtained sponge cakes showed the following results. That is, all the sponge cakes of Trial Production Example 2-1 to 2-4, in which any one of the starches prepared in Examples 1-3, 2A, 3A-3 and 5A was added, showed nice swelling after baking and had a large volume, and also had soft and puffy nice texture as compared with the sponge cakes of Comparative Trial Production Example 2-1 and Comparative Trial Production Example 2-2.

Trial Production Example 3: Preparation of Custard Cream

Among the formulations shown in Table 12 below, granulated sugar was added to egg yolk beaten well by a beater, followed by mixing by the beater. To the mixture, a powder sample obtained by previously mixing soft wheat flour and a starch was added through sieving, followed by mixing. Furthermore, warmed milk was added and mixed with them, the mixture was filtered and put in a pan, and then heated. The mixture was stirred by a wooden spatula until the mixture become to a mixture that has a viscosity and a smooth state. Finally, butter, a food color and vanilla essence were added and mixed with them to prepare a custard cream.

TABLE 12

| Formulation (Parts) | Comparative Trial Production Example 3-1 | Comparative Trial Production Example 3-2 | Trial Production Example 3-1 | Trial Production Example 3-2 |
|---|---|---|---|---|
| Milk | 300 | 300 | 300 | 300 |
| Egg yolk | 35 | 35 | 35 | 35 |
| Granulated sugar | 60 | 60 | 60 | 60 |
| Soft wheat flour | 10 | 10 | 10 | 10 |
| Chemically unmodified wheat starch Note (3) | 10 | — | — | — |
| Chemically modified wheat starch Note (1) | — | 10 | — | — |
| Starch prepared in Example 1-3 | — | — | 10 | — |
| Starch prepared in Example 3A-3 | — | — | — | 10 |
| Salt-free butter | 15 | 15 | 15 | 15 |
| KUCHINA COLOR 400LS Note (2) | appropriate amount | appropriate amount | appropriate amount | appropriate amount |
| Vanilla essence | appropriate amount | appropriate amount | appropriate amount | appropriate amount |

Note (1)
Chemically modified wheat starch: "MIDSOL 1020", manufactured by GLICO FOODS CO., LTD.

Note (2)
KUCHINA COLOR 400LS: Gardenia yellow food color. "KUCHINA COLOR" is a registered trademark of GLICO FOODS CO., LTD.

Note (3)
Chemically unmodified wheat starch: Untreated native wheat starch.

The obtained custard creams showed the following results. That is, both the custard creams of Trial Production Example 3-1 and 3-2, in which any one of starches prepared in Examples 1-3 and 3A-3 was added, had appropriate body and shape retention, and had nice melt in mouth and smooth texture. On the other hand, the custard cream of Comparative Trial Production Example 3-1 had gel-like physical properties and heavy texture, and also had poor melt in mouth and poor smoothness. Also, the custard cream of Comparative Trial Production Example 3-2 had poor body and shape retention, and had texture with stickiness and poor melt in mouth.

Trial Production Example 4: Preparation of Milk Pudding

Among the formulations shown in Table 13 below, granulated sugar was added to milk and mixed well using a wooden spatula to dissolve the granulated sugar. To the mixture, a starch sample was added and mixed well using the wooden spatula. The mixture was heated while stirring by the wooden spatula until the mixture become to a mixture having a viscosity and a smooth state. The mixture was filled in a jelly cup and quenched in an ice bath to prepare a milk pudding.

TABLE 13

| Formulation □(Parts) | Comparative Trial Production Example 4-1 | Comparative Trial Production Example 4-2 | Trial Production Example 4-1 | Trial Production Example 4-2 |
|---|---|---|---|---|
| Milk | 170 | 170 | 170 | 170 |
| Granulated sugar | 10 | 10 | 10 | 10 |
| Chemically unmodified wheat starch Note (2) | 10 | — | — | — |
| Chemically Modified wheat starch Note (1) | — | 10 | — | — |
| Starch prepared in Example 1-3 | — | — | 10 | — | prepared in Examples 1-3 and 3A-3 was added, had sticky and chewy and also had nice melt in mouth and smooth texture. On the other hand, the milk pudding of Comparative Trial Production Example 4-1 was sticky but had texture with hard yogurt-like hardness and was therefore inferior in both melt in mouth and smoothness as compared with those of Trial Production Examples. Also, the milk pudding of Comparative Trial Production Example 4-2 was not firmly gelled and had a texture with stickiness, and also had poor melt in mouth.

Trial Production Example 5: Preparation of Kudzu Starch Cake

Among the formulations shown in Table 14 below, a mixture of a starch sample and white soft sugar was added to water and white soft sugar was dissolved by well mixing using a wooden spatula. The mixture was heated while stirring using the wooden spatula until the mixture become a pasty mixture with a viscosity and a transparency state. The mixture was poured into a mold and quenched in an ice bath to prepare a kudzu starch cake.

TABLE 14

| Formulation (Parts) | Comparative Trial Production Example 5-1 | Comparative Trial Production Example 5-2 | Comparative Trial Production Example 5-3 | Trial Production Example 5-1 | Trial Production Example 5-2 | Trial Production Example 5-3 | Trial Production Example 5-4 |
|---|---|---|---|---|---|---|---|
| Fermented wheat starch | 56 | — | — | — | — | — | — |
| Chemically unmodified wheat starch Note (2) | — | 56 | — | — | — | — | — |
| Chemically unmodified wheat starch Note (1) | — | — | 56 | — | — | — | — |
| Starch prepared in Example 1-3 | — | — | — | 56 | — | — | — |
| Starch prepared in Example 2A | — | — | — | — | 56 | — | — |
| Starch prepared in Example 3A-3 | — | — | — | — | — | 56 | — |
| Starch prepared in Example 5A | — | — | — | — | — | — | 56 |
| White soft sugar | 32 | 32 | 32 | 32 | 32 | 32 | 32 |
| Water | 280 | 280 | 280 | 280 | 280 | 280 | 280 |

Note (1)
Chemically modified wheat starch: "MIDSOL 1020", manufactured by GLICO FOODS CO., LTD.
Note (2)
Chemically unmodified wheat starch: Untreated native wheat starch.

TABLE 13-continued

| Formulation □(Parts) | Comparative Trial Production Example 4-1 | Comparative Trial Production Example 4-2 | Trial Production Example 4-1 | Trial Production Example 4-2 |
|---|---|---|---|---|
| Starch prepared in Example 3A-3 | — | — | — | 10 |

Note (1)
Chemically modified wheat starch: "MIDSOL 1020", manufactured by GLICO FOODS CO., LTD.
Note (2)
Chemically unmodified wheat starch: Untreated native wheat starch.

The obtained milk puddings showed the following results. That is, both the milk puddings of Trial Production Examples 4-1 and 4-2, in which any one of the starches The obtained kudzu starch cakes showed the following results. That is, all the kudzu starch cakes of Trial Production Example 5-1 to 5-4, in which any one of the starches prepared in Examples 1-3, 2A, 3A-3 and 5A was added, had a appropriate hardness and brittleness, and had appropriate viscoelasticity and sticky texture. As compared with a kudzu starch cake so called in the Kanto area in Comparative Trial Production Examples 5-1, in which a fermented wheat starch obtained by fermenting for a long period, for example, one or more years was used, the kudzu starch cakes having the identical texture could be prepared without requiring fermentation for a long period in Trial Production Examples. Furthermore, the obtained kudzu starch cakes had nice flavor without having peculiar flavor derived from a fermented wheat starch and fermentation odor. On the other hand, the kudzu starch cake of Comparative Trial Production Example 5-2 was hard and brittle, and had texture with stickiness in the mouth. Also, the kudzu starch cake of Comparative Trial Production Example 5-3 had soft and brittle texture and showed texture far different from that of the kudzu starch cake so called in the Kanto area, together with those of Comparative Trial Production Example 5-2 and Comparative Trial Production Example 5-3.

Trial Production Example 6: Preparation of Goma-Dofu

Among the formulation shown in Table 15 below, a starch sample was added to water and the mixture was heated while stirring using a wooden spatula until the mixture become a pasty mixture with a viscosity and a transparency state. A sesame paste was added to them and mixed well. The mixture was filled in a container and then cooled to obtain a goma-dofu.

TABLE 15

| Formulation (Parts) | Comparative Trial Production Example 6-1 | Comparative Trial Production Example 6-2 | Trial Production Example 6-1 | Trial Production Example 6-2 |
|---|---|---|---|---|
| Sesame paste | 50 | 50 | 50 | 50 |
| Chemically unmodified wheat starch Note (2) | 30 | — | — | — |
| Chemically modified wheat starch Note (1) | — | 30 | — | — |
| Starch prepared in Example 1-3 | — | — | 30 | — |
| Starch prepared in Example 3A-3 | — | — | — | 30 |
| Water | 300 | 300 | 300 | 300 |

Note (1)
Chemically modified wheat starch: "MIDSOL 1020", manufactured by GLICO FOODS CO., LTD.
Note (2)
Chemically unmodified wheat starch: Untreated native wheat starch.

The obtained goma-dofus showed the following results. That is, both the goma-dofus of Trial Production Examples 6-1 and 6-2, in which any one of starches prepared in Examples 1-3 and 3A-3 was added, had appropriately sticky texture and appropriate crispy sensation in contrast to a texture with rich elasticity like texture obtained by the addition of a kudzu powder, and had readily edible texture with less stickiness and sticking in the mouth. Thus, it could be expected for the obtained goma-dofus to be applied to foods for advanced aged persons, for example. On the other hand, the goma-dofu of Comparative Trial Production Example 6-1 has soft and strong sticky texture and the goma-dofu of Comparative Trial Production Example 6-2 had hard and brittle texture, but had neither elasticity nor sticky texture, and thus both goma-dofus of Comparative Trial Production Example 6-1 and Comparative Trial Production Example 6-2 were inferior in deliciousness and ease of eating.

Trial Production Example 7: Preparation of Kamaboko

Among the formulations shown in Table 16 below, a fish paste, common salt, sugar, monosodium glutamate and potassium sorbate were put in a (silent) mixer and well mixed until the mixture had a viscosity. In order to inhibit a temperature rise of the fish paste, a half amount of moisture with ice was added to them and mixed. Then, egg white, Mirin and a starch previously suspended in the remaining water with ice were added to them and mixed well until a homogeneous mixture was obtained. Indication of the temperature of the fish paste after mixing was within a range from 10 to 15° C. The mixed fish paste was deaerated and filled in a cage. After filling, the cage filled with a mixed fish paste was subjected to a sterilization step (at 90° C. for 40 minutes) and cooled to prepare a kamaboko.

TABLE 16

| Formulation (Parts) | Comparative Trial Production Example 7-1 | Comparative Trial Production Example 7-2 | Comparative Trial Production Example 7-3 | Trial Production Example 7-1 | Trial Production Example 7-2 |
|---|---|---|---|---|---|
| Fish paste | 100 | 100 | 100 | 100 | 100 |
| Chemically unmodified wheat starch Note (3) | 15 | — | — | — | — |
| Chemically modified wheat starch 1 Note (1) | — | 15 | — | — | — |
| Chemically modified wheat starch 2 Note (2) | — | — | 15 | — | — |
| Starch prepared in Example 1-3 | — | — | — | 15 | — |
| Starch prepared in Example 3A-3 | — | — | 3 | — | 15 |
| Common salt | 3 | 3 | — | 3 | 3 |
| Sugar | 2.5 | 2.5 | 2.5 | 2.5 | 2.5 |
| Egg white | 5 | 5 | 5 | 5 | 5 |
| Mirin | 4 | 4 | 4 | 4 | 4 |
| Monosodium glutamate | 0.5 | 0.5 | 0.5 | 0.5 | 0.5 |
| Potassium sorbate | 0.3 | 0.3 | 0.3 | 0.3 | 0.3 |
| Water with ice | 40 | 40 | 40 | 40 | 40 |

Note (1)
Chemically modified wheat starch 1: "MIDSOL 1020", manufactured by GLICO FOODS CO., LTD.
Note (2)
Chemically modified wheat starch 2: "Ginrin", manufactured by GLICO FOODS CO., LTD. "Ginrin" is a registered trademark of GLICO FOODS CO., LTD.
Note (3)
Chemically unmodified wheat starch: Untreated native wheat starch.

On the next day of production and after one week, the obtained kamabokos were subjected to a sensory test. The kamaboko of Comparative Trial Production Example 7-1 had texture with slightly poor elasticity and also had no good chewiness. The kamaboko of Comparative Trial Production Example 7-2 had hardness but had stiff texture, and also retrogradation of the starch arose in a sensory test after refrigeration for one week, and thus the kamaboko showed dry and tasteless texture with water separation. The kamaboko of Comparative Trial Production Example 7-3 was less likely to cause change with time due to retrogradation because of the structure of the starch, but showed greasy texture with poor elasticity. As compared with these Comparative Trial Production Examples, both the kamabokos of Trial Production Examples 7-1 and 7-2, in which any one of the starches prepared in Examples 1-3 and 3A-3 was added, had elasticity with nice chewiness and also caused less change with time.

Trial Production Example 8: Preparation of Glaze for Mitarashi Dango

Among the formulation shown in Table 17 below, a starch sample was previously suspended in a part of water. The total amount of white soft sugar, dark soy sauce, Mirin, starch syrup and the remaining water were put in a pan and then mixed well by a wooden spatula. Furthermore, the starch sample previously suspended in water was added to them and heated while stirring using the wooden spatula. The mixture was heated until the mixture becomes a pasty mixture with a viscosity and a transparency state, to prepare a glaze for mitarashi dango.

TABLE 17

| Formulation (Parts) | Comparative Trial Production Example 8-1 | Comparative Trial Production Example 8-2 | Trial Production Example 8-1 | Trial Production Example 8-2 |
| --- | --- | --- | --- | --- |
| White soft sugar | 95 | 95 | 95 | 95 |
| Dark soy sauce | 80 | 80 | 80 | 80 |
| Mirin | 35 | 35 | 35 | 35 |
| Starch syrup | 8 | 8 | 8 | 8 |
| Chemically unmodified cassava starch [Note (2)] | 10 | — | — | — |
| Chemically modified cassava starch [Note (1)] | — | 10 | — | — |
| Starch prepared in Example 9 | — | — | 10 | — |
| Starch prepared in Example 10-2 | — | — | — | 10 |
| Water | 70 | 70 | 70 | 70 |

Note (1)
Chemically modified cassava starch: "RK-08", manufactured by GLICO FOODS CO., LTD.
Note (2)
Chemically unmodified cassava starch: Untreated native cassava starch.

The obtained glaze for mitarashi dango showed the following results. That is, both the glazes for mitarashi dango of Trial Production Example 8-1 and 8-2, in which any one of the starches prepared in Examples 9 and 10-2 was added, had nice body and shape retention, and were less likely to drop because of nice adhesion onto the dango, and also had less stickiness and thread-forming sensation and had smooth texture. On the other hand, the glaze for mitarashi dango of Comparative Trial Production. Example 8-1 had gel-like physical properties and heavy texture, and also had poor melt in mouth and no smoothness. The glaze for mitarashi dango of Comparative Trial Production Example 8-2 had poor body and poor shape retention and caused dropping because of poor adhesion onto a dango, and also had texture with stickiness and poor melt in mouth. For example, in freezing distribution of a split and broiled eel, in order to prevent a salsa for the split and broiled eel from dropping at the time of thawing, a salsa having a high viscosity and nice body and shape retention may be sometimes used in the final step of baking. However there is a problem that the salsa having a high viscosity usually has strong stickiness or in a gel-like form, and also has jellied fish-like physical properties and heavy texture. Use of the enzyme-treated starch in the present invention makes it possible to prepare a split and broiled fish which is less likely to drop because of nice adhesion onto the eel and the like, and has less stickiness and thread-forming sensation, and has smooth texture.

Trial Production Example 9: Preparation of Fruit Sauce

Among the formulations shown in Table 18 below, a starch sample was previously suspended in a part of water. Fruit puree, white soft sugar, lemon juice and the total amount of the remaining water were put in a pan and heated with stirring using the wooden spatula. Furthermore, the starch sample previously suspended in water was added to them. The mixture was heated until the mixture become a pasty mixture with a viscosity and a transparency state to prepare a fruit sauce.

TABLE 18

| Formulation (Parts) | Comparative Trial Production Example 9-1 | Comparative Trial Production Example 9-2 | Trial Production Example 9-1 | Trial Production Example 9-2 |
| --- | --- | --- | --- | --- |
| Fruit puree | 100 | 100 | 100 | 100 |
| White soft sugar | 10 | 10 | 10 | 10 |
| Chemically unmodified cassava starch [Note (2)] | 3 | — | — | — |
| Chemically modified cassava starch [Note (1)] | — | 3 | — | — |
| Starch prepared in Example 9 | — | — | 3 | — |
| Starch prepared in Example 10-2 | — | — | — | 3 |
| Lemon juice | 2 | 2 | 2 | 2 |
| Water | 10 | 10 | 10 | 10 |

Note (1)
Chemically modified cassava starch: "RK-08", manufactured by GLICO FOODS CO., LTD.
Note (2)
Chemically unmodified cassava starch: Untreated native cassava starch.

The obtained fruit sauces showed the following results. That is, both the fruit sauces of Trial Production Example 9-1 and 9-2, in which any one of the starches prepared in Examples 9 and 10-2 was added, had nice body and shape retention, and had nice adhesion onto a food such as dessert, and had less stickiness and thread-forming sensation, and smooth texture. On the other hand, the fruit sauce of Comparative Trial Production Example 9-1 had gel-like physical properties and heavy texture, and also had poor melt in mouth and no smoothness. The fruit sauce of Comparative Trial Production Example 9-2 had poor body and poor shape retention, and caused dropping because of poor adhesion onto a food such as dessert, and also had texture with stickiness, and poor melt in mouth.

Trial Production Example 10: Preparation of Dressing

Among the formulations shown in Table 19 below, white soft sugar and a starch sample which are previously mixed in powder state was added to water, and heated with stirring at 90° C. for 10 minutes. Brewed vinegar, common salt, lemon juice, and seasonings including monosodium glutamate and the like were added and further heated with stirring for 5 minutes. After cooling it to room temperature, egg yolk was added to them and mixed well. Using a homomixer manufactured by Tokushu Kika Kogyo Co., Ltd. (Now in the name of: PRIMIX Corporation), salad oil was slowly added dropwise while mixing with stirring at 8,000 rpm. After dropwise addition of the entire amount of salad oil, the mixture was mixed with stirring at 8,000 rpm further for 5 minutes to prepare a dressing.

TABLE 19

| Formulation (Parts) | Comparative Trial Production Example 10-1 | Comparative Trial Production Example 10-2 | Trial Production Example 10-1 | Trial Production Example 10-2 |
|---|---|---|---|---|
| Salad oil | 38 | 38 | 38 | 38 |
| Brewed vinegar (acidity: 4.2) | 10 | 10 | 10 | 10 |
| Egg yolk | 5 | 5 | 5 | 5 |
| White soft sugar | 5 | 5 | 5 | 5 |
| Common Salt | 3 | 3 | 3 | 3 |
| Lemon juice | 2 | 2 | 2 | 2 |
| Chemically unmodified cassava starch Note (2) | 2.5 | — | — | — |
| Chemically modified cassava starch Note (1) | — | 2.5 | — | — |
| Starch prepared in Example 9 | — | — | 2.5 | — |
| Starch prepared in Example 10-2 | — | — | — | 2.5 |
| Monosodium glutamate | 0.2 | 0.2 | 0.2 | 0.2 |
| Pepper | Suitable amount | Suitable amount | Suitable amount | Suitable amount |
| Mustard | Suitable amount | Suitable amount | Suitable amount | Suitable amount |
| Water | 33.8 | 33.8 | 33.8 | 33.8 |

Note (1)
Chemically modified cassava starch: "RK-08", manufactured by GLICO FOODS CO., LTD.
Note (2)
Chemically unmodified cassava starch: Untreated native cassava starch.

The obtained dressings showed the following results. That is, both the dressings of Trial Production Examples 10-1 and 10-2, in which each of the starches prepared in Examples 9 and 10-2 was added, had nice body and nice shape retention, and were less likely to drop because of nice adhesion onto vegetables and the like, and caused less stickiness and thread-forming sensation, and had smooth texture. On the other hand, the dressing of Comparative Trial Production Example 10-1 had gel-like physical properties and heavy texture, and also had poor melt in mouth and no smoothness. Also, the dressing of Comparative Trial Production Example 10-2 had poor body and poor shape retention and caused dropping because of poor adhesion onto vegetables and the like, and also had texture with stickiness, and poor melt in mouth.

Trial Production Example 11: Preparation of Batter for Deep-Fried Food)

Among the formulations shown in Table 20 below, soft wheat flour and a starch sample previously mixed in a powder state were suspended in cold water and mixed well to prepare a batter for deep-fried food.

TABLE 20

| Formulation (Parts) | Comparative Trial Production Example 11-1 | Comparative Trial Production Example 11-2 | Trial Production Example 11-1 | Trial Production Example 11-2 |
|---|---|---|---|---|
| Soft wheat flour | 150 | 95 | 95 | 95 |
| Chemically unmodified cassava starch Note (2) | 30 | — | — | — |
| Chemically modified cassava starch Note (1) | — | 30 | — | — |
| Starch prepared in Example 9 | — | — | 30 | — |
| Starch prepared in Example 10-2 | — | — | — | 30 |
| Cold water | 230 | 230 | 230 | 230 |

Note (1)
Chemically modified cassava starch: "RK-08", manufactured by GLICO FOODS CO., LTD.
Note (2)
Chemically unmodified cassava starch: Untreated native cassava starch.

The obtained batters for deep-fried food showed the following results. That is, both the tempuras obtained by dipping ingredients such as prawn in the batters for deep-fried food of Trial Production Examples 11-1 and 11-2, in which the starch prepared in Example 9 or 10-2 was added, thereby coating the ingredients with the batters, and frying in oil, or the fried foods obtained by dipping ingredients such as prawn in the batters for deep-fried food of Trial Production Examples 11-1 and 11-2, in which the starch prepared in Example 9 or 10-2 was added, thereby coating the ingredients with the batters, further coating this with a bread crumbs and frying in oil, had a crispy and light texture. On the other hand, tempuras and fried foods, in which the batters for deep-fried food of Comparative Trial Production Example 11-1 and Comparative Trial Production Example 11-2 were used, had poor crispy texture, and hardly made users feel lightness.

Trial Production Example 12: Preparation of Sausage

Among the formulations shown in Table 21 below, pork arm meat was put in a silent cutter, while cutting the pork arm meat at a high speed, casein sodium, common salt, white soft sugar, a seasoning, a pickle solution, a pork powder, spice, potassium sorbate, a pH adjusting agent and a food color were added and mixed well. When the mixture was formed into a paste, water with ice and lard were added and cutting was continued. Finally, a starch sample was added to them and mixed well to give a homogeneous paste. The paste was filled in a casing and then sterilized at 80° C. for 40 minutes to prepare a sausage by cooling with running water.

TABLE 21

| Formulation (Parts) | Comparative Trial Production Example 12-1 | Comparative Trial Production Example 12-2 | Trial Production Example 12-1 | Trial Production Example 12-2 |
|---|---|---|---|---|
| Pork arm meat | 60 | 60 | 60 | 60 |
| Lard | 10 | 10 | 10 | 10 |
| Casein sodium | 1 | 1 | 1 | 1 |
| Chemically unmodified cassava starch [Note (3)] | 3 | — | — | — |
| Chemically modified cassava starch [Note (1)] | — | 3 | — | — |
| Starch prepared in Example 9 | — | — | 3 | — |
| Starch prepared in Example 10-2 | — | — | — | 3 |
| Water with ice | 25 | 25 | 25 | 25 |
| Common salt | 1.4 | 1.4 | 1.4 | 1.4 |
| White soft sugar | 1 | 1 | 1 | 1 |
| Seasoning | 0.3 | 0.3 | 0.3 | 0.3 |
| pickle solution | 0.5 | 0.5 | 0.5 | 0.5 |
| Pork powder | 1 | 1 | 1 | 1 |
| Spice | 0.5 | 0.5 | 0.5 | 0.5 |
| Potassium sorbate | 0.15 | 0.15 | 0.15 | 0.15 |
| pH adjusting agent | 0.15 | 0.15 | 0.15 | 0.15 |
| Creation Color RC [Note (2)] | appropriate amount | appropriate amount | appropriate amount | appropriate amount |

Note (1)

Chemically modified cassava starch: "RK-08", manufactured by GLICO FOODS CO., LTD.

Note (2)

Creation Color RC: Cochineal food color. "Creation" is a registered trademark of GLICO FOODS CO., LTD.

Note (3)

Chemically unmodified cassava starch: Untreated native cassava starch.

On the next day of production and after one week, the obtained sausages were subjected to a sensory test. The sausage of Comparative Trial Production Example 12-1 had texture with slightly poor elasticity and had no good chewiness. The sausage of Comparative Trial Production Example 12-2 had hardness but had stiff texture, and retrogradation of the starch arose in a sensory test after refrigeration for one week, and thus the sausage showed dry and tasteless texture with water separation. As compared with those of these Comparative Trial Production Examples, both the sausages of Trial Production Examples 12-1 and 12-2, in which the starch prepared in Example 9 or 10-2 was added, had elasticity with nice chewiness and also caused less change with time.

Trial Production Example 13: Preparation of Raw Udon

To a powder mixture obtained by mixing a starch, medium wheat flour and a powdered gluten in the following ratio in accordance with the formulation shown in Table 22 below, water for kneading obtained by dissolving 2 parts of common salt in 40 parts of water was added, followed by kneading in a vacuum mixer for 12 minutes. Using a noodle making machine, the obtained kneaded mixture was subjected to compound and rolling to obtain a noodle strip, which was cut using a cutting-tooth No. 10 to obtain a raw udon.

TABLE 22

| Formulation (Parts) | Comparative Trial Production Example 13-1 | Comparative Trial Production Example 13-2 | Comparative Trial Production Example 13-3 | Trial Production Example 13-1 |
|---|---|---|---|---|
| Wheat flour | 80 | 80 | 80 | 80 |
| Chemically unmodified cassava starch [Note (3)] | 20 | — | — | — |
| Chemically modified cassava starch 1 [Note (1)] | — | 20 | — | — |
| Chemically modified cassava starch 2 [Note (2)] | — | — | 20 | — |
| Starch prepared in Example 10-2 | — | — | — | 20 |
| Powdered gluten | 2 | 2 | 2 | 2 |
| Salt | 2 | 2 | 2 | 2 |
| Water | 40 | 40 | 40 | 40 |

Note (1)

Chemically modified cassava starch 1: "CHEMISTAR 280", manufactured by GLICO FOODS CO., LTD. "CHEMISTAR" is a registered trademark of GLICO FOODS CO., LTD.

Note (2)

Chemically modified cassava starch 2: "RK-08", manufactured by GLICO FOODS CO., LTD.

Note (3)

Chemically unmodified cassava starch: Untreated native cassava starch.

The obtained raw udon was boiled in boiling water for 10 minutes and dipped in a hot soup, and then texture was evaluated. The udon of Comparative Trial Production Example 13-1 and Comparative Trial Production Example 13-2 was poor in elasticity and texture was hardly improved. Regarding the udon of Comparative Trial Production Example 13-3, a slight effect of imparting elasticity was recognized. However, rigid hardness was merely imparted and this effect may have a bad effect on noodles. On the other hand, regarding the udon of Trial Production Example 13-1, the effect of imparting sticky texture with excellent chewiness was recognized.

Trial Production Example 14: Preparation of Jelly Candy

In accordance with the formulations shown in Table 23 below, white sugar, starch syrup, a starch and water were mixed with stirring in the following ratio, the mixture was dissolved by heating up to Bx (Brix) 75. The obtained solution was filled in a mold, and left at normal temperature for 24 hours. After confirming that the solution has been solidified, it was removed from the mold to obtain a jelly candy.

TABLE 23

| Formulation (Parts) | Comparative Trial Production Example 14-1 | Comparative Trial Production Example 14-2 | Trial Production Example 14-1 | Trial Production Example 14-2 |
|---|---|---|---|---|
| Sugar | 34 | 34 | 34 | 34 |
| Starch syrup | 30 | 30 | 30 | 30 |
| Chemically unmodified cassava starch [Note (2)] | 21 | — | — | — |

TABLE 23-continued

| Formulation (Parts) | Comparative Trial Production Example 14-1 | Comparative Trial Production Example 14-2 | Trial Production Example 14-1 | Trial Production Example 14-2 |
| --- | --- | --- | --- | --- |
| Chemically modified cassava starch [Note (1)] | — | 21 | — | — |
| Starch prepared in Example 9 | — | — | 21 | — |
| Starch prepared in Example 10-2 | — | — | — | 21 |
| Water | 15 | 15 | 15 | 15 |

Note (1)
Chemically modified cassava starch: "CHEMISTAR 300S" manufactured by GLICO FOODS CO., LTD. "CHEMISTAR" is a registered trademark of GLICO FOODS CO., LTD.

Note (2)
Chemically unmodified cassava starch: Untreated native cassava starch.

The obtained jelly candies showed the following results. That is, both the jelly candles of Trial Production Example 14-1 and 14-2 had appropriate viscoelasticity and nice melt texture in mouth. On the other hand, the jelly candy of Comparative Trial Production Example 14-1 had strong elastic sensation, and the jelly candy of Comparative Trial Production Example 14-2 had strong sticky textures, but both the jelly candies had strong pasty sensation and poor melt in mouth.

Trial Production Example 15: Preparation of Frozen Dessert

In accordance with the formulation shown in Table 24 below, while raw materials and water were mixed with stirring in the following ratio, the mixture was dissolved by heating up to Bx (Brix) 40. The obtained solution was put in an ice cream maker and cooled with stirring for 35 minutes. The obtained materials was transferred to a container and then frozen to obtain a frozen dessert.

TABLE 24

| Formulation (Parts) | Comparative Trial Production Example 15-1 | Comparative Trial Production Example 15-2 | Trial Production Example 15-1 | Trial Production Example 15-2 |
| --- | --- | --- | --- | --- |
| Starch syrup | 18 | 18 | 18 | 18 |
| Granulated sugar | 12 | 12 | 12 | 12 |
| Fresh cream | 12 | 12 | 12 | 12 |
| Vegetable oil and fat | 6 | 6 | 6 | 6 |
| Chemically unmodified cassava starch [Note (2)] | 2.4 | — | — | — |
| Chemically modified cassava starch [Note (1)] | — | 2.4 | — | — |
| Starch prepared in Example 9 | — | — | 2.4 | — |
| Starch prepared in Example 10-2 | — | — | — | 2.4 |
| Guar gum | 0.4 | 0.4 | 0.4 | 0.4 |
| Emulsifier | 0.2 | 0.2 | 0.2 | 0.2 |
| Water | 49 | 49 | 49 | 49 |

Note (1)
Chemically modified cassava starch: "CHEMISTAR 300S", manufactured by GLICO FOODS CO., LTD. "CHEMISTAR" is a registered trademark of GLICO FOODS CO., LTD.

Note (2)
Chemically unmodified cassava starch: Untreated native cassava starch.

The obtained frozen desserts showed the following results. That is, both the frozen desserts of Trial Production Examples 15-1 and 15-2 had appropriate viscoelasticity and sticky texture, and had nice melt texture in mouth. On the other hand, the frozen dessert of Comparative Trial Production Example 15-1 had sticky texture and the frozen dessert of Comparative Trial Production Example 15-2 also had sticky texture and spinnability. However, both the frozen desserts had strong pasty sensation and poor melt in mouth.

Example 13-1

To 400 g of an untreated native wheat starch of the same lot as what was used in Comparative Example 1, 900 g of ion-exchange water was added to prepare a starch suspension. After adjusting the pH of the suspension to 5.0, 1% by weight (based on starch solid content) of cyclodextrin glucanotransferase ("Toruzyme 3.0 L" derived from *Bacillus licheniformis*, manufactured by Novo; optimum pH of 6.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined by a part of a reaction solution. The results are shown in Table 2-2. As a result, the setback viscosity of it was 7.0 (BU).

Example 13-2

To 400 g of an untreated native wheat starch of the same lot as what was used in Comparative Example 1, 900 g of ion-exchange water was added to prepare a starch suspension. After adjusting the pH of the suspension to 6.0, 1% by weight (based on starch solid content) of cyclodextrin glucanotransferase (Cyclodextrin glucanotransferase "Amano" derived from *Paenibacillus macerans* (*Bacillus macerans*), manufactured by Amano Enzyme) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined by a part of a reaction solution. The results are shown in Table 2-2.

Example 14

To 400 g of an untreated native corn starch of the same lot as what was used in Comparative Example 12, 900 g of ion-exchange water was added to prepare a starch suspension. After adjusting the pH of the suspension to 5.0, 1% by weight (based on starch solid content) of cyclodextrin glucanotransferase ("Toruzyme 3.0 L" derived from *Bacillus licheniformis*, manufactured by Novo; optimum pH of 6.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined by a part of a reaction solution. The results are shown in Table 3-2. As a result, the setback viscosity of it was 0 (BU).

Example 15

To 400 g of an untreated native cassava starch of the same lot as what was used in Comparative Example 15, 900 g of ion-exchange water was added to prepare a starch suspension. After adjusting the pH of the suspension to 5.0, 1% by weight (based on starch solid content) of cyclodextrin glucanotransferase ("Toruzyme 3.0 L" derived from *Bacillus licheniformis*, manufactured by Novo; optimum pH of 6.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined by a part of a reaction solution. The results are shown in Table 4-2. As a result, the setback viscosity of it was 2 (BU).

Comparative Example 18

To 500 g of an untreated native cassava starch of the same lot as what was used in Comparative Example 15, 750 g of an aqueous 6.7% (w/w) sodium sulfate solution was added to prepare a starch suspension. After adjusting the pH of the suspension to 8.5, 7.36 g of a vinyl acetate monomer was added and stirred at 30° C. for 40 minutes to allow a reaction proceed. After 40 minutes, the pH of the suspension was adjusted to 6.0 and the reaction was terminated. After completion of the reaction, acetylated starch granules were obtained by centrifugal filtration and blow drying. Viscosity characteristics of the obtained acetylated starch granules (starch acetate granules) were analyzed by the amylograph and the rheometer.

Comparative Example 19

To 500 g of an untreated native cassava starch of the same lot as what was used in Comparative Example 15, 785 g of an aqueous 11% (w/w) sodium sulfate solution was added to prepare a starch suspension. After adjusting the pH of the suspension to 11.0, 24 g of propylene oxide was added and stirred at 42° C. for 16 hours to allow a reaction proceed. After 16 hours, the pH of the suspension was adjusted to 6.0 and the reaction was terminated. After completion of the reaction, hydroxypropylated starch granules (hydroxypropyl starch granules) were obtained by centrifugal filtration and blow drying. Viscosity characteristics of the obtained hydroxypropylated starch granules were analyzed by the amylograph and the rheometer.

Comparative Example 20

To 500 g of an untreated native cassava starch of the same lot as what was used in Comparative Example 15, 750 g of an aqueous 6.7% (w/w) sodium sulfate solution was added to prepare a starch suspension. After adjusting the pH of the suspension to 11.0, 10 µl of phosphorus oxychloride was added and stirred at 30° C. for 1 hour to allow a reaction proceed. After 1 hour, the pH of the suspension was adjusted to 6.0 and the reaction was terminated. After completion of the reaction, phosphate-crosslinking starch granules (distarch phosphate granules) were obtained by centrifugal filtration and blow drying. Viscosity characteristics of the obtained phosphate-crosslinking starch granules were analyzed by the amylograph and the rheometer.

Comparative Example 21

To 500 g of an untreated native cassava starch of the same lot as what was used in Comparative Example 15, 910 g of an aqueous 10% (w/w) sodium sulfate solution was added to prepare a starch suspension. After adjusting the pH of the suspension to 11.0, 16 g of propylene oxide was added and stirred at 42° C. for 16 hours to allow an etherification reaction proceed. After 16 hours, the temperature of the starch suspension was adjusted to 30° C., 5 µl of phosphorus oxychloride was added and stirred at 30° C. for 1 hour to carry out a crosslinking reaction proceed. After 1 hour, the pH of the suspension was adjusted to 6.0 and the entire reaction was terminated. After completion of the reaction, hydroxypropylated phosphate-crosslinking starch granules (hydroxypropyl distarch phosphate granules) were obtained by centrifugal filtration and blow drying. Viscosity characteristics of the obtained hydroxypropylated phosphate-crosslinking starch granules were analyzed by the amylograph and the rheometer.

Example 16

To 4 Kg of an untreated native cassava starch of the same lot as what was used in Comparative Example 15, 9 Kg of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, enzyme-treated starch granules were obtained by centrifugal filtration and blow drying. It is noted that the degradation ratio of the obtained sample was 21% by weight.

Example 17

To 400 g of the acetylated starch granules (starch acetate granules) prepared in Comparative Example 18, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. After completion of the reaction, a degradation ratio was determined using a part of the reaction solution.

Example 18

To 400 g of the acetylated starch granules (starch acetate granules) prepared in Comparative Example 18, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined using a part of the reaction solution.

Example 19

To 400 g of the hydroxypropylated starch granules prepared in Comparative Example 19, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined using a part of the reaction solution.

Example 20

To 400 g of the hydroxypropylated starch granules prepared in Comparative Example 19, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined using a part of the reaction solution.

Example 21

To 400 g of the phosphate-crosslinking starch granules (distarch phosphate granules) prepared in Comparative Example 20, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined using a part of the reaction solution.

Example 22

To 400 g of the phosphate-crosslinking starch granules (distarch phosphate granules) prepared in Comparative Example 20, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined using a part of the reaction solution.

Example 23

To 400 g of the hydroxypropylated phosphate-crosslinking starch granules (hydroxypropyl distarch phosphate granules) prepared in Comparative Example 21, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined, using a part of the reaction solution.

Example 24

To 400 g of the hydroxypropylated phosphate-crosslinking starch granules (hydroxypropyl distarch phosphate granules) prepared in Comparative Example 21, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined using a part of the reaction solution.

Example 25

To 500 g of the enzyme-treated starch granules prepared in Example 16, 750 g of an aqueous 6.7% (w/w) sodium sulfate solution was added to prepare a starch suspension. After adjusting the pH of the suspension to 8.5, 7.36 g of a vinyl acetate monomer was added and stirred at 30° C. for 40 minutes to carry out a reaction. After 40 minutes, the pH of the suspension was adjusted to 6.0 and the reaction was terminated. After completion of the reaction, enzyme-treated-acetylated starch granules were obtained by centrifugal filtration and blow drying. Viscosity characteristics of the obtained enzyme-treated acetylated starch granules were analyzed by the amylograph and the rheometer. Also, after completion of the reaction, a degradation ratio was determined by a part of the reaction solution.

Example 26

To 500 g of the enzyme-treated starch granules prepared in Example 16, 785 g of an aqueous 11% (w/w) sodium sulfate solution was added to prepare a starch suspension. After adjusting the pH of the suspension to 11.0, 24 g of propylene oxide was added and stirred at 42° C. for 16 hours to carry out a reaction. After 16 hours, the pH of the suspension was adjusted to 6.0 and the reaction was terminated. After completion of the reaction, enzyme-treated-hydroxypropylated starch granules were obtained by centrifugal filtration and blow drying. Viscosity characteristics of the obtained enzyme-treated-hydroxypropylated starch granules were analyzed by the amylograph and the rheometer. Also, after completion of the reaction, a degradation ratio was determined by a part of the reaction solution.

Example 27

To 500 g of the enzyme-treated starch granules prepared in Example 16, 750 g of an aqueous 6.7% (w/w) sodium sulfate solution was added to prepare a starch suspension. After adjusting the pH of the suspension to 11.0, 10 µl of phosphorus oxychloride was added and stirred at 30° C. for 1 hour to carry out a reaction. After 1 hour, the pH of the suspension was adjusted to 6.0 and the reaction was terminated. After completion of the reaction, enzyme-treated-phosphate-crosslinking starch granules were obtained by centrifugal filtration and blow drying. Viscosity characteristics of the obtained enzyme-treated-phosphate-crosslinking starch granules were analyzed by the amylograph and the rheometer. Also, after completion of the reaction, a degradation ratio was determined by a part of the reaction solution.

Example 28

To 500 g of the enzyme-treated starch granules prepared in Example 16, 910 g of an aqueous 10% (w/w) sodium sulfate solution was added to prepare a starch suspension. After adjusting the pH of the suspension to 11.0, 16 g of propylene oxide was added and stirred at 42° C. for 16 hours to carry out an etherification reaction. After 16 hours, the temperature of the starch suspension was adjusted to 30° C. and 5 µl of phosphorus oxychloride was added and stirred at 30° C. for 1 hour to carry out a crosslinking reaction. After 1 hour, the pH of the suspension was adjusted to 6.0 and the entire reaction was terminated. After completion of the reaction, enzyme-treated hydroxypropylated phosphate-crosslinking starch granules were obtained by centrifugal filtration and blow drying. Viscosity characteristics of the obtained enzyme-treated hydroxypropylated phosphate-crosslinking starch granules were analyzed by the amylograph and the rheometer. Also, after completion of the reaction, a degradation ratio was determined by a part of the reaction solution.

The measurement results of Comparative Examples 18 to 21 and Examples 17 to 28 are shown in Table 25-2. It is noted that in an analysis by the rheometer of the present starch which used the chemical modification and the enzymatic treatment in combination, after refrigeration storage at 5° C. for 16 hours the gel did not have the hardness sufficient for the measurement. Therefore, it was difficult to compare physical properties of the gels. Therefore, confirmation was carried out after refrigeration storage at 5° C. for 21 days. The details are as follows.

A starch paste was prepared so that the concentration of the starch was 20% by weight on the dry matter basis, and then filled in a Krehalon casing having a folding width of 45 mm. This starch paste filled in the casing was heated to 90° C. at 1° C./min and maintained at 90° C. for 30 minutes. Then, the starch paste was left to cool in a constant-temperature water bath at 20° C. for 30 minutes, and then it was cooled to 5° C. in a refrigerator. After cooling, it was refrigerated at 5° C. for 21 days, then it was left at room temperature (about 25° C.) for 4 hours to return the temperature of it to room temperature, and then the measurement was carried out with a rheometer (RT-2010J-CW) manufactured by Rheotech Inc. The measurement was carried out under the measurement conditions of the rheometer: a test item: a rupture test; a height of a sample: 25 mm; and a movement rate (rupture rate) of a sample: 6 cm/min, using an adapter of a spherical jig for measurement viscosity φ5 (diameter: 5 mm, area: 19.635 mm$^2$). At the measurement, the hardness of the starch gel was evaluated by a rupture stress (g) and a Young's modulus (dyn/cm$^2$).

TABLE 25-1

Summary of Names, Origins and Product Names of Enzymes used for Chemical Modification and Enzymatic Treatment in combination

| Example | Name of enzyme | Origin | Kind of chemical modification |
|---|---|---|---|
| Comp. Ex. 18 | — | — | Acetylation |
| Example 17 | amyloglucosidase | *Aspergillus niger* | Acetylation |
| Example 18 | α-amylase | *Aspergillus niger* | Acetylation |
| Example 25 | amyloglucosidase | *Aspergillus niger* | Acetylation |
| Comp. Ex. 19 | — | — | Hydroxypropylation |
| Example 19 | amyloglucosidase | *Aspergillus niger* | Hydroxypropylation |
| Example 20 | α-amylase | *Aspergillus niger* | Hydroxypropylation |
| Example 26 | amyloglucosidase | *Aspergillus niger* | Hydroxypropylation |
| Comp. Ex. 20 | — | — | Phosphate-crosslinking |
| Example 21 | amyloglucosidase | *Aspergillus niger* | Phosphate-crosslinking |
| Example 22 | α-amylase | *Aspergillus niger* | Phosphate-crosslinking |
| Example 27 | amyloglucosidase | *Aspergillus niger* | Phosphate-crosslinking |
| Comp. Ex. 21 | — | — | Hydroxypropylation, phosphate-crosslinking |
| Example 23 | amyloglucosidase | *Aspergillus niger* | Hydroxypropylation, phosphate-crosslinking |
| Example 24 | α-amylase | *Aspergillus niger* | Hydroxypropylation, phosphate-crosslinking |
| Example 28 | amyloglucosidase | *Aspergillus niger* | Hydroxypropylation, phosphate-crosslinking |
| Comp. Ex. 22 | — | — | Oxidized starch |
| Example 29 | amyloglucosidase | *Aspergillus niger* | Oxidized starch |
| Example 30 | α-amylase | *Aspergillus niger* | Oxidized starch |
| Comp. Ex. 23 | — | — | (Bleached starch) |
| Example 31 | amyloglucosidase | *Aspergillus niger* | (Bleached starch) |
| Example 32 | α-amylase | *Aspergillus niger* | (Bleached starch) |

Comp. Ex. = Comparative Example

TABLE 25-2

Summary of combined use of chemical modification and
enzymatic treatment (Starch Concentration for Amylograph: 6.0%)

| | | Maximum viscosity | | | Rupture stress | | Young's modulus | |
|---|---|---|---|---|---|---|---|---|
| Example | Degradation ratio (%) | Measured value (BU) | Relative % (%) | Breakdown viscosity (BU) | Measured value (g) | Relative % (%) | Measured value (dyn/cm$^2$) | Relative % (%) |
| Comp. Ex. 18 | — | 895 | 100 | 606 | 121 | 100 | 2,499,026 | 100 |
| Example 17 | 7 | 727 | 81 | 433 | 145 | 120 | 2,923,860 | 117 |
| Example 18 | 9 | 693 | 77 | 429 | 142 | 117 | 3,023,821 | 121 |
| Example 25 | 21 | 797 | 89 | 472 | 215 | 178 | 4,169,554 | 167 |
| Comp. Ex. 19 | — | 1004 | 100 | 670 | 33 | 100 | 373,715 | 100 |
| Example 19 | 20 | 845 | 84 | 550 | 47 | 142 | 483,149 | 129 |
| Example 20 | 21 | 661 | 66 | 470 | 43 | 130 | 669,986 | 179 |
| Example 26 | 21 | 824 | 82 | 525 | 71 | 215 | 573,625 | 153 |
| Comp. Ex. 20 | — | 903 | 100 | 0 | 170 | 100 | 3,943,691 | 100 |
| Example 21 | 21 | 908 | 101 | 0 | 283 | 166 | 5,319,388 | 135 |
| Example 22 | 15 | 871 | 96 | 0 | 337 | 198 | 7,529,620 | 191 |
| Example 27 | 21 | 898 | 99 | 0 | 554 | 326 | 10,027,924 | 254 |
| Comp. Ex. 21 | — | 769 | 100 | 403 | 31 | 100 | 250,328 | 100 |
| Example 23 | 19 | 740 | 96 | 413 | 45 | 145 | 391,117 | 156 |
| Example 24 | 21 | 524 | 68 | 356 | 64 | 206 | 1,218,285 | 487 |
| Example 28 | 21 | 784 | 102 | 207 | 125 | 403 | 1,497,293 | 598 |
| Comp. Ex. 22 | — | 317 | 100 | 227 | 91 | 100 | 4,468,130 | 100 |
| Example 29 | 7 | 419 | 132 | 324 | 119 | 131 | 5,953,997 | 133 |
| Example 30 | 9 | 411 | 130 | 315 | 101 | 111 | 5,048,987 | 113 |
| Comp. Ex. 23 | — | 715 | 100 | 181 | 137 | 100 | 4,494,603 | 100 |
| Example 31 | 22 | 673 | 94 | 138 | 224 | 164 | 5,293,378 | 118 |
| Example 32 | 31 | 630 | 88 | 143 | 237 | 173 | 6,764,052 | 150 |

* Degradation ratios in Examples 25 to 28 each refer to a degradation ratio of an enzyme-treated starch used as a base material.

It was confirmed that when the chemical modification and the enzymatic treatment are used in combination, particularly when the phosphate-crosslinking starch is subjected to the enzymatic treatment, gel forming ability can be enhanced while maintaining a maximum viscosity. This is an extremely excellent advantage as compared with the fact that when phosphate-crosslinking is increased in a conventional chemical modification, the gel becomes harder but the maximum viscosity drastically decreases, thus leading to the cause of powderiness. It was also confirmed for not only the phosphate-crosslinking starch but also other chemically modified starches that, by carrying out an enzymatic treatment, it is possible to enhance gel forming ability while relatively maintaining the viscosity as compared with a conventional chemically modified starch.

By the same method as that for the starches of Comparative examples 1 to 17 and Examples 1-1 to 15, retrogradation resistance, transparency and film property of the starches of Comparative examples 18 to 21 and Examples 17 to 28 were assessed. The results are shown in following Table 25-3.

TABLE 25-3

Retrogradation resistance, transparency and film property of the
starches of Comparative examples 18 to 21 and Examples 17 to 28

| Example | | Retrogradation resistance | Transparency | Film property |
|---|---|---|---|---|
| Comparative example 18 | Acetylation | Yes | Transparent | Yes |
| Example 17 | Acetylation | Yes | Transparent | Yes |
| Example 18 | Acetylation | Yes | Transparent | Yes |
| Example 25 | Acetylation | Yes | Transparent | Yes |
| Comparative example 19 | Hydroxypropylation | Yes | Transparent | Yes |
| Example 19 | Hydroxypropylation | Yes | Transparent | Yes |
| Example 20 | Hydroxypropylation | Yes | Transparent | Yes |
| Example 26 | Hydroxypropylation | Yes | Transparent | Yes |
| Comparative example 20 | Phosphate-crosslinking | No | Opaque in white | No |
| Example 21 | Phosphate-crosslinking | No | Opaque in white | No |
| Example 22 | Phosphate-crosslinking | No | Opaque in white | No |
| Example 27 | Phosphate-crosslinking | No | Opaque in white | No |
| Comparative example 21 | Hydroxypropylated phosphate-crosslinking | Yes | Transparent | Yes |
| Example 23 | Hydroxypropylated phosphate-crosslinking | Yes | Transparent | Yes |
| Example 24 | Hydroxypropylated phosphate-crosslinking | Yes | Transparent | Yes |
| Example 28 | Hydroxypropylated phosphate-crosslinking | Yes | Transparent | Yes |
| Comparative example 22 | Oxidized starch | No | Transparent | No |
| Example 29 | Oxidized starch | No | Transparent | No |
| Example 30 | Oxidized starch | No | Transparent | No |
| Comparative example 23 | (bleached starch) | No | slightly opaque | No |
| Example 31 | (bleached starch) | No | slightly opaque | No |
| Example 32 | (bleached starch) | No | slightly opaque | No |

Generally, it is known that particular chemical modifications affect retrogradation resistance, transparency and film property. Particularly, as shown in Comparative examples 18, 19 and 21, esterification and etherification have an effect to give retrogradation resistance, transparency and film property. In Examples 17, 18, 25, 19, 20, 26, 23, 24, and 28, there are retrogradation resistance, transparency and film property. Therefore, it was confirmed that the enzyme-treatment did not adversely affect the effects (retrogradation resistance, transparency and film-related grant) provided by the chemical modification. Particularly, it was confirmed that impartment of retrogradation resistance and improvement of transparency obtained esterification or etherification were maintained even if an enzyme-treatment was used in combination.

On the other hand, it is conventionally known that chemical modification such as phosphate-crosslinking, oxidation, or bleaching has no effect on retrogradation resistance, transparency and film property. Actually, as for phosphate-crosslinking in Comparative example 20, Examples 21, 22, and 27, each starch granule showed slightly lower values than natural starch granules which have not been treated with the enzyme regarding retrogradation resistance, transparency and film property. However, when Comparative Example 20 (without enzyme-treatment) and Examples 21, 22 and 27 (with enzyme-treatment) are compared, regarding all of the retrogradation resistance, transparency and film property, no deterioration of the properties due to the enzyme-treatment was observed.

In the oxidized starches of Comparative example 22, Examples 29 and 30 and bleaching starches of Comparative example 23, Examples 31 and 32, regarding each starch granule, in comparison with the natural starch granule which has not been enzyme-treated, transparency was improved, while retrogradation resistance and film property were slightly lowered. However, when Comparative Example 22 (without enzyme treatment) and Examples 29 and 30 (with enzyme-treatment) are compared, regarding all of retrogradation resistance, transparency and film property, there was no deterioration of properties due to the enzyme treatment. Further, when Comparative Example 23 and Examples 31 and 32 are compared, regarding all of retrogradation resistance, transparency and film property, there was no deterioration of properties due to the enzyme treatment. As described above, regarding all chemical modifications, no difference due to enzyme-treatment was observed.

Comparative Example 22: Oxidized Starch

To 500 g of an untreated native cassava starch of the same lot as what was used in Comparative Example 15, 750 g of ion-exchange water was added to prepare a starch suspension. After adjusting the of the suspension to 10.0, 25 g of sodium hypochlorite whose effective chlorine amount is 10% by weight vas added and stirred at 30° C. for 2 hours to carry out a reaction, while maintaining the pH of the suspension at 10.0. After 2 hours, the pH of the suspension was adjusted to 6.0 and then 2 g of sodium hydrogen sulfite was added. Immediately after stirring, the pH of the suspension was adjusted to 6.0 and the reaction was terminated. After completion of the reaction, the oxidized starch was obtained by centrifugal filtration and blow drying. Viscosity characteristics of the obtained oxidized starch were analyzed by the amylograph and the rheometer.

Comparative Example 23: Bleached Starch

To 500 g of an untreated native cassava starch of the same lot as what was used in Comparative Example 15, 700 g of ion-exchange water was added to prepare a starch suspension. After adjusting the pH of the suspension to 11.0, 2.5 g of sodium hypochlorite whose effective chlorine amount is 10% by weight was added and stirred at 30° C. for 5 minutes while maintaining the pH of the suspension at 11. Then, 0.25 g of sodium metabisulfite was added and stirred for 10 minutes, the pH of the suspension was adjusted to 6.0 and the reaction was terminated. After completion of the reaction, the bleached starch was obtained by centrifugal filtration and blow drying. Viscosity characteristics of the obtained bleached starch were analyzed by the amylograph and the rheometer.

Example 29: In the Case where an Oxidized Starch was Treated with an Amyloglucosidase To 400 g of the oxidized starch prepared in Comparative Example 22, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined using a part of the reaction solution.

Example 30: In the Case where an Oxidized Starch was Treated with an α-Amylase

To 400 g of the oxidized starch prepared in Comparative Example 22, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined using a part of the reaction solution.

Example 31: In the Case where a Bleached Starch was Treated with an Amyloglucosidase To 400 g of the bleached starch prepared in Comparative Example 23, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined using a part of the reaction solution.

Example 32: In the Case where a Bleached Starch was Treated with an α-Amylase To 400 g of the bleached starch prepared in Comparative Example 23, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, enzyme-treated starch granules were obtained by centrifugal filtration and blow drying. Viscosity characteristics of the obtained enzyme-treated starch granules were analyzed by the amylograph and the rheometer. Also, after completion of the reaction, a degradation ratio was determined using a part of the reaction solution. The measurement results of Comparative Examples 22 to 23 and Examples 29 to 32 are shown in Table 25-2.

Comparative Example 24

To 2 kg of an untreated native corn starch of the same lot as what was used in Comparative Example 12, ion-exchange water was added thereby adjusting the water content to 21% by weight. The resultant was filled in a 3 L glass beaker in a state where blank space was as small as possible, and the upper portion was covered with an aluminum foil, and then heated at 120° C. for 15 minutes to carry out a heat-moisture treatment. After completion of the heat-moisture treatment, the heat-moisture-treated starch granules were obtained by blow drying.

Example 33

To 4 Kg of an untreated native corn starch of the same lot as what was used in Comparative Example 12, 9 Kg of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, enzyme-treated starch granules were obtained by centrifugal filtration and blow drying. It is noted that the degradation ratio of the obtained sample was 34% by weight.

Example 34

To 4 Kg of an untreated native corn starch of the same lot as what was used in Comparative Example 12, 9 Kg of on-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, enzyme-treated starch granules were obtained by centrifugal filtration and blow drying. It is noted that the degradation ratio of the obtained sample was 28% by weight.

Example 35

To 400 g of the heat-moisture-treated starch granules prepared in Comparative Example 24, 900 g of ion-exchange water was added to prepare a starch suspension. After adjusting the pH of the suspension to 5.0, 1% by weight (based on starch solid content) of amyloglucosidase ("OPTIDEX L-400" derived from *Aspergillus niger*, manufactured by Genencor; optimum pH of 4.4) was added and stirred at 50° C. for 18 hours to carry out an enzyme reaction. After completion of the reaction, enzyme-heat-moisture-treated starch granules were obtained by centrifugal filtration and blow drying. Viscosity characteristics of the obtained enzyme-heat-moisture-treated starch granules were analyzed by the amylograph and the rheometer. Also, after completion of the reaction, a degradation ratio was determined using a part of the reaction solution.

Example 36

To 400 g of the heat-moisture-treated starch granules prepared in Comparative Example 24, 900 g of ion-exchange water was added to prepare a starch suspension. After adjusting the pH of the suspension to 5.0, 1% by weight (based on starch solid content) of α-amylase ("AMYLEX A3" derived from *Aspergillus niger*, manufactured by DANISCO; optimum pH of 5.0) was added and stirred at 50° C. for 18 hours to carry out an enzyme reaction. After completion of the reaction, enzyme-heat-moisture-treated starch granules were obtained by centrifugal filtration and blow drying. Viscosity characteristics of the obtained enzyme-heat-moisture-treated starch granules were analyzed by the amylograph and the rheometer. Also, after completion of the reaction, a degradation ratio was determined using a part of the reaction solution.

Example 37

To 400 g of the enzyme-treated starch granules prepared in Example 33, ion-exchange water was added thereby adjusting the water content to 21% by weight. The resultant was filled in a 1 L glass beaker in a state where blank space was as small as possible, and the upper portion was covered with an aluminum foil, and then heated at 120° C. for 15 minutes to carry out a heat-moisture treatment. After completion of the heat-moisture treatment, heat-moisture-enzyme-treated starch granules were obtained by blow drying. Viscosity characteristics of the obtained heat-moisture-enzyme-treated starch granules were analyzed by the amylograph and the rheometer. Also, after completion of the reaction, a degradation ratio was determined by a part of the reaction solution.

Example 38

To 400 g of the enzyme-treated starch granules prepared in Example 34, ion-exchange water was added thereby adjusting the water content to 20% by weight. The resultant was filled in a 1 L glass beaker in a state where blank space was as small as possible, and the upper portion was covered with an aluminum foil, and then heated at 120° C. for 15 minutes to carry out a heat-moisture treatment. After completion of the heat-moisture treatment, heat-moisture-enzyme-treated starch granules were obtained by blow drying. Viscosity characteristics of the obtained heat-moisture-enzyme-treated starch granules were analyzed by the amylograph and the rheometer. Also, after completion of the reaction, a degradation ratio was determined by a part of the reaction solution. The measurement results of Comparative Example 24 and Examples 35 to 38 are shown in Table 26-2.

TABLE 26-1

Summary of Names, Origins and Product Names of Enzymes Used for a Treatment of Heat-moisture-treated Starch Granules

| Example | Name of enzyme | Origin | Product name of enzyme (manufacture) |
|---|---|---|---|
| Comparative Example 24 | — | — | Untreated corn starch |
| Example 35 | amyloglucosidase | *Aspergillus niger* | OPTIDEX L-400 (Genencor) |
| Example 36 | α-amylase | *Aspergillus niger* | AMYLEX A3 (DANISCO) |
| Example 37 | amyloglucosidase | *Aspergillus niger* | OPTIDEX L-400 (Genencor) |
| Example 38 | α-amylase | *Aspergillus niger* | AMYLEX A3 (DANISCO) |

TABLE 26-2

| | | Maximum viscosity | | Next Day | | | |
|---|---|---|---|---|---|---|---|
| | | | | Rupture stress | | Young's modulus | |
| Example | Degradation ratio (% by weight) | Measured value (BU) | Relative % (%) | Breakdown viscosity (BU) | Measured value (g) | Relative % (%) | Measured value (dyn/cm²) | Relative % (%) |
| Comparative Example 24 | — | 401 | 100 | 108 | 230 | 100 | 6,091,460 | 100 |
| Example 35 | 39 | 351 | 88 | 96 | 439 | 191 | 6,566,419 | 108 |
| Example 36 | 33 | 351 | 88 | 91 | 436 | 190 | 6,788,705 | 111 |
| Example 37 | 34 | 327 | 82 | 74 | 420 | 182 | 6,690,934 | 110 |
| Example 38 | 28 | 349 | 87 | 79 | 428 | 186 | 7,132,581 | 117 |

* Degradation ratios in Examples 37 and 38 each refer to a degradation ratio of enzyme-treated starch granules used as a base material.

(Comparative Example 25-1) Preparation of Hydroxypropylated Starch Granule

To 700 g of untreated native wheat starch granules, 157.5 g of sodium sulfate and 1,300 g of water were added to prepare a starch suspension. After adjusting the pH of the suspension to 11.0, 52.5 g of propylene oxide was added and stirred at 40° C. for 24 hours to allow a reaction to proceed. After the reaction, the pH of the suspension was adjusted to 5.5 and the reaction was terminated.

(Comparative Example 25-2) Preparation of Hot-Water-Treated Hydroxypropylated Starch Granule To 700 g of untreated native wheat starch granules of the same lot as what was used in Comparative Example 25-1, 1,300 g of water was added to prepare a starch suspension. The suspension was heated in hot-water bath of 50° C. for 16 hours. Water was added thereto. The products were washed by centrifugal filtration, dried and then triturated to obtain hot-water-treated starch granules. To 700 g of the obtained hot-water-treated starch granules, 157.5 g of sodium sulfate and 1,300 g of water were added to prepare a starch suspension. After adjusting the pH of the suspension to 11.0, 52.5 g of propylene oxide was added and stirred at 40° C. for 24 hours to allow a reaction to proceed. After the reaction, the pH of the suspension was adjusted to 5.5 and the reaction was terminated.

(Examples 39-1, 39-2, 39-3, 39-4 and 39-5) Preparation of Enzyme-Treated Hydroxypropylated Starch Granule To 1,000 g of untreated native wheat starch granules of the same lot as what was used in Comparative Example 25-1, 1,850 g of water was added to prepare a starch suspension. After adjusting the pH of the suspension to 5.0, 0.5% by weight (based on starch dry weight) of amyloglucosidase (derived from *Aspergillus niger*) prepared in Example 12C was added and allowed the enzyme reaction to proceed at 50° C. so that the degradation ratio became 2% by weight, 3% by weight, 5% by weight, 10% by weight or 20% by weight. After finishing the reaction, water was added. The products were washed by centrifugal filtration, dried and then triturated to prepare enzyme-treated starch granules having each of the degradation ratios. To 700 g of the prepared enzyme-treatment starch granules having each of the degradation ratios, 157.5 g of sodium sulfate and 1,300 g of water were added to prepare a starch suspension. After adjusting the pH of the suspension to 11.0, 52.5 g of propylene oxide was added and stirred at 40° C. for 24 hours to allow a reaction to proceed. After the reaction, the pH of the suspension was adjusted to 5.5 and the reaction was terminated.

(Comparative Example 26) Preparation of Acetylated Starch Granule

To 700 g of untreated native cassava starch granules, 14 g of sodium chloride and 1,300 g of water were added to prepare a starch suspension. After adjusting the pH of the suspension to pH 11.0, 3.5 g of vinyl acetate monomer was added and stirred at 30° C. for 4 hours to allow a reaction to proceed. After the reaction, the pH of the suspension was adjusted to 5.5 and the reaction was terminated.

(Examples 40-1, 40-2, 40-3, 40-4 and 40-5) Preparation of Enzyme-Treated Acetic Acid Treated Starch Granule To 1,000 g of untreated native cassava starch granules of the same lot as what was used in Comparative Example 26, 1,850 g of water was added to prepare a starch suspension. The pH of the suspension was adjusted to 5.0, 0.5% by weight (based on starch dry weight) of α-amylase (derived from *Aspergillus niger*) prepared in Example 12B was added and allowed the enzyme reaction to proceed at 50° C. so that the degradation ratio became 2% by weight, 3% by weight, 5% by weight, 10% by weight or 20% by weight. After finishing the reaction, water was added. The products were washed by centrifugal filtration, dried and then triturated to prepare enzyme-treated starch granules having each of the degradation ratios. To 700 g of the enzyme-treated starch granules prepared having each degradation ratio, 14 g of sodium chloride and 1,300 g of water were added to prepare a starch suspension. After adjusting the pH of the suspension to 11.0, 3.5 g of vinyl acetate monomer was added and stirred at 30° C. for 4 hours to allow a reaction to proceed. After the reaction, the pH of the suspension was adjusted to 5.5 and the reaction was terminated.

(Comparative Example 27) Preparation of Hydroxypropylated Starch Granule

To 700 g of untreated native corn starch, 157.5 g of sodium sulfate and 1,300 g of water were added to prepare a starch suspension. After adjusting the pH of the suspension to 11.0, 52.5 g of propylene oxide was added and stirred at 40° C. for 24 hours to allow a reaction to proceed. After the reaction, the pH of the suspension was adjusted to 5.5 and the reaction was terminated.

(Examples 41-1 and 41-2) Preparation of Enzyme-Treated-Hydroxypropylated Starch Granule To 1,000 g of untreated native corn starch of the same lot as what was used in Comparative Example 27, 1,850 g of water was added to prepare a starch suspension. The pH of the suspension was adjusted to 5.0. 0.5% by weight (based on starch dry weight) of amyloglucosidase (derived from *Aspergillus niger*) prepared in Example 12C was added and allowed the enzyme reaction to proceed at 50° C. so that the degradation ratio became 5% by weight or 20% by weight. After finishing the reaction, water was added, washed by centrifugal filtration, dried and then triturated to obtain enzyme-treated starch granules having each of the degradation ratios. To 700 g of the prepared enzyme-treated starch granules having each degradation ratio, 157.5 g of sodium sulfate and 1,300 g of water were added to prepare a starch suspension. After adjusting the pH of the suspension to 11.0, 52.5 g of propylene oxide was added and stirred at 40° C. for 24 hours to allow a reaction to proceed. After the reaction, the pH of the suspension was adjusted to 5.5 and the reaction was terminated.

Examination of the Easiness of Precipitation of the Starches of Examples 39 to 41

Easiness of precipitation was examined for the etherified starch granules obtained in Comparative Examples 25 to 27 and the enzyme-treated-etherified starch granules obtained in Examples 39 to 41. As indications of the easiness of precipitation, turbid liquid volume, turbidity of the supernatant and amount of all saccharides in the supernatant were examined.

At first, immediately after the chemical modification reaction (i.e., immediately after pH adjustment), 100 ml of the reaction liquid was put in a graduated cylinder, left for 70 hours at room temperature and then the height of interface of the supernatant part which is seen to be transparent and the suspension part which is seen to be turbid was read. It was considered as a turbid liquid volume. Furthermore, the supernatant was taken and absorbance at 720 nm was measured. The value was considered as turbidity. Furthermore, the amount of all saccharides in the supernatant was measured by a phenol-sulfuric acid method to determine the amount of all saccharides in the supernatant.

As for filtration time, after chemical modification reaction (i.e., immediately after pH adjustment), 400 g of the reaction liquid was filtered with No. 2 filter paper to measure a time period until the filtrate amount arriving at 100 ml or 200 ml. Furthermore, filtration velocity per minute was calculated from the time taken to arrive at 200 ml, and the values were compared.

Results of these experiments are shown in following Tables 27 to 29.

TABLE 27

Confirmation of State of reaction liquid
Raw material: Untreated wheat starch; with etherification (hydroxypropylated) treatment.

|  | Enzyme-treatment (degradation ratio) (% by weight) | Room temperature, stand alone, 70 hrs | | | |
| --- | --- | --- | --- | --- | --- |
|  |  | Turbid liquid volume (per 100 ml) | Turbidity of Supernatant (Abs 720 nm) | Amount of all saccharides in the supernatant (mg/100 ml) | Comparison of amounts of all saccharides in the supernatant |
| Comparative example 25-1 | — | 60 ml | 0.953 | 1229 | 1 |
| Example 39-1 | 2 | 59 ml | 0.185 | 442 | 0.36 |
| Example 39-2 | 3 | 57 ml | 0.138 | 409 | 0.33 |
| Example 39-3 | 5 | 51 ml | 0.159 | 209 | 0.17 |
| Example 39-4 | 10 | 55 ml | 0.104 | 313 | 0.25 |
| Example 39-5 | 20 | 54 ml | 0.062 | 149 | 0.12 |
| Comparative example 25-2 | hot-water treatment | 62 ml | — | — | — |

|  | Filtration time | | Filtration velocity | Comparison of Filtration |
| --- | --- | --- | --- | --- |
|  | Time arriving at 100 ml filtrate | Time arriving at 200 ml filtrate | calculated from the time taken to arrive at 200 ml filtrate | velocity calculated from the time taken to arrive at 200 ml filtrate |
| Comparative example 25-1 | 12 min | 72 min | 2.8 ml/min | 1 |
| Example 39-1 | 11 min | 49 min | 4.1 ml/min | 1.46 |
| Example 39-2 | 10 min | 40 min | 5.0 ml/min | 1.79 |

TABLE 27-continued

Confirmation of State of reaction liquid
Raw material: Untreated wheat starch; with etherification (hydroxypropylated) treatment.

| | | | | |
|---|---|---|---|---|
| Example 39-3 | 10 min | 40 min | 5.0 ml/min | 1.79 |
| Example 39-4 | 7 min | 35 min | 5.7 ml/min | 2.04 |
| Example 39-5 | 4 min | 20 min | 10.0 ml/min | 3.57 |
| Comparative example 25-2 | 12 min | 70 min | 2.9 ml/min | 1.04 |

TABLE 28

Confirmation of State of reaction liquid
Raw material: Untreated cassava starch; with etherification (acetylated) treatment.

| | Enzyme-treatment (degradation ratio) (% by weight) | Room temperature, stand alone, 70 hrs | | | |
|---|---|---|---|---|---|
| | | Turbid liquid volume (per 100 ml) | Turbidity of Supernatant (Abs 720 nm) | Amount of all saccharides in the supernatant (mg/100 ml) | Comparison of amounts of all saccharides in the supernatant |
| Comparative example 26 | — | 60 ml | 0.051 | 218 | 1 |
| Example 40-1 | 2 | 61 ml | 0.047 | 112 | 0.51 |
| Example 40-2 | 3 | 60 ml | 0.027 | 147 | 0.67 |
| Example 40-3 | 5 | 58 ml | 0.025 | 73 | 0.34 |
| Example 40-4 | 10 | 66 ml | 0.029 | 105 | 0.48 |
| Example 40-5 | 20 | 65 ml | 0.045 | 143 | 0.66 |

| | Filtration time | | Filtration velocity | Comparison of Filtration |
|---|---|---|---|---|
| | Time arriving at 100 ml filtrate | Time arriving at 200 ml filtrate | calculated from the time taken to arrive at 200 ml filtrate | velocity calculated from the time taken to arrive at 200 ml filtrate |
| Comparative example 26 | 50 sec | 170 sec | 71 ml/min | 1 |
| Example 40-1 | 40 sec | 95 sec | 126 ml/min | 1.77 |
| Example 40-2 | 40 sec | 112 sec | 107 ml/min | 1.51 |
| Example 40-3 | 40 sec | 116 sec | 103 ml/min | 1.45 |
| Example 40-4 | 35 sec | 101 sec | 119 ml/min | 1.68 |
| Example 40-5 | 35 sec | 88 sec | 136 ml/min | 1.92 |

TABLE 29

Confirmation of State of reaction liquid
Raw material: Untreated corn starch; with etherification (hydroxypropylated) treatment.

| | Enzyme-treatment (degradation ratio) (% by weight) | Room temperature, stand alone, 70 hrs | | | |
|---|---|---|---|---|---|
| | | Turbid liquid volume (per 100 ml) | Turbidity of Supernatant (Abs 720 nm) | Amount of all saccharides in the supernatant (mg/100 ml) | Comparison of amounts of all saccharides in the supernatant |
| Comparative example 27 | — | 46 ml | 0.651 | 201 | 1 |
| Example 41-1 | 5 | 51 ml | 0.149 | 107 | 0.53 |
| Example 41-2 | 20 | 55 ml | 0.064 | 59 | 0.29 |

| | Filtration time | | Filtration velocity | Comparison of Filtration |
|---|---|---|---|---|
| | Time arriving at 100 ml filtrate | Time arriving at 200 ml filtrate | calculated from the time taken to arrive at 200 ml filtrate | velocity calculated from the time taken to arrive at 200 ml filtrate |
| Comparative example 27 | 37 sec | 88 sec | 136 ml/min | 1 |
| Example 41-1 | 22 sec | 66 sec | 182 ml/min | 1.34 |
| Example 41-2 | 30 sec | 65 sec | 185 ml/min | 1.36 |

In the above-described results, in comparison with an enzyme-untreated starch granule, the turbid liquid volume was smaller, and the turbidity of supernatant and amount of all saccharides in the supernatant were also smaller. When the degradation ratio is higher, the turbid liquid volume tends to be smaller, and the turbidity of supernatant and amount of all saccharides in the supernatant also tend to be smaller. From these results, it was found that the step of enzyme-treatment gives properties of easiness of precipitation and easiness of solid-liquid separation to the obtained enzyme-treated-chemically modified starch granules. Furthermore, when the degradation ratio is higher, the filtration velocity tends to be quicker. From these facts, it was found that enzyme-treatment before chemical modification can make the filtration velocity of the obtained starch granules quicker. Conventionally, it was a problem in the industrial production that the chemically modified starch granules have slow filtration velocity. However, it is considered that if enzyme-treatment is performed before a chemical modification, this problem is resolved.

Example 42

Centrifugal filtration and blow-drying of the starch granules prepared in Comparative Examples 25 and 26, and the starch granules prepared in Examples 39 and 40, respectively provided hydroxypropylated starch granules, acetylated starch granules as well as enzyme-treated hydroxypropylated starch granules and enzyme-treated acetylated starch granules as dry powder. Amounts of maximum viscosity increase of these dry powdered starches were measured using RVA (Rapid visco analyzer "TEC MASTER", Perten). Amounts of maximum viscosity increase were analyzed with RVA using 7.5% by weight starch suspension. Immediately after initiation of measurement, it was heated to 50° C. and thereafter, temperature was raised to 95° C. in 4.5° C./min with rotating at 120 rpm. Meanwhile, the starch was gelatinized and viscosity was increased. Amounts of increase of viscosity during every four seconds were measured from a time point when the viscosity arrived at 20 cp until a time point when the viscosity arrived at the highest viscosity, and the maximum value of them was considered as the "maximum viscosity increase". The results are shown in following Table 30.

Furthermore, retrogradation resistance, transparency and film property of the starches of Comparative Examples 28 and 29 and Examples 42-1 to 42-10 were assessed by the method similar to those used for the starches of Comparative Examples 1 to 17 and Examples 1-1 to 15.

TABLE 30

Maximum viscosity increase, retrogradation resistance, transparency and film property of the starch paste using the dry powder

| | Enzyme-treatment (degradation ratio) (% by weight) | Maximum viscosity increase (cP/4 sec) | retrogradation resistance | transparency | film property |
|---|---|---|---|---|---|
| Raw material: Untreated wheat starch; with etherification (hydroxypropylated) treatment. | | | | | |
| Comparative example 28 | — | 33 | Yes | transparent | Yes |
| Example 42-1 | 2 | 43 | Yes | transparent | Yes |
| Example 42-2 | 3 | 47 | Yes | transparent | Yes |
| Example 42-3 | 5 | 50 | Yes | transparent | Yes |

TABLE 30-continued

Maximum viscosity increase, retrogradation resistance, transparency and film property of the starch paste using the dry powder

| | Enzyme-treatment (degradation ratio) (% by weight) | Maximum viscosity increase (cP/4 sec) | retrogradation resistance | transparency | film property |
|---|---|---|---|---|---|
| Example 42-4 | 10 | 50 | Yes | transparent | Yes |
| Example 42-5 | 20 | 54 | Yes | transparent | Yes |
| Raw material: Untreated cassava starch; with esterification (acetylated) treatment. | | | | | |
| Comparative example 29 | — | 55 | Yes | transparent | Yes |
| Example 42-6 | 2 | 75 | Yes | transparent | Yes |
| Example 42-7 | 3 | 85 | Yes | transparent | Yes |
| Example 42-8 | 5 | 90 | Yes | transparent | Yes |
| Example 42-9 | 10 | 89 | Yes | transparent | Yes |
| Example 42-10 | 20 | 101 | Yes | transparent | Yes |

From these results, it was found that the maximum viscosity increase is significantly increased by enzyme-treatment. From this, it is considered that the enzyme-treated-chemically modified starch granules of the present invention can be gelatinized faster than conventional starch to form starch paste. Furthermore, even if enzymatic treatment was performed, there was no inferiority in retrogradation resistance, transparency, and the film property in comparison with those which have not been enzyme-treated. This shows that enzyme-treatment does not adversely affect the effects of the chemical treatment.

Comparative Example 43-1

To 700 g of untreated native wheat starch granules of the same lot as what was used in Comparative Example 25-1, 157.5 g of sodium sulfate and 1,300 g of water were added to prepare a starch suspension. After adjusting the pH of the suspension to 11.0, 17.5 g (2.5% by weight based on starch dry weight) of propylene oxide was added and stirred at 40° C. for 24 hours to allow a reaction to proceed. After the reaction, the pH of the suspension was adjusted to 5.5 and the reaction was terminated. Then, washing and dehydration were carried out by centrifugal filtration, blow-dried and then triturated to obtain hydroxypropylated starch granules as dry powder.

Example 43-2

To 1,000 g of untreated native wheat starch of the same lot as what was used in Comparative Example 25-1, 1,850 g of water was added to prepare a starch suspension. After adjusting the pH of the suspension to 5.0, 0.5% by weight (based on starch dry weight) of amyloglucosidase (derived from *Aspergillus niger*) prepared in Example 12C was added and allowed the enzyme reaction to proceed at 50° C. so that the degradation ratio became 20% by weight. Then, washing and dehydration were carried out by centrifugal filtration, blow-dried and then triturated to obtain enzyme-treated starch granules as dry powder.

To 700 g of the prepared enzyme-treated starch granules, 157.5 g of sodium sulfate and 1,300 g of water were added to prepare a starch suspension. After adjusting the pH of the suspension to 11.0, 17.5 g (2.5% by weight based on starch dry weight) of propylene oxide was added and stirred at 40° C. for 24 hours to allow a reaction to proceed. After the reaction, the pH of the suspension was adjusted to 5.5 and the reaction was terminated. Then, washing and dehydration were carried out by centrifugal filtration, blow-dried and then triturated to obtain enzyme-treated-hydroxypropylated starch granules as dry powder.

Example 43-3

To 1,000 g of untreated native wheat starch granules of the same lot as what was used in Comparative Example 25-1, 225 g of sodium sulfate and 1,850 g of water were added to prepare a starch suspension. After adjusting the pH of the suspension to 11.0, 17.5 g (2.5% by weight based on starch dry weight) of propylene oxide was added and stirred at 40° C. for 24 hours to allow a reaction to proceed. After the reaction, the pH of the suspension was adjusted to 5.5 and the reaction was terminated. Then, washing and dehydration were carried out by centrifugal filtration, blow-dried and then triturated to obtain hydroxypropylated starch granules as dry powder. To 700 g of the prepared hydroxypropylated starch granules, 1,300 g of water was added to prepare a starch suspension. After adjusting the pH of the suspension to 5.0, 0.5% by weight (based on starch dry weight) of amyloglucosidase (derived from *Aspergillus niger*) prepared in Example 12C was added and allowed the enzyme reaction to proceed at 50° C. so that the degradation ratio became 20% by weight. Then, washing and dehydration were carried out by centrifugal filtration, blow-dried and then triturated to obtain enzyme-treated-hydroxypropylated starch granules.

Comparative Example 43-4

To 700 g of untreated native wheat starch granules of the same lot as what was used in Comparative Example 25-1, 157.5 g of sodium sulfate and 1,300 g of water were added to prepare a starch suspension. After adjusting the pH of the suspension to 11.0, 35 g (5% by weight based on starch dry weight) of propylene oxide was added and stirred at 40° C. for 24 hours to allow a reaction to proceed. After the reaction, the pH of the suspension was adjusted to 5.5 and the reaction was terminated. Then, washing and dehydration were carried out by centrifugal filtration, blow-dried and then triturated to obtain hydroxypropylated starch granules as dry powder.

Example 43-5

To 1,000 g of untreated native wheat starch granules of the same lot as what was used in Comparative Example 25-1, 1,850 g of water was added to prepare a starch suspension. After adjusting the pH of the suspension to 5.0, 0.5% by weight (based on starch dry weight) of amyloglucosidase (derived from *Aspergillus niger*) prepared in Example 12C was added and allowed the enzyme reaction to proceed at 50° C. so that the degradation ratio became 20% by weight. Then, washing and dehydration were carried out by centrifugal filtration, blow-dried and then triturated to obtain enzyme-treated starch granules.

To 700 g of the prepared enzyme-treated starch granules, 157.5 g of sodium sulfate and 1,300 g of water were added to prepare a starch suspension. After adjusting the pH of the suspension to 11.0, 35 g (5% by weight based on starch dry weight) of propylene oxide was added and stirred at 40° C. for 24 hours to allow a reaction to proceed. After the reaction, the pH of the suspension was adjusted to 5.5 and the reaction was terminated. Then, washing and dehydration were carried out by centrifugal filtration, blow-dried and then triturated to obtain enzyme-treated-hydroxypropylated starch granules as dry powder.

Example 43-6

To 1,000 g of untreated native wheat starch granules of the same lot as what was used in Comparative Example 25-1, 225 g of sodium sulfate and 1,850 g of water were added to prepare a starch suspension. After adjusting the pH of the suspension to 11.0, 35 g (0.5% by weight based on starch dry weight) of propylene oxide was added and stirred at 40° C. for 24 hours to allow a reaction to proceed. After the reaction, the pH of the suspension was adjusted to 5.5 and the reaction was terminated. Then, washing and dehydration were carried out by centrifugal filtration, blow-dried and then triturated to obtain hydroxypropylated starch granules as dry powder. To 700 g of the prepared hydroxypropylated starch granules, 1,300 g of water was added to prepare a starch suspension. After adjusting the pH of the suspension to 5.0, 0.5% by weight (based on starch dry weight) of amyloglucosidase (derived from *Aspergillus niger*) prepared in Example 12C was added and allowed the enzyme reaction to proceed at 50° C. so that the degradation ratio became 20% by weight Then, washing and dehydration were carried out by centrifugal filtration, blow-dried and then trituiated to obtain hydroxypropylated-enzyme-treated starch granules.

Example 43-7

To 1,000 g of untreated native wheat starch granules of the same lot as what was used in Comparative Example 25-1, 1,850 g of water was added to prepare a starch suspension. After adjusting the pH of the suspension to 5.0, 0.5% by weight (based on starch dry weight) of amyloglucosidase (derived from *Aspergillus niger*) prepared in Example 12C was added and allowed the enzyme reaction to proceed at 50° C. so that the degradation ratio became 20% by weight. Then, washing and dehydration were carried out by centrifugal filtration, blow-dried and then triturated to obtain enzyme-treated starch granules.

To 700 g of the prepared enzyme-treated starch granules, 157.5 g of sodium sulfate and 1,300 g of water were added to prepare a starch suspension. After adjusting the pH of the suspension to 11.0, 52.5 g (7.5% by weight based on starch dry weight) of propylene oxide was added and stirred at 40° C. for 24 hours to allow a reaction to proceed. After the reaction, the pH of the suspension was adjusted to 5.5 and the reaction was terminated. Then, washing and dehydration were carried out by centrifugal filtration, blow-dried and then triturated to obtain enzyme-treated-hydroxypropylated starch granules as dry powder.

The amounts of maximum viscosity increase of the starch paste of these hydroxypropylated starch granules, enzyme-treated-hydroxypropylated starch granules and hydroxypropylated-enzyme-treated starch granules were measured. Amounts of maximum viscosity increase were analyzed with RVA using 7.5% by weight starch suspension. Immediately after initiation of the measurement, it was heated to 50° C. and thereafter, the temperature was raised to 95° C. in 4.5° C./min with rotating at 120 rpm. Meanwhile, the starches were gelatinized and viscosity was increased. Amounts of increase of viscosity during every four seconds were measured from a time point when the viscosity arrived at 20 cp until a time point when the viscosity arrived at the highest viscosity, and the maximum value of them was considered as the "maximum viscosity increase". The results are shown in following Table 31.

TABLE 31

Maximum viscosity increase depends on the presence or absence of enzyme treatment, and the timing of the enzyme-treatment Raw material: Untreated wheat starch; with etherification (hydroxypropylated) treatment.

|  | Amount of added propylene oxide (% by weigh: based on starch weight) | Enzyme-treatment | Maximum viscosity increase (cp/4 sec) |
|---|---|---|---|
| Comparative Example 43-1 | 2.5 | No | 42 |
| Example 43-2 | 2.5 | After Chemical Modification | 45 |
| Example 43-3 | 2.5 | Before Chemical Modification | 45 |
| Comparative Example 43-4 | 5.0 | No | 42 |
| Example 43-5 | 5.0 | After Chemical Modification | 42 |
| Example 43-6 | 5.0 | Before Chemical Modification | 72 |
| Comparative Example 28 | 7.5 | No | 33 |
| Example 43-7 | 7.5 | After Chemical Modification | 39 |
| Example 42-5 | 7.5 | Before Chemical Modification | 54 |

Usually, etherification with propylene oxide results in a decrease in the maximum viscosity increase in comparison with the untreated starch. The tendency will be significant when the amount of propylene oxide added is increased. However, it was found that if an enzyme-treatment is performed before the chemical modification, the maximum viscosity increase is not significantly lowered, and in some cases it is increased. Furthermore, if the enzyme-treatment was performed after the chemical modification, a decrease in the maximum viscosity increase was not prevented. From these facts, it is clear that it is important to perform the enzyme-treatment before chemical modification in order not to spoil easiness of gelatinization of the starch granules.

Comparative Example 30

To 700 g of untreated native wheat starch granules of the same lot as what was used in Comparative Example 25-1, 2.94 g of calcium chloride and 1,300 g of water were added to prepare a starch suspension. After adjusting the pH of the suspension to 11.0, 1.4 g of sodium trimetaphosphate was added and stirred at 35° C. for 2 hours to allow a reaction to proceed. After the reaction, the pH of the suspension was adjusted to 5.5 and the reaction was terminated. Then, washing and dehydration were carried out by centrifugal filtration, blow-dried and then triturated to obtain phosphate-crosslinking starch granules as dry powder.

To 700 g of the prepared phosphate-crosslinking starch granules, 157.5 g of sodium sulfate and 1,300 g of water were added to prepare a starch suspension. After adjusting the pH of the suspension to 11.0, 52.5 g of propylene oxide was added and stirred at 40° C. for 24 hours to allow a reaction to proceed. After the reaction, the pH of the suspension was adjusted to 5.5 and the reaction was terminated. Then, washing and dehydration were carried out by centrifugal filtration, blow-dried and then triturated to obtain phosphate-crosslinking-hydroxypropylated starch granules as dry powder.

Example 44

To 1,000 g of untreated native wheat starch granules of the same lot as what was used in Comparative Example 25-1, 4.2 g of calcium chloride and 1,850 g of water were added to prepare a starch suspension. After adjusting the pH of the suspension to 11.0, 2.0 g of sodium trimetaphosphate was added and stirred at 35° C. for 2 hours to allow a reaction to proceed. After the reaction, the pH of the suspension was adjusted to 5.5 and the reaction was terminated. Then, washing and dehydration were carried out by centrifugal filtration, blow-dried and then triturated to obtain phosphate-crosslinking starch granules as dry powder. To 1,000 g of the obtained phosphate-crosslinking starch granules, 1,850 g of water was added to prepare a starch suspension. After adjusting the pH of the suspension to 5.0, 0.5% by weight (based on starch dry weight) of amyloglucosidase (derived from *Aspergillus niger*) prepared in Example 12C was added and allowed the enzyme reaction to proceed at 50° C. so that the degradation ratio became 20% by weight. Then, washing and dehydration were carried out by centrifugal filtration, blow-dried and then triturated to obtain phosphate-crosslinking-enzyme-treated starch granules. To 700 g of the obtained phosphate-crosslinking-enzyme-treated starch granules, 157.5 g of sodium sulfate and 1,300 g of water were added to prepare a starch suspension. After adjusting the pH of the suspension to 11.0, 52.5 g of propylene oxide was added and stirred at 40° C. for 24 hours to allow a reaction to proceed. After the reaction, the pH of the suspension was adjusted to 5.5 and the reaction was terminated. Then, washing and dehydration were carried out by centrifugal filtration, blow-dried and then triturated to obtain phosphate-crosslinking-enzyme-treated-hydroxypropylated starch granules as dry powder.

The phosphate-crosslinking-hydroxypropylated starch granules obtained by Comparative Example 30 or the phosphate-crosslinking-enzyme-treated-hydroxypropylated starch granules obtained by Example 44 were added to water to prepare 40% by weight of starch suspension, put in a graduated cylinder, and left stand at room temperature for 30 hours. Then, the height of interface of the supernatant part which is seen to be transparent and the suspension part which is seen to be turbid was read. It was considered as a turbid liquid volume. Furthermore, the supernatant was taken and the absorbance at 720 nm was measured. The value was considered as turbidity. Furthermore, the amount of all saccharides in the supernatant was measured by a phenol-sulfuric acid method. The results are shown in following Table 32.

TABLE 32

Confirmation of State at the time of resuspension of the product
Raw material: phosphate-crosslinking wheat starch; with etherification (hydroxypropylation) treatment.

|  | Enzyme-treatment (degradation ratio) (% by weight) | Room temperature, stand alone, 30 hrs | | |
|---|---|---|---|---|
|  |  | Turbid liquid volume (per 100 ml) | Turbidity of Supernatant (Abs 720 nm) | Amount of all saccharides in the supernatant (mg/100 ml) |
| Comparative example 30 | — | 85 ml | 2.267 | 1811 |
| Example 44 | 20 | 54 ml | 0.172 | 64 |

As a result of these, also in the case of resuspension, for the enzyme-treated starch granules, the turbid liquid volume was decreased and turbidity of the supernatant and the amount of all saccharides in the supernatant were decreased, in comparison with enzyme-untreated starch granules. It was found from these results that the obtained enzyme-treated-chemically modified starch granules are easily precipitated and have a property that it is easy to perform solid-liquid separation, as a result or the enzyme-treatment.

As described above, the present invention has been exemplified using a preferred embodiment of the present invention, but the present invention should not be construed to be limited to this embodiment. It is understood that the present invention should be construed for its scope only by the claims. It is understood that those skilled in the art can practice an equivalent range based on the description of the invention and the technical common knowledge, from the description of the specific preferable embodiment of the present invention. It is understood that patents, patent applications and publications cited in the present specification should be herein incorporated a reference for the content thereof as if the contents themselves were specifically described in the present specification.

INDUSTRIAL APPLICABILITY

As described above, the present invention provides various industrial advantages by using an enzyme having characteristics capable of increasing a maximum viscosity of a starch.

According to the present invention, it becomes possible to provide a food having new textures which could not be obtained by a conventional chemically unmodified starch and a chemically modified starch. For example, use of the enzyme-treated cassava starch in the present invention makes it possible to prepare a cookie which is very light and soft and has texture with nice melt in mouth, and to provide a cookie having readily edible texture which is also suited for persons of advanced age and infants. In addition, since the dough at the time of shaping a cookie is very dry and not sticky, the water addition amount at the time of preparing the dough can be further increased, thus making it possible to increase a yield factor. Furthermore, for a food such as kudzu starch cake so-called in the Kanto area, which requires long time and much labor heretofore because the preparation of a wheat starch as a raw material requires a fermentation process for a long period such as one or more years, use of an enzyme-treated wheat starch of the present invention makes it possible to easily prepare a kudzu starch cake so-called in the Kanto area which does not have fermentation odor derived from a fermented wheat starch and has nice flavor, without requiring such long time and much labor.

Furthermore, when the enzyme-treated cassava starch of the present invention is used in noodles, for example, raw udon, the texture improving effect of impairing sticky texture with rich chewiness is recognized, and no adverse influence was exerted on factors of the quality of noodles, such as "slippery and smooth" and "sogginess". Thus, it has been found that the addition of this enzyme-treated starch easily improve the texture of the noodle to those favored by Japanese.

The starch granules of the present invention can be preferably used not only for food application but also for various other applications. The starch granules of the present invention can be preferably used, for example, for a biodegradable article. Particularly, the enzyme-treated-chemically modified starch granules of the present invention have characteristics that solid-liquid separation from suspension is easy, precipitation speed is fast and a viscosity increase in water is rapid. Therefore, the enzyme-treated-chemically modified starch granules of the present invention can be preferably used in applications in need of quick solid-liquid separation or the precipitation. The enzyme-treated-chemically modified starch granules of the present invention also can be preferably used in the applications in need of a quick viscosity increase.

The invention claimed is:

1. A method of producing a starch gel-containing food, the method comprising the steps of:
   treating starch granules with an enzyme at a temperature of about 10° C. or higher and about 70° C. or lower to obtain enzyme-treated starch granules having improved gel forming ability, wherein the enzyme-treated starch granules form a gel having a rupture stress higher than that of the starch granules before the treatment with the enzyme when measured by a rheometer;
   mixing a food material, the enzyme-treated starch granules and water to obtain a mixture;
   heating the mixture thereby gelatinizing the enzyme-treated starch granules in the mixture; and
   cooling the mixture containing the gelatinized enzyme-treated starch granules thereby gelling the starch to obtain a starch gel-containing food, wherein
   the enzyme is selected from the group consisting of α-amylase having a characteristic capable of improving a gel forming ability of a starch, amyloglucosidase, α-glucosidase, isoamylase, and cyclodextrin glucanotransferase.

2. The method according to claim 1, wherein the enzyme is selected from the group consisting of α-amylase derived from the genus *Aspergillus*, amyloglucosidase, α-glucosidase, isoamylase, and cyclodextrin glucanotransferase.

3. The method according to claim 1, wherein the enzyme is selected from the group consisting of α-amylase derived from *Aspergillus oryzae*, α-amylase derived from *Aspergillus niger*, amyloglucosidase, α-glucosidase, isoamylase, and cyclodextrin glucanotransferase.

4. The method according to claim 1, wherein the enzyme is selected from the group consisting of
   α-amylase derived from *Aspergillus oryzae* or *Aspergillus niger*;
   amyloglucosidase derived from *Aspergillus niger*, *Rhizopus niveus* or *Rhizopus oryzae*;
   α-glucosidase derived from *Aspergillus niger*;
   isoamylase derived from *Flavobacterium* sp. or *Pseudomonas amyloderamosa*; and
   cyclodextrin glucanotransferase derived from *Bacillus licheniformis* or *Paenibacillus macerans* (*Bacillus macerans*).

5. The method according to claim 1, wherein the enzyme is selected from the group consisting of
   α-amylase derived from *Aspergillus oryzae* commercially available from Amano Enzyme as Biozyme A, α-amylase derived from *Aspergillus oryzae* commercially available from SHIN NIHON CHEMICALS Corporation as Sumizyme L, α-amylase derived from *Aspergillus niger* commercially available from Danisco as AMYLEX A3, α-amylase derived from *Aspergillus niger* commercially available from SHIN NIHON CHEMICALS Corporation as Sumizyme AS,
   amyloglucosidase derived from *Aspergillus niger* commercially available from Novozyme as AMG, amyloglucosidase derived from *Aspergillus niger* commercially available from Genencor as OPTIDEX L-400, amyloglucosidase derived from *Aspergillus niger* commercially available from DANISCO as DIAZYME X4NP,
   amyloglucosidase derived from *Aspergillus niger* commercially available from Amano Enzyme as glucoamylase "Amano" SD, amyloglucosidase derived from *Rhizopus niveus* commercially available from Amano Enzyme as Gluczyme AF6,
   amyloglucosidase derived from *Rhizopus oryzae* commercially available from SHIN NIHON CHEMICALS Corporation as Sumizyme, α-glucosidase derived from *Aspergillus niger* commercially available from Amano Enzyme as transglucosidase L "Amano", α-glucosidase derived from *Aspergillus niger* commercially available from Genencor as Transglucosidase L-500,
isoamylase derived from *Pseudomonas amyloderamosa* commercially available from Sigma as isoamylase, cyclodextrin glucanotransferase derived from *Bacillus licheniformis* commercially available from Novozyme as Toruzyme, and cyclodextrin glucanotransferase derived from *Paenibacillus macerans* (*Bacillus macerans*) commercially available from Amano Enzyme as Cyclodextrin glucanotransferase "Amano".

6. The method according to claim 1, wherein:
(1) the enzyme is encoded by a nucleic acid molecule which is capable of hybridizing under stringent conditions with a nucleic acid molecule consisting of a base sequence complementary to a base sequence of SEQ ID NO: 1, 3, 5, 11, 7, or 9, and has a starch hydrolysis activity; or
(2) the enzyme is encoded by a nucleic acid molecule which is capable of hybridizing under stringent conditions with a nucleic acid molecule consisting of a base sequence complementary to a base sequence of SEQ ID NO: 13, and has a transglycosylation activity;
wherein the stringent conditions of (1) and (2) are hybridization in a solution containing 50% formamide, 5×SSC (750 mM NaCl, 75 mM trisodium citrate), 50 mM sodium phosphate (pH 7.6), 5×Denhardt's solution (0.2% BSA, 0.2% Ficoll 400 and 0.2% polyvinylpyrrolidone), 10% dextran sulfate and 20 µg/ml denatured sheared salmon sperm DNA at 65° C., and subsequent washing under the condition of 65° C. using an SSC solution having a 0.1 to 2-fold concentration (a composition of an SSC solution having a 1-fold concentration is 150 mM sodium chloride and 15 mM sodium citrate).

7. The method according to claim 1, wherein:
(1) the enzyme has an amino acid sequence having at least 95% or more of homology with an amino acid sequence of SEQ ID NO: 2, 4, 6, 12, 8, or 10, and has a starch hydrolysis activity; or
(2) the enzyme has an amino acid sequence having at least 95% or more of homology with an amino acid sequence of SEQ ID NO: 14, and has a transglycosylation activity.

8. The method according to claim 1, wherein the starch granules to be enzyme-treated are starch granules of an untreated starch, a physically treated starch or a chemically modified starch.

9. The method according to claim 1, wherein the starch granules to be enzyme-treated are starch granules of an untreated starch, and the starch granules have been neither chemically modified nor physically treated in any stage until the starch gel-containing food is obtained by the method.

10. The method according to claim 1, wherein the starch granules to be enzyme-treated are starch granules of an untreated starch or a physically treated starch, the method further comprises the step of chemically modifying the enzyme-treated starch granules, and the chemically modified enzyme-treated starch granules are mixed with the food material and water.

11. The method according to claim 1, wherein the starch granules to be enzyme-treated are starch granules of an untreated starch or a chemically modified starch, the method further comprises the step of physically treating the enzyme-treated starch granules, and the physically treated enzyme-treated starch granules are mixed with the food material and water.

12. The method according to claim 1, further comprising the step of removing a carbohydrate eluted by enzymatic degradation from the product comprising enzyme-treated starch granules, before the step of mixing the food material, the enzyme-treated starch granules and water to obtain the mixture.

13. A starch gel-containing food produced by the method according to claim 1.

14. The food according to claim 13, wherein the food is a high moisture content type food and the amount of moisture of the food is more than 40 g and less than 95 g per 100 g of the edible portion.

15. The food according to claim 13, wherein the food is selected from the group consisting of traditional Japanese-style confectioneries, fat- or oil-containing foods, gelatinous foods, fish meat and animal meat processed foods, salsa and sauces, and noodles.

16. The food according to claim 13, wherein the food is a low moisture content type food and the amount of moisture of the food is 1 g or more and 40 g or less per 100 g of the edible portion.

17. The food according to claim 13, wherein the food is selected from the group consisting of bakeries, Western-style confectioneries, and fried foods.

18. The food according to claim 13, wherein the enzyme is selected from the group consisting of α-amylase derived from the genus *Aspergillus*, amyloglucosidase, α-glucosidase, isoamylase, and cyclodextrin glucanotransferase.

19. The food according to claim 13, wherein the enzyme is selected from the group consisting of α-amylase derived from *Aspergillus oryzae*, α-amylase derived from *Aspergillus niger*, amyloglucosidase, α-glucosidase, isoamylase, and cyclodextrin glucanotransferase.

20. The food according to claim 13, wherein the starch granules are derived from cassava, corn or wheat.

21. A method of producing enzyme-treated starch granules, the method comprising the steps of:
treating starch granules with an enzyme at a temperature of about 10° C. or higher and about 70° C. or lower to obtain enzyme-treated starch granules having improved gel forming ability, wherein the enzyme-treated starch granules form a gel having a rupture stress higher than that of the starch granules before the treatment with the enzyme when measured by a rheometer; and
removing a carbohydrate eluted by enzymatic degradation from the enzyme-treated starch granules, wherein
the enzyme is selected from the group consisting of α-amylase having a characteristic capable of improving a gel forming ability of a starch, amyloglucosidase, α-glucosidase, isoamylase, and cyclodextrin glucanotransferase.

22. The method according to claim 21, wherein the starch granules are starch granules of an untreated starch, a physically treated starch or a chemically modified starch.

23. The method according to claim 21, wherein the starch granules are starch granules of an untreated starch, and the starch granules have been neither chemically modified nor physically treated in any stage until the final product is obtained by the method.

24. The method according to claim 21, wherein the starch granules are starch granules of an untreated starch or a physically treated starch, the method further comprises the step of chemically modifying the enzyme-treated starch granules.

25. The method according to claim 21, wherein the starch granules are starch granules of an untreated starch or a chemically modified starch, the method further comprises the step of physically treating the enzyme-treated starch granules.

26. A method of producing enzyme-treated-chemically modified starch granules, the method comprising the steps of:
(a) treating starch granules with an enzyme at a temperature of about 10° C. or higher and about 70° C. or lower to obtain enzyme-treated starch granules having improved gel forming ability, wherein the enzyme-treated starch granules form a gel having a rupture stress higher than that of the starch granules before the treatment with the enzyme when measured by a rheometer; and
(b) etherifying or esterifying the enzyme-treated starch granules to obtain an enzyme-treated-chemically modified starch granules, wherein
the method further comprises the step of removing a carbohydrate eluted by enzymatic degradation from the enzyme-treated starch granules, between the steps (a) and (b), or after the step (b), and
the enzyme is selected from the group consisting of α-amylase having a characteristic capable of improving a gel forming ability of a starch, amyloglucosidase, α-glucosidase, isoamylase, and cyclodextrin glucanotransferase.

27. Enzyme-treated starch granules produced by the method according to claim 21.

28. Enzyme-treated and chemically modified starch granules produced by the method according to claim 26.

29. A biodegradable article which was prepared using the enzyme-treated and chemically modified starch granules according to claim 28.

30. The biodegradable article according to claim 29, wherein the biodegradable article is a hydrogel, powder, a film, a sheet, a thread, a fiber or a nonwoven fabric.

31. The biodegradable article according to claim 29, wherein the biodegradable article is a paint or adhesive.

32. The biodegradable article according to claim 29, wherein the biodegradable article is a pharmaceutical drug, a pharmaceutical drug additive, a quasi-drug, a quasi-drug additive, a cosmetic, a cosmetic additive, an agricultural chemical or a fertilizer.

33. The biodegradable article according to claim 29, wherein the biodegradable article is a medical material.

34. The biodegradable article according to claim 29, wherein the biodegradable article is a capsule.

35. The biodegradable article according to claim 29, wherein the biodegradable article is a thickening agent composition for use in a hydrogel for hydraulic fracturing.

36. The biodegradable article according to claim 29, wherein the biodegradable article is a composition to be injected into a human body to form a hydrogel.

* * * * *